(12) United States Patent
Zhang et al.

(10) Patent No.: US 12,180,272 B2
(45) Date of Patent: *Dec. 31, 2024

(54) ANTIGEN BINDING MOLECULE FORMATS

(71) Applicant: Regeneron Pharmaceuticals, Inc., Tarrytown, NY (US)

(72) Inventors: Tong Zhang, New Rochelle, NY (US); Erica Pyles, New City, NY (US); Michael Rosconi, New City, NY (US); Nina Liu, Chappaqua, NY (US); Supriya Patel, Elmsford, NY (US); Eric Smith, New York, NY (US); Andrew Murphy, Croton-on-Hudson, NY (US); Chia-Yang Lin, Scarsdale, NY (US); Samuel Davis, New York, NY (US)

(73) Assignee: Regeneron Pharmaceuticals, Inc., Tarrytown, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 17/666,107

(22) Filed: Feb. 7, 2022

(65) Prior Publication Data

US 2022/0235126 A1 Jul. 28, 2022

Related U.S. Application Data

(63) Continuation of application No. PCT/US2020/045309, filed on Aug. 7, 2020.

(60) Provisional application No. 63/050,483, filed on Jul. 10, 2020, provisional application No. 62/884,496, filed on Aug. 8, 2019.

(51) Int. Cl.
| | |
|---|---|
| *C07K 16/00* | (2006.01) |
| *A61K 39/395* | (2006.01) |
| *A61K 47/68* | (2017.01) |
| *C07K 16/24* | (2006.01) |
| *C07K 16/28* | (2006.01) |
| *C07K 16/30* | (2006.01) |
| *C12P 21/08* | (2006.01) |
| *C07K 1/00* | (2006.01) |

(52) U.S. Cl.
CPC .......... *C07K 16/244* (2013.01); *A61K 39/395* (2013.01); *A61K 47/6845* (2017.08); *C07K 16/2809* (2013.01); *C07K 16/30* (2013.01); *C07K 2317/31* (2013.01); *C07K 2317/35* (2013.01); *C07K 2317/52* (2013.01); *C07K 2317/522* (2013.01); *C07K 2317/53* (2013.01); *C07K 2317/55* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 6,992,174 B2* | 1/2006 | Gillies | C07K 16/30 424/134.1 |
| 2016/0009824 A1* | 1/2016 | Lo | C07K 16/2863 435/69.6 |
| 2016/0194396 A1* | 7/2016 | Johnson | C07K 16/2803 530/387.3 |
| 2016/0355600 A1 | 12/2016 | Moore et al. | |
| 2017/0073418 A1* | 3/2017 | Gao | A61P 43/00 |

FOREIGN PATENT DOCUMENTS

| | | |
|---|---|---|
| WO | 2010/136172 | 12/2010 |
| WO | WO2010145792 A1 | 12/2010 |
| WO | 2011/138392 | 11/2011 |
| WO | 2016/087416 | 6/2016 |
| WO | WO2017049004 A1 | 3/2017 |
| WO | WO2019086362 A1 | 5/2019 |

OTHER PUBLICATIONS

Bates et al., 2019, "David vs. Goliath: The Structure, Function, and Clinical Prospects of Antibody Fragments," Antibodies 8(28):2-3188.
Chiu et al., 2016, "Engineering Antibody Therapeutics," Current Opinion in Structural Biology 38:163-173.
Cuesta et al., 2010, "Multivalent Antibodies: When Design Surpasses Evolution," Trends in Biology 28(7):355-362.
Dimasi et al., 2019, "Molecular Engineering Strategies and Methods for the Expression and Purification of IgG1-Based Bispecific Bivalent Antibodies," Methods 154: 77-86.
Elgundi et al., 2017, "The State-of-play and Future of Antibody Therapeutics," Advanced Drug Delivery Reviews 122:2-19.
Gu et al., 2010, "Rationale and Development of Multispecific Antibody Drugs," Expert Review of Clinical Pharmacology 1-2.
Ha et al., 2016, "Immunoglobulin Fc Heterodimer Platform Technology: From Design to Applications in Therapeutic Antibodies and Proteins," Frontiers in Immunology 7:1-16.
Huang et al., 2016, "Bispecific Antibody Case Studies," Lake Pharma: The Biologics Company, PowerPoint 1-28.

(Continued)

*Primary Examiner* — Chun W Dahle

(74) *Attorney, Agent, or Firm* — Biospark Intellectual Property Law

(57) ABSTRACT

Antigen binding molecules (ABMs) comprising Fab domains in non-native configurations, ABM conjugates comprising the ABMs and cytotoxic or cytostatic agents, pharmaceutical compositions containing the ABMs and ABM conjugates, methods of using the ABMs, ABM conjugates and pharmaceutical compositions for treating cancer, nucleic acids encoding the ABMs, cells engineered to express the ABMs, and methods of producing ABMs.

11 Claims, 43 Drawing Sheets

Figure 1A:
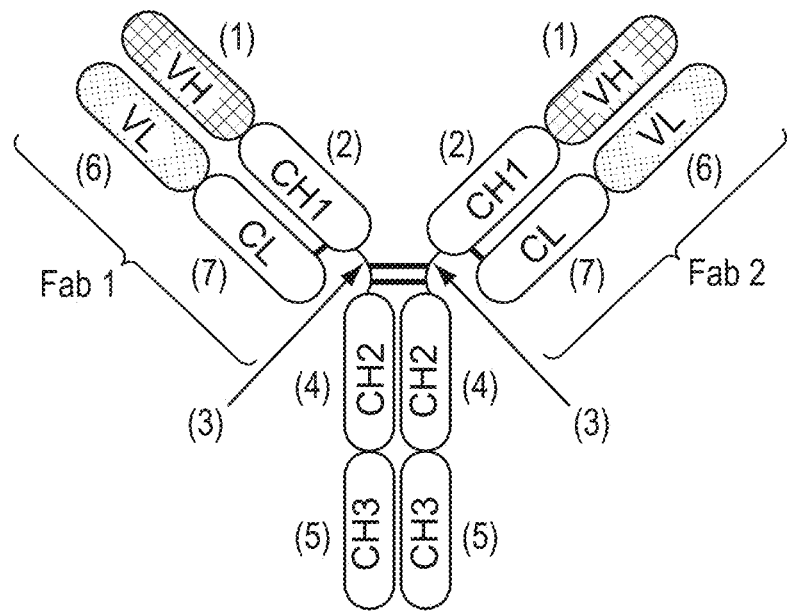

Specification includes a Sequence Listing.

(56) References Cited

OTHER PUBLICATIONS

Notification of Transmittal of the International Search Report and Written Opinion of the International Searching Authority for International Application No. PCT/US2020/045309, dated Nov. 10, 2020, including International Search Report and Written Opinion.
Kareva et al., 2018, "Guiding Principles for Mechanistic Modeling of Bispecific Antibodies," ScienceDirect 139:59-72.
Klein et al., 2019, "Engineering Therapeutic Bispecific Antibodies Using CrossMab Technology," Methods 154:21-31.
Koch et al., 2017, "Recombinant Antibodies to Arm Cytotoxic Lymphocytes in Cancer Immunotherapy," Transfusion Medicine and Hemotherapy 44:337-350.
Kontermann et al., 2012, "Dual Targeting Strategies with Bispecific Antibodies," mAbs 4(2):182-197.
Kontermann et al., 2015, "Bispecific Antibodies," Drug Discovery Today 20(7):838-847.
Labrijn et al., 2019, "Bispecific Antibodies: a Mechanistic Review of the Pipeline," Nature Reviews Drug Discovery 1-24.
Liu et al., 2017, "Fc Engineering for Developing Therapeutic Bispecific Antibodies and Novel Scaffolds," Frontiers in Immunology 8(38): 1-15.
Mertens, Nico, 2011, "Tribodies: Fab-scFv Fusion Proteins as a Platform to Create Multi-functional Pharmaceuticals," Bispecific Antibodies 135-149.
Middleburg et al., 2021, "Overcoming Challenges for CD3-Bispecific Antibody Therapy in Solid Tumors," Cancers 13(287):1-25.
Moore et al., 2019, "A Robust Heterodimeric Fc Platform Engineered for Efficient Development of Bispecific Antibodies of Multiple Formats," Methods 154:38-50.
Nyakatura et al., 2018, "Design and Evaluation of Bio and Trispecific Antibodies Targeting Multiple Filovirus Glycoproteins," JBC Papers 1-19.
Oganesyan et al., 2018 "Structural insights into the mechanism of action of a biaparatopic anti-HER2 antibody" Journal of Biological Chemistry 293(22): 8439-8448.
Padte et al., 2018, "Engineering Multi-specific Antibodies Against HIV-1," Retrovirology 15(60):1-17.
Runcie et al., 2018, "Bi-specific and Tri-specific Antibodies—the Next Big Thing in Solid Tumor Therapeutics," Molecular Medicine 24(50):1-15.
Schanzer et al., 2014, "A Novel Glycoengineering Bispecific Antibody Format for Targeted Inhibition of Epidermal Growth Factor Receptor (EGFR) and Insulin-like Growth Factor Receptor Type I (IGF-1R) Demonstrating Unique Molecular Properties," The Journal of Biological Chemistry 289(27): 18693-18706.
Smith et al., 2015, "A Novel, Native-format Bispecific Antibody Triggering T-cell Killing of B-cells is Robustly Active in Mouse Tumor Models and Cynomolgus Monkeys," Scientific Reports 5(17943):1-12.
Spiess et al., 2015, "Alternative Molecular Formats and Therapeutic Applications for Bispecific Antibodies," Molecular Immunology 67:95-106.
Steinmetz et al., 2016, "COVG-Ig, a Universal Bispecific Tetravalent and Multifunctional Immunoglobulin Format for Medical Applications," mAbs 8(5): 867-878.
Weidle et al., 2013, "The Intriguing Options of Multispecific Antibody Formats for Treatment of Cancer," Cancer Genomics & Proteomics 10: 1-18.
Weidle et al., 2014, "Tumor-Antigen-Binding Bispecific Antibodies for Cancer Treatment," Seminars in Oncology 41(5):653-660.
Wu et al., 2015, "Fab-based Bispecific Antibody Formats with Robust Biophysical Properties and Biological Activity," mAbs 7(3):470-482.
Wu et al., 2019, "Building Blocks for Bispecific and Trispecific Antibodies," Methods 154:3-9.
You et al., 2021, "Bispecific Antibodies: A Smart Arsenal for Cancer Immunotherapies," Vaccines 724:1-28.

* cited by examiner

2+2 Tandem Fab

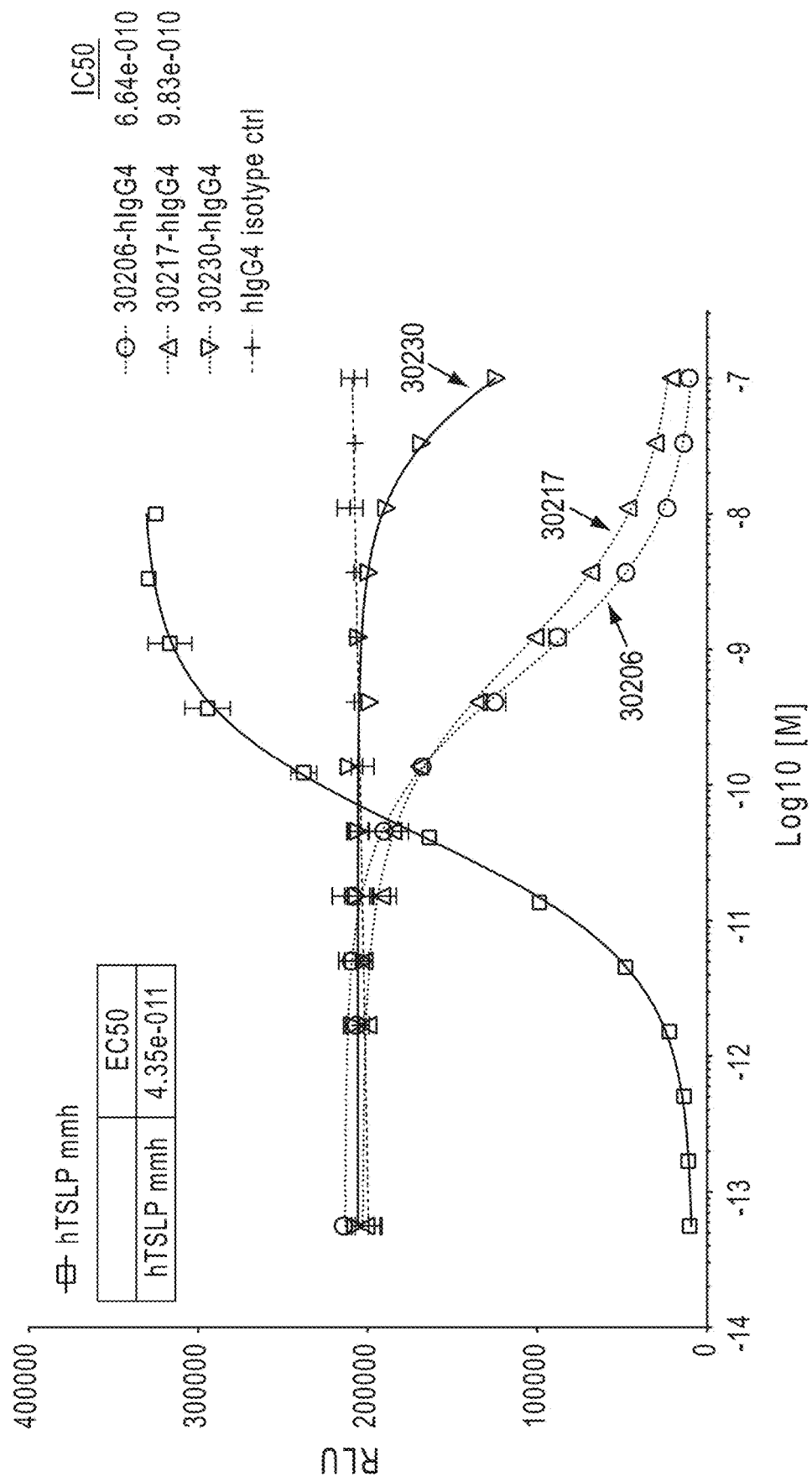

SEQUENCE LISTING

```
<160> NUMBER OF SEQ ID NOS: 39

<210> SEQ ID NO 1
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Gly Gly Gly Gly Ser Cys Pro Pro Cys
1               5

<210> SEQ ID NO 2
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Glu Ser Lys Tyr Gly Pro Pro Cys Pro Pro Cys
1               5                   10

<210> SEQ ID NO 3
```

```
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Gly Gly Gly Gly Ser
1               5

<210> SEQ ID NO 4
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Gly Gly Gly Gly Ser Gly Gly Gly Gly Ser Gly Gly Gly Gly Ser
1               5                   10                  15

<210> SEQ ID NO 5
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Gly Gly Gly Gly
1

<210> SEQ ID NO 6
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Gly Gly Gly Gly Gly
1               5

<210> SEQ ID NO 7
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Gly Gly Gly Gly Gly Gly
1               5

<210> SEQ ID NO 8
<211> LENGTH: 7
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 8

Gly Gly Gly Gly Gly Gly Gly
1               5

<210> SEQ ID NO 9
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Gly Gly Gly Gly Gly Gly Gly Gly
1               5

<210> SEQ ID NO 10
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Gly Gly Gly Gly Gly Gly Gly Gly Gly
1               5

<210> SEQ ID NO 11
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Gly Gly Gly Ser
1

<210> SEQ ID NO 12
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Ser Gly Gly Gly
1

<210> SEQ ID NO 13
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 13

Ser Gly Gly Gly Gly
1               5

<210> SEQ ID NO 14
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Gly Gly Gly Gly Gly Ser
1               5

<210> SEQ ID NO 15
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Ser Gly Gly Gly Gly Gly
1               5

<210> SEQ ID NO 16
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Gly Gly Gly Gly Gly Gly Ser
1               5

<210> SEQ ID NO 17
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Ser Gly Gly Gly Gly Gly Gly
1               5

<210> SEQ ID NO 18
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Gly Gly Gly Gly Ser Gly Gly Gly Gly Ser
1               5                   10
```

```
<210> SEQ ID NO 19
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Gly Gly Gly Gly Ser Gly Gly Gly Ser Gly Gly Gly Ser Gly
1               5                   10                  15

Gly Gly Gly Ser
            20

<210> SEQ ID NO 20
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Cys Pro Pro Cys
1

<210> SEQ ID NO 21
<211> LENGTH: 4
<212> TYPE: PRT
<213> ORGANISM: Homo sapiens

<400> SEQUENCE: 21

Cys Pro Ser Cys
1

<210> SEQ ID NO 22
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Glu Pro Lys Ser Cys Asp Lys Thr His Thr Cys Pro Pro Cys Pro Ala
1               5                   10                  15

Pro Pro Val Ala
            20

<210> SEQ ID NO 23
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Glu Ser Lys Tyr Gly Pro Pro Cys Pro Pro Cys Pro Ala Pro Pro Val
1               5                   10                  15

Ala
```

```
<210> SEQ ID NO 24
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Cys Pro Pro Cys Pro Ala Pro Gly Gly Gly Gly Pro Ser Val Phe
1               5                   10                  15

<210> SEQ ID NO 25
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Cys Pro Pro Cys Pro Ala Pro Gly Gly Gly Pro Ser Val Phe
1               5                   10

<210> SEQ ID NO 26
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Cys Pro Pro Cys Pro Ala Pro Gly Gly Pro Ser Val Phe
1               5                   10

<210> SEQ ID NO 27
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Cys Pro Pro Cys Pro Ala Pro Gly Pro Ser Val Phe
1               5                   10

<210> SEQ ID NO 28
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Asp Lys Arg Val Glu Ser Lys Tyr Gly Pro Pro Cys Pro Pro Cys Pro
1               5                   10                  15

Ala Pro Pro Val Ala Gly Pro Ser Val Phe Leu Phe Pro Pro Lys Pro
                20                  25                  30
```

-continued

```
Lys Asp Thr Leu Met Ile Ser Arg Thr Pro Glu Val Thr Cys Val Val
         35                  40                  45

Val Asp Val Ser Gln Glu Asp Pro Glu Val Gln Phe Asn Trp Tyr Val
 50                  55                  60

Asp Gly Val Glu Val His Asn Ala Lys Thr Lys Pro Arg Glu Glu Gln
65                  70                  75                  80

Phe Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Gly
             100                 105                 110

Leu Pro Ser Ser Ile Glu Lys Thr Ile Ser Lys Ala Lys Gly Gln Pro
         115                 120                 125

Arg Glu Pro Gln Val Tyr Thr Leu Pro Pro Ser Gln Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Arg Leu Thr Val Asp Lys Ser Arg Trp Gln Glu Gly Asn Val Phe
        195                 200                 205

Ser Cys Ser Val Met His Glu Ala Leu His Asn His Tyr Thr Gln Lys
    210                 215                 220

Ser Leu Ser Leu Ser Leu Gly Lys
225                 230

<210> SEQ ID NO 29
<211> LENGTH: 235
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Asp Lys Lys Val Glu Pro Lys Ser Cys Asp Lys Thr His Thr Cys Pro
1               5                   10                  15

Pro Cys Pro Ala Pro Pro Val Ala Gly Pro Ser Val Phe Leu Phe Pro
            20                  25                  30

Pro Lys Pro Lys Asp Thr Leu Met Ile Ser Arg Thr Pro Glu Val Thr
        35                  40                  45

Cys Val Val Val Asp Val Ser Gln Glu Asp Pro Glu Val Gln Phe Asn
 50                  55                  60

Trp Tyr Val Asp Gly Val Glu Val His Asn Ala Lys Thr Lys Pro Arg
65                  70                  75                  80

Glu Glu Gln Phe Asn Ser Thr Tyr Arg Val Val Ser Val Leu Thr Val
                85                  90                  95

Leu His Gln Asp Trp Leu Asn Gly Lys Glu Tyr Lys Cys Lys Val Ser
            100                 105                 110

Asn Lys Gly Leu Pro Ser Ser Ile Glu Lys Thr Ile Ser Lys Ala Lys
        115                 120                 125

Gly Gln Pro Arg Glu Pro Gln Val Tyr Thr Leu Pro Pro Ser Arg Asp
    130                 135                 140

Glu Leu Thr Lys Asn Gln Val Ser Leu Thr Cys Leu Val Lys Gly Phe
```

```
                145                 150                 155                 160
Tyr Pro Ser Asp Ile Ala Val Glu Trp Glu Ser Asn Gly Gln Pro Glu
                    165                 170                 175

Asn Asn Tyr Lys Thr Thr Pro Pro Val Leu Asp Ser Asp Gly Ser Phe
                    180                 185                 190

Phe Leu Tyr Ser Lys Leu Thr Val Asp Lys Ser Arg Trp Gln Gln Gly
                    195                 200                 205

Asn Val Phe Ser Cys Ser Val Met His Glu Ala Leu His Asn His Tyr
                    210                 215                 220

Thr Gln Lys Ser Leu Ser Leu Ser Pro Gly Lys
225                 230                 235

<210> SEQ ID NO 30
<211> LENGTH: 329
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Pro Val Ala Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser Gln Glu Asp Pro Glu Val Gln Phe Asn Trp Tyr
145                 150                 155                 160

Val Asp Gly Val Glu Val His Asn Ala Lys Thr Lys Pro Arg Glu Glu
                165                 170                 175

Gln Phe Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Gly Leu Pro Ser Ser Ile Glu Lys Thr Ile Ser Lys Ala Lys Gly Gln
    210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270
```

```
Tyr Lys Thr Thr Pro Pro Val Leu Asp Ser Asp Gly Ser Phe Leu
        275                 280                 285

Tyr Ser Lys Leu Thr Val Asp Lys Ser Arg Trp Gln Gln Gly Asn Val
290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325
```

<210> SEQ ID NO 31
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
        275                 280                 285
```

```
Leu Thr Val Asp Lys Ser Arg Trp Gln Glu Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Leu Gly Lys
                325

<210> SEQ ID NO 32
<211> LENGTH: 329
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Pro Val Ala Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser Gln Glu Asp Pro Glu Val Gln Phe Asn Trp Tyr
145                 150                 155                 160

Val Asp Gly Val Glu Val His Asn Ala Lys Thr Lys Pro Arg Glu Glu
                165                 170                 175

Gln Phe Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Gly Leu Pro Ser Ser Ile Glu Lys Thr Ile Ser Lys Ala Lys Gly Gln
    210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn Arg Phe Thr Gln
```

```
                305                 310                 315                 320
Lys Ser Leu Ser Leu Ser Pro Gly Lys
                    325

<210> SEQ ID NO 33
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
        275                 280                 285

Leu Thr Val Asp Lys Ser Arg Trp Gln Glu Gly Asn Val Phe Ser Cys
    290                 295                 300

Ser Val Met His Glu Ala Leu His Asn Arg Phe Thr Gln Lys Ser Leu
305                 310                 315                 320

Ser Leu Ser Leu Gly Lys
                    325
```

```
<210> SEQ ID NO 34
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 5xHis tag"

<400> SEQUENCE: 34

His His His His His
1               5

<210> SEQ ID NO 35
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 35

His His His His His His
1               5

<210> SEQ ID NO 36
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
        35

<210> SEQ ID NO 37
<211> LENGTH: 40
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser
        35                  40

<210> SEQ ID NO 38
<211> LENGTH: 30
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic polypeptide"

<400> SEQUENCE: 38

Gly Gly Gly Gly Ser Gly Gly Gly Ser Gly Gly Gly Gly Ser Gly
1               5                   10                  15

Gly Gly Gly Ser Gly Gly Gly Ser Gly Gly Gly Gly Ser
            20              25                  30

<210> SEQ ID NO 39
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20              25
```

ANTIGEN BINDING MOLECULE FORMATS

1. CROSS-REFERENCE TO RELATED APPLICATIONS

This application is a continuation of international application no. PCT/US2020/045309 filed Aug. 7, 2020, which claims the priority benefit under 35 U.S.C. § 119 (e) of U.S. provisional application Nos. 62/884,496, filed Aug. 8, 2019, and 63/050,483, filed Jul. 10, 2020, the contents of each of which are incorporated herein in their entireties by reference thereto.

2. SEQUENCE LISTING

The instant application contains a Sequence Listing which has been submitted electronically in ASCII format and is hereby incorporated by reference in its entirety. Said ASCII copy, created on Aug. 6, 2020, is named RGN-001WO-_SL.txt and is 25,358 bytes in size.

3. BACKGROUND

Most naturally occurring antibody molecules in general comprise two so called light chain polypeptides (light chain) and two so called heavy chain polypeptides (heavy chain). Each of the heavy and light chain polypeptides contains a variable domain (variable region) (generally the amino terminal portion of the polypeptide chain) comprising binding regions that are able to interact with an antigen. Each of the heavy and light chain polypeptides comprises a constant region (generally the carboxyl terminal portion).

Recombinant monoclonal antibodies, which are produced by a single clone of cells or cell line, have emerged as a very successful class of biological drugs for the treatment of a variety of different diseases during the past two decades. Monoclonal antibodies (mAbs) are a significant class of biotherapeutic products, and they have achieved outstanding success in treating many life-threatening and chronic diseases.

Increases in affinity and/or avidity take place when the epitopes are accessible by the antigen binding portions, for example Fab domains, of the antibody. The geometry of conventional antibody formats, however, limits the ability of antibodies to recognize multiple epitopes on a single target molecule, particularly when the target is of small size, or when desirable epitopes (including those on multiple target molecules) are in relatively close physical proximity, or desired to be brought into close physical proximity. Thus, an efficient platform for the generation of binding molecules that might improve affinity, avidity, or antibody function, through alternative antibody-antigen binding geometries, would be useful.

4. SUMMARY

The present disclosure provides antigen binding molecules ("ABMs") containing at least two Fab domains in a non-native configuration. The ABMs comprise at least two polypeptide chains, each comprising an Fc domain and one component of the at least two Fab domains. Exemplary ABMs of the disclosure are illustrated in FIGS. 1B, 2B and 3A through 3D.

Each polypeptide chain comprising an Fc domain and any associated polypeptide chains is referred to herein as a "half antibody". A typical ABM of the disclosure comprises two half antibodies associated through their Fc domains. The associated Fc domains together form an Fc region. In addition to the Fc region, a typical ABM of the disclosure comprises at least one Fab domain in a non-native configuration in each half antibody. At least one of the Fab domains or both such Fab domains in the non-native configuration bind to a target molecule. By "native configuration" or "native immunoglobulin configuration" means the configuration of antibody domains in a naturally-occurring IgG antibody. In the accompanying schematic drawings, VH domains are labeled with the numeral (1), CH1 domains are labeled with the numeral (2), hinge domains are labeled with the numeral (3), CH2 domains are labeled with the numeral (4), CH3 domains are labeled with the numeral (5), VL domains are labeled with the numeral (6), CL domains are labeled with the numeral (7), and linkers that are not hinge domains are labeled with the numeral (8). Thus, by reference to the labeling in the accompanying figures, a native immunoglobulin configuration consists essentially of:

A first (heavy chain) polypeptide consisting essentially of, in an N-to-C terminal orientation, a VH domain (1), a CH1 domain (2), a hinge region (3) linked via a disulfide bridge to the hinge region of the second (heavy chain) polypeptide; a CH2 domain (4), and a CH3 domain (5);

A second (heavy chain) polypeptide consisting essentially of, in an N-to-C terminal orientation, a VH domain (1), a CH1 domain (2), a hinge region (3) linked via a disulfide bridge to the hinge region of the first (heavy chain) polypeptide; a CH2 domain (4), and a CH3 domain (5);

A third (light chain) polypeptide consisting essentially of, in an N-to-C terminal orientation, a VL domain (6) and a CL domain (7), associated with the first (heavy chain) polypeptide; and A fourth (light chain) polypeptide consisting essentially of, in an N-to-C terminal orientation, a VL domain (6) and a CL domain (7), associated with the second (heavy chain) polypeptide.

Figure 2A:
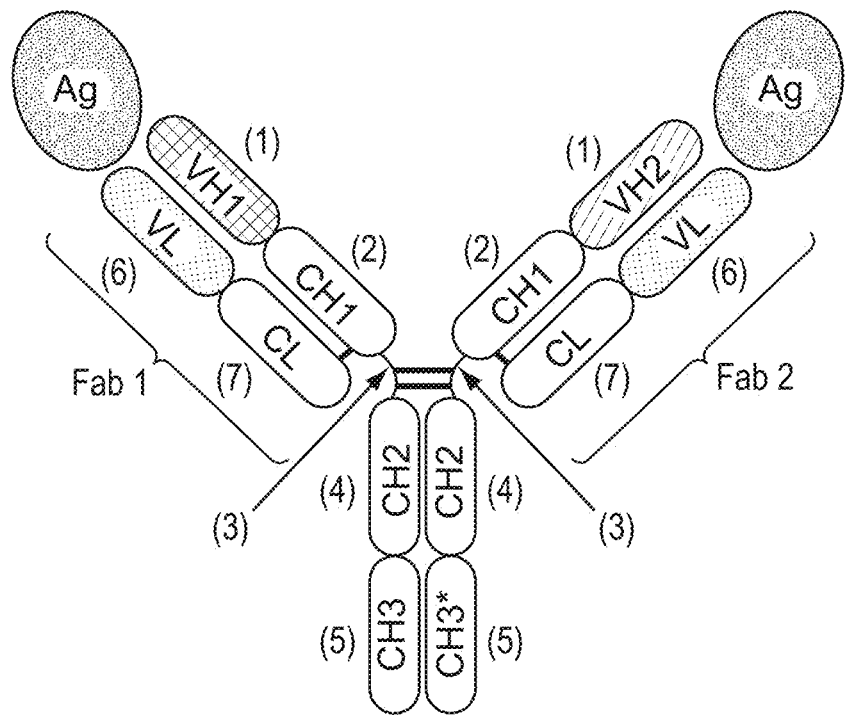
Figure 2B:
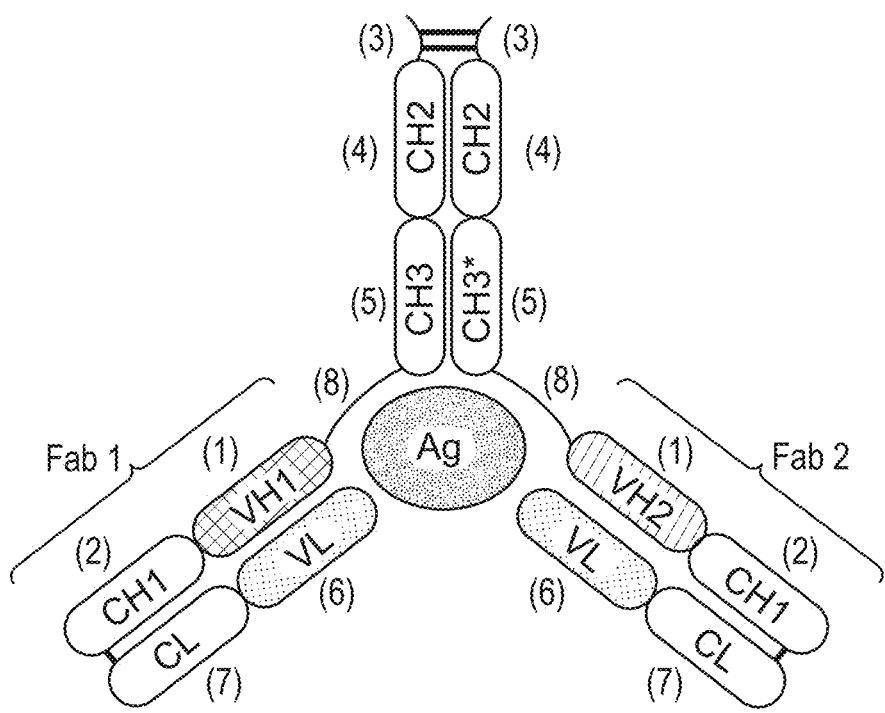

The reference to a "native configuration" or a "native immunoglobulin configuration" is not intended to limit the term to wild type antibody sequences or only monospecific antibodies. Rather, as shown in FIG. 1A and FIG. 2A, the format can apply to both a monospecific antibody (FIG. 1A) or a traditional bispecific antibody with variant sequences (FIG. 2B). The fundamental difference between the monospecific antibody format of FIG. 1A and the bispecific antibody format of FIG. 2A is not their configuration but the use of an Fc heterodimer (e.g., as described in Section 6.2.7.2), in which each Fc region linked to different VH domain, allowing the binding to different epitopes. For clarity, as used herein, the term "bispecific" refers to binding to any two different epitopes, whether on the same antigen or target molecule or on different antigens or target molecules.

The ABMs of the disclosure are particularly useful for binding to a small soluble target molecule, for example a cytokine or chemokine, and find applications in antagonizing the activity of the target molecule, for example by blocking the binding of the target molecule to a binding partner such as a receptor. Without being bound by theory, it is believed that the binding formats of the disclosure permit binding to a target molecule with greater affinity and/or avidity than a native immunoglobulin comprising the same at least two Fab domains.

TABLE A

Terminology Key for ABM Formats Illustrated in FIGS. 1-3

| Format | Sub-format | Illustrative FIGS. | Alternative Name |
|---|---|---|---|
| Format A | N/A | 1B (Homodimer configuration) 2B (Heterodimer configuration) | Fc-Fab |
| Format B | N/A | 3A | Reach |
| Format C | Format C1 | 3B | Clamp |
| Format C | Format C2 | 3C (Configuration 1 (1-1-2-2 Configuration)) 3D (Configuration 2 (1-2-1-2 Configuration)) | 2 + 2 Tandem Fab |

These ABM formats are described in greater detail below. In a first aspect, an ABM of the disclosure comprises:
a first half antibody comprising in an N-to-C terminal orientation:
an optional hinge domain;
a first Fc domain; and
a first Fab (Fab1) domain comprising a first heavy chain variable region (VH) associated with a first light chain variable region (VL); and
a second half antibody comprising in an N-to-C terminal orientation:
an optional hinge domain;
a second Fc domain; and
a second Fab ("Fab2") domain comprising a second VH associated with a second VL,
wherein the first Fc domain and second Fc domain are associated with one another to form an Fc region and wherein the optional hinge domains, if present, can be associated with one another through a disulfide bridge.

Figure 1B:
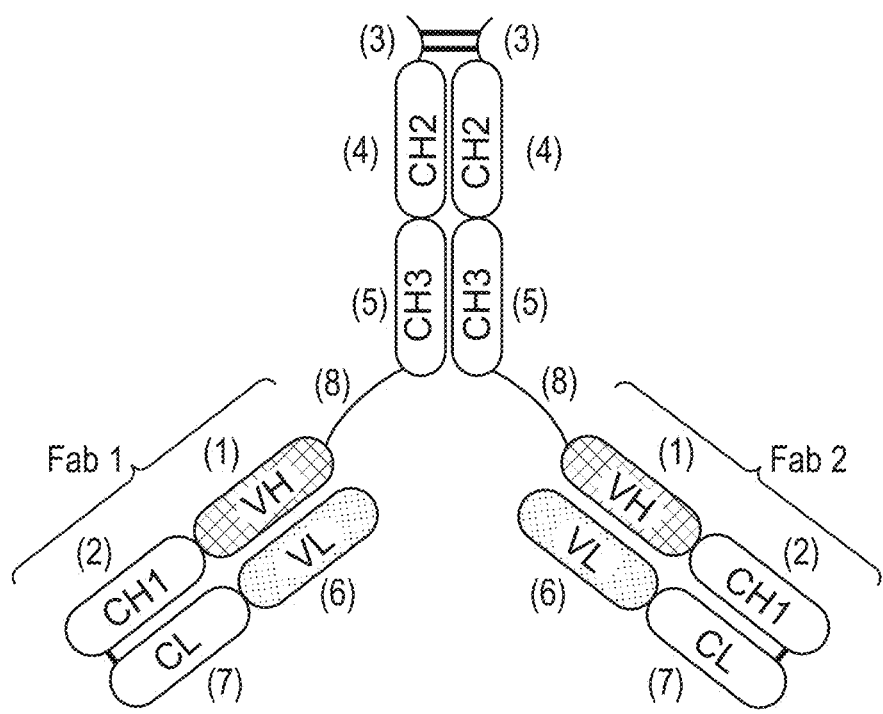
Figure 13A:
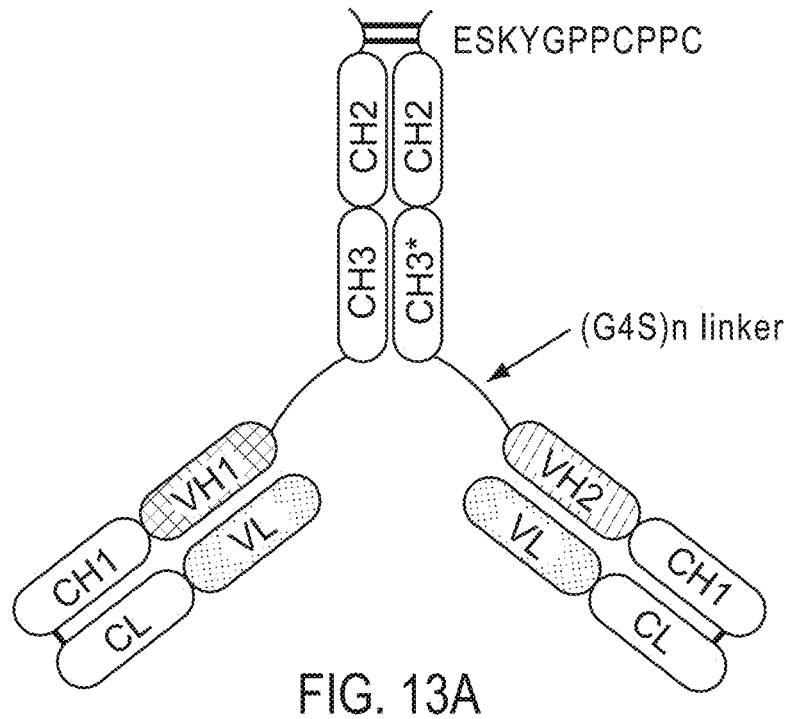
Figure 13B:
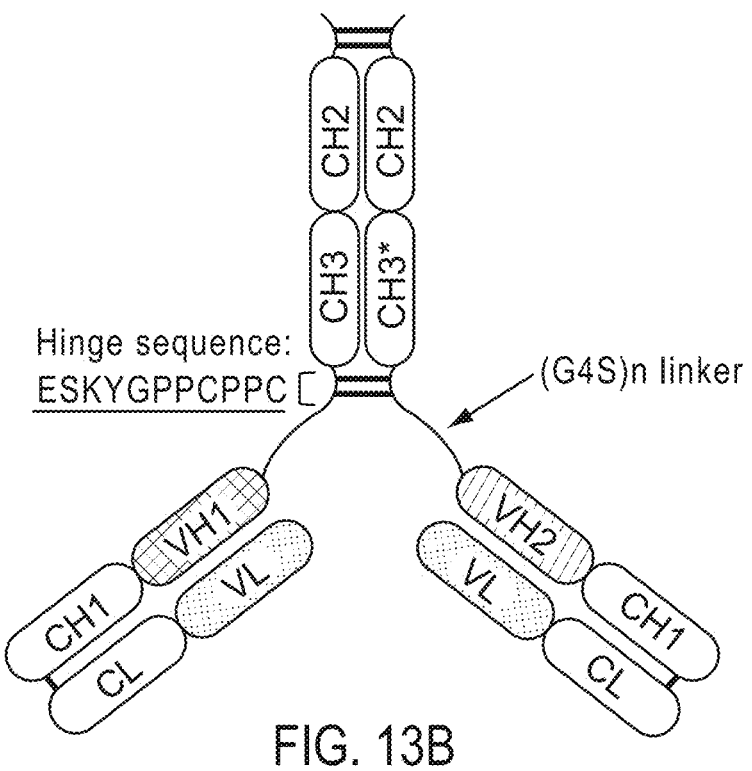
Figure 13C:
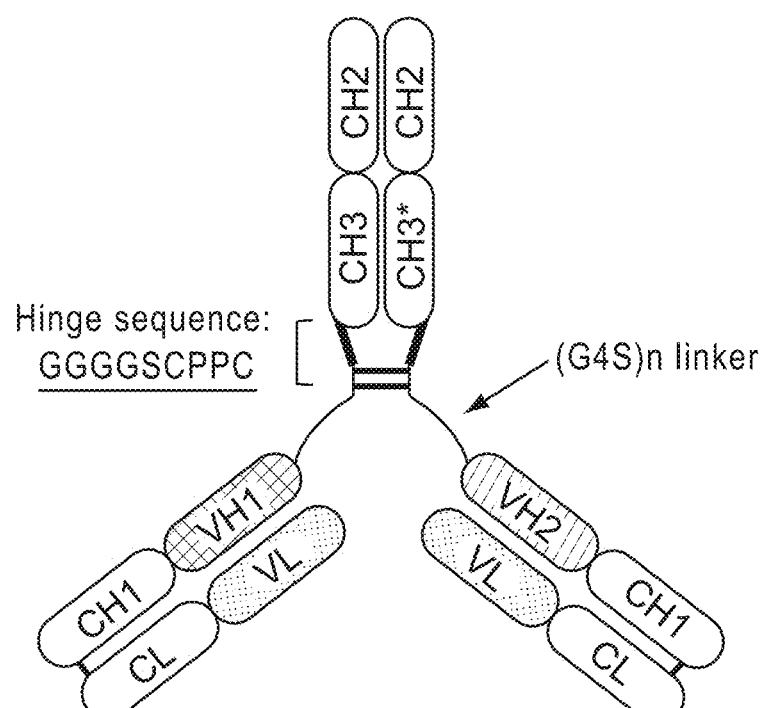

Two embodiments of this type of ABM, generally referred to herein as ABM format "A" ("Format A") and sometimes referred to herein as the "Fc-Fab" format, are illustrated in FIG. 1B and FIG. 2B, as well as variations thereof depicted in FIG. 13A, FIG. 13B and FIG. 13C. Accordingly, the present disclosure provides Format A ABMs depicted in FIG. 1B and FIG. 2B comprising:
a first polypeptide comprising in an N-to-C terminal orientation:
an optional hinge domain (3) linked via a disulfide bond to a hinge domain in the second polypeptide;
an Fc domain comprising a CH2 domain (4) and a CH3 domain (5);
an optional hinge domain (3) linked via a disulfide bond to a hinge domain in the second polypeptide;
a linker (8); and
the heavy chain component of a Fab1 domain comprising a Fab1 VH domain (1) and a Fab1 CH1 domain (2) associated with the light chain component of the Fab1 domain, the light chain component in the form of a polypeptide comprising, in an N-to-C terminal orientation, a Fab1 VL domain (6) and a Fab1 CL domain (7); and
a second polypeptide comprising in an N-to-C terminal orientation:
an optional hinge domain (3) linked via a disulfide bond to a hinge domain in the first polypeptide;
a second Fc domain comprising a CH2 domain (4) and a CH3 domain (5);
an optional hinge domain (3) linked via a disulfide bond to a hinge domain in the first polypeptide;
a linker (8); and
the heavy chain component of a Fab2 domain comprising a Fab2 VH domain (1) and a Fab2 CH1 domain (2) associated with the light chain component of the Fab2 domain, the light chain component in the form of a polypeptide comprising, in an N-to-C terminal orientation, a Fab2 VL domain (6) and a Fab2 CL domain (7);
wherein the first Fc domain and second Fc domain are associated with one another to form an Fc region.

In the embodiment of FIG. 1B both half antibodies are identical, including the Fc domains which form an Fc homodimer, and the resulting ABM is monospecific. In the embodiment of FIG. 2B, the ABM comprises an Fc heterodimer, allowing the use of different Fab1 and Fab2 VH domains and production of a multispecific, e.g., bispecific, molecule. While FIG. 1B, FIGS. 2B and 13A illustrate embodiments in which the ABM has a hinge region composed of hinge domains N-terminal to the Fc domain, the Format A ABMs can have no hinge region (not illustrated), a hinge region C-terminal to the Fc region (FIG. 13C), or hinge regions N- and C-terminal to the Fc region (FIG. 13B). Exemplary hinge domains that can be used N- and/or C-terminal to the Fc region comprise the amino acid sequence GGGGSCPPC (SEQ ID NO:1) and ESKYGPPCPPC (SEQ ID NO:2), as depicted in FIGS. 13A-13C, although the Format A ABMs can have alternative hinge region sequences. Likewise, although FIGS. 13A-13C depict (G4S)$_n$ linkers (G4S is disclosed as SEQ ID NO:3), other linker sequences can be used.

While FIG. 1B and FIG. 2B illustrate embodiments of Format A ABMs that contain only two binding domains (Fab1 and Fab2), the ABMs of the disclosure may contain additional binding domains, e.g., an scFv or Fab domain. However, in certain aspects, Fab1 and Fab2 are the sole binding domains of a Format A ABM.

In a second aspect, an ABM of the disclosure comprises:
a first half antibody comprising in an N-to-C terminal orientation:
a first Fab (Fab1) domain comprising a first VH associated with a first VL;
a first spacer domain; and
a first Fc domain; and
a second polypeptide comprising in an N-to-C terminal orientation:
a second Fab (Fab2) domain comprising a second VH associated with a second VL;
a second spacer domain; and
a second Fc domain; and
wherein the first Fc domain and second Fc domain are associated with one another to form an Fc region.

Without being bound by theory, it is believed that the inclusion of a spacer domain between the Fc domain and the Fab domain gives results in greater flexibility between the Fc region and the antigen binding site of the Fab and consequently higher affinity and/or avidity of binding of the ABM to its antigen or target molecule. The terms "antigen" and "target molecule" are used interchangeably herein.

Figure 3A:
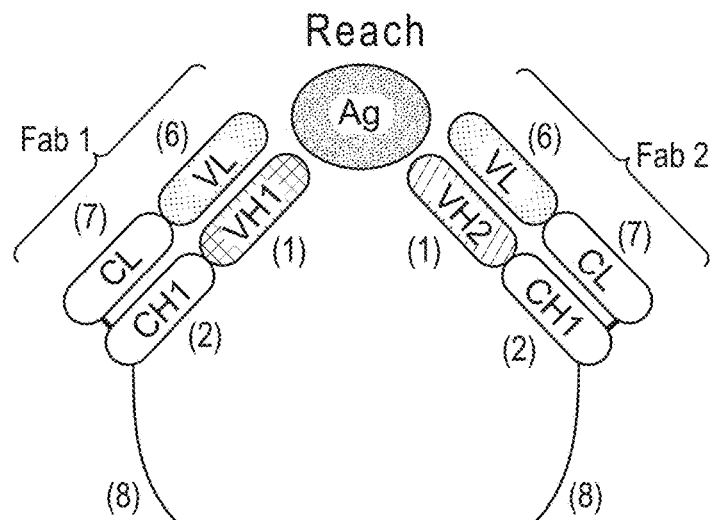

In certain embodiments, the spacer domains are extended linkers. This format of ABM, generally referred to herein as format "B" ("Format B") and sometimes referred to herein as the "Reach" format, is illustrated in FIG. 3A. Accordingly, the present disclosure provides embodiments Format B ABMs depicted in FIG. 3A comprising:
a first polypeptide comprising in an N-to-C terminal orientation:
the heavy chain component of a Fab1 domain comprising a Fab1 VH domain (1) and a Fab1 CH1 domain (2) associated with the light chain component of the Fab1 domain, the light chain component in the form of a polypeptide comprising, in an N-to-C terminal orientation, a Fab1 VL domain (6) and a Fab1 CL domain (7);
a linker domain (8) which is an extended linker;
a hinge domain (3) linked via a disulfide bond to a hinge domain in the second polypeptide; and
a first Fc domain comprising a CH2 domain (4) and a CH3 domain (5); and a second polypeptide comprising in an N-to-C terminal orientation:
the heavy chain component of a Fab2 domain comprising a Fab2 VH domain (1) and a Fab2 CH1 domain (2) associated with the light chain component of the Fab2 domain, the light chain component in the form of a polypeptide comprising, in an N-to-C terminal orientation, a Fab2 VL domain (6) and a Fab2 CL domain (7);
a linker domain (8) which is an extended linker;
a hinge domain (3) linked via a disulfide bond to a hinge domain in the second polypeptide; and
a second Fc domain comprising a CH2 domain (4) and a CH3 domain (5).

While the embodiment of Format B ABMs depicted in FIG. 3A contains only two binding domains (Fab1 and Fab2), the Format B ABMs of the disclosure may contain additional binding domains, e.g., an scFv or Fab domain. However, in certain aspects, Fab1 and Fab2 are the sole binding domains of a Format B ABM of the disclosure.

Figure 3B:
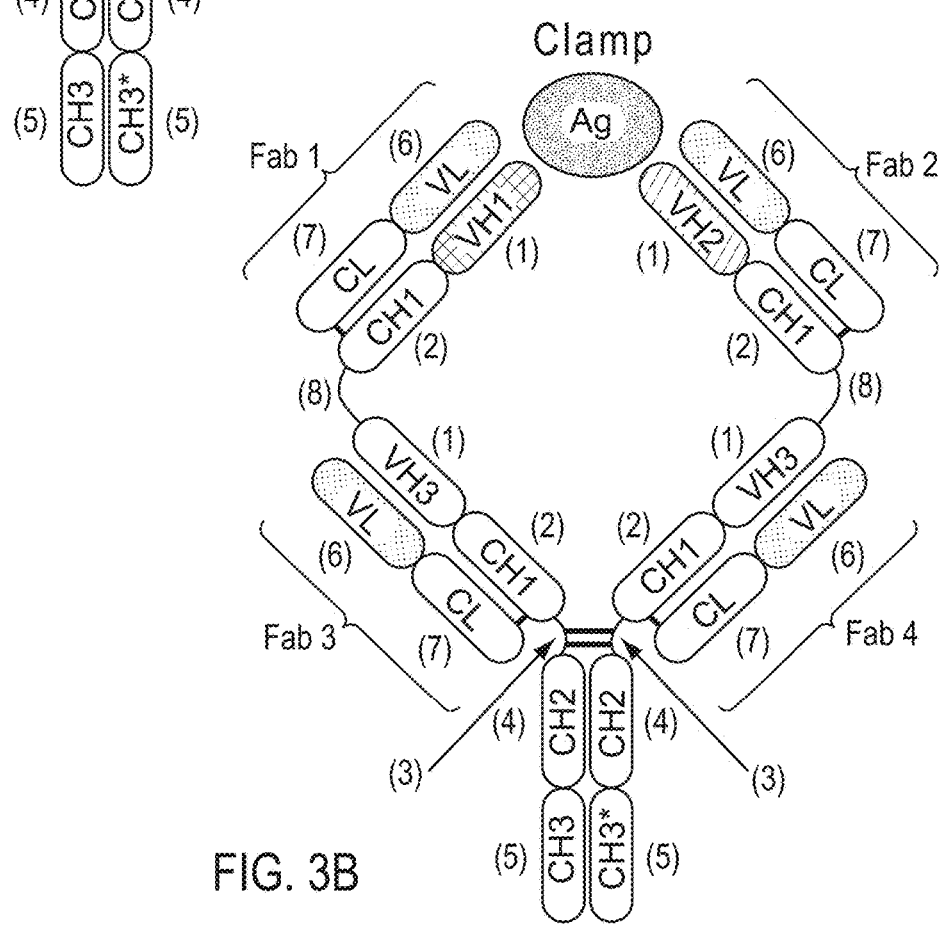
Figure 3C:
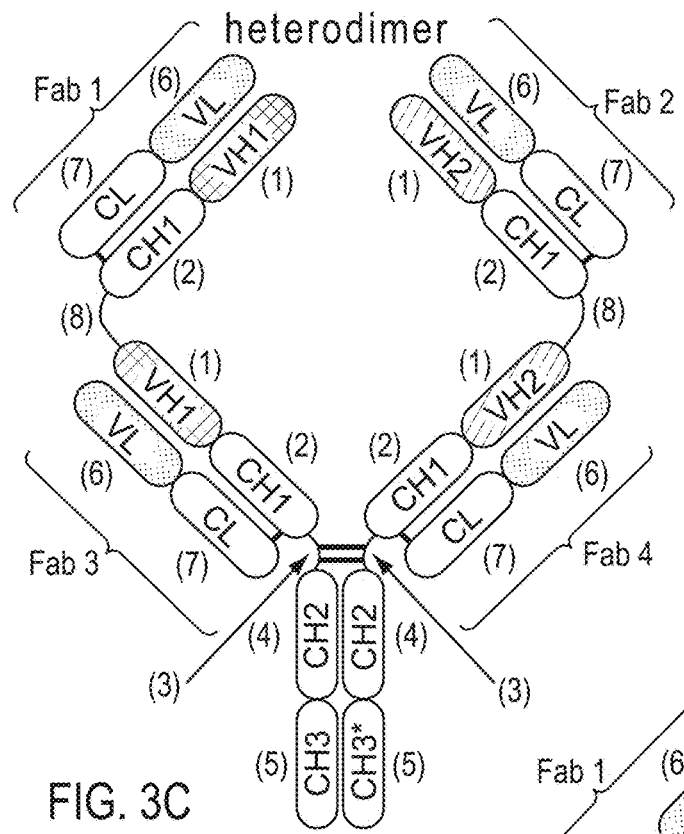
Figure 3D:
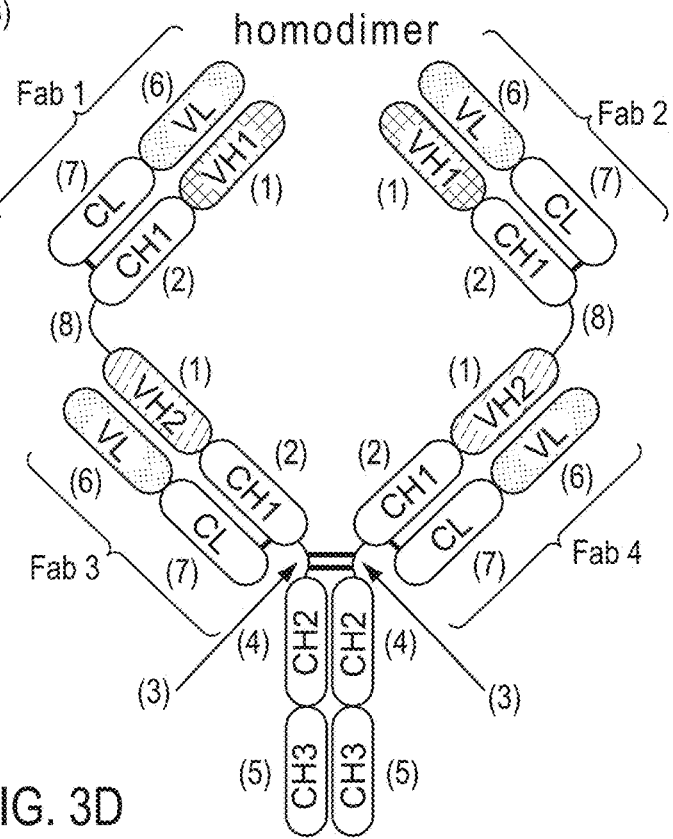

In other embodiments, the spacer domains are Fab domains. Different variations of this format of ABM, referred to herein as format "C" ("Format C"), are illustrated in FIGS. 3B-3D. Format C ABMs thus comprise a third Fab (Fab3) domain and a fourth Fab (Fab4) domain, configured as follows:
a first half antibody comprising in an N-to-C terminal orientation
a first Fab (Fab1) domain comprising a first VH associated with a first VL;
a third Fab (Fab3) domain comprising a third VH associated with a third VL; and
a first Fc domain; and
a second half antibody comprising in an N-to-C terminal orientation:
a second Fab (Fab2) domain comprising a second VH associated with a second VL;
a fourth Fab (Fab4) domain comprising a fourth VH associated with a fourth VL; and
a second Fc domain.

Accordingly, the present disclosure provides embodiments Format C ABMs depicted in FIGS. 3B-3D, comprising:
a first polypeptide comprising in an N-to-C terminal orientation:
the heavy chain component of a Fab1 domain comprising a Fab1 VH domain (1) and a Fab1 CH1 domain (2) associated with the light chain component of the Fab1 domain, the light chain component in the form of a polypeptide comprising, in an N-to-C terminal orientation, a Fab1 VL domain (6) and a Fab1 CL domain (7);
a linker domain (8);
the heavy chain component of a Fab3 domain comprising a Fab3 VH domain (1) and a Fab3 CH1 domain (2) associated with the light chain component of the Fab3 domain, the light chain component in the form of a polypeptide comprising, in an N-to-C terminal orientation, a Fab3 VL domain (6) and a Fab3 CL domain (7);
a hinge domain (3) linked via a disulfide bond to a hinge domain in the second polypeptide; and
a first Fc domain comprising a CH2 domain (4) and a CH3 domain (5); and a second polypeptide comprising in an N-to-C terminal orientation:
the heavy chain component of a Fab2 domain comprising a Fab2 VH domain (1) and a Fab2 CH1 domain (2) associated with the light chain component of the Fab2 domain, the light chain component in the form of a polypeptide comprising, in an N-to-C terminal orientation, a Fab2 VL domain (6) and a Fab2 CL domain (7);
a linker domain (8);
the heavy chain component of a Fab4 domain comprising a Fab4 VH domain (1) and a Fab4 CH1 domain (2) associated with the light chain component of the Fab4 domain, the light chain component in the form of a polypeptide comprising, in an N-to-C terminal orientation, a Fab4 VL domain (6) and a Fab4 CL domain (7);
a hinge domain (3) linked via a disulfide bond to a hinge domain in the second polypeptide; and
a second Fc domain comprising a CH2 domain (4) and a CH3 domain (5);
wherein the first Fc domain and second Fc domain are associated with one another to form an Fc region.

While the embodiments of Format C ABMs depicted in FIGS. 3B-3D contain four binding domains (Fab1, Fab2, Fab3 and Fab4), the Format C ABMs of the disclosure may contain additional binding domains, e.g., an scFv or Fab domain. However, in certain aspects, Fab1, Fab2, Fab3 and Fab4 are the sole binding domains of a Format C ABM of the disclosure.

The Fab3 and Fab4 domains of Format C ABMs can be non-binding (as illustrated in FIG. 3B) or binding (as illustrated in FIG. 3C and FIG. 3D). Those embodiments in which Fab3 and Fab4 are non-binding are generally referred to herein as Format C1 ABMs and this format sometimes referred to herein as the "Clamp" format. Those embodiments in which Fab3 and Fab4 are binding are generally referred to herein as Format C2 ABMs and this format sometimes referred to herein as the "Tandem Fab" format. The term "2+2 Tandem Fab" refers to embodiments, illustrated in FIGS. 3C and 3D, where Fab1, Fab2, Fab3 and Fab 4 are the sole binding domains in a Tandem Fab. Each of Format C1 and Format C2 ABMs can be homodimeric or heterodimeric.

In certain embodiments of Format C1 ABMs, the Fab1 and Fab2 domains are non-identical (e.g., bind to different epitopes, whether on the same target molecule or on different target molecules) and the Fab3 and Fab4 domains are identical non-binding domains. In other embodiments, the Fab3 and Fab4 domains are different non-binding domains.

In certain embodiments of the Format C2 ABMs, the Fab1 and Fab3 domains comprise identical VH domains and the Fab2 and Fab4 domains comprise identical VH domains, as shown in FIG. 3C. This configuration is referred to as Configuration 1, or the 1-1-2-2 Configuration. In alternative embodiments of the Format C2 ABMs, the Fab1 and Fab2 domains comprise identical VH domains and Fab3 and Fab4 domains comprise identical VH domains, as shown in FIG. 3D. This configuration is referred to as Configuration 2, or the 1-2-1-2 Configuration.

The complete ABM is formed by association of the two half antibodies through the two Fc domains to form an Fc region. When the two half antibodies are non-identical, for example when Fab1 and Fab2 include different VH domains, an Fc heterodimerization approach, for example as described in Section 6.2.7.2, can be utilized to facilitate correct half antibody pairings and/or their purification. Examples of heterodimerization approaches are star mutations (as described in Section 6.2.7.2) or knob-in-hole mutations.

While FIGS. 2B, 3A, 3B and 3C show ABMs comprising non-identical VH domains in each half antibody paired through Fc heterodimers, this format can be also used for Fc homodimers. For instance, while FIG. 2B and FIG. 3A respectively show a Format A ABM and a Format B ABM comprising an Fc heterodimer, allowing the incorporation of different VH domains in Fab1 and Fab2 and production of a multispecific, e.g., bispecific, binding molecule, this format can be also used for monospecific Format A and Format B ABMs with Fc homodimers and identical VH domains. Similarly, Fc homodimers can be used to produce monospecific Format C ABMs, with identical Fab1, Fab2, Fab3 and Fab4 VH domains or identical Fab1 and Fab2 VH domains and non-binding Fab3 and Fab4 VH domains.

Further, different strategies can be used to permit correct VH-VL pairings in multispecific binding molecules when the first and second polypeptides include different VH domains. For example, a common light chain can be used that is capable of operably pairing with more than one type of VH domain in an ABM. In such embodiments, the light chain polypeptides (e.g., the light chains associated with Fab1 and Fab2 and, if present, Fab3 and Fab4), can be identical. Alternatively, single domain Fabs can be used in which the heavy chain components ((1) and (2)) can be expressed as a fusion with the light chain components ((6) and (7)).

The variations of the ABMs of the disclosure shown in FIGS. 1-3 are not intended to be limiting; the ABMs of the disclosure can include any combination of modifications illustrated in FIGS. 1-3 and in Section 6.2, infra, among others. Further, referencing a first or second polypeptide chain or a left or right half antibody is for the sake of convenience only and is not intended to convey that the polypeptide chains or half antibodies are produced or assembled in any particular order.

In some embodiments the first Fab (Fab1) domain and the second Fab (Fab2) domain of the ABMs of the disclosure can each bind to the same target molecule, for example a small soluble molecule. The first Fab (Fab1) domain and second Fab (Fab2) domain can bind to the same epitope (e.g., in the embodiment depicted in FIG. 1B and FIG. 3D, or a variation of FIG. 3A or FIG. 3B in which both Fab1 and Fab2 have identical VH domains (not shown)) or they can bind to different epitopes (e.g., in the embodiments depicted in FIG. 2B, FIG. 3A, FIG. 3B, and FIG. 3C), whether on the same target molecule or on different target molecules. Where the first Fab (Fab1) domain and second Fab (Fab2) domain bind to different epitopes, e.g., two different epitopes on the same target molecule or on different target molecules, they can be selected so that Fabs are capable of binding to their epitopes at the same time.

In some embodiments, for example of Format C ABMs, the ABMs of the disclosure can include a third Fab (Fab3) domain and a fourth Fab (Fab4) domain as depicted in FIG. 3B, FIG. 3C and FIG. 3D. The third and fourth Fab domains can be non-binding, as depicted in FIG. 3B, or they can be binding, as depicted in FIG. 3C and FIG. 3D. When Fab3 and Fab4 are present, they can bind to the same or different epitopes from the epitopes bound by Fab1 and Fab2 domains, respectively. For example, Fab1 and Fab 3 can share an epitope and Fab 2 and Fab 4 can share an epitope, as illustrated in the embodiment of FIG. 3C. Alternatively, example, Fab1 and Fab 2 can share an epitope and Fab 3 and Fab 4 can share an epitope, as illustrated in the embodiment of FIG. 3D. As used herein, in reference to the Format C ABMs, the terms "first and second Fab domains" and "Fab1 and Fab2 domains" typically refers to the most N-terminal Fab domains, and reference to the "third and fourth Fab domains" and "Fab3 and Fab4 domains" typically refers to inner Fab domains.

Exemplary antigen binding molecules of the disclosure, including their components and configurations, and their target molecules are described in Sections 6.2 and 6.3, as well as in "A" specific embodiments 1 to 138 and "B" specific embodiments 1 to 72, infra.

The present disclosure further provides conjugates, e.g., drug conjugates, comprising the ABMs of the disclosure (drug conjugates referred to herein as "antibody-drug conjugates" or "ADCs" for convenience). Exemplary features of conjugates are described in Section 6.4 as well as "A" specific embodiment 139 and "B" specific embodiment 73, infra.

The disclosure further provides nucleic acids encoding the ABMs of the disclosure. The nucleic acids encoding the ABMs can be a single nucleic acid (e.g., a vector encoding all polypeptide chains of an ABM) or a plurality of nucleic acids (e.g., two or more vectors encoding the different polypeptide chains of an ABM). The disclosure further provides host cells and cell lines engineered to express the nucleic acids and ABMs of the disclosure. The disclosure further provides methods of producing an ABM of the disclosure. Exemplary nucleic acids, host cells, cell lines, and methods of producing an ABM are described in Section 6.5, "A" specific embodiments 144-145, and "B" specific embodiments 75-81, infra.

The disclosure further provides pharmaceutical compositions comprising the ABMs and ADCs of the disclosure. Exemplary pharmaceutical compositions are described in Section 6.6, "A" specific embodiment 140, and "B" specific embodiment 74, infra.

Further provided herein are methods of using the ABMs, the conjugates, and the pharmaceutical compositions of the disclosure, e.g., for treating conditions associated with aberrant expression or activity of the target molecules to which they bind. Exemplary methods are described in Section 6.7, "A" specific embodiments 141-143 and "B" specific embodiments 82-85, infra.

5. BRIEF DESCRIPTION OF THE FIGURES

FIGS. 1A-1B: Schematic representation of an exemplary homodimeric (monospecific bivalent) Format A ABM of the disclosure (FIG. 1B) and corresponding native antibody format (FIG. 1A). Figure legend: (1)=VH; (2)=CH1; (3)=Hinge; (4)=CH2; (5)=CH3; (6)=VL; (7)=CL; (8)=Linker.

FIGS. 2A-2B: Schematic representation of a heterodimeric bispecific Format A ABM of the disclosure (FIG. 2B) and the corresponding traditional bispecific antibody format (FIG. 2A). A small antigen (Ag) is shown to indicate potential ways the bispecific ABMs could interact with a small antigen. Figure legend: (1)=VH; (2)=CH1; (3)=Hinge; (4)=CH2; (5)=CH3; (6)=VL; (7)=CL; (8)=Linker. The asterisk in one of the CH3 domains indicates that the two CH3 are not identical and contain one or more mutations that permit heterodimerization (e.g., knob-in-hole mutations, a star mutation, etc.).

FIGS. 3A-3D: Schematic representation of exemplary Format B ABM of the disclosure (FIG. 3A) and an exemplary Format C ABMs of the disclosure (FIGS. 3B-3D). The particular embodiments of Format C ABMs shown are an exemplary heterodimeric Format C1 ABM (FIG. 3B), an exemplary heterodimeric Format C2 ABM (FIG. 3C), and an exemplary homodimeric Format C2 ABM (FIG. 3D). In some embodiments, these bispecific ABMs use a common light chain VL-CL. In some embodiments of all formats, VH1-CH1/VL-CL and VH2-CH1/VL-CL are Fab fragments from non-competing mAbs to the antigen. In the format shown in FIG. 3B (sometimes referred to herein as the "clamp" format), the inner Fab fragment VH3-CH1/VL-CL does not bind to the target molecule. In the format shown in FIG. 3A (sometimes referred to herein as the "Reach" format), the inner Fabs are replaced with a flexible long linker. Figure legend: (1)=VH; (2)=CH1; (3)=Hinge; (4)=CH2; (5)=CH3; (6)=VL; (7)=CL; (8)=Linker. The asterisk in one of the CH3 domains indicates that the two CH3 are not identical and contain one or more mutations that permit heterodimerization (e.g., knob-in-hole mutations, a star mutation, etc.).

Figure 4A:
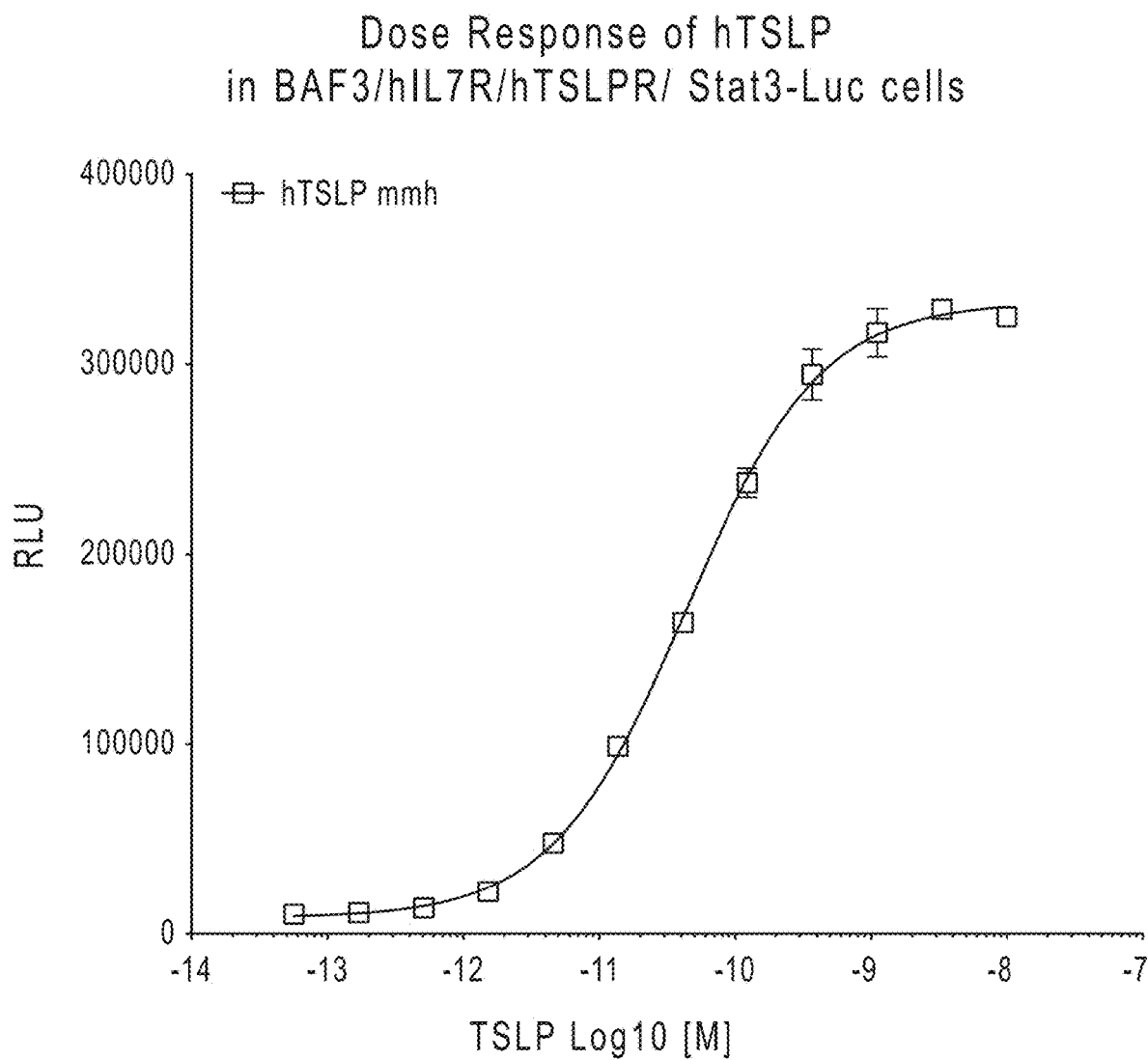

FIGS. 4A-4B: FIGS. 4A and 4B are graphs showing activity of TSLP parental Abs in TSLP blocking bioassay. FIG. 4A, dose response curve of hTSLP in a STAT3-Luciferase reporter assay using Baf3 cells expressing both hIL7R and hTSLPR. FIG. 4B, activity of selected TSLP Abs in a TSLP blocking bioassay. TSLP Abs were incubated with the Baf3/hIL7R/hTSLPR/STAT3-Luciferase reporter cell line in the presence of 100 pM constant hTSLP. Luciferase activity was measured after 5.5 hour incubation.

Figure 5:
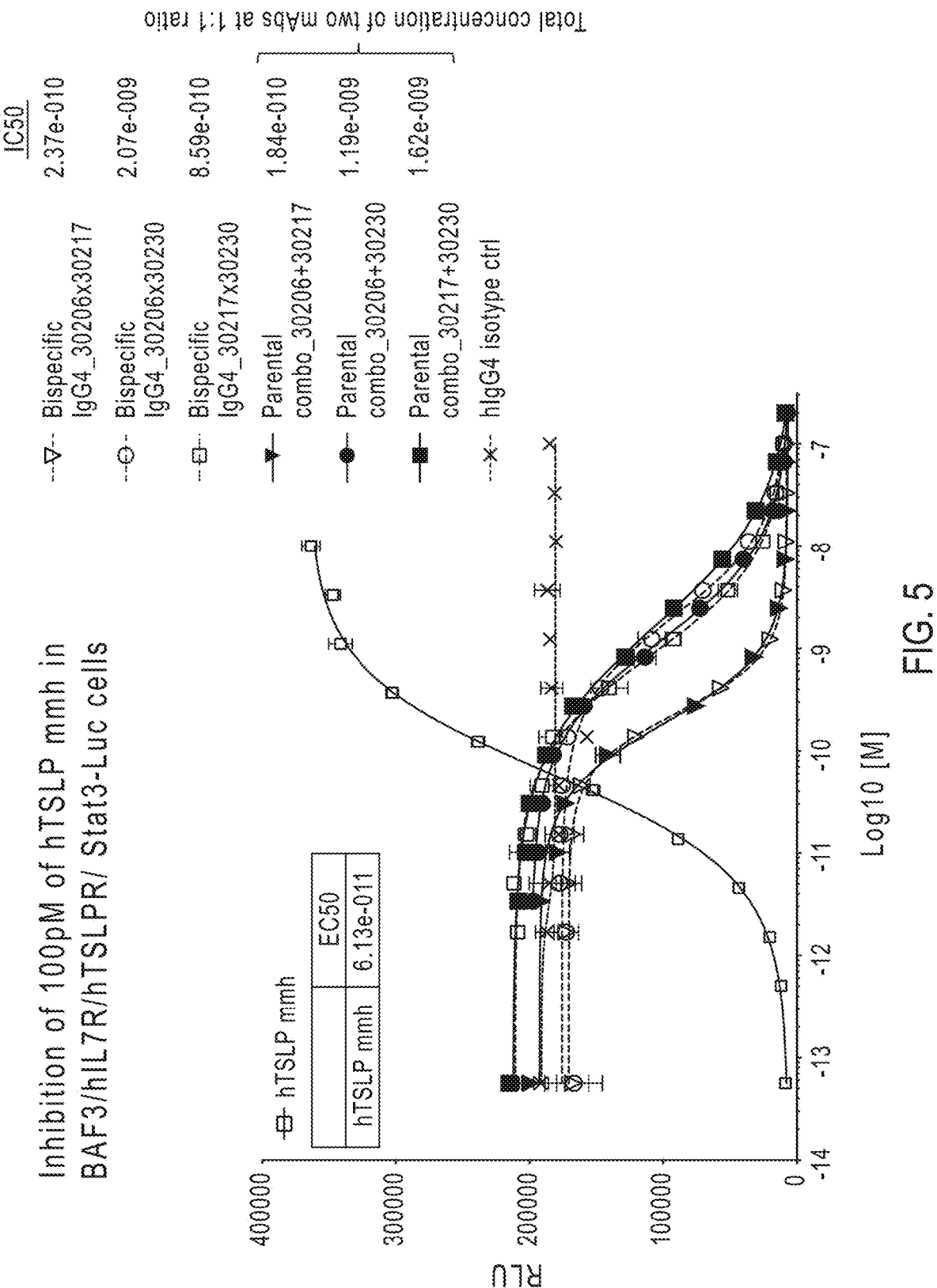

FIG. 5: FIG. 5 is a graph demonstrating that anti-hTSLP bispecific IgG4 Abs showed similar TSLP blocking activity as the corresponding parental Ab combinations. Anti-hTSLP parental Ab combinations and bispecific IgG4 Abs were compared for their activity in a hTSLP blocking bioassay. TSLP Abs were incubated with the Baf3/hIL7R/hTSLPR/STAT3-Luciferase reporter cell line in the presence of 100 pM hTSLP. Luciferase activity was measured after 5.5 hour incubation.

Figure 6A:
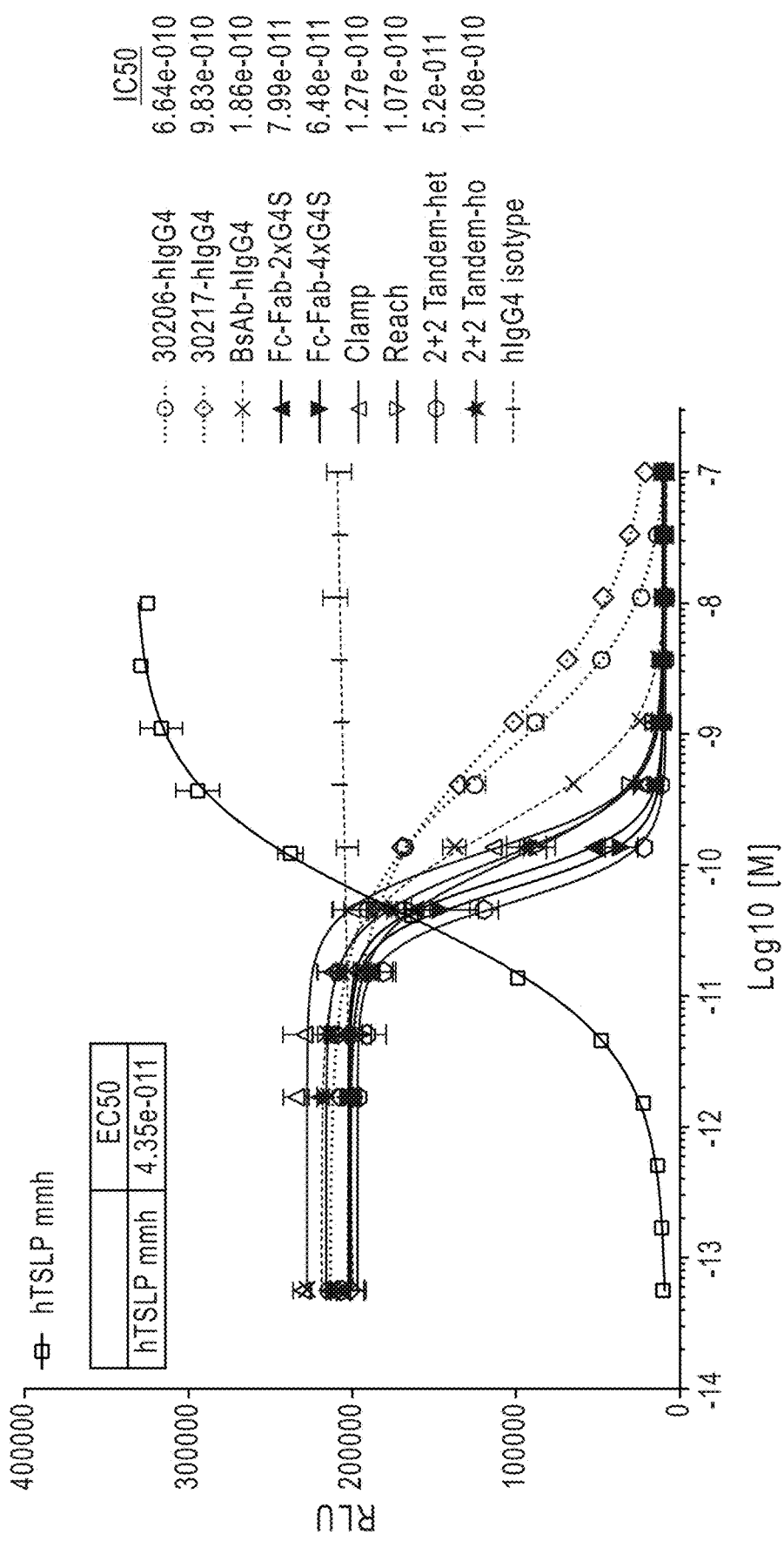
Figure 6B:
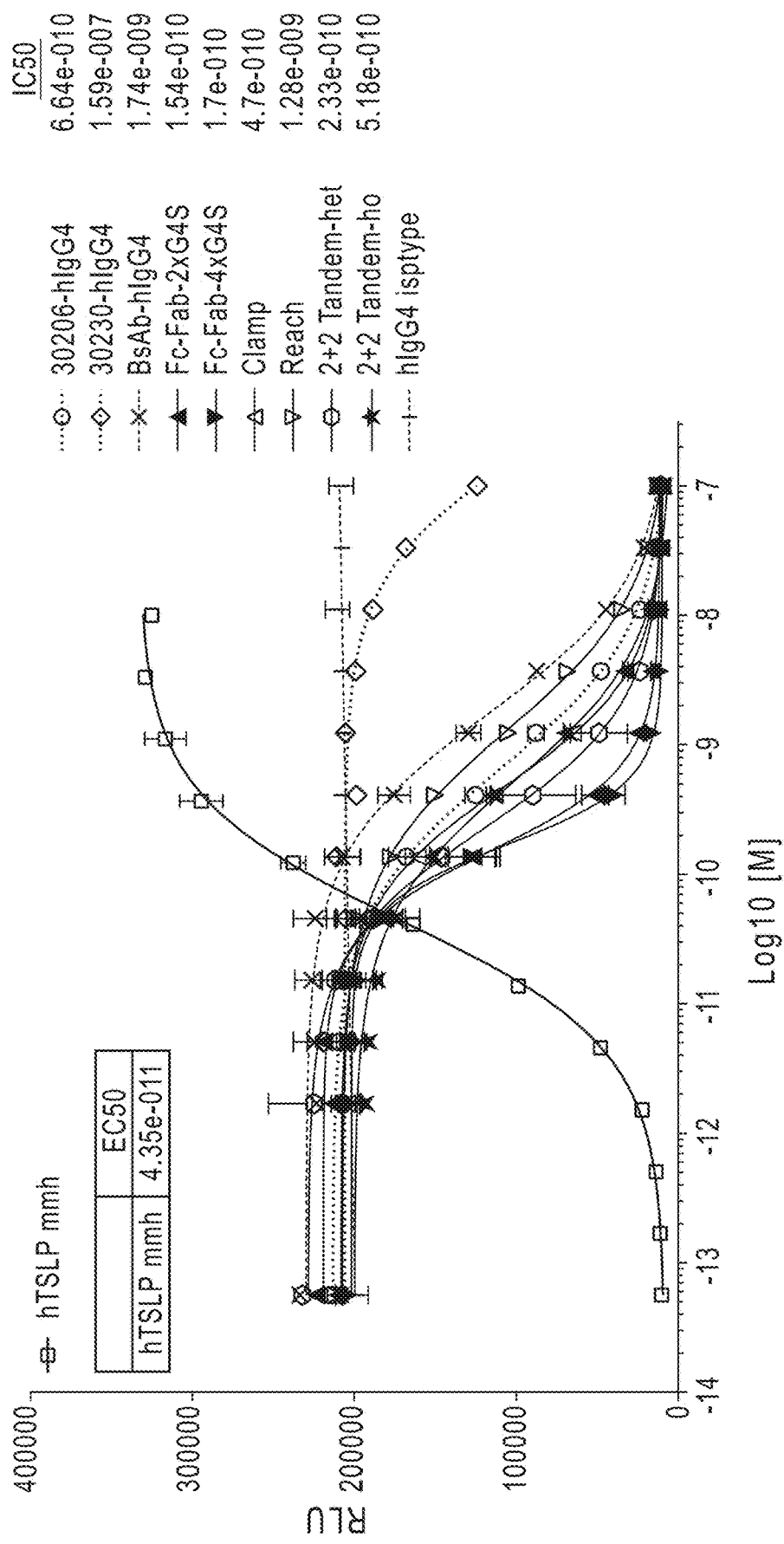
Figure 6C:
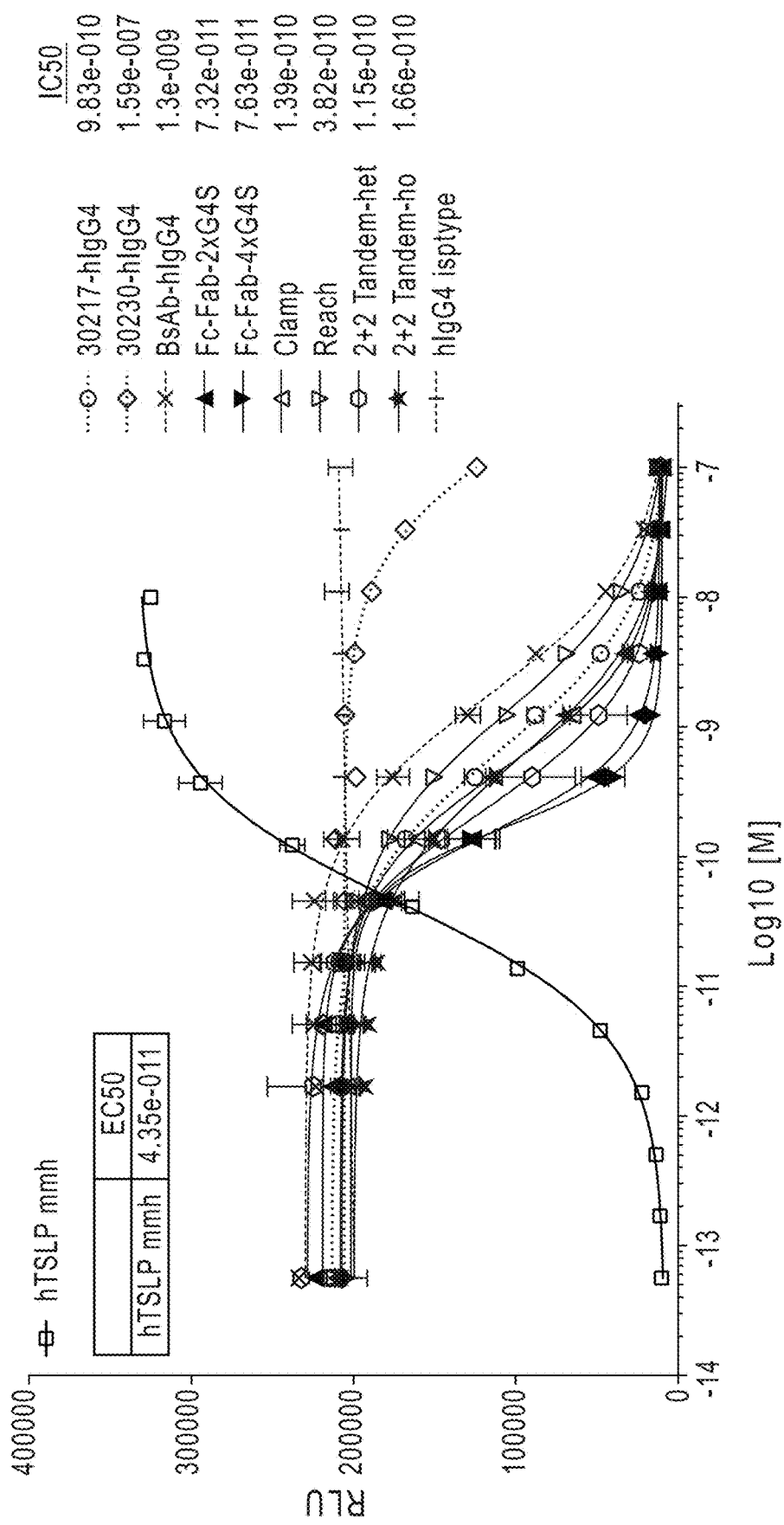

FIGS. 6A-6C: FIGS. 6A-6C are graphs comparing different format bispecific anti-hTSLP Abs in a TSLP blocking bioassay. Several parental Ab pairings were tested: 30206× 30217 (FIG. 6A), 30206×30230 (FIG. 6B), 30217×30230 (FIG. 6C). TSLP Abs were incubated with the Baf3/hIL7R/hTSLPR/STAT3-Luciferase reporter cell line in the presence of 100 pM hTSLP. Luciferase activity was measured after 5.5 hour incubation. "2xG4S" and "4xG4S" disclosed in FIGS. 6A-6C are SEQ ID NO:18 and SEQ ID NO:19, respectively.

Figure 7:
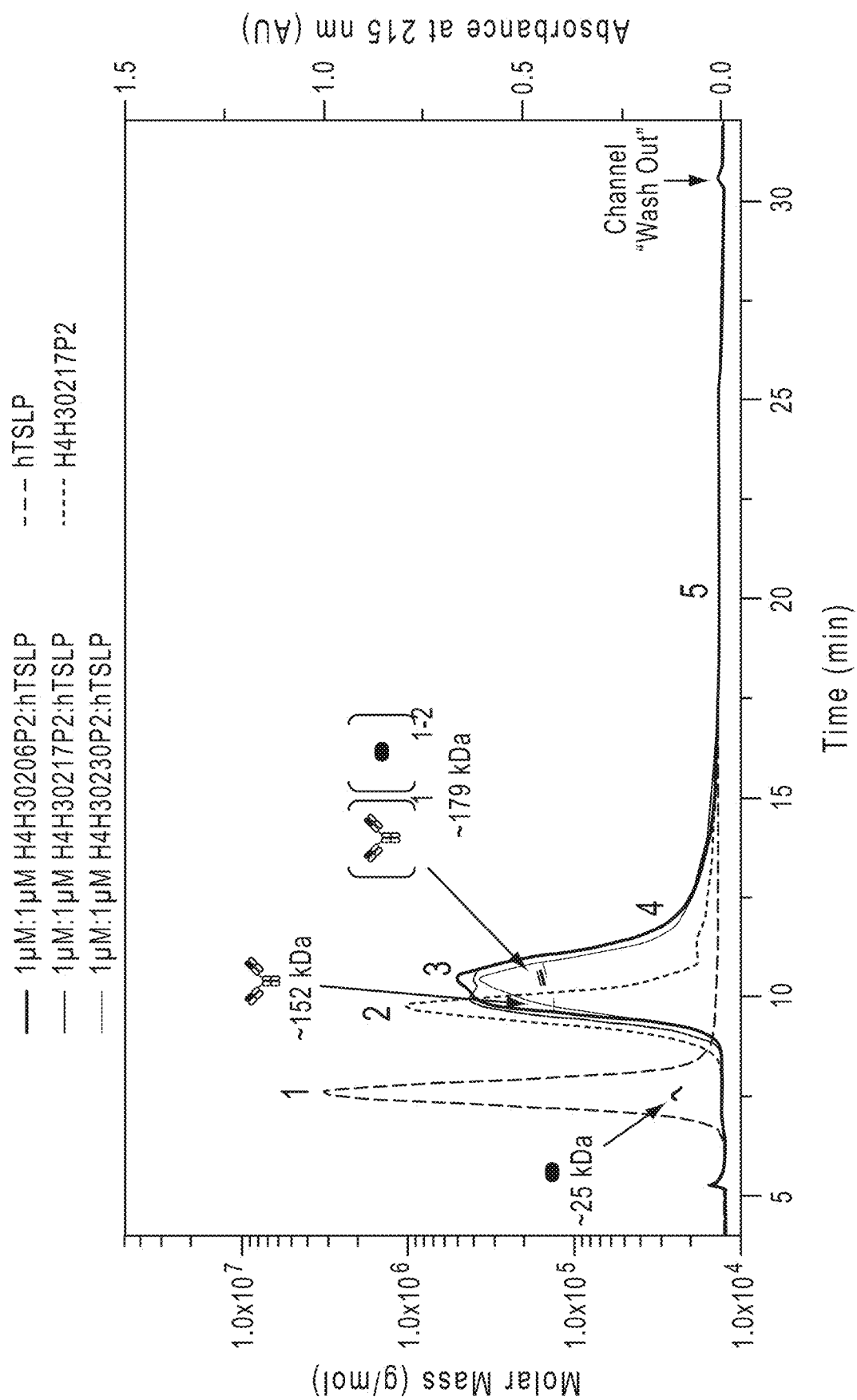

FIG. 7: FIG. 7 is a graph showing fractograms of individual parental mAbs in the presence of hTSLP (REGN4009). Anti-TSLP mAb:hTSLP complexes (solid lines) were analyzed by asymmetric flow field-flow fractionation coupled to multi-angle light scattering (A4F-MALS). Fractograms from individual samples of H4H30217P2 (grey dashed line) and hTSLP (black dashed line) are also overlaid. Relative UV absorbance at 215 nm as a function of retention time is shown for each sample and the measured molar masses of resolved peaks are indicated.

Figure 8:
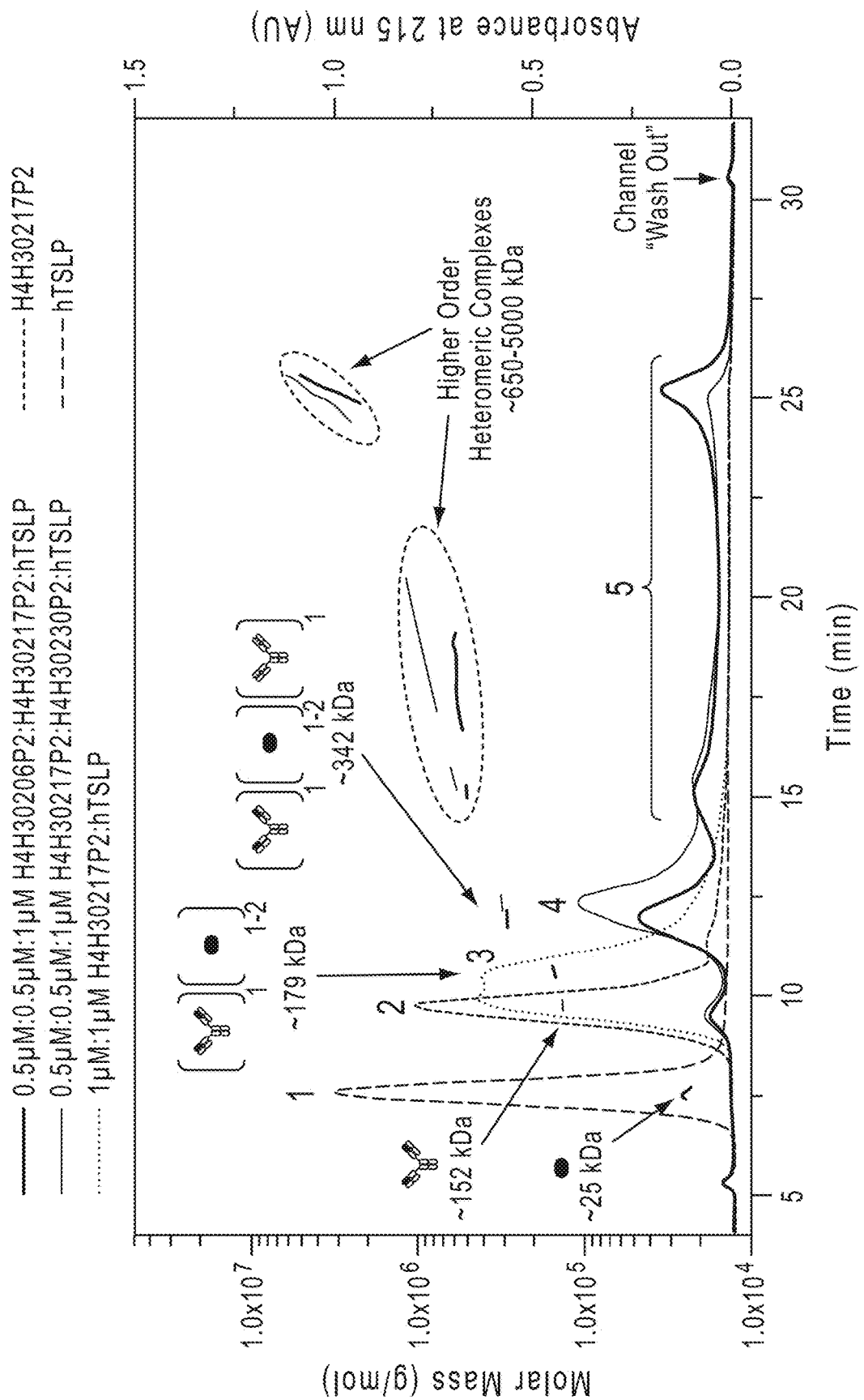

FIG. 8: FIG. 8 is a graph showing fractograms of parental mAb combinations in the presence of hTSLP. Anti-TSLP mAb combination:hTSLP complexes (solid lines) were analyzed by asymmetric flow field-flow fractionation coupled to multi-angle light scattering (A4F-MALS). Fractograms from individual samples of H4H30217P2 (grey dashed line) and hTSLP (black dashed line), and H4H30217P2:hTSLP complex (black dotted line) are also overlaid. Relative UV absorbance at 215 nm as a function of retention time is shown for each sample and the measured molar masses of resolved peaks are indicated.

Figure 9:
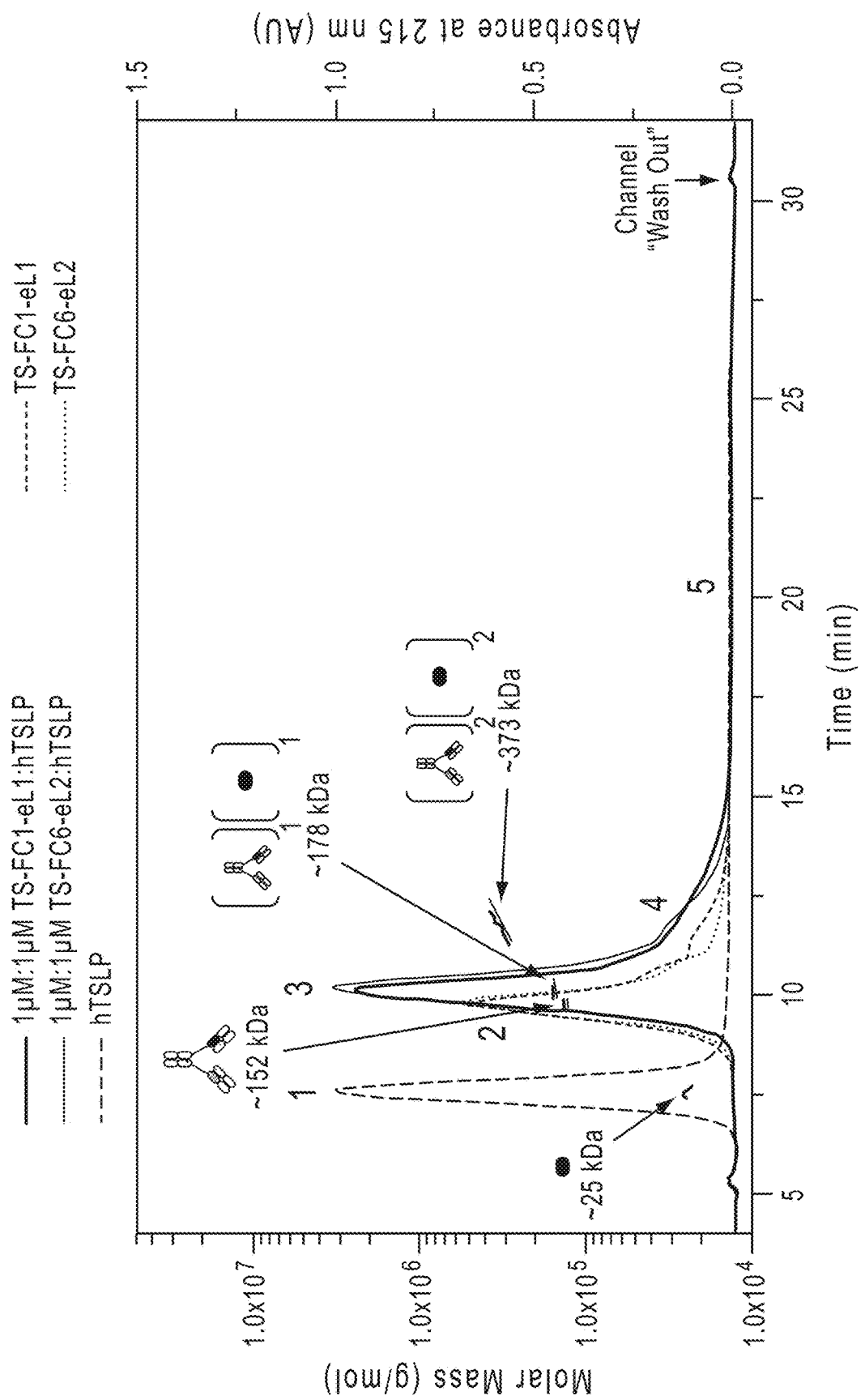

FIG. 9: FIG. 9 is a graph showing fractograms of Fc-Fab bispecific Abs in the presence of hTSLP. Anti-TSLP Fc-Fab: hTSLP complexes (solid lines) were analyzed by asymmetric flow field-flow fractionation coupled to multi-angle light scattering (A4F-MALS). Fractograms from individual samples of TS-FC1-eL1 (black dotted line), TS-FC6-eL2 (grey dotted line) and hTSLP (black dashed line) are also overlaid. Relative UV absorbance at 215 nm as a function of retention time is shown for each sample and the measured molar masses of resolved peaks are indicated.

Figure 10:
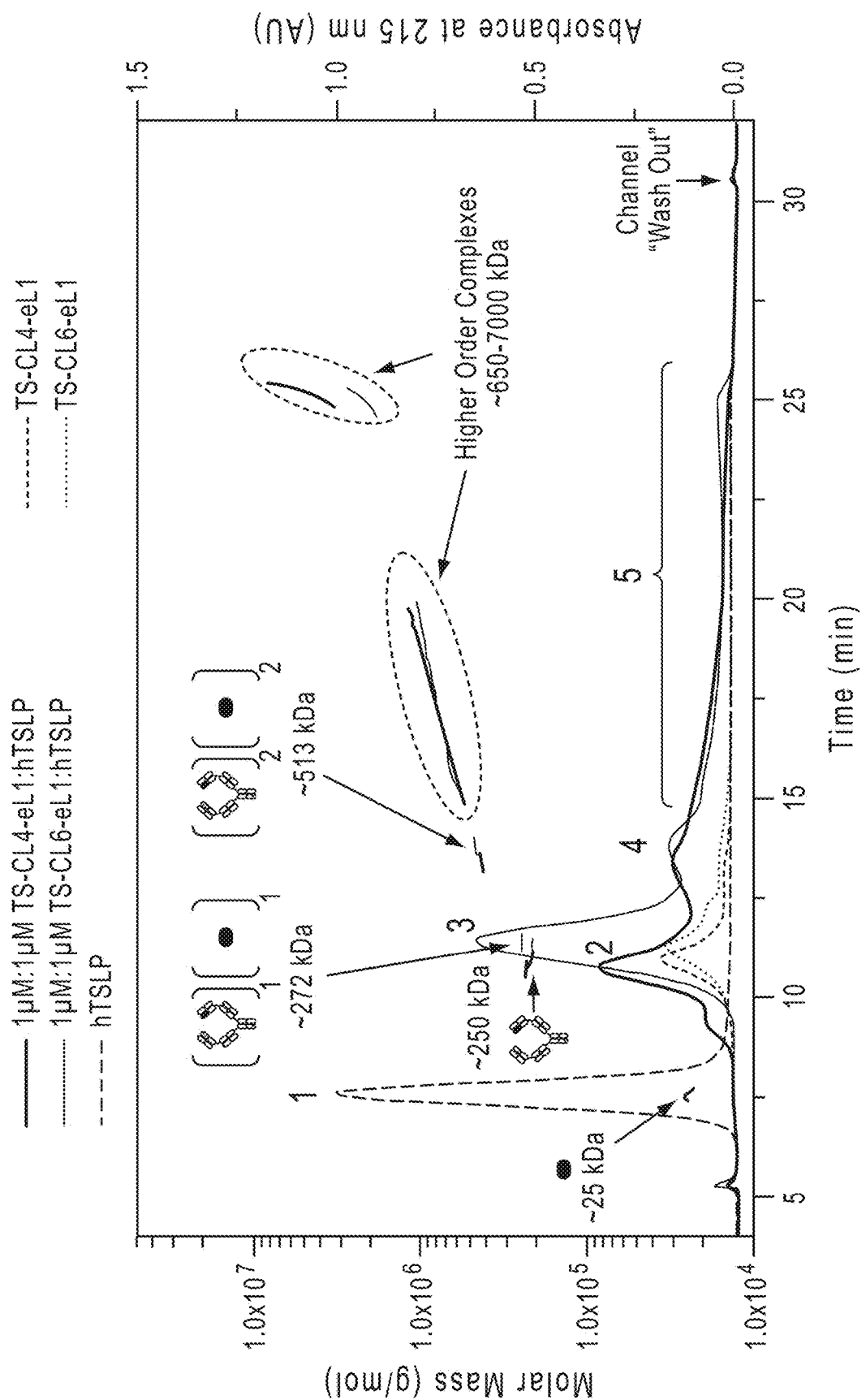

FIG. 10: FIG. 10 is a graph showing fractograms of Clamp bispecific Abs in the presence of hTSLP. Anti-TSLP Clamp:hTSLP complexes (solid lines) were analyzed by asymmetric flow field-flow fractionation coupled to multi-angle light scattering (A4F-MALS). Fractograms from individual samples of TS-CL4-eL1 (black dotted line), TS-CL6-eL1 (grey dotted line) and hTSLP (black dashed line) are also overlaid. Relative UV absorbance at 215 nm as a function of retention time is shown for each sample and the measured molar masses of resolved peaks are indicated.

Figure 11:
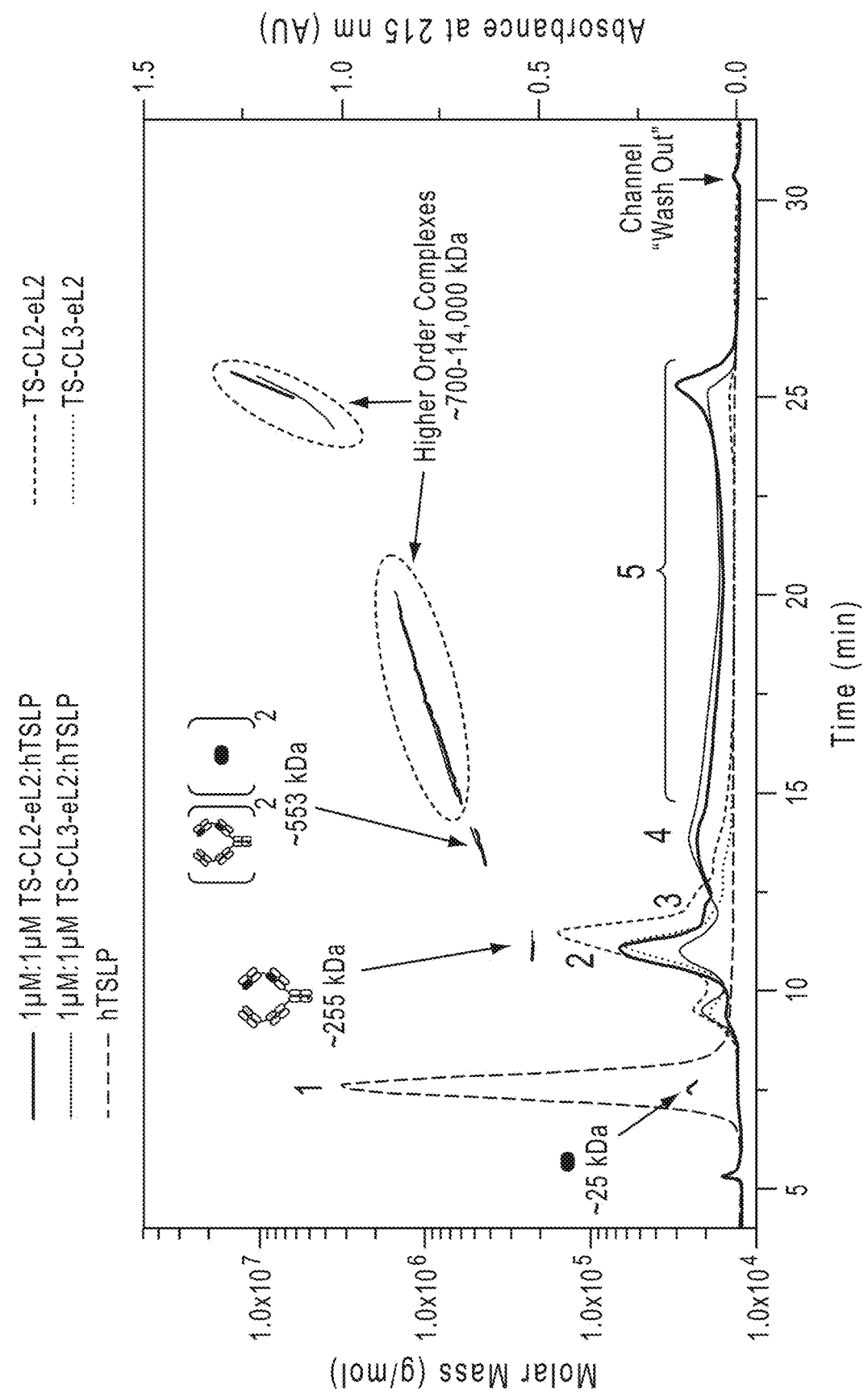

FIG. 11: FIG. 11 is a graph showing fractograms of 2+2 Tandem Fabs bispecific Abs in the presence of hTSLP. Anti-TSLP 2+2 Tandem Fabs:hTSLP complexes (solid lines) were analyzed by asymmetric flow field-flow fractionation coupled to multi-angle light scattering (A4F-MALS). Fractograms from individual samples of TS-CL2-eL2 (black dotted line), TS-CL3-eL2 (grey dotted line) and hTSLP (black dashed line) are also overlaid. Relative UV absorbance at 215 nm as a function of retention time is shown for each sample and the measured molar masses of resolved peaks are indicated.

Figure 12:
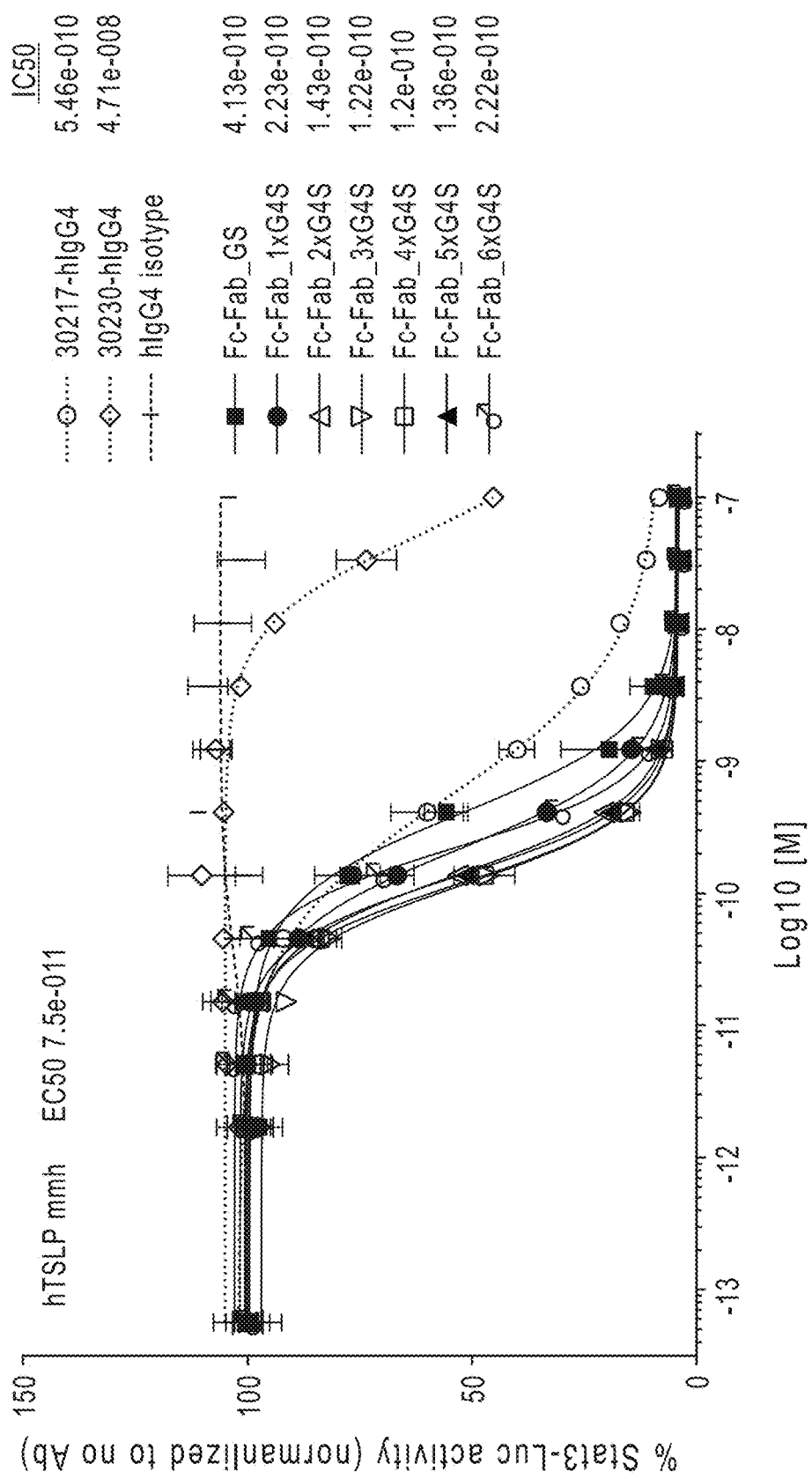

FIG. 12: FIG. 12 is a graph comparing activity of anti-hTSLP 30217×30230 bispecific Fc-Fabs with different linker lengths in a TSLP blocking bioassay. TSLP Abs were incubated with the Baf3/hIL7R/hTSLPR/STAT3-Luciferase reporter cell line in the presence of 120 pM constant hTSLP. Luciferase activity was measured after 5.5 hour incubation. All values were normalized to STAT3-Luciferase activity in the absence of TSLP blocking Ab, and expressed as percentage of STAT3-Luc activity. G4S, (G4S)$_2$, (G4S)$_3$, (G4S)$_4$, (G4S)$_5$, and (G4S)$_6$ linkers disclosed in FIG. 12 are SEQ ID NOS:3, 18, 4, 19, 39, and 38, respectively.

Figure 13D:
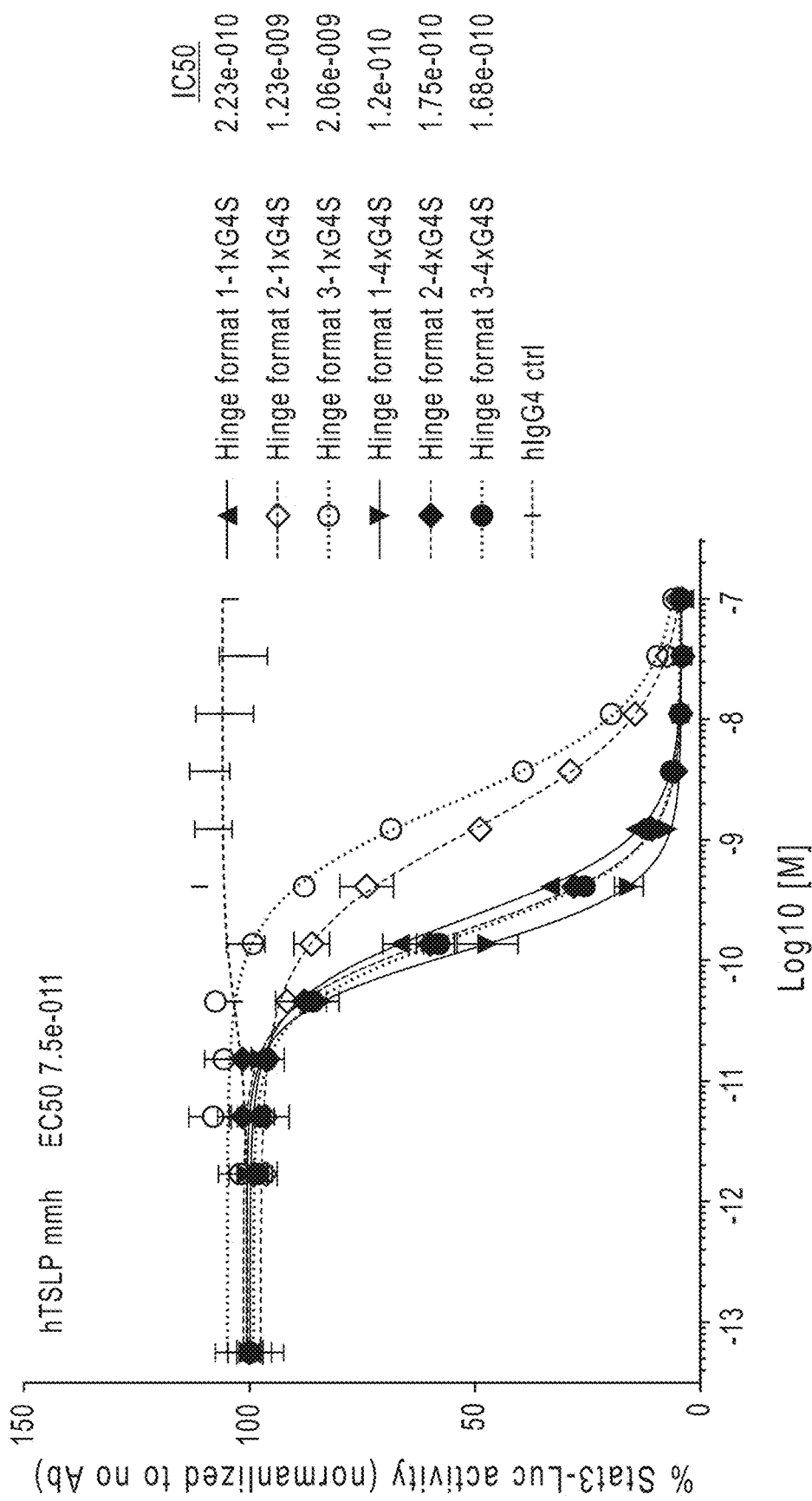

FIGS. 13A-13D: FIGS. 13A-13C are schematics of different hinge formats. FIG. 13A: Hinge Format 1, shown with hinge sequence ESKYGPPCPPC (SEQ ID NO:2) and (G4S)$_n$ linker (G4S is disclosed as SEQ ID NO:3); FIG. 13B: Hinge Format 2, shown with hinge sequence ESKYGPPCPPC (SEQ ID NO:2) and (G4S)$_n$ linker (G4S is disclosed as SEQ ID NO:3); FIG. 13C: Hinge Format 3, shown with hinge sequence GGGGSCPPC (SEQ ID NO:1) and (G4S)$_n$ linker (G4S is disclosed as SEQ ID NO:3). FIG. 13D is a graph showing activity of 30217×30230 Fc-Fabs with different hinge formats (Hinge Format 1 with a G4S linker (SEQ ID NO:3), Hinge Format 2 with a G4S linker (SEQ ID NO:3), Hinge Format 3 with a G4S linker (SEQ ID NO:3), Hinge Format 1 with a (G4S)$_4$ linker (SEQ ID NO:19), Hinge Format 2 with a (G4S)$_4$ linker (SEQ ID NO:19), and Hinge Format 3 with a (G4S)$_4$ linker (SEQ ID NO:19)). TSLP Abs were incubated with the Baf3/hIL7R/hTSLPR/STAT3-Luciferase reporter cell line in the presence of 120 pM hTSLP. Luciferase activity was measured after 5.5 hour incubation. All values were normalized to STAT3-Luciferase activity in the absence of TSLP blocking Ab, and expressed as percentage of STAT3-Luc activity.

Figure 14:
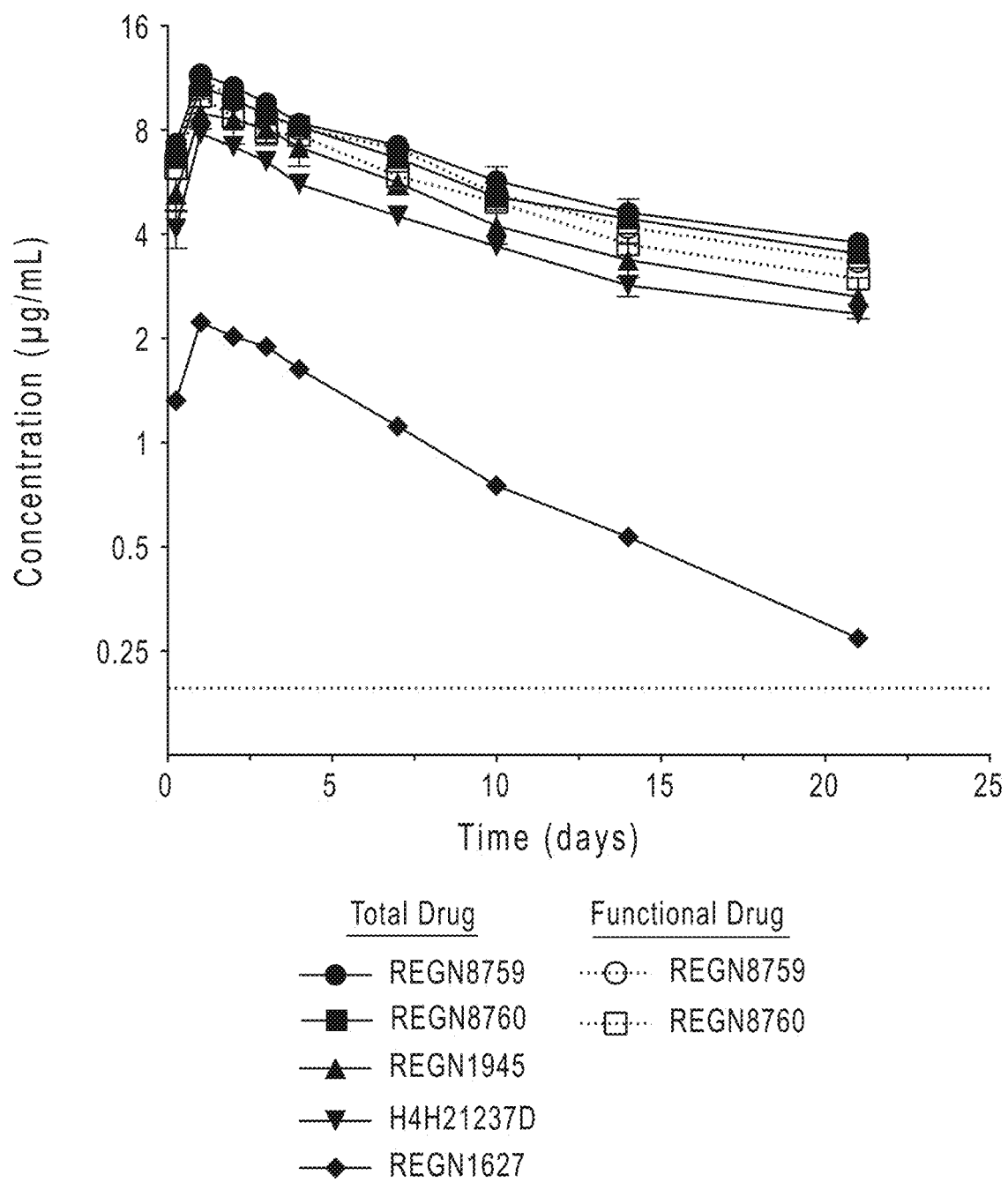

FIG. 14: FIG. 14 shows pharmacokinetic profiles of anti-TSLP bispecific Fc-Fab molecules REGN8759 and REGN8760; hIgG4 Isotype control REGN1945; conventional hIgG4 bispecific isotype control H4H21237D; and hFcγ homodimer REGN1627 in WT mice.

Figure 15:
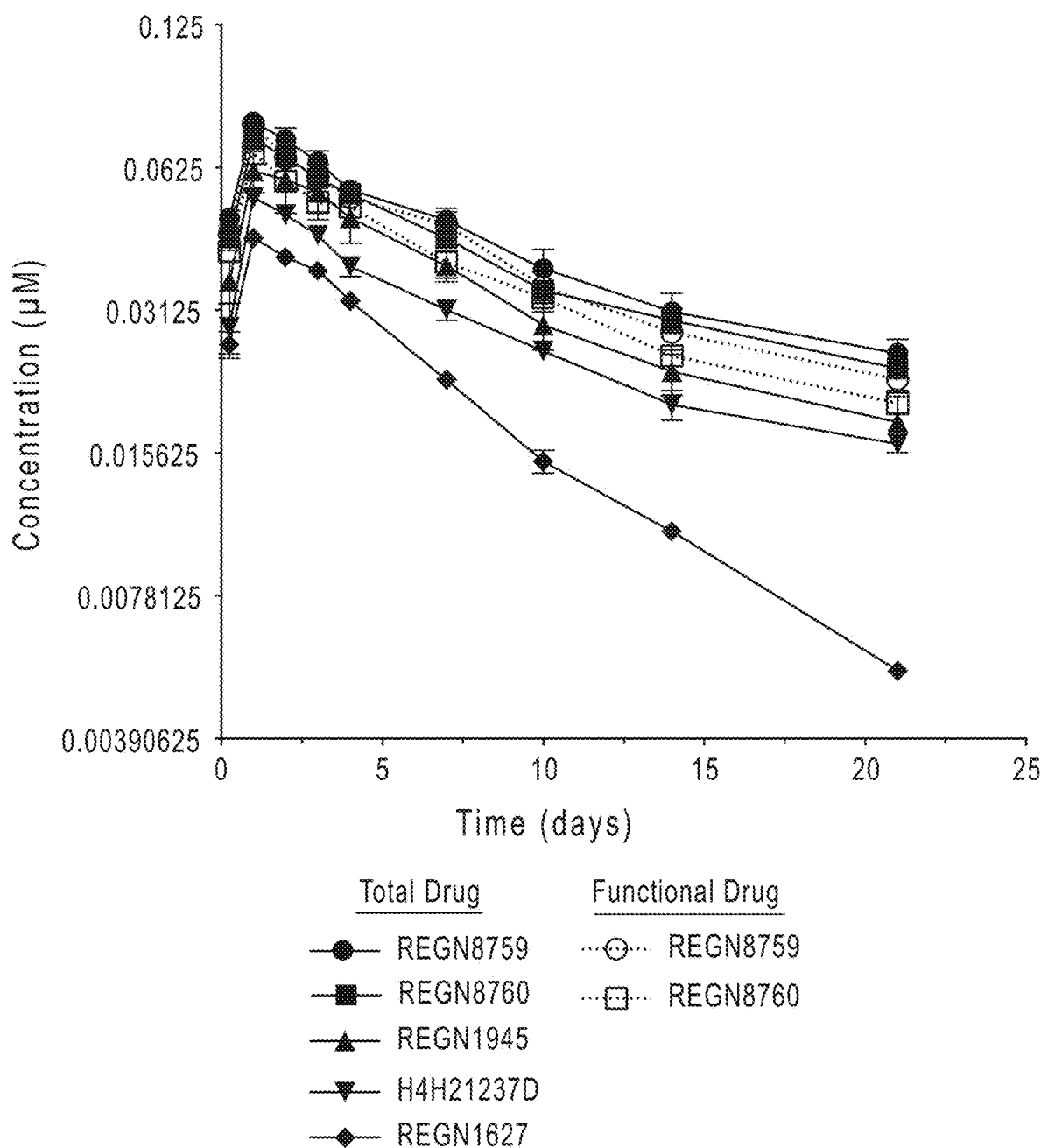

FIG. 15: FIG. 15 shows molar equivalent pharmacokinetic profiles of anti-TSLP Fc-Fab antibodies REGN8759 and REGN8760; hIgG4 Isotype control REGN1945; conventional hIgG4 bispecific isotype control H4H21237D; and hFcγ homodimer REGN1627 in WT mice.

Figure 16A:
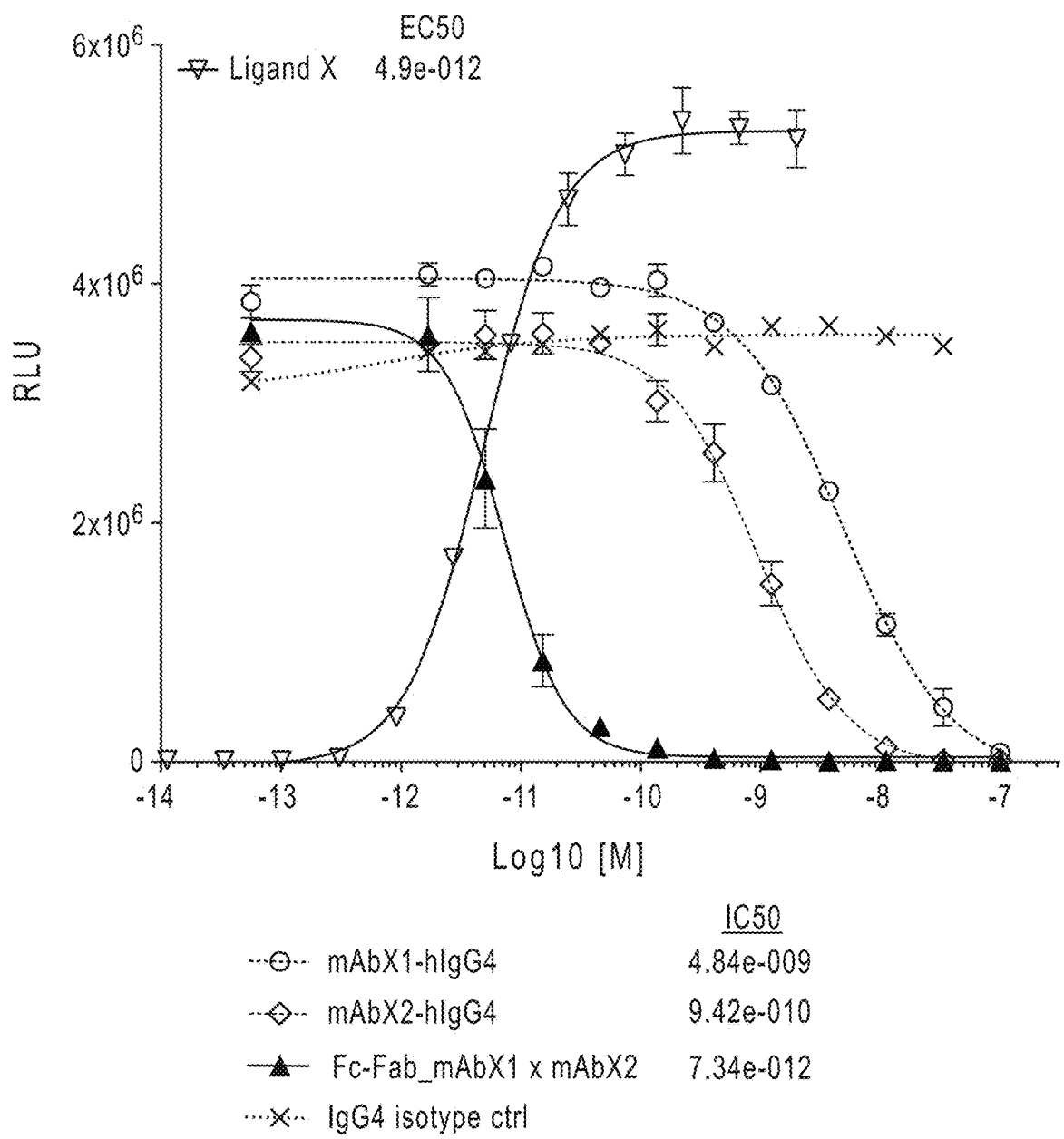
Figure 16B:
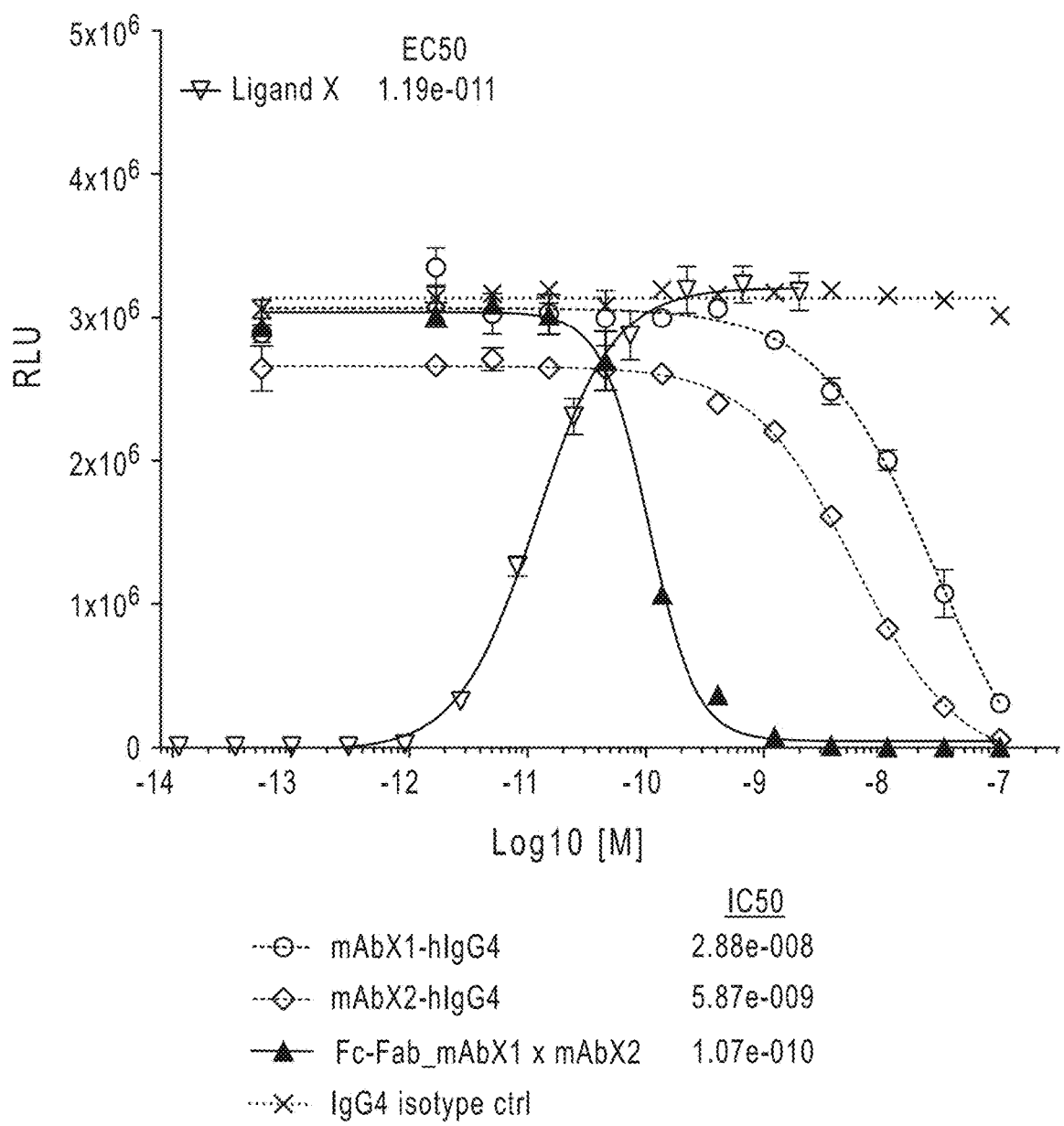
Figure 16C:
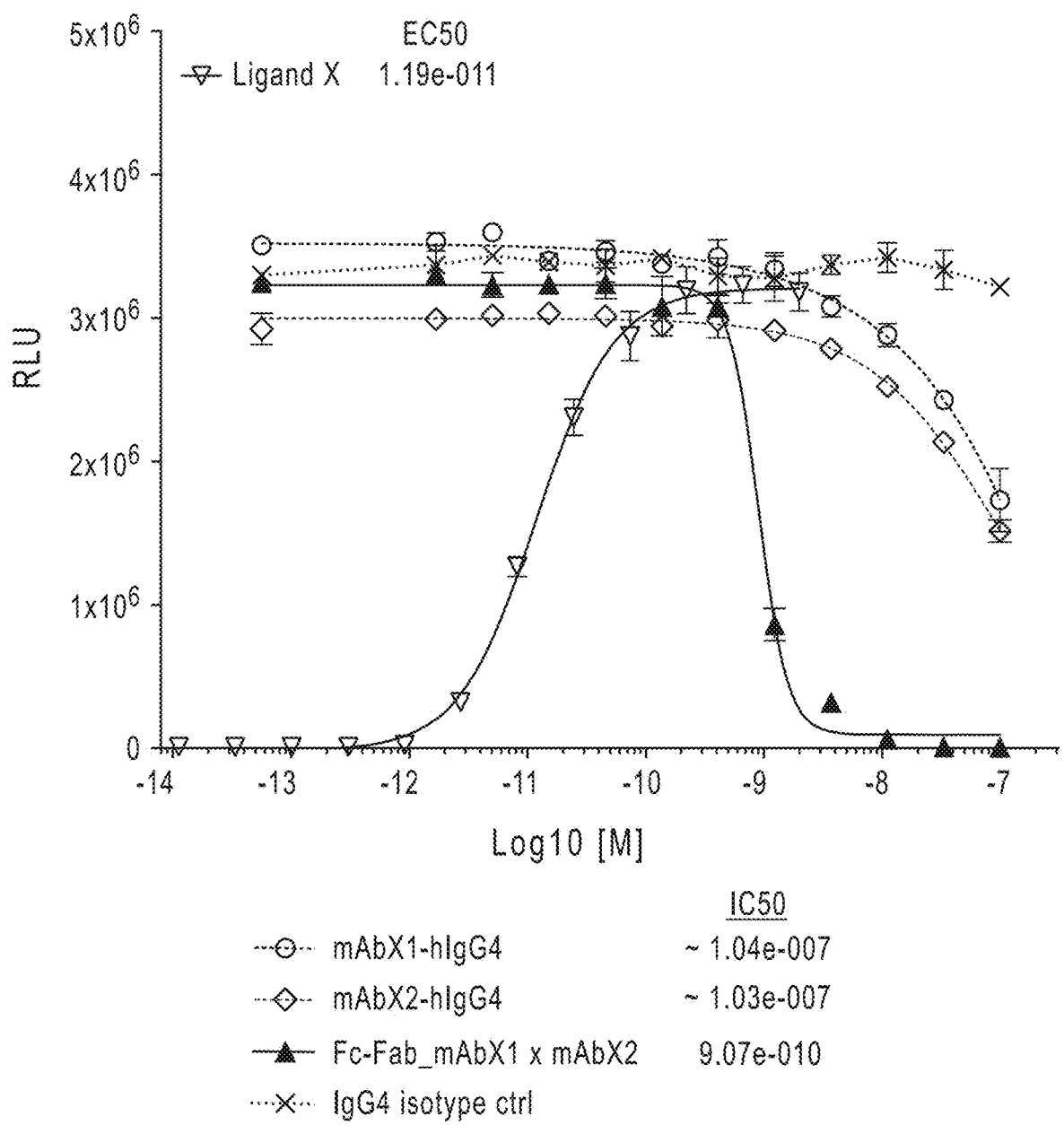

FIGS. 16A-16C: FIGS. 16A-16C are graphs comparing inhibitory activity of anti-Ligand X parental mAbs mAbX1, mAbX2, and the bispecific Fc-Fab mAbX1 x mAbX2 in Ligand X signaling bioassays. Anti-Ligand X Abs were incubated with an engineered luciferase reporter cell line for Receptor X signaling in the presence of 10 pM (FIG. 16A), 100 pM (FIG. 16B) or 1 nM (FIG. 16C) constant human Ligand X. Luciferase activity was measured after a 5.5 hour incubation.

Figure 17A:
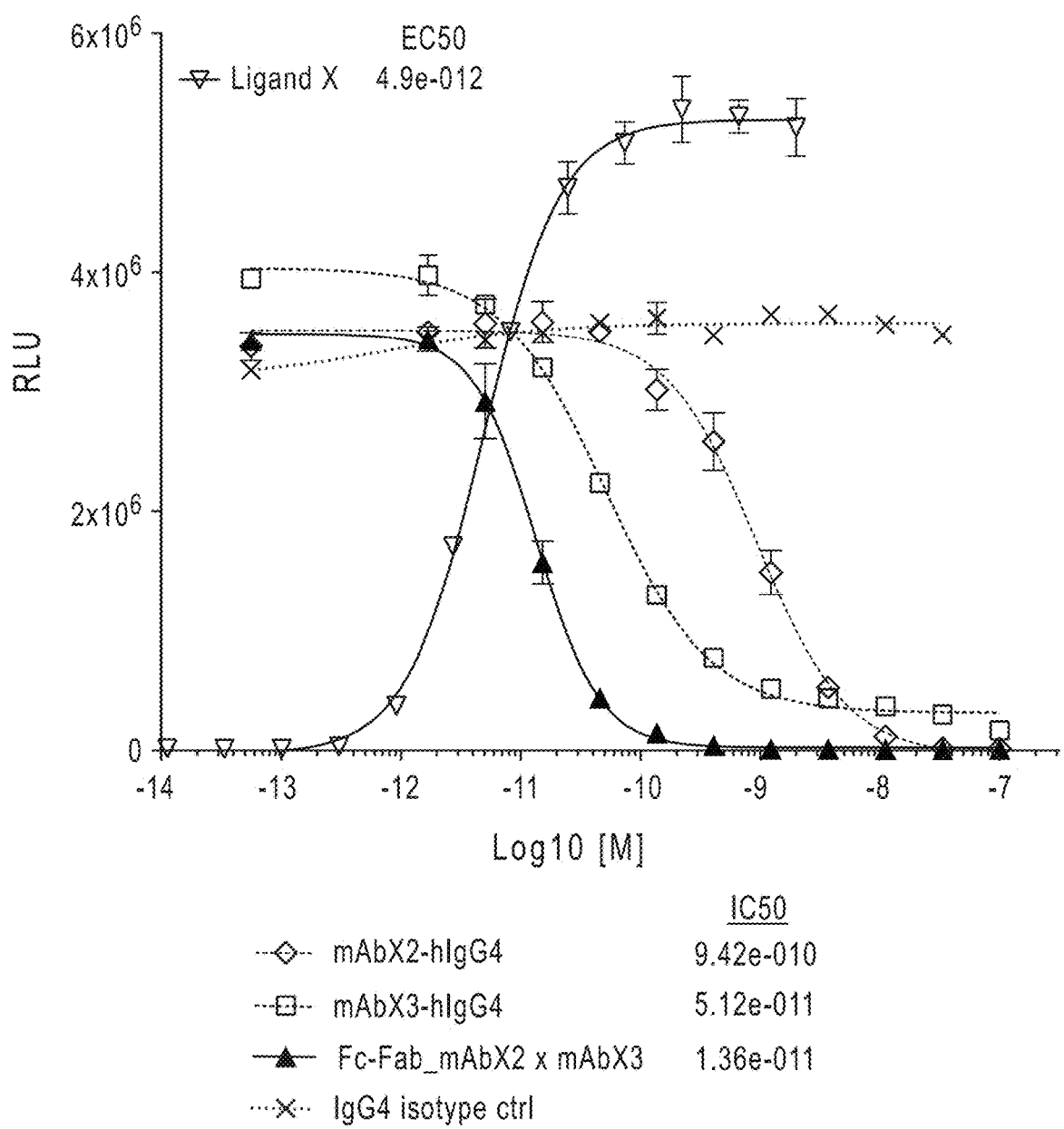
Figure 17B:
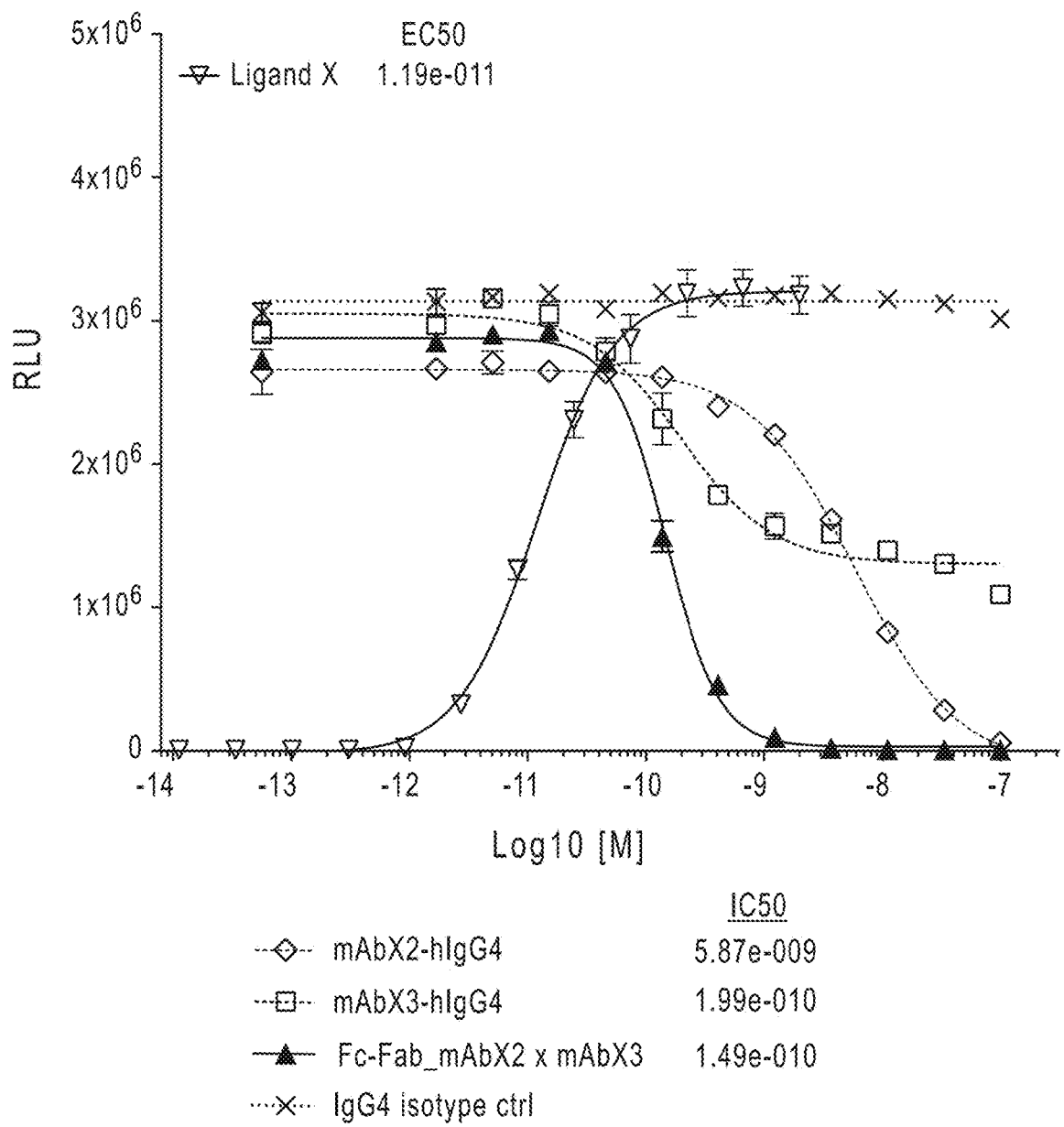
Figure 17C:
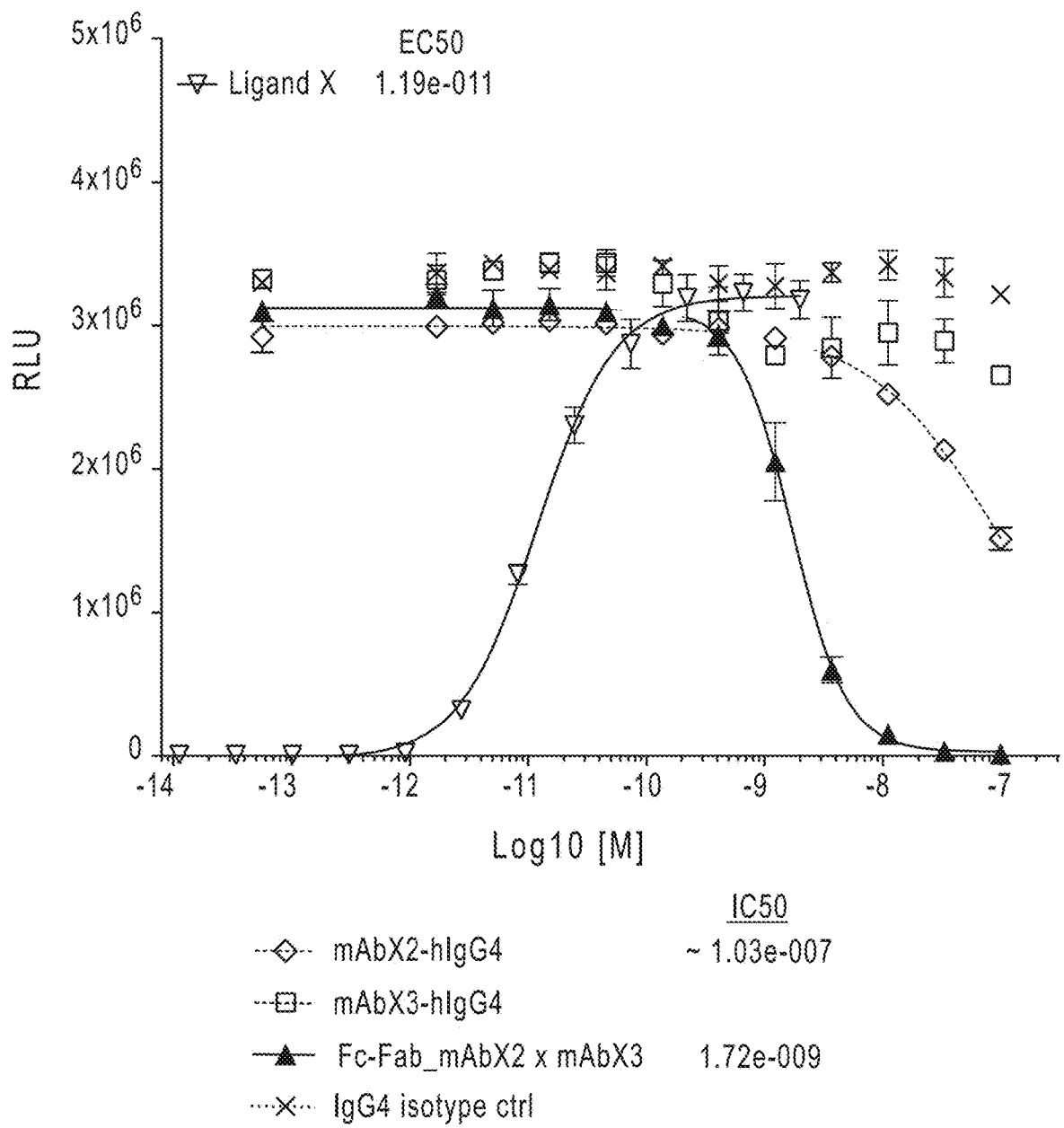

FIGS. 17A-17C: FIGS. 17A-17C are graphs comparing inhibitory activity of anti-Ligand X parental mAbs mAbX2, mAbX3, and the bispecific Fc-Fab mAbX2 x mAbX3 in Ligand X signaling bioassays. Anti-Ligand X Abs were incubated with an engineered luciferase reporter cell line for Receptor X signaling in the presence of 10 pM (FIG. 17A), 100 pM (FIG. 17B) or 1 nM (FIG. 17C) constant human Ligand X. Luciferase activity was measured after a 5.5 hour incubation.

Figure 18A:
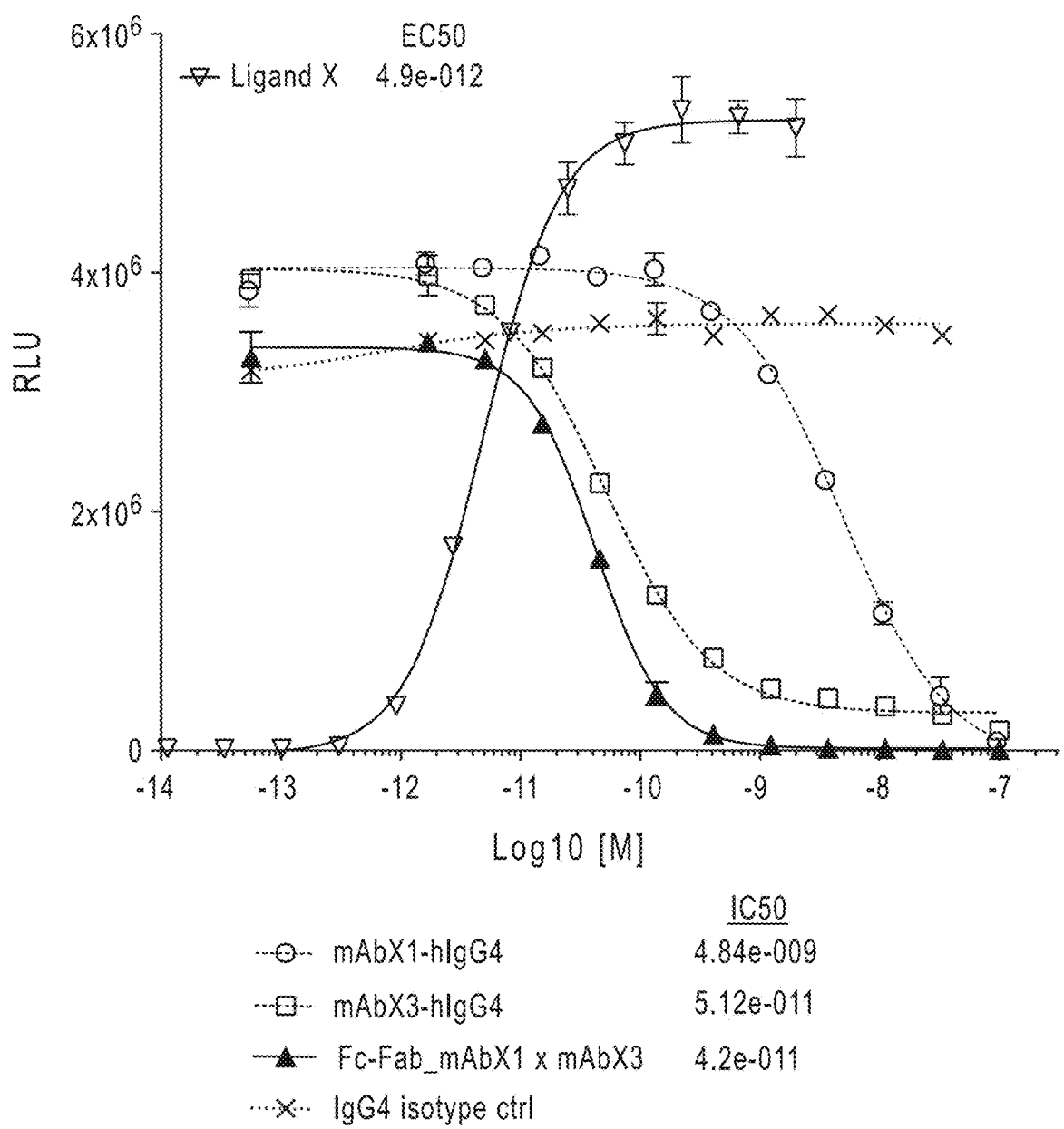
Figure 18B:
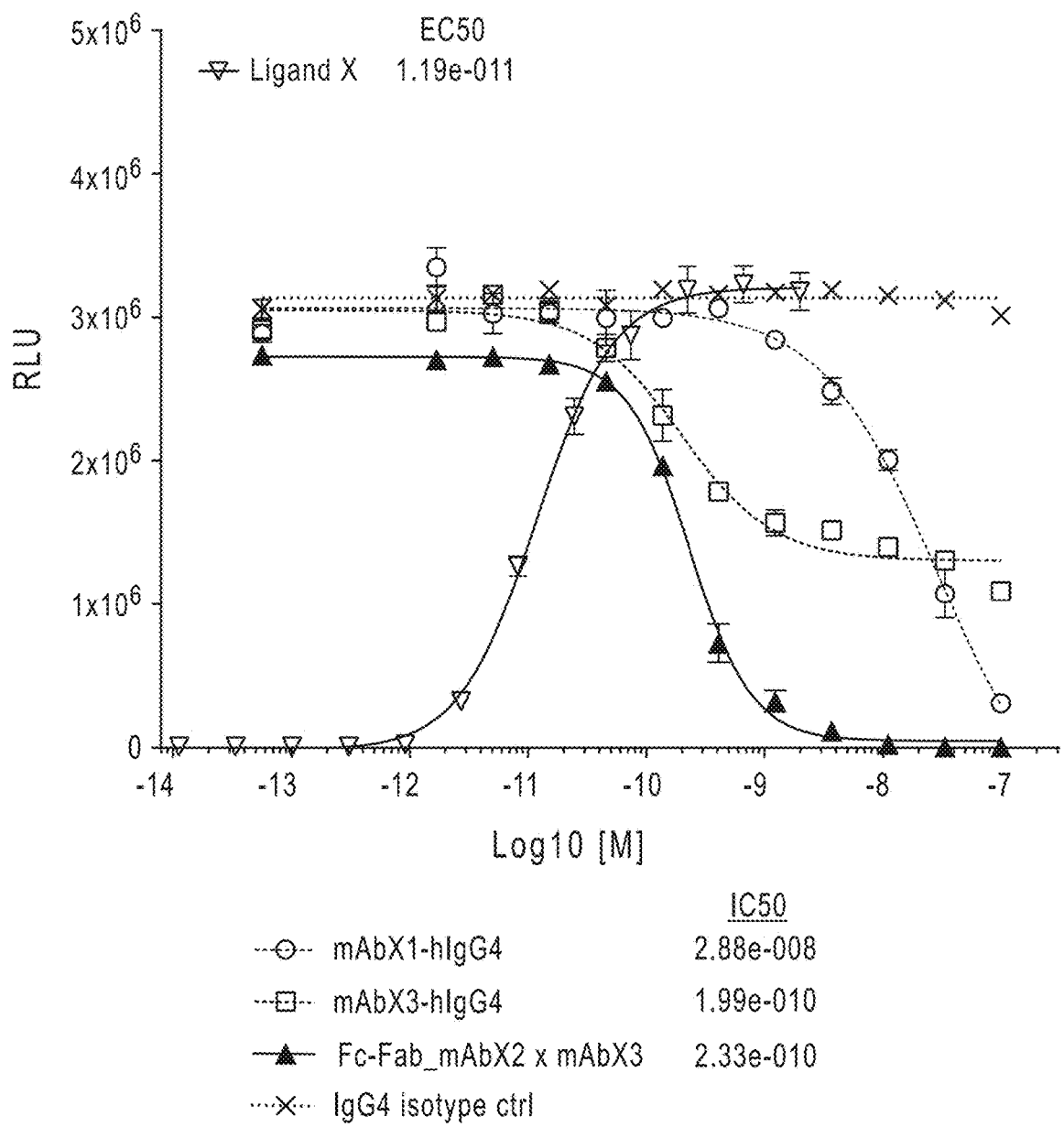
Figure 18C:
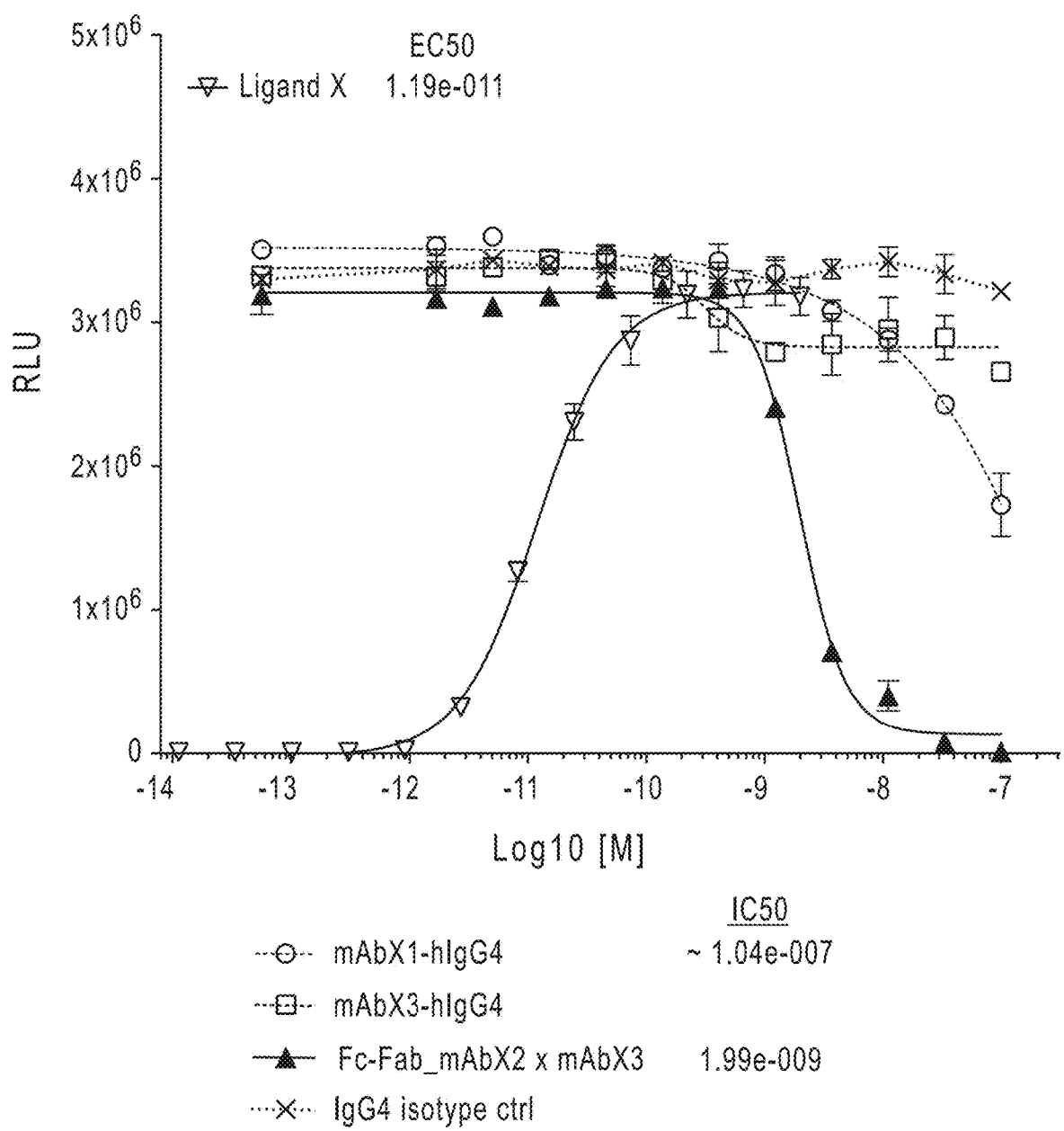

FIGS. 18A-18C: FIGS. 18A-18C are graphs comparing inhibitory activity of anti-Ligand X parental mAbs mAbX1, mAbX3, and the bispecific Fc-Fab mAbX1 x mAbX3 in Ligand X signaling bioassays. Anti-Ligand X Abs were incubated with an engineered luciferase reporter cell line for Receptor X signaling in the presence of 10 pM (FIG. 18A), 100 pM (FIG. 18B) or 1 nM (FIG. 18C) constant human Ligand X. Luciferase activity was measured after a 5.5 hour incubation.

Figure 19A:
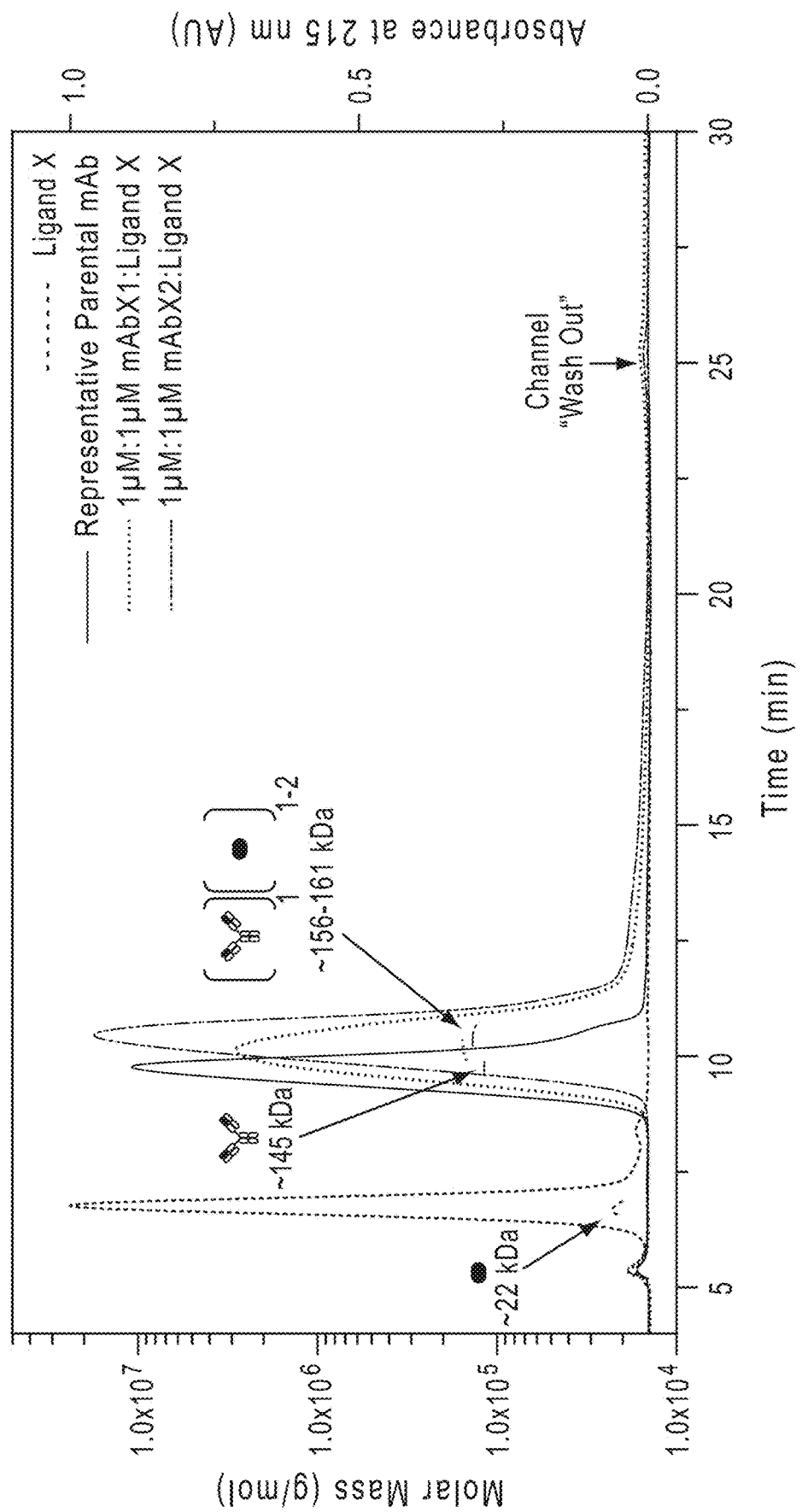
Figure 19B:
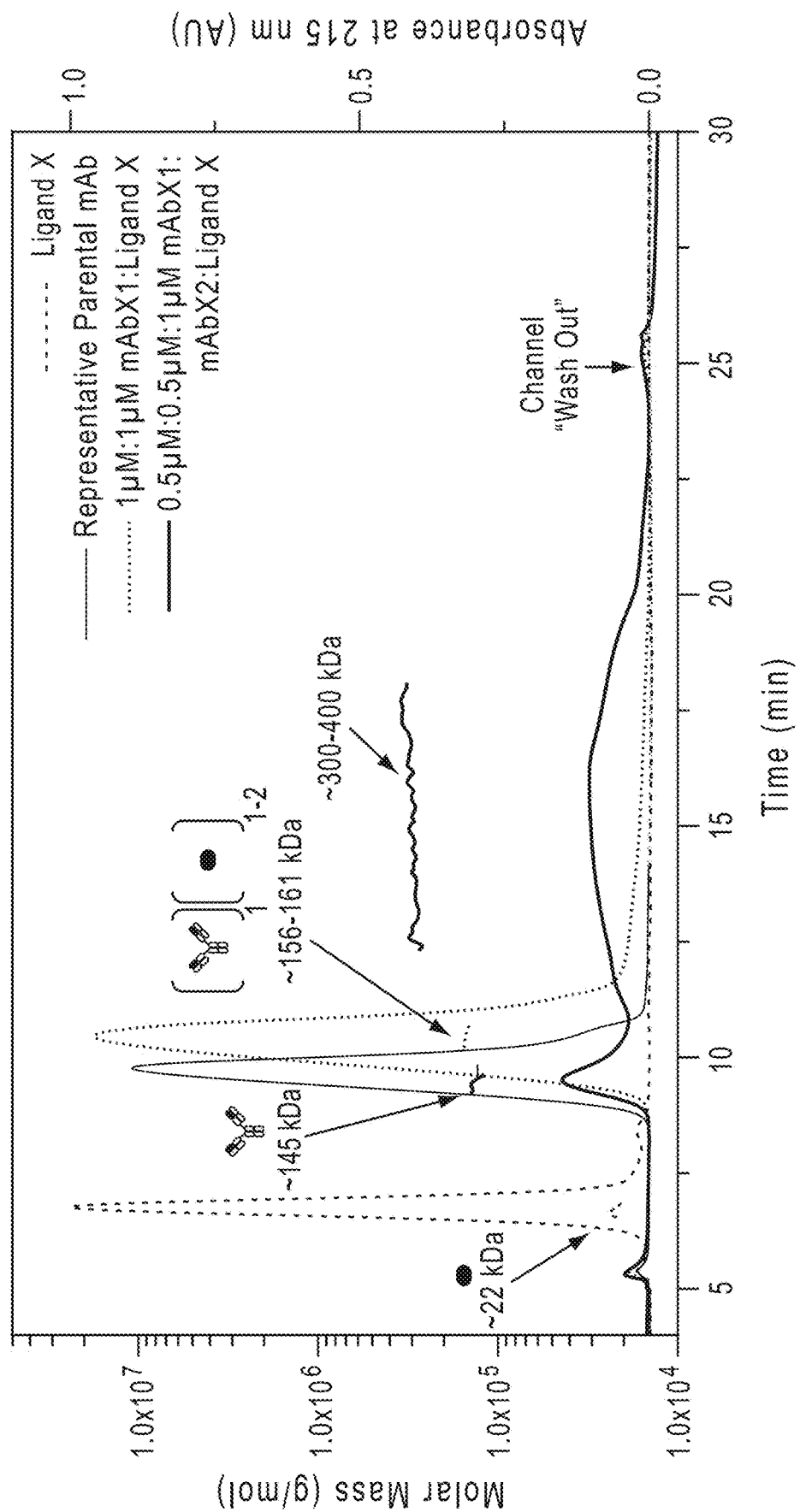
Figure 19C:
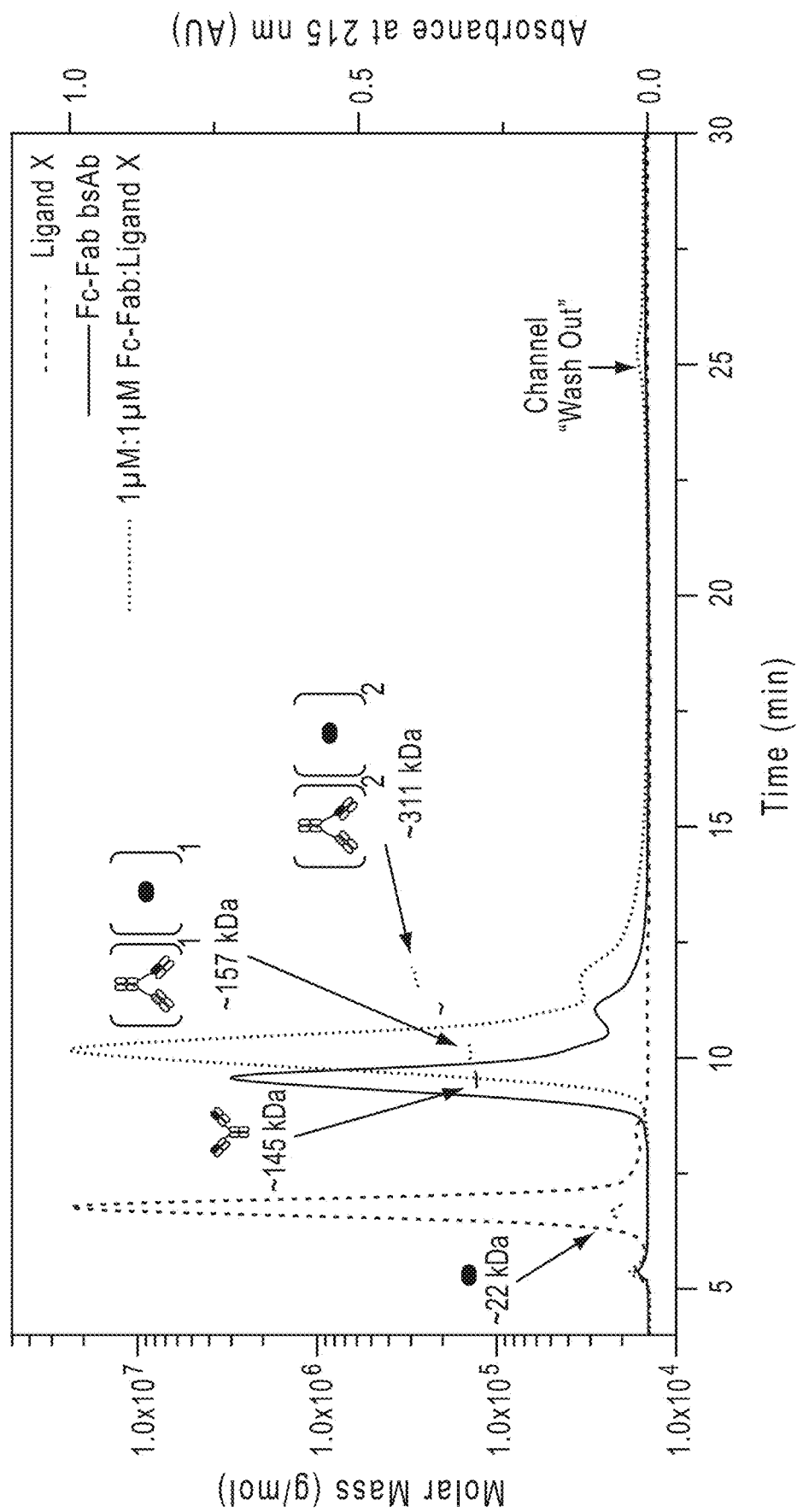
Figure 19D:
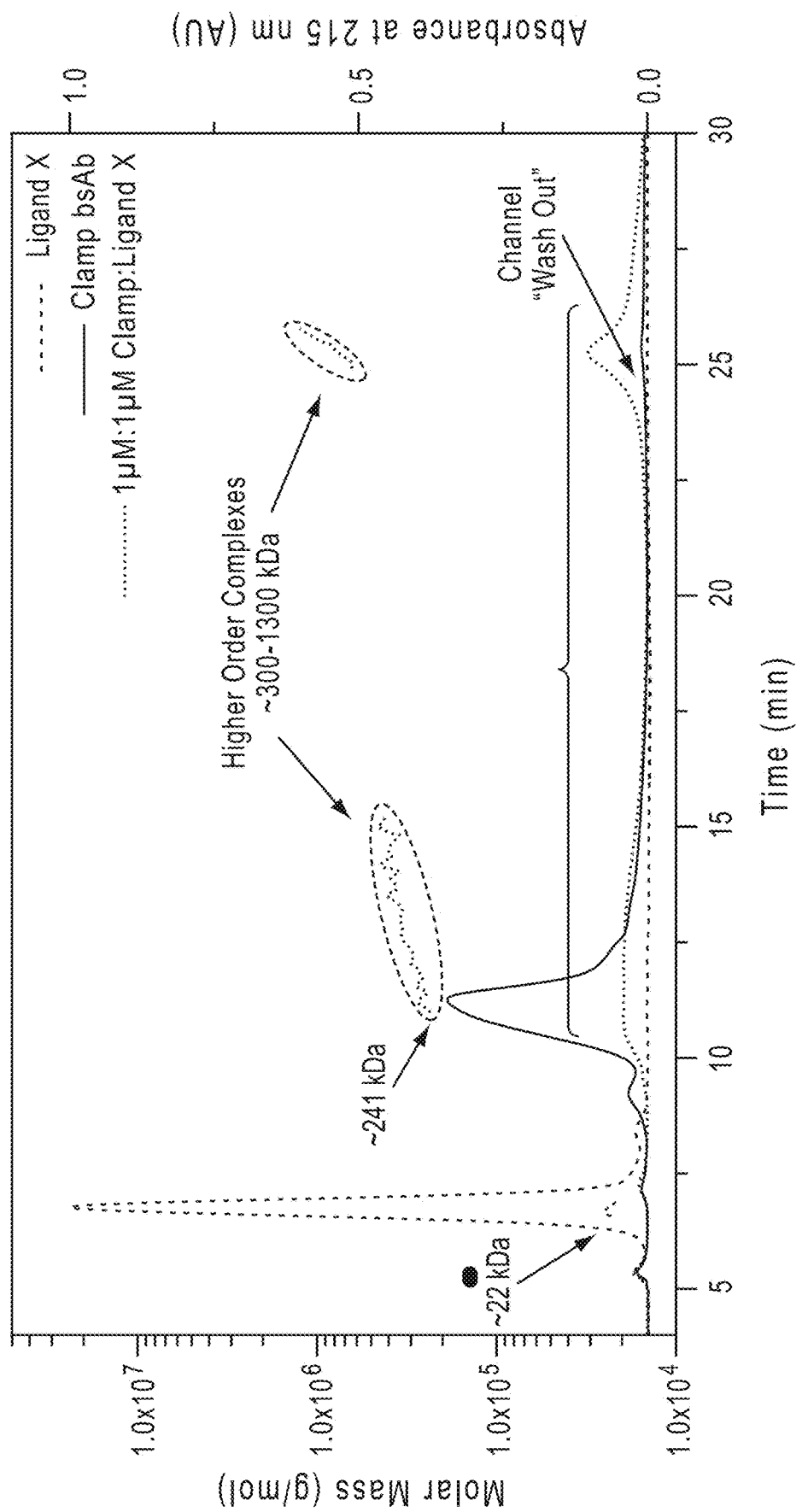
Figure 19E:
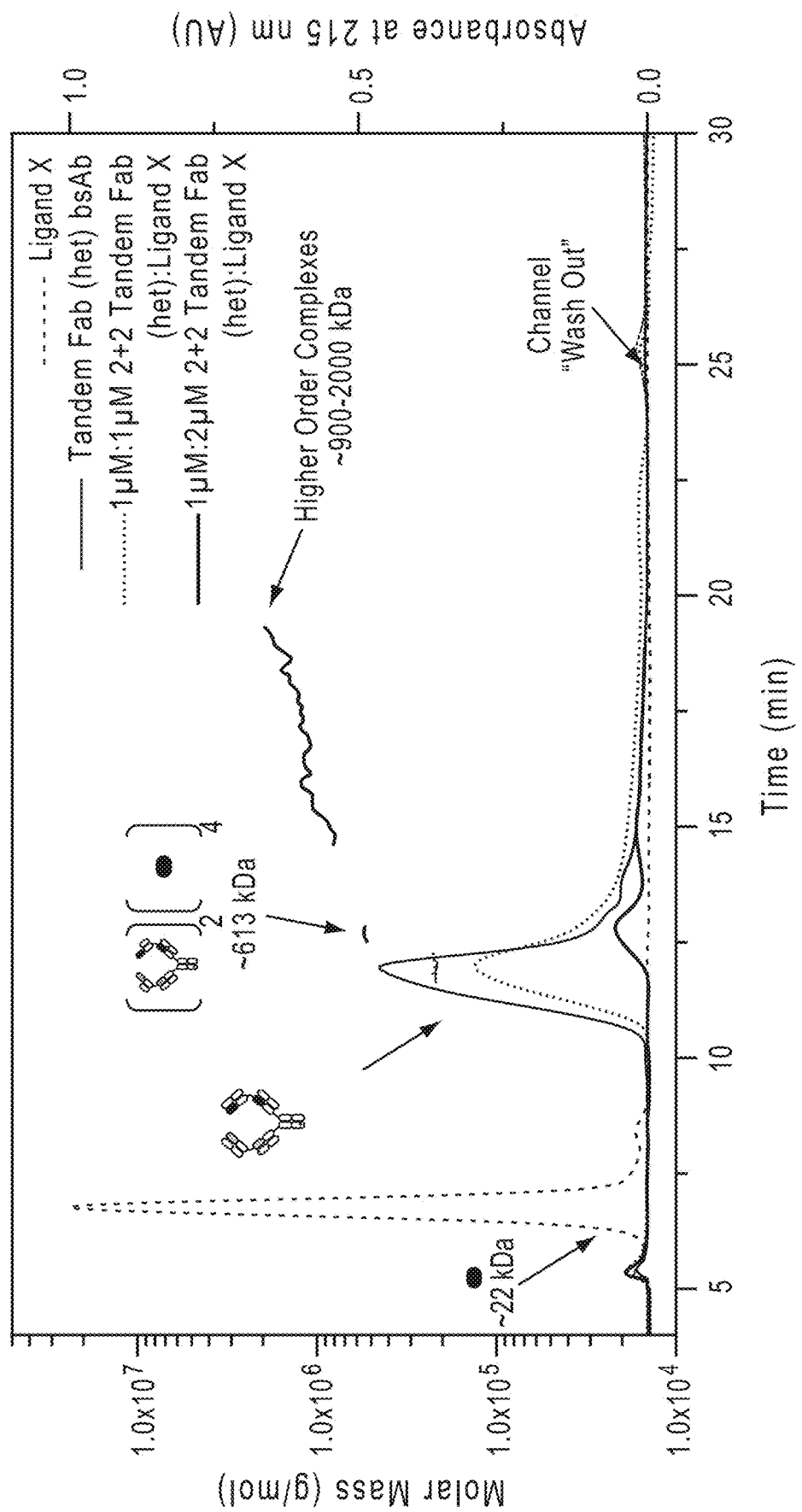

FIGS. 19A-19E: FIGS. 19A-19E are graphs showing fractograms of complexes of Ligand X with anti-Ligand X antibodies. Anti-Ligand X antibodies in combination with Ligand X were analyzed by asymmetric flow field-flow fractionation coupled to multi-angle light scattering (A4F-MALS). Fractograms from individual samples of the antibodies and Ligand X are also overlaid. Relative UV absorbance at 215 nm as a function of retention time is shown for each sample and the measured molar masses of resolved peaks are indicated. FIGS. 19A and 19B show fractograms of the parental antibodies mAbX1, mAbX2 and Ligand X; FIG. 19C show a fractogram of mAbX1 x mAbX2 Fc-Fab and Ligand X; FIG. 19D shows a fractogram of mAbX1 x mAbX2 Clamp and Ligand X; and FIG. 19E shows a fractogram of mAbX1 x mAbX2 2+2 Tandem Fab heterodimer and Ligand X.

Figure 20A:
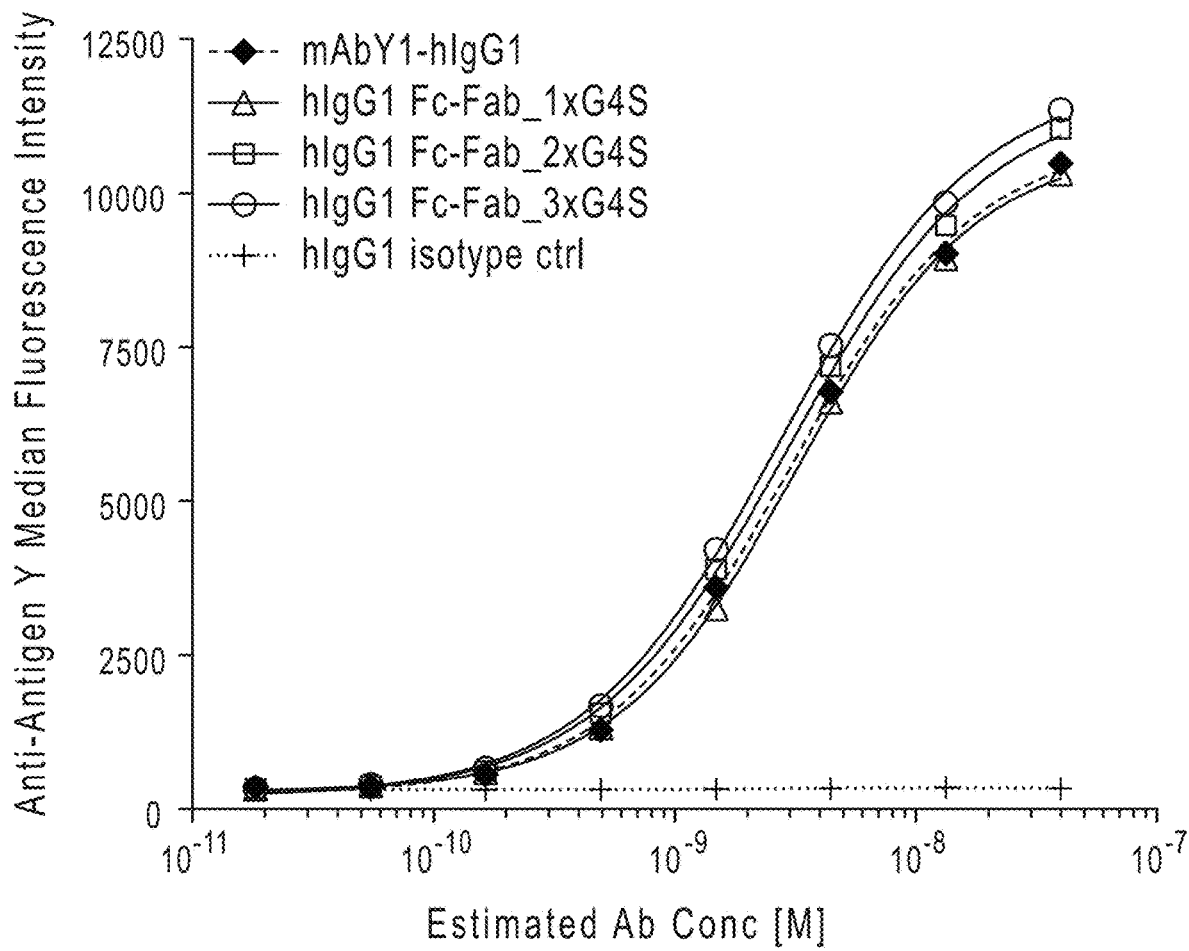
Figure 20B:
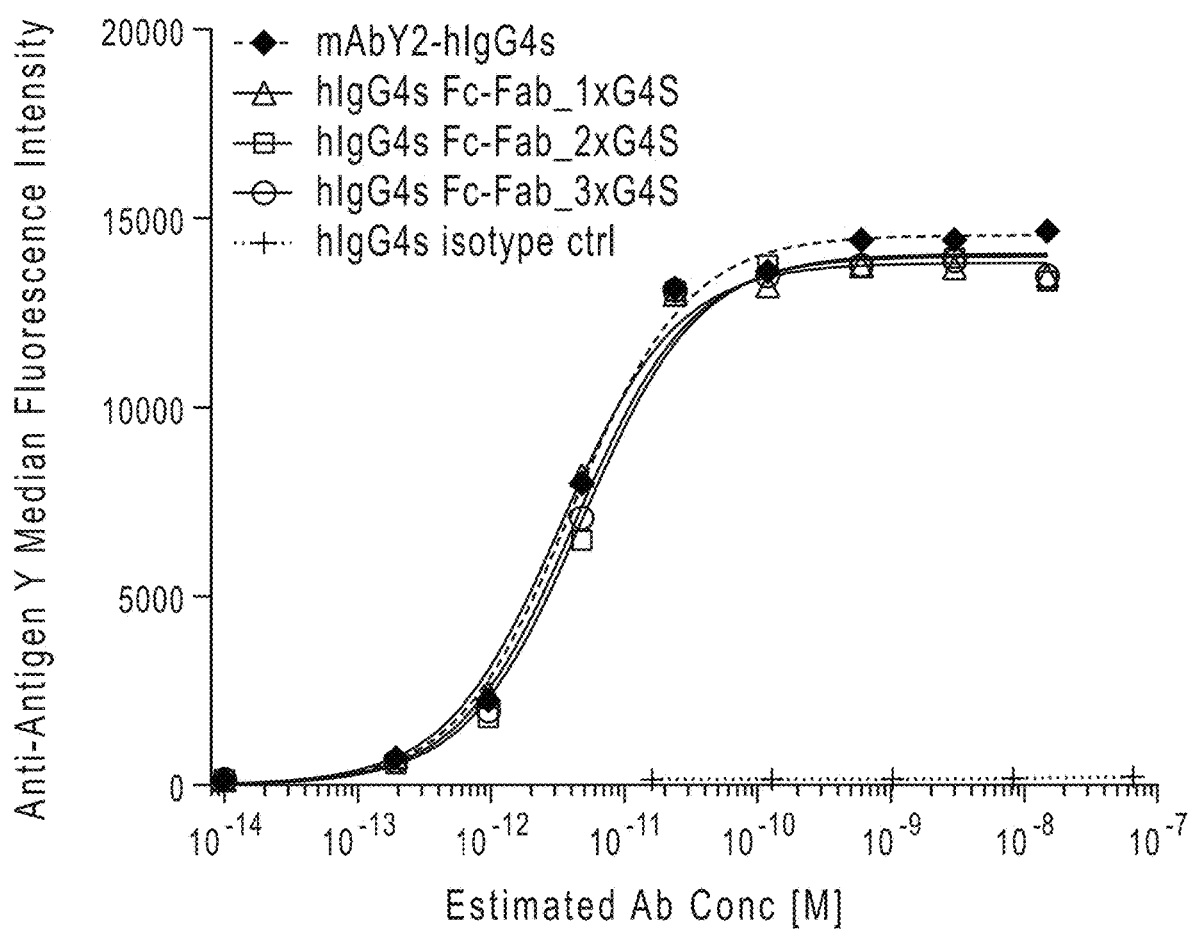
Figure 20C:
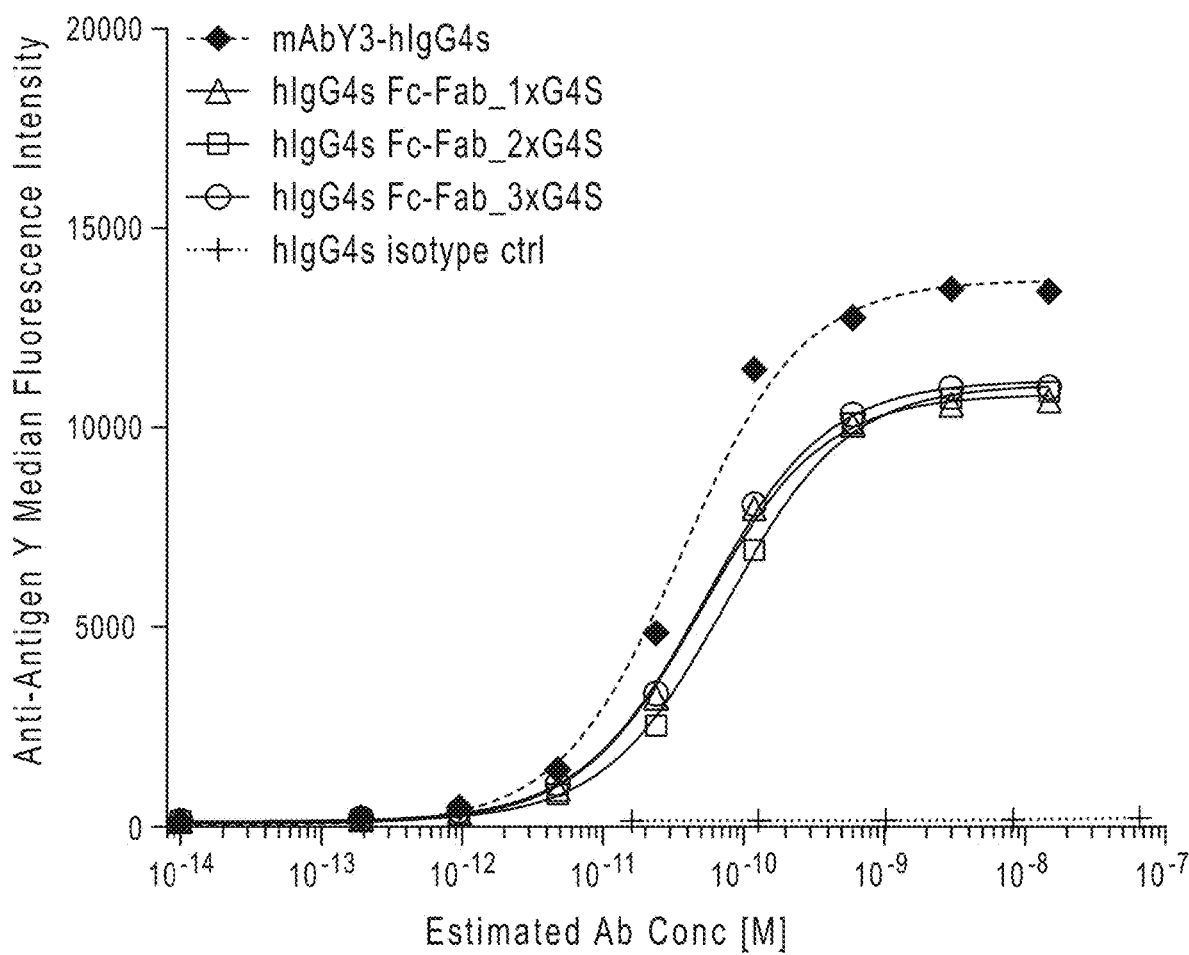
Figure 20D:
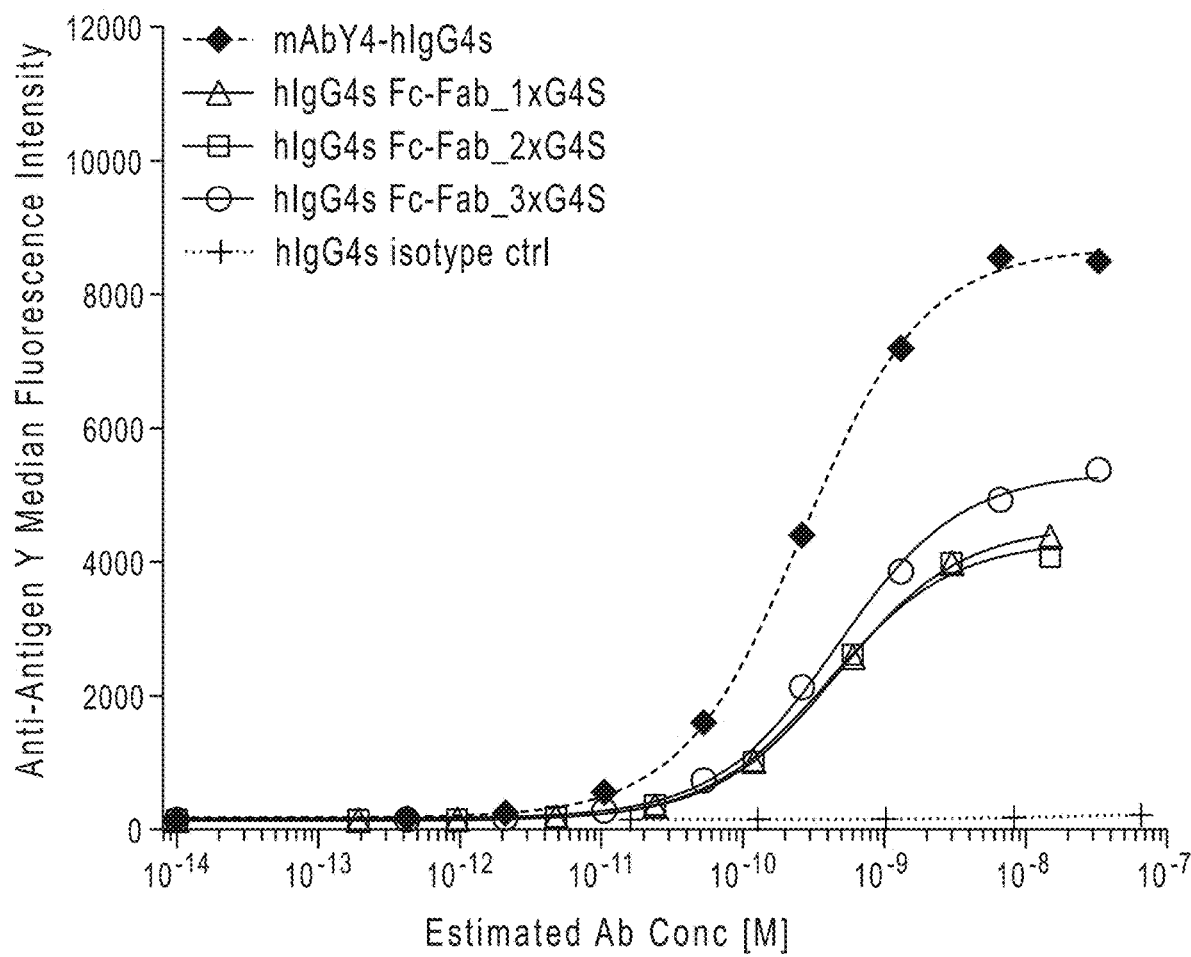

FIGS. 20A-20D: FIGS. 20A-20D are graphs showing binding of Antigen Y Fc-Fabs to Antigen Y-expressing cells, as measured in a FACS-based assay. FIG. 20A, anti-Antigen Y IgG1 mAb mAbY1 was cloned as IgG1 Fc-Fabs with different length G4S linkers (G4S is disclosed as SEQ ID NO:3). The Fc-Fabs and parental IgG1 mAb showed similar binding to cell surface Antigen Y. FIGS. 20B, 20C, 20D, anti-Antigen Y IgG4s mAbs mAbY2, mAbY3, and mAbY4 were cloned as IgG4s Fc-Fabs with different G4S linkers (G4S is disclosed as SEQ ID NO:3). All Fc-Fabs showed strong activity in the Antigen Y FACS binding assay. "1xG4S", "2xG4S", "3xG4S", "4xG4S" and "5xG4S" disclosed in FIGS. 20A-20D are SEQ ID NOS:3, 18, 4, 19, and 39, respectively.

Figure 21A:
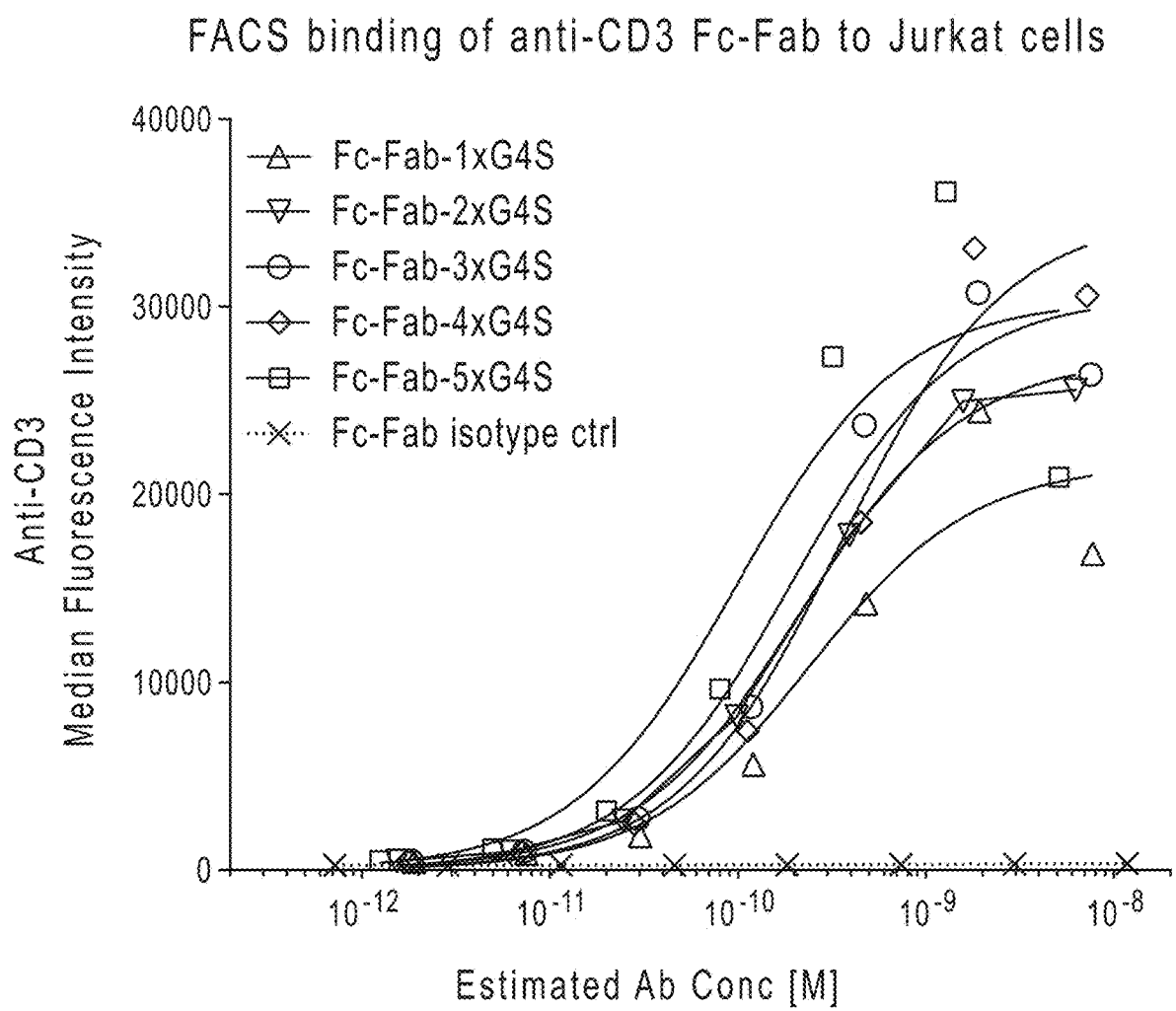
Figure 21B:
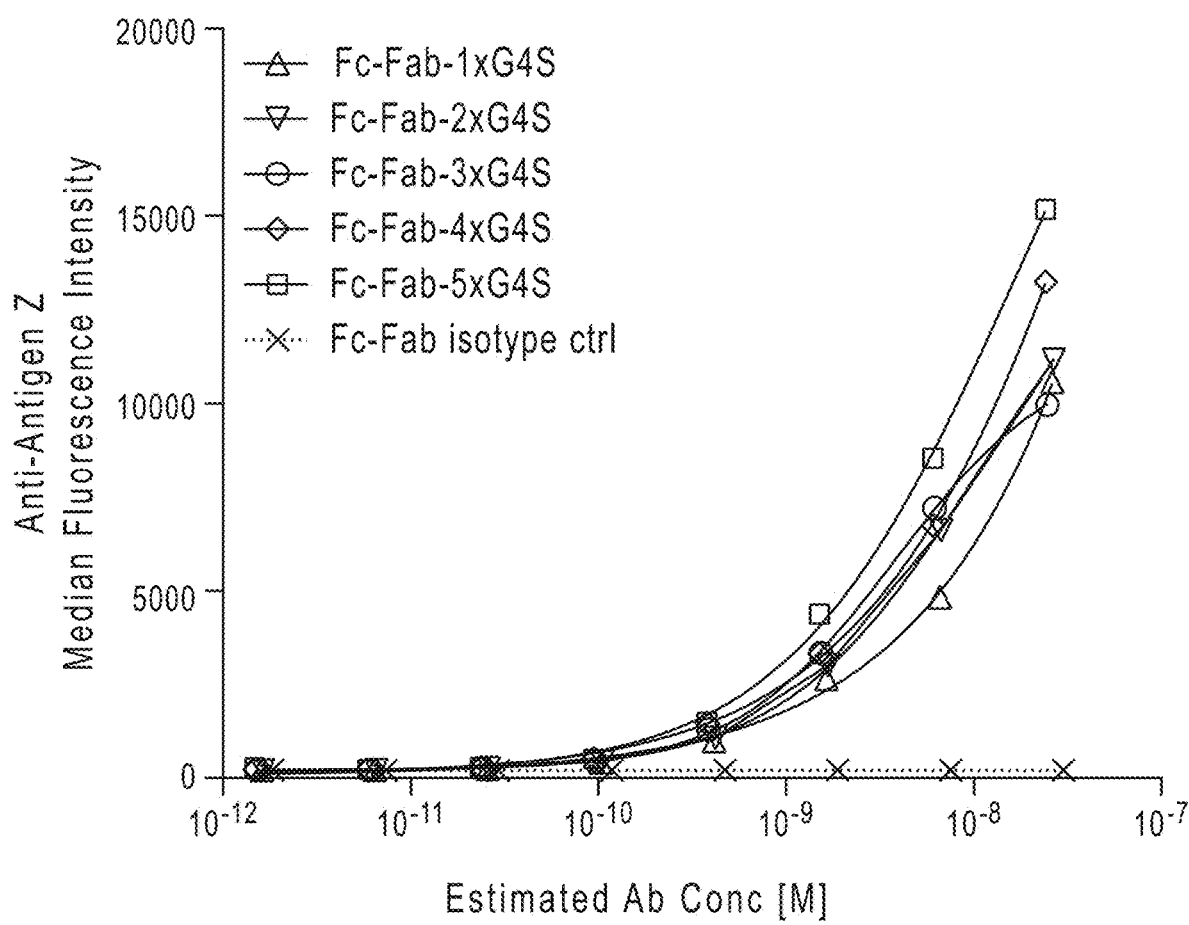

FIGS. 21A-21B: FIGS. 21A-21B are graphs showing binding of anti-CD3 and anti-Antigen Z Fc-Fabs to cell surface epitopes in a FACS-based assay. Anti-CD3 (FIG. 21A) and anti-Antigen Z (FIG. 21B) Abs were cloned as IgG1 Fc-Fabs with G4S linkers (G4S is disclosed as SEQ ID NO:3) of different length. These Fc-Fabs showed specific binding to cell surface CD3 (FIG. 21A) and Antigen Z (FIG. 21B). "1xG4S", "2xG4S", "3xG4S", "4xG4S" and "5xG4S" disclosed in FIGS. 21A-21B are SEQ ID NOS:3, 18, 4, 19, and 39, respectively.

Figure 22A:
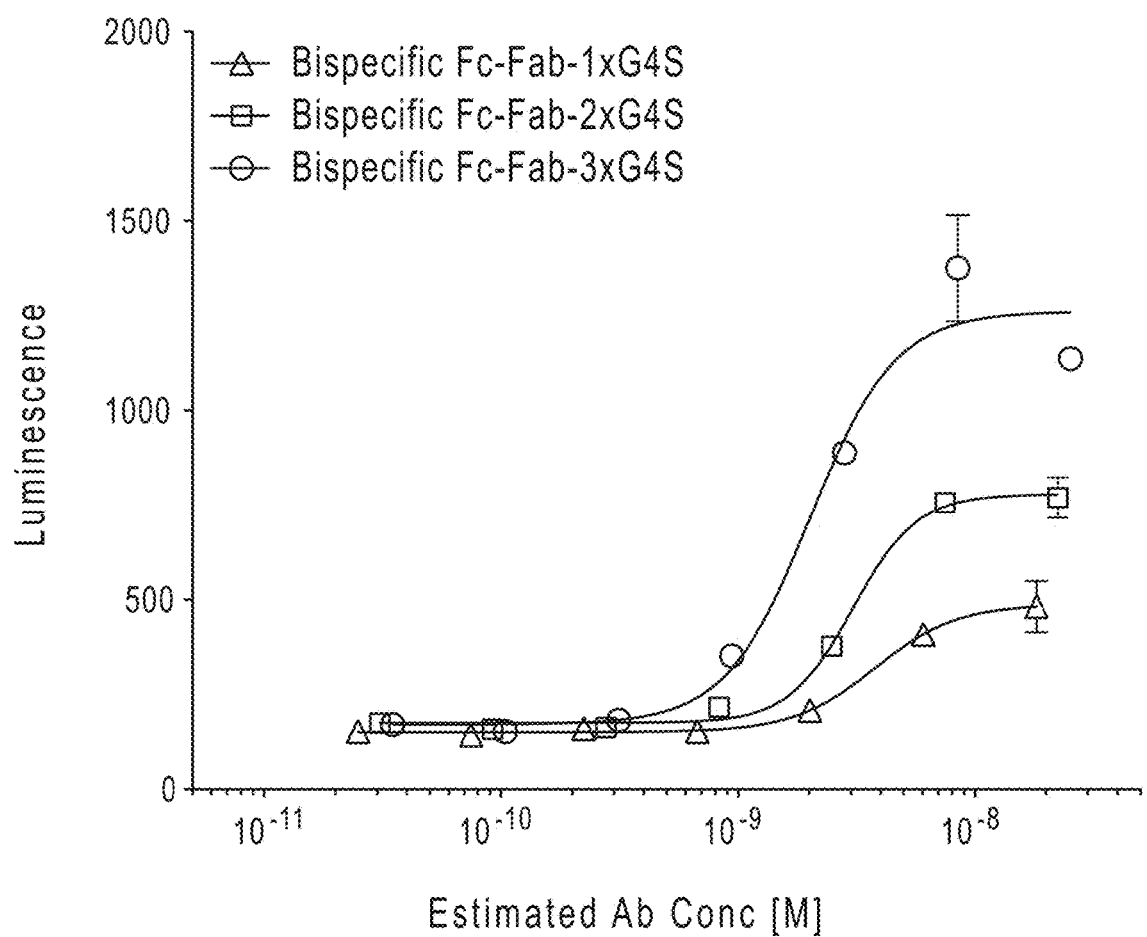
Figure 22B:
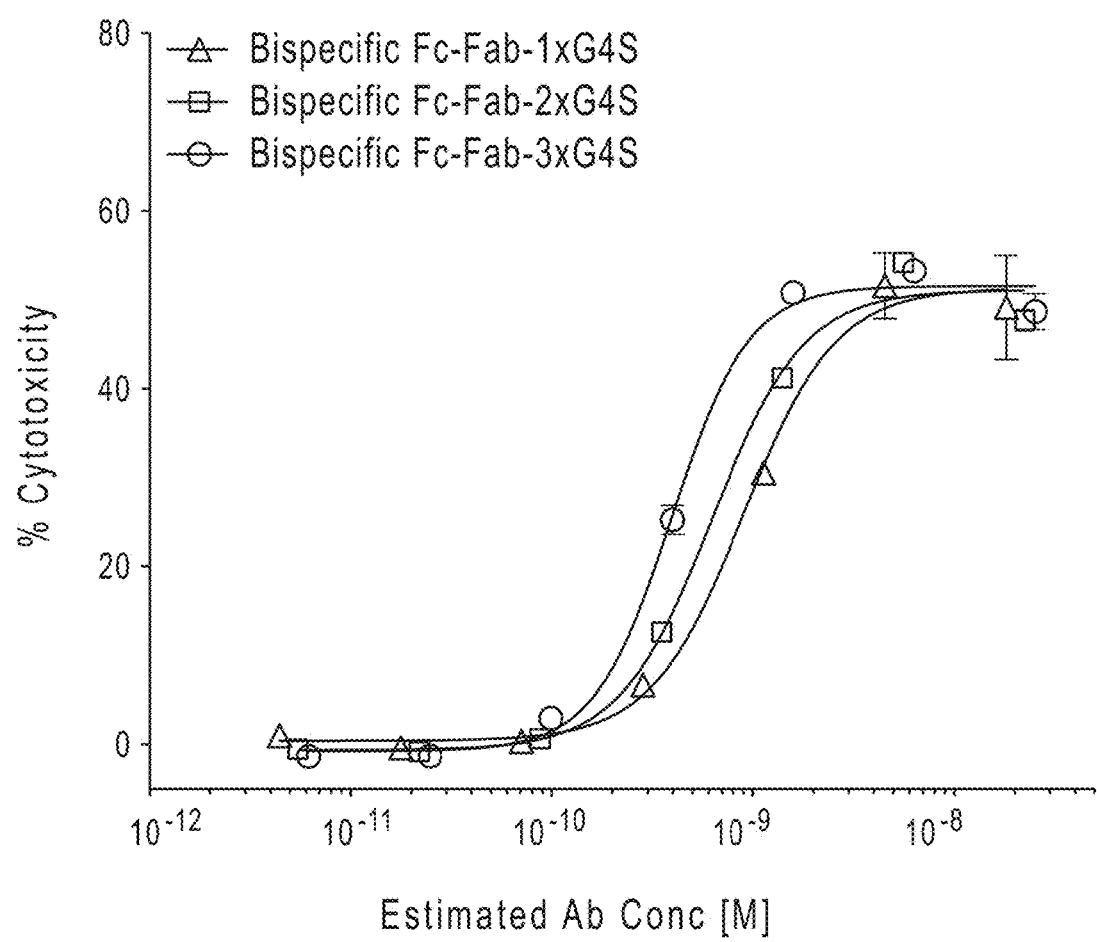

FIGS. 22A-22B: FIGS. 22A and 22B are graphs showing CD3 x Antigen Z bispecific Fc-Fabs were active in bioassays. FIG. 22A, CD3 x Antigen Z bispecific Fc-Fabs activated TCR signaling in Jurkat/NFAT-Luciferase reporter cells in the presence of Antigen Z+ cells. FIG. 22B, CD3 x Antigen Z bispecific Fc-Fabs triggered killing of Antigen Z+ cells by pre-activated human donor T cells in a 3 hr calcein release assay. "1xG4S", "2xG4S", and "3xG4S" disclosed in FIGS. 22A-22B are SEQ ID NOS:3, 18, and 4, respectively.

6. DETAILED DESCRIPTION

6.1. Definitions

As used herein, the following terms are intended to have the following meanings:

Antibody: The term "antibody", as used herein, means any antigen-binding molecule or molecular complex comprising at least one complementarity determining region (CDR) that specifically binds to or interacts with a particular antigen. The term "antibody" includes immunoglobulin molecules of conventional format, which comprise four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain (CL1). The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. An amino acid consensus sequence may be defined based on a side-by-side analysis of two or more CDRs.

The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a VH domain associated with a VL domain, the VH and VL domains may be situated relative to one another in any suitable arrangement. For example, the variable region may be dimeric and contain VH-VH, VH-VL or VL-VL dimers. Alternatively, the antigen-binding fragment of an antibody may contain a monomeric VH or VL domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present disclosure include: (i) VH-CH1; (ii) VH-CH2; (iii) VH-CH3; (iv) VH-CH1-CH2; (v) VH-CH1-CH2-CH3; (vi) VH-CH2-CH3; (vii) VH-CL; (viii) VL-CH1; (ix) VL-CH2; (x) VL-CH3; (xi) VL-CH1-CH2; (xii) VL-CH1-CH2-CH3; (xiii) VL-CH2-CH3; and (xiv) VL-CL. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present disclosure may comprise a homo-dimer or hetero-dimer (or other multimer) of any of the variable and constant domain configurations listed above in non-covalent association with one another and/or with one or more monomeric VH or VL domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present disclosure using routine techniques available in the art.

Antigen Binding Molecule or ABM: The term "antigen binding molecule" or "ABM" as used herein refers to molecules (e.g., assemblies of multiple polypeptide chains) comprising two half antibodies. Typically, each half antibody comprises at least one antigen-binding site. The ABMs of the disclosure can be monospecific or multispecific (e.g., bispecific). The antigen binding sites in monospecific binding molecules all bind to the same epitope whereas multispecific binding molecules have at least two antigen-binding sites that bind to different epitopes, which can be one the same or different target molecules.

Associated: The term "associated" in the context of an ABM refers to a functional relationship between two or more polypeptide chains. In particular, the term "associated" means that two or more polypeptides are associated with one another, e.g., non-covalently through molecular interactions or covalently through one or more disulfide bridges or chemical cross-linkages, so as to produce a functional ABM in which the antigen-binding sites can bind their respective targets. Examples of associations that might be present in an ABM of the disclosure include (but are not limited to) associations between homodimeric or heterodimeric Fc domains in an Fc region, associations between VH and VL regions in a Fab domain, associations between CH1 and CL in a Fab domain, and associations between CH3 and CH3 in a domain substituted Fab.

Bivalent: The term "bivalent" as used herein refers to refers to an ABM that has two antigen binding sites. In some embodiments, the two antigen binding sites bind to the same epitope of the same target. In other embodiments, the two antigen binding sites specifically bind to different epitopes, whether of the same target molecule or different target molecules.

Complementarity Determining Region or CDR: The terms "complementarity determining region" or "CDR," as used herein, refer to the sequences of amino acids within antibody variable regions which confer antigen specificity and binding affinity. In general, there are three CDRs in each heavy chain variable region (CDR-H1, CDR-H2, HCDR-H3) and three CDRs in each light chain variable region (CDR1-L1, CDR-L2, CDR-L3). Exemplary conventions that can be used to identify the boundaries of CDRs include, e.g., the Kabat definition, the Chothia definition, the ABS definition and the IMGT definition. See, e.g., Kabat, 1991, "Sequences of Proteins of Immunological Interest," National Institutes of Health, Bethesda, Md. (Kabat numbering scheme); Al-Lazikani et al., 1997, J. Mol. Biol. 273:927-948 (Chothia numbering scheme); Martin et al., 1989, Proc. Natl. Acad. Sci. USA 86:9268-9272 (ABS numbering scheme); and Lefranc et al., 2003, Dev. Comp. Immunol. 27:55-77 (IMGT numbering scheme). Public databases are also available for identifying CDR sequences within an antibody.

Cytokine: The term "cytokine" refers to a member of a group of low molecular weight extracellular polypeptides/glycoproteins with cell signaling activity that includes chemokines, interferons, interleukins, lymphokines, and tumor necrosis factors. Cytokines are responsible for regulating the immune response (e.g., activity, differentiation, proliferation and production of cells and other cytokines) and are typically synthesized by immune cells, mainly by T cells, neutrophils and macrophages, but may also be synthesized by non-immune cells. Cytokines exist as monomers, dimers (both homodimers and heterodimers), trimers (including homotrimers), and tetramers (including homotetramers). Cytokines range from approximately 5 to 70 kDa in molecular weight, although the majority range from approximately 5 to approximately 20 kDa. Many cytokines share a four-a-helix bundle structure. Other cytokines are characterized by a cysteine knot, containing three disulfide bridges formed from pairs of cysteine residues. Further cytokines are characterized by a homotrimeric pyramidal structure, a feature sometimes present in cell surface proteins.

EC50: The term "EC50" refers to the half maximal effective concentration of an antibody or ABM which induces a response halfway between the baseline and maximum after a specified exposure time. The EC50 essentially represents the concentration of an antibody or ABM where 50% of its maximal effect is observed. In certain embodiments, the EC50 value equals the concentration of an antibody or ABM that gives half-maximal binding to cells expressing the target molecules that can be specifically bound by an antibody or ABM, e.g., as determined by FACS binding assay. Thus, reduced or weaker binding is observed with an increased EC50, or half maximal effective concentration value. EC50 values of ABMs of the disclosure can in some embodiments be characterized by EC50 values of about $10^{-5}$M or less (e.g., less than $10^{-5}$M, less than $10^{-6}$M, less than $10^{-7}$M, less than $10^{-8}$M, or less than $10^{-9}$M).

Epitope: The term "epitope" refers to an antigenic determinant that interacts with a specific antigen binding site in the variable region of an antibody or a antigen-binding molecule known as a paratope. A single antigen or target molecule may have more than one epitope. Thus, different antibodies or antigen-binding molecules may bind to different areas on an antigen or target molecule and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen or target molecule.

Fab: The term "Fab" in the context of an ABM of the disclosure refers to a pair of polypeptide chains, the first comprising a variable heavy (VH) domain of an antibody N-terminal to a first constant domain (referred to herein as C1), and the second comprising variable light (VL) domain of an antibody N-terminal to a second constant domain (referred to herein as C2) capable of pairing with the first constant domain. In a native immunoglobulin, the VH is N-terminal to the first constant domain (CH1) of the heavy chain and the VL is N-terminal to the constant domain of the light chain (CL). The Fabs of the disclosure can be arranged according to the native orientation or include domain substitutions or swaps on that facilitate correct VH and VL pairings, particularly where the ABMs of the disclosure comprise non-identical Fabs. For example, it is possible to replace the CH1 and CL domain pair in a Fab with a CH3-domain pair to facilitate correct modified Fab-chain pairing in heterodimeric ABMs. It is also possible to reverse CH1 and CL, so that the CH1 is attached to VL and CL is attached to the VH, a configuration generally known as Crossmab. Alternatively, or in addition to, the use of substituted or swapped constant domains, correct chain pairing can be achieved by the use of universal light chains that can pair with both variable regions of a heterodimeric ABM of the disclosure. In describing the ABMs of the disclosure, C1 domains are referred elsewhere in the specification as CH1 domains and C2 domains are referred to herein as CL domains for each of description; however, it is intended that domain swapped formats are also included. Other forms of engineered Fabs are exemplified in Section 6.2.1.

Fc: The term "Fc" refers to a portion of a heavy chain constant region that comprises at least the CH2 and CH3 domains that typically bind to an Fc receptor, e.g., an FcγR, namely FcγRI (CD64), FcγRII (CD32), FcγRIII (CD16) or an FcRn, i.e., a neonatal Fc receptor. The term "Fc" also encompasses engineered Fcs that differ from Fcs of native immunoglobulins. For example, the CH2 and CH3 region can be engineered to include deletions, substitutions, and/or insertions or other modifications that render it unable to bind any Fc receptor, then the CH2 and CH3 region is considered to be non-functional in terms of its typical biological function. Other forms of engineered Fc are exemplified in Section 6.2.7.

Fc Domain and Fc Region: The term "Fc domain" refers to a portion of the heavy chain that pairs with the corresponding portion of another heavy chain. The term "Fc region" refers to the region of antibody-based binding molecules formed by association of two heavy chain Fc domains. The two Fc domains within the Fc region may be the same or different from one another. In a native antibody the Fc domains are typically identical, but for the purpose of producing the ABMs of the disclosure, one or both Fc domains might advantageously be modified to allow for heterodimerization.

Half Antibody: The term "half antibody" refers to a molecule that comprises at least Fc domain and can associate with another molecule comprising an Fc domain through, e.g., a disulfide bridge or molecular interactions (e.g., knob-in-hole interactions between Fc heterodimers). A half antibody can be composed of one polypeptide chain or more than one polypeptide chains (e.g., a heavy chain and a light chain).

Heavy Chain: The term "heavy chain" or "immunoglobulin (Ig) heavy chain", as used herein, includes Ig heavy chain constant region sequence from any organism, and unless otherwise specified includes a heavy chain variable domain. Heavy chain variable domains include three heavy chain complementary determining regions (CDRs) and four framework regions (FRs), unless otherwise specified. Fragments of heavy chain variable domains include CDRs, or both CDRs and FRs. A typical heavy chain constant region (CH) has, following the variable domain, from N-terminal to C-terminal: a CH1 domain, a hinge, a CH2 domain, and a CH3 domain (see, for example FIGS. 1A and 2A). A non-typical heavy chain, such as disclosed herein with respect to the antigen-binding molecules and bispecific heavy antigen-binding molecules has a variable domain (VH) between any two of the heavy chain constant region (CH), for example, from N-terminal to C-terminal: a CH2 domain, a CH3 domain, a VH domain, and a CH2 domain (see, for example FIG. 1B and FIG. 2B). In an embodiment, the Fc portion comprises at least the CH2 and CH3 domains.

Hinge: The term "hinge", as used herein, is intended to include the region of consecutive amino acid residues that connect the C-terminus of the CH1 to the N-terminus of the CH2 domain of an immunoglobulin. Several amino acids of the N-terminus of the CH2 domain, which are coded by the CH2 exon, are also considered part of the "lower hinge". Without being bound by any one theory, amino acids of the hinge region of IgG1, IgG2 and IgG4 have been characterized as comprising 12-15 consecutive amino acids encoded by a distinct hinge exon, and several N-terminal amino acids of the CH2 domain (encoded by the CH2 exon) (Brekke et al., 1995, Immunology Today 16(2):85-90). On the other hand, IgG3 comprises a hinge region consisting of four segments: one upper segment resembling the hinge region of IgG1, and 3 segments that are identical amino acid repeats unique to IgG3.

Host cell: The term "host cell" as used herein refers to cells into which a nucleic acid of the disclosure has been introduced. The terms "host cell" and "recombinant host cell" are used interchangeably herein. It is understood that such terms refer to the particular subject cell and to the progeny or potential progeny of such a cell. Because certain modifications may occur in succeeding generations due to either mutation or environmental influences, such progeny may not, in fact, be identical to the parent cell, but are still included within the scope of the term as used herein. Typical host cells are eukaryotic host cells, such as mammalian host cells. Exemplary eukaryotic host cells include yeast and mammalian cells, for example vertebrate cells such as a mouse, rat, monkey or human cell line, for example HKB11 cells, PER.C6 cells, HEK cells or CHO cells.

Immunoglobulin: The term "immunoglobulin" (Ig) refers to a class of structurally related glycoproteins consisting of two pairs of polypeptide chains, one pair of light (L) chains and one pair of heavy (H) chains, which may all four be inter-connected by disulfide bonds. The structure of immunoglobulins has been well characterized. See for instance Fundamental Immunology Ch. 7 (Paul, W., ed., 2nd ed. Raven Press, N.Y. (1989)). Each heavy chain typically comprises a heavy chain variable region (abbreviated herein as VH or VH) and a heavy chain constant region (CH or CH). The heavy chain constant region typically comprises three domains, CH1, CH2, and CH3. The CH1 and CH2 domains are linked by a hinge. The Fc portion comprises at least the CH2 and CH3 domains.

Typically, the numbering of amino acid residues of immunoglobulins is according to IMGT, Sequences of Proteins of Immunological Interest, 5th Ed. Public Health Service, National Institutes of Health, Bethesda, MD (1991), or by the EU numbering system of Kabat (also known as "EU numbering" or "EU index"), e.g., as in Kabat et al. Sequences of Proteins of Immunological interest. 5th ed. US Department of Health and Human Services, NIH publication No. 91-3242 (1991).

Isotype: The term "isotype" refers to the immunoglobulin class or subclass (for instance, IgG1, IgG2, IgG3, IgG4, IgD, IgA, IgE, or IgM) that is encoded by heavy chain constant region genes.

Operably linked: The term "operably linked" refers to a physical or functional juxtaposition of the components so described as to permit them to function in their intended manner. In relation to a polypeptide, the term "operably linked" can refer to a functional relationship between two or more regions of a polypeptide chain in which the two or more regions are linked so as to produce a functional polypeptide. In relation to a nucleic acid, such as in the context of DNA expression vector construct, the term "operably linked", refers to, e.g., a control sequence, e.g., a promoter or operator, is appropriately placed at a position relative to a coding sequence such that the control sequence directs the production of a polypeptide encoded by the coding sequence.

Polypeptide and Protein: The term "protein" is meant to include quaternary structures, ternary structures and other complex macromolecules composed of at least one polypeptide. The term "protein" includes polypeptide.

The term "polypeptide" refers to a single linear polymer chain of amino acids bonded together by peptide bonds between the carboxyl and amino groups of adjacent amino acid residues. The polypeptides of the disclosure comprise amino acid sequences that are derived from an immunoglobulin domain. A polypeptide or amino acid sequence "derived from" a designated protein or polypeptide refers to the origin of the polypeptide.

The term "protein" may also be used to describe a large polypeptide, such one composed of one or multiple polypeptides.

Single Chain Fab: The term "single chain Fab" or "scFab" as used herein refers to a polypeptide chain comprising the VH, CH1, VL and CL domains of antibody, where these domains are present in a single polypeptide chain.

Single Chain Fv or scFv: The term "single chain Fv" or "scFv" as used herein refers to a polypeptide chain comprising the VH and VL domains of antibody, where these domains are present in a single polypeptide chain.

Specifically (or selectively) binds: The term "specifically (or selectively) binds" as used herein means that an ABM or antigen binding site ("ABS") thereof forms a complex with a target molecule that is relatively stable under physiologic conditions. Specific binding can be characterized by a KD of about $5 \times 10^{-2}$M or less (e.g., less than $5 \times 10^{-2}$M, less than $10^{-2}$M, less than $5 \times 10^{-3}$M, less than $10^{-3}$M, less than $5 \times 10^{-4}$M, less than $10^{-4}$M, less than $5 \times 10^{-5}$M, less than $10^{-5}$M, less than $5 \times 10^{-6}$M, less than $10^{-6}$M, less than $5 \times 10^{-7}$M, less than $10^{-7}$M, less than $5 \times 10^{-8}$M, less than $10^{-8}$M, less than $5 \times 10^{-9}$M, less than $10^{-9}$M, or less than $10^{-10}$M). Methods for determining the binding affinity of an antibody or an antibody fragment, e.g., an ABM or ABS, to a target molecule are well known in the art and include, for example, equilibrium dialysis, surface plasmon resonance (e.g., Biacore assays), fluorescent-activated cell sorting (FACS) binding assays and the like. An ABM or ABS thereof antibody that specifically binds a target molecule from one species can, however, have cross-reactivity to the target molecule from one or more other species.

Target Molecule: The term "target molecule" as used herein refers to any biological molecule (e.g., protein, carbohydrate, lipid or combination thereof) that can be specifically bound by an antigen binding site of an ABM. Exemplary target molecules include, but are not limited to, ABCF1, ACVR1, ACVR1B, ACVR2, ACVR2B, ACVRLI, ADORA2A, Aggrecan, AGR2, AICDA, AIF1, AIG1, AKAP1, AKAP2, AMH, AMHR2, ANGPT1, ANGPT2, ANGPTL3, ANGPTL4, ANPEP, APC, APOC1, AR, AZGP1 (zinc-a-glycoprotein), ART-4, B7, B7.1, B7.2, BAD, BAFF, BAGI, BAIi, BCL2, BCL6, BDNF, BLNK, BLRI (MDRIS), BlyS, BMPI, BMP2, BMP3B (GDF10), BMP4, BMP6, BMPS, BMPR1A, BMPR1B, BMPR2, BPAG1 (plectin), BRCA1, Ba-733, BAGE, BrE3-antigen, CA125, CAMEL, CAP-I, CASP-8/m, CCCL19, CCCL21, CD1, CD1a, CD2, CD3, CD4, CDS, CD8, CDI-IA, CD14, CD15, CD16, CD18, CD19, CD20, CD21, CD22, CD23, CD25, CD29, CD30, CD32b, CD33, CD37, CD38, CD40, CD40L, CD45, CD46, CD54, CD55, CD59, CD64, CD66a-e, CD67, CD70, CD74, CD79a, CD80, CD83, CD95, CD126, CD133, CD138, CD147, CD154, CDC27, CDK-4/m, CDKN2A, CXCR4, CXCR7, CXCL12, C19orfl0 (IL27w), C3, C4A, CS, CSR1, CANT1, CASPI, CASP4, CAV1, CCBP2 (D6/ JAB61), CCLI (I-309), CCLII (eotaxin), CCL13 (MCP-4), CCLIS (MIP-1d), CCL16 (HCC-4), CCL17 (TARC), CCLIS (PARC), CCL19 (MIP-3b), CCL2 (MCP-1), MCAF, CCL20 (MIP-3a), CCL21 (MIP-2), SLC, exodus-2, CCL22 (MDC/STC-1), CCL23 (MPIF-1), CCL24 (MPIF-2/eotaxin- 2), CCL2S (TECK), CCL26 (eotaxin-3), CCL27 (CTACK/ILC), CCL2S, CCL3 (MIP1a), CCL4 (MIP-1b), CCLS (RANTES), CCL7 (MCP-3), CCLS (mcp-2), CCNA1, CCNA2, CCND1, CCNE1, CCNE2, CCR1 (CKR1/HM14S), CCR2 (mcp-1RB/RA), CCR3 (CKR3/CMKBR3), CCR4, CCRS (CMKBRSI ChemR13), CCR6 (CMKBR6/CKR-L3/STRL22/DRY6), CCR7 (CKR7/EB1), CCRS (CMKBRS/TER1/CKR-LI), CCR9 (GPR-9-6), CCRLI (VSHK1), CCRL2 (L-CCR), CD164, CDIC, CD200, CD-22, CD24, CD2S, CD3S, CD3E, CD3G, CD3Z, CD4, CD44, CD4SRB, CD47, CD4S, CDS2, CD69, CD72, CD79A, CD79B, CDSO, CDS1, CDS3, CDS6, CD137, CD13S, B7-1, B7-2, ICOSL, B7-H3, B7-H4, CD137L, OX40L, CDH1 (E-cadherin), CDH10, CDH12, CDH13, CDHIS, CDH19, CDH20, CDHS, CDH7, CDHS, CDH9, CDK2, CDK3, CDK4, CDKS, CDK6, CDK7, CDK9, CDKN1A (p21 Wapl/Cip1), CDKN1B (p27Kip1), CDKN1C, CDKN2A (p16INK4a), CDKN2B, CDKN2C, CDKN3, CEBPB, CER1, CHGA, CHGB, Chitinase, CHST10, CKLFSF2, CKLFSF3, CKLFSF4, CKLFSFS, CKLFSF6, CKLFSF7, CKLFSFS, CLDN3, CLDN7 (claudin-7), CLN3, CLU (clusterin), CMKLR1, CMKOR1 (RDC1), CNR1, COLISA1, COLIA1, COL4A3, COL6A1, CR2, CRP, CSF1 (M-CSF), CSF2 (GM-CSF), CSF3 (GCSF), CTLA-4, CTNNB1 (b-catenin), CTSB (cathepsin B), CX3CLI (SCYD1), CX3CR1 (V2S), CXCLI (GRO1), CXCLIO (IP-10), CXCL11 (I-TAC/IP-9), CXCL13, CXCL14, CXCL16, CXCL2 (GR02), CXCL3 (GR03), CXCLS (ENA-7S/LIX), CXCL6 (GCP-2), CXCL9 (MIG), CXCR3 (GPR9/CKR-L2), CXCR6 (TYMSTR/STRL33/Bonzo), CYBS, CYC1, CYSLTR1, HIF-1-a, colon-specific antigen-p (CSAp), CEA (CEACAM5), CEACAM6, c-met, DAB2IP, DES, DKFZp4S1J011S, DNCLI, DPP4, DAM, EGFR, EGFRvIII, EGP-1, EGP-2, ELF2-M, Ep-CAM, E2F1, ECGF1, EDG1, EFNA1, EFNA3, EFNB2, EGF, EGFR, ELAC2, ENG, EN01, EN02, EN03, EPHB4, EPO, EREG, ERKS, ESR1, ESR2, F3 (TF), FADD, FasL, FASN, FCER1A, FCER2, FCGR3A, FGF, FGF1 (aFGF), FGF10, FGF11, FGF12, FGF12B, FGF13, FGF14, FGF16, FGF17, FGF1S, FGF19, FGF2 (bFGF), FGF20, FGF21, FGF22, FGF23, FGF3 (int-2), FGF4 (HST), FGFS, FGF7 (KGF), FGFS, FGF9, FGFR3, FIGF (VEGFD), FILI (EPSILON), FILI (ZETA), FLJ12SS4, FLJ2SS30, FLRT1 (fibronectin), FOS, FOSLI (FRA-1), FY (DARC), FIt-1, FIt-3, folate receptor, G250 antigen, GAGE, GROB, GABRP (GABAa), GAGEB1, GAGEC1, GALNAC4S-6ST, GATA3, GDFS, GFiI, GGTI, GM-CSF, GNAS1, GNRH1, GPR2 (CCR10), GPR31, GPR44, GPRS1 (FKSGSO), GRCC10 (C10), GRP, GSN (Gelsolin), GSTP1, HAVCR2, HDAC4, HDACS, HDAC7A, HDAC9, HGF, HIP1 histamine and histamine receptors, HLA-A, HLA-DRA, HM74, HMOX1, HUMCYT2A, HLA-DR, HMI 24, human chorionic gonadotropin (HCG) and its subunits, HER2/neu, HMGB-1, hypoxia inducible factor (HIF-1), HSP70-2M, HST-2 or 1a, IGF-IR, IFN-γ, IFN-α, IL-2, IL-4R, IL-6R, IL-13R, IL-15R, IL-17R, IL-18R, IL-6, IL-8, IL-12, IL-15, IL-17, IL-18, IL-25, IGBP1, IGF1, IGF1R, IGF2, IGFBP2, IGFBP3, IGFBP6, IL-1, IL-10, IL-10RA, IL-10RB, IL-11, IL-11RA, IL-12, IL-12A, IL-12B, IL-12RB1, IL-12RB2, IL-13, IL-13RA1, IL-13RA2, IL-14, IL-1S, IL-1SRA, IL-16, IL-17, IL-17B, IL-17C, IL-17R, IL-18, IL-18BP, IL-18R1, IL-18RAP, IL-19, IL-IA, IL-1B, IL-1F10, IL-1FS, IL-1F6, IL-1F7, IL-1F8, IL-1F9, IL-1HY1, IL-1R1, IL-1R2, IL-1RAP, IL-1RAPL1, IL-1RAPL2, IL-1RL1, IL-1RL2 IL-1RN, IL-2, IL-20, IL-20RA, IL-21R, IL-22, IL-22R, IL-22RA2, IL-23, IL-24, IL-2S, IL-26, IL-27, IL-28A, IL-28B, IL-29, IL-2RA, IL-2RB, IL-2RG, IL-3, IL-30, IL-3RA, IL-4, IL-4R, IL-S, IL-5RA, IL-6, IL-6R, IL-6ST (glycoprotein 130), IL-7, IL-7R, IL-S, IL-SRA, IL-SRB, IL-9, IL-9R, IL-K, INHA, INHBA, INSL3, INSL4, IRAK1, IRAK2, ITGA1, ITGA2, ITGA3, ITGA6 (a6 integrin), ITGAV, ITGB3, ITGB4 (b 4 integrin) insulin-like growth factor-I (IGF-1), ICEBERG, ICOSL, ID2, IFN-a, IFNA1, IFNA2, IFNA4 IFNAS, IFNA6, IFNA7, IFNB1, IFNW1, JAG1, JAK1, JAK3, JUN, K6HF, KAiI, KDR, KITLG, KLFS (GC Box BP), KLF6, KLK10, KLK12, KLK13, KLK14, KLK1S, KLK3, KLK4, KLKS, KLK6, KLK9, KRT1, KRT19 (Keratin 19), KRT2A, KRTHB6 (hair-specific type II keratin), KC4-antigen, KS-1-antigen, KS 1-4, Le-Y, LDR/FUT, LAMAS, LEP (leptin), Lingo-p7S, Lingo-Troy, LPS, LTA (TNF-b), LTB, LTB4R (GPR16), LTB4R2, LTBR, MACMARCKS, MAG or Omgp, MAP2K7 (c-Jun), MDK, MIB1, midkine, MIF, MIP-2, MKI67 (Ki-67), MMP2, MMP9, MS4A1, MSMB, MT3 (metallothionectin-III), MTSS1, MUC1 (mucin), MYC, MYD88, macrophage migration inhibitory factor (MIF), MAGE, MAGE-3, MART-1, MART-2, NY-ES0-1, TRAG-3, mCRP, MCP-1, MIP-1A, MIP-1B, MIF, MUC1, MUC2, MUC3, MUC4, MUC5, MUM-1/2, MUM-3, NCA66, NCA95, NCA90, NCK2, neurocan, NFKB1, NFKB2, NGFB (NGF), NGFR, NgR-Lingo, NgR-Nogo66 (Noga), NgRp7S, NgR-Troy, NME1 (NM23A), NOXS, NPPB, NROB1, NROB2, NR1D1, NR1D2, NRIH2, NRIH3, NRIH4, NR1I2, NR1I3, NR2C1, NR2C2, NR2E1, NR2E3, NR2F1, NR2F2, NR2F6, NR3C1, NR3C2, NR4A1, NR4A2, NR4A3, NRSA1, NRSA2, NR6A1, NRP1, NRP2, NTSE, NTN4, ODZ1, OPRD1, PCSK9, P2RX7, PAP, PART1, PATE, PAWR, PCA3, PCNA, PD-1, PD-L1, alpha4beta7, OX40, GITR, TIM-3, Lag-3, B7-H3, B7-H4, GDFS, CGRP, Lingo-I, Factor IXa, Factor X, ICOS, GARP, BTLA, CD160, RORI, 2B4, KIR, CD27, OX40, A2aR, PDGFA, PDGFB, PECAM1, PF4 (CXCL4), PGF, PGR, phosphacan, PIAS2, PIK3CG, PLAU (uPA), PLG, PLXDC1, PPBP (CXCL7), PPID, PR1, PRKCQ, PRKD1, PRL, PROC, PROK2, PSAP, PSCA, PTAFR, PTEN, PTGS2 (COX-2), PTN, pancreatic cancer mucin, placental growth factor, p53, PLAGL2, prostatic acid phosphatase, PSA, PRAME, PSMA, 10 PIGF, ILGF, ILGF-IR, IL-6, RS5, RANTES, RAC2 (p21Rac2), RARB, RGS1, RGS13, RGS3, RNFI10 (ZNF144), ROB02, S100A2, SCGB1D2 (lipophilin B), SCGB2A1 (mammaglobin 2), SCGB2A2 (mammaglobin 1), SCYE1 (endothelial monocyte-activating cytokine), SDF2, SERPINA1, SERPINA3, SERPINBS (maspin), SERPINE1 (PAI-1), SERPINF1, SHBG, SLA2, SLC2A2, SLC33A1, SLC43A1, SLIT2, SPP1, SPRR1B (SprI), ST6GAL1, STAB1, STATE, STEAP, STEAP2, TIOI, SAGE, 5100, survivin, survivin-2B, TAC, TAG-72, tenascin, TRAIL receptors, TNF-α, Tn-antigen, ThomsonFriedenreich antigens, tumor necrosis antigens, TB4R2, TBX21, TCP10, TDGF1, TEK, TGFA, TGFB1, TGFBIiI, TGFB2, TGFB3, TGFBI, TGFBR1, TGFBR2, TGFBR3, TH1L, THBS1 (thrombospondin-1), THBS2, THBS4, THPO, TIE (Tie-1), TIMP3, tissue factor, TLR10, TLR2, TLR3, TLR4, TLRS, TLR6, TLR7, TLRS, TLR9, TNF, TNF-a, TNFAIP2 (B94), TNFAIP3, TNFRSF11A, TNFRSF1A, TNFRSF1B, TNFRSF21, TNFRSFS, TNFRSF6 (Fas), TNFRSF7, TNFRSFS, TNFRSF9, TNFSF10 (TRAIL), TNFSF11 (TRANCE), TNFSF12 (APO3L), TNFSF13 (April), TNFSF13B, TNFSF14 (HVEM-L), TNFSF1S (VEGI), TNFSF18, TNFSF4 (OX40 ligand), TNFSFS (CD40 ligand), TNFSF6 (FasL), TNFSF7 (CD27 ligand), TNFSFS (CD30 ligand), TNFSF9 (4-IBB ligand), TOLLIP, Toll-like receptors, TOP2A (topoisomerase Iia), TPS3, TPM1, TPM2, TRADD, TRAF1, TRAF2, TRAF3, TRAF4, TRAPS, TRAF6, TREM1, TREM2, TRPC6, TSLP, TWEAK, VEGFR, ED-B fibronectin, WT-1, 17-IA antigen, complement factors C3, C3a, C3b, C5a, CS, an angiogenesis marker, bcI-2, bcI-6, Kras, cMET, CD19/CD3, BCMA/CD3, EGFR, HER3, IL17RA/IL7R, IL-6/IL-23, IL1/IL-8, IL-6, IL-6R/IL-21, IL-21R, ANG2/VEGF, VEGF/PDGFR-beta, Vascular Endothelial Growth Factor (VEGF) acceptor 2/CD3, PSMA/CD3, EPCAM/CD3, VEGFR-1, VEGFR-2, VEGFR-3, VEGFB, VEGFC, versican, VHL CS, VLA-4, c-FMS/CS-FlR, RET, HER3, HER4, IGFR, PDGFR, c-KIT, BCR, integrin, MMPs VEGF, EGF, PlGF, PDGF, HGF, angiopoietin, ERBB-3/C-MET, ERBB-2/C-MET, EGF receptor I/CD3, EGFR/HER3, PSCA/CD3, C-MET/CD3, ENDOSIALIN/CD3, EPCAM/CD3, IGF-1R/CD3, FAPALPHA/CD3, EGFR/IGF-IR, IL 25 17A/F, EGF receptor I/CD3, and CD19/CD16, KHI, Tn-antigen, TF-antigen, CD44, glycolipids, glycosphingolipids such as 30 Gg3, Gb3, GD3, GD2, Gb5, Gm1, Gm2, sialyltetraosylceramide, XCL1 (lymphotactin), XCL2 (SCM-1b), XCR1 (GPRS/CCXCR1), YY1, and ZFPM2. In some embodiments, the target molecule is a small soluble (i.e., not membrane-bound) molecule.

Tetravalent: The term "tetravalent" as used herein refers to refers to an ABM that has four antigen binding sites. In some embodiments, two of the antigen binding sites bind to the same epitope and the other two binding site bind to different epitopes, whether of the same target molecule or different target molecules.

Universal Heavy Chain: The term "universal heavy chain" as used herein in the context of an ABM refers to a heavy chain with a rearranged heavy chain variable region, e.g., a human heavy chain with a rearranged Ig heavy chain variable region. Exemplary rearranged Ig heavy chain variable regions are provided in U.S. Patent Pub. No. 2014/0245468 and U.S. Pat. Nos. 9,204,624 and 9,930,871, each of which is hereby incorporated by reference herein in its entirety. Universal heavy chains are also known as "common heavy chains."

Universal Light Chain: The term "universal heavy chain" as used herein in the context of an ABM refers to a light chain with a rearranged light chain variable region, e.g., a human light chain with a rearranged Ig light chain variable region. Universal light chains are also known as "common heavy chains." In the context of an ABM refers to a light chain polypeptide capable of pairing with the heavy chain region of two different Fab domains with different variable regions in the same ABM. Universal light chains are also known as "common light chains." Exemplary rearranged Ig light chain variable regions are provided in, e.g., U.S. Pat. Nos. 9,969,814; 10,130,181, and 10,143,186 and U.S. Patent Pub. Nos. 2012/0021409, 2012/0192300, 2013/0045492, 2013/0185821, 2013/0302836, and 2015/0313193, each of which is hereby incorporated by reference herein in its entirety.

VH: The term "VH" refers to the variable region of an immunoglobulin heavy chain of an antibody, including the heavy chain of a Fab.

VL: The term "VL" refers to the variable region of an immunoglobulin light chain, including the light chain of a Fab.

6.2. Antigen Binding Molecules (ABMs)

Disclosed herein are an antigen-binding molecules, such as monospecific and bispecific antigen-binding molecules. The disclosed antigen binding molecules have binding domain arrangements that differ from the typical antibody architecture. The disclosed antigen binding molecules can bispecifically bind to a single target molecule or antigen, which can result in increased affinity and/or avidity for the antigen or target molecule. For example, for a bispecific antigen-binding molecule where both Fabs bind the same antigen at different epitopes, affinity for the antigen would be expected to increase relative to an antibody that only bound to only one of the epitopes. Without being bound by theory, it is believed that the ABMs disclosed herein have increased avidity for an antigen or target molecule resulting from either increased proximity and/or greater flexibility of the Fab1 and Fab2 domains, which would increase the local concentration of antigen binding sites relative to an antibody of conventional format, in which the binding sites of the Fab domains are spaced apart.

In a first aspect, an ABM of the disclosure comprises:
a first half antibody comprising in an N-to-C terminal orientation:
an optional hinge domain;
a first Fc domain; and
a first Fab (Fab1) domain comprising a first heavy chain variable region (VH) associated with a first light chain variable region (VL); and
a second half antibody comprising in an N-to-C terminal orientation:
an optional hinge domain;
a second Fc domain; and
a second Fab ("Fab2") domain comprising a second VH associated with a second VL,
wherein the first Fc domain and second Fc domain are associated with one another to form an Fc region and wherein the optional hinge domains, if present, can be associated with one another through a disulfide bridge.

Two embodiments of this type of ABM, generally referred to herein as ABM format "A" ("Format A") and sometimes referred to herein as the "Fc-Fab" format, are illustrated in FIG. 1B and FIG. 2B, as well as variations thereof depicted in FIG. 13A, FIG. 13B and FIG. 13C. Accordingly, the present disclosure provides Format A ABMs depicted in FIG. 1B and FIG. 2B comprising:
a first polypeptide comprising in an N-to-C terminal orientation:
an optional hinge domain (3) linked via a disulfide bond to a hinge domain in the second polypeptide;
an Fc domain comprising a CH2 domain (4) and a CH3 domain (5);
an optional hinge domain (3) linked via a disulfide bond to a hinge domain in the second polypeptide;
a linker (8); and
the heavy chain component of a Fab1 domain comprising a Fab1 VH domain (1) and a Fab1 CH1 domain (2) associated with the light chain component of the Fab1 domain, the light chain component in the form of a polypeptide comprising, in an N-to-C terminal orientation, a Fab1 VL domain (6) and a Fab1 CL domain (7); and
a second polypeptide comprising in an N-to-C terminal orientation:
an optional hinge domain (3) linked via a disulfide bond to a hinge domain in the first polypeptide;
a second Fc domain comprising a CH2 domain (4) and a CH3 domain (5);
an optional hinge domain (3) linked via a disulfide bond to a hinge domain in the first polypeptide;
a linker (8); and
the heavy chain component of a Fab2 domain comprising a Fab2 VH domain (1) and a Fab2 CH1 domain (2) associated with the light chain component of the Fab2 domain, the light chain component in the form of a polypeptide comprising, in an N-to-C terminal orientation, a Fab2 VL domain (6) and a Fab2 CL domain (7);

wherein the first Fc domain and second Fc domain are associated with one another to form an Fc region.

In the embodiment of FIG. 1B both half antibodies are identical, including the Fc domains which form an Fc homodimer, and the resulting ABM is monospecific. In the embodiment of FIG. 2B, the ABM comprises an Fc heterodimer, allowing the use of different Fab1 and Fab2 VH domains and production of a multispecific, e.g., bispecific, molecule. While FIG. 1B, FIGS. 2B and 13A illustrate embodiments in which the ABM has a hinge region composed of hinge domains N-terminal to the Fc domain, the Format A ABMs can have no hinge region (not illustrated), a hinge region C-terminal to the Fc region (FIG. 13C), or hinge regions N- and C-terminal to the Fc region (FIG. 13B). Exemplary hinge domains that can be used N- and/or C-terminal to the Fc region comprise the amino acid sequence GGGGSCPPC (SEQ ID NO:1) and ESKYGPPCPPC (SEQ ID NO:2), as depicted in FIGS. 13A-13C, although the Format A ABMs can have alternative hinge region sequences. Likewise, although FIGS. 13A-13C depict (G4S)$_n$ linkers (G4S is disclosed as SEQ ID NO:3), other linker sequences can be used.

While FIG. 1B and FIG. 2B illustrate embodiments of Format A ABMs that contain only two binding domains (Fab1 and Fab2), the ABMs of the disclosure may contain additional binding domains, e.g., an scFv or Fab domain. However, in certain aspects, Fab1 and Fab2 are the sole binding domains of a Format A ABM.

In a second aspect, an ABM of the disclosure comprises:
a first half antibody comprising in an N-to-C terminal orientation:
a first Fab (Fab1) domain comprising a first VH associated with a first VL;
a first spacer domain; and
a first Fc domain; and
a second polypeptide comprising in an N-to-C terminal orientation:
a second Fab (Fab2) domain comprising a second VH associated with a second VL;
a second spacer domain; and
a second Fc domain; and
wherein the first Fc domain and second Fc domain are associated with one another to form an Fc region.

Without being bound by theory, it is believed that the inclusion of a spacer domain between the Fc domain and the Fab domain gives results in greater flexibility between the Fc region and the antigen binding site of the Fab and consequently higher affinity and/or avidity of binding of the ABM to its target molecule.

In certain embodiments, the spacer domains are extended linkers. This format of ABM, generally referred to herein as format "B" ("Format B") and sometimes referred to herein as the "Reach" format, is illustrated in FIG. 3A. Accordingly, the present disclosure provides embodiments Format B ABMs depicted in FIG. 3A comprising:
a first polypeptide comprising in an N-to-C terminal orientation:
the heavy chain component of a Fab1 domain comprising a Fab1 VH domain (1) and a Fab1 CH1 domain (2) associated with the light chain component of the Fab1 domain, the light chain component in the form of a polypeptide comprising, in an N-to-C terminal orientation, a Fab1 VL domain (6) and a Fab1 CL domain (7);
a linker domain (8) which is an extended linker;
a hinge domain (3) linked via a disulfide bond to a hinge domain in the second polypeptide; and
a first Fc domain comprising a CH2 domain (4) and a CH3 domain (5); and
a second polypeptide comprising in an N-to-C terminal orientation:
the heavy chain component of a Fab2 domain comprising a Fab2 VH domain (1) and a Fab2 CH1 domain (2) associated with the light chain component of the Fab2 domain, the light chain component in the form of a polypeptide comprising, in an N-to-C terminal orientation, a Fab2 VL domain (6) and a Fab2 CL domain (7);
a linker domain (8) which is an extended linker;
a hinge domain (3) linked via a disulfide bond to a hinge domain in the second polypeptide; and
a second Fc domain comprising a CH2 domain (4) and a CH3 domain (5).

While the embodiment of Format B ABMs depicted in FIG. 3A contains only two binding domains (Fab1 and Fab2), the Format B ABMs of the disclosure may contain additional binding domains, e.g., an scFv or Fab domain. However, in certain aspects, Fab1 and Fab2 are the sole binding domains of a Format B ABM of the disclosure.

In other embodiments, the spacer domains are Fab domains. Different variations of this format of ABM, referred to herein as format "C" ("Format C"), are illustrated in FIGS. 3B-3D. Format C ABMs thus comprise a third Fab (Fab3) domain and a fourth Fab (Fab4) domain, configured as follows:
a first half antibody comprising in an N-to-C terminal orientation
a first Fab (Fab1) domain comprising a first VH associated with a first VL;
a third Fab (Fab3) domain comprising a third VH associated with a third VL; and
a first Fc domain; and
a second half antibody comprising in an N-to-C terminal orientation:
a second Fab (Fab2) domain comprising a second VH associated with a second VL;
a fourth Fab (Fab4) domain comprising a fourth VH associated with a fourth VL; and
a second Fc domain.

Accordingly, the present disclosure provides embodiments Format C ABMs depicted in FIGS. 3B-3D, comprising:
a first polypeptide comprising in an N-to-C terminal orientation:
the heavy chain component of a Fab1 domain comprising a Fab1 VH domain (1) and a Fab1 CH1 domain (2) associated with the light chain component of the Fab1 domain, the light chain component in the form of a polypeptide comprising, in an N-to-C terminal orientation, a Fab1 VL domain (6) and a Fab1 CL domain (7);
a linker domain (8);
the heavy chain component of a Fab3 domain comprising a Fab3 VH domain (1) and a Fab3 CH1 domain (2) associated with the light chain component of the Fab3 domain, the light chain component in the form of a polypeptide comprising, in an N-to-C terminal orientation, a Fab3 VL domain (6) and a Fab3 CL domain (7);

a hinge domain (3) linked via a disulfide bond to a hinge domain in the second polypeptide; and a first Fc domain comprising a CH2 domain (4) and a CH3 domain (5); and a second polypeptide comprising in an N-to-C terminal orientation:

the heavy chain component of a Fab2 domain comprising a Fab2 VH domain (1) and a Fab2 CH1 domain (2) associated with the light chain component of the Fab2 domain, the light chain component in the form of a polypeptide comprising, in an N-to-C terminal orientation, a Fab2 VL domain (6) and a Fab2 CL domain (7);

a linker domain (8);

the heavy chain component of a Fab4 domain comprising a Fab4 VH domain (1) and a Fab4 CH1 domain (2) associated with the light chain component of the Fab4 domain, the light chain component in the form of a polypeptide comprising, in an N-to-C terminal orientation, a Fab4 VL domain (6) and a Fab4 CL domain (7);

a hinge domain (3) linked via a disulfide bond to a hinge domain in the second polypeptide; and a second Fc domain comprising a CH2 domain (4) and a CH3 domain (5);

wherein the first Fc domain and second Fc domain are associated with one another to form an Fc region.

While the embodiments of Format C ABMs depicted in FIGS. 3B-3D contain four binding domains (Fab1, Fab2, Fab3 and Fab4), the Format C ABMs of the disclosure may contain additional binding domains, e.g., an scFv or Fab domain. However, in certain aspects, Fab1, Fab2, Fab3 and Fab4 are the sole binding domains of a Format C ABM of the disclosure.

The Fab3 and Fab4 domains of Format C ABMs can be non-binding (as illustrated in FIG. 3B) or binding (as illustrated in FIG. 3C and FIG. 3D). Those embodiments in which Fab3 and Fab4 are non-binding are generally referred to herein as Format C1 ABMs and this format sometimes referred to herein as the "Clamp" format. Those embodiments in which Fab3 and Fab4 are binding are generally referred to herein as Format C2 ABMs and this format sometimes referred to herein as the "Tandem Fab" format. The term "2+2 Tandem Fab" refers to embodiments, illustrated in FIGS. 3C and 3D, where Fab1, Fab2, Fab3 and Fab 4 are the sole binding domains in a Tandem Fab. Each of Format C1 and Format C2 ABMs can be homodimeric or heterodimeric.

In certain embodiments of Format C1 ABMs, the Fab1 and Fab2 domains are non-identical (e.g., bind to different epitopes, whether on the same target molecule or on different target molecules) and the Fab3 and Fab4 domains are identical non-binding domains. In other embodiments, the Fab3 and Fab4 domains are different non-binding domains.

In certain embodiments of the Format C2 ABMs, the Fab1 and Fab3 domains comprise identical VH domains and the Fab2 and Fab4 domains comprise identical VH domains, as shown in FIG. 3C. This configuration is referred to as Configuration 1, or the 1-1-2-2 Configuration. In alternative embodiments of the Format C2 ABMs, the Fab1 and Fab2 domains comprise identical VH domains and Fab3 and Fab4 domains comprise identical VH domains, as shown in FIG. 3D. This configuration is referred to as Configuration 2, or the 1-2-1-2 Configuration.

The complete ABM is formed by association of the two half antibodies through the two Fc domains to form an Fc region. When the two half antibodies are non-identical, for example when Fab1 and Fab2 include different VH domains, an Fc heterodimerization approach, for example as described in Section 6.2.7.2, can be utilized to facilitate correct half antibody pairings or their purification. Examples of heterodimerization approaches are star mutations (as described in Section 6.2.7.2) or knob-in-hole mutations.

While FIGS. 2B, 3A, 3B and 3C show ABMs comprising non-identical VH domains in each half antibody paired through Fc heterodimers, this format can be also used for Fc homodimers. For instance, while FIG. 2B and FIG. 3A respectively show a Format A ABM and a Format B ABM comprising an Fc heterodimer, allowing the incorporation of different VH domains in Fab1 and Fab2 and production of a multispecific, e.g., bispecific, binding molecule, this format can be also used for monospecific Format A and Format B ABMs with Fc homodimers and identical VH domains. Similarly, Fc homodimers can be used to produce monospecific Format C ABMs, with identical Fab1, Fab2, Fab3 and Fab4 VH domains or identical Fab1 and Fab2 VH domains and non-binding Fab3 and Fab4 VH domains.

Further, different strategies can be used to permit correct VH-VL pairings in multispecific binding molecules when the first and second polypeptides include different VH domains. For example, a common light chain can be used that is capable of operably pairing with more than one type of VH domain in an ABM. In such embodiments, the light chain polypeptides (e.g., the light chains associated with Fab1 and Fab2 and, if present, Fab3 and Fab4), can be identical. Alternatively, single domain Fabs can be used in which the heavy chain components ((1) and (2)) can be expressed as a fusion with the light chain components ((6) and (7)).

The variations of the ABMs of the disclosure shown in FIGS. 1-3 are not intended to be limiting; the ABMs of the disclosure can include any combination of modifications illustrated in FIGS. 1-3 and in Section 6.2, infra, among others. Further, referencing a first or second polypeptide chain or a left or right half antibody is for the sake of convenience only and is not intended to convey that the polypeptide chains or half antibodies are produced or assembled in any particular order.

In some embodiments the first Fab (Fab1) domain and the second Fab (Fab2) domain of the ABMs of the disclosure can each bind to the same target molecule, for example a small soluble molecule. The first Fab (Fab1) domain and second Fab (Fab2) domain can bind to the same epitope (e.g., in the embodiment depicted in FIG. 1B and FIG. 3D, or a variation of FIG. 3A or FIG. 3B in which both Fab1 and Fab2 have identical VH domains (not shown)) or they can bind to different epitopes (e.g., in the embodiments depicted in FIG. 2B, FIG. 3A, FIG. 3B, and FIG. 3C), whether on the same target molecule or on different target molecules. Where the first Fab (Fab1) domain and second Fab (Fab2) domain bind to different epitopes, e.g., two different epitopes on the same target molecule or on different target molecules, they can be selected so that Fabs are capable of binding to their epitopes at the same time.

In some embodiments, for example of Format C ABMs, the ABMs of the disclosure can include a third Fab (Fab3) domain and a fourth Fab (Fab4) domain as depicted in FIG. 3C, FIG. 3A and FIG. 3D. The third and fourth Fab domains can be non-binding, as depicted in FIG. 3C, or they can bind to the same or different epitopes from the epitopes bound by the first and second Fab (Fab1 and Fab2) domains, respectively. As used herein, in reference to the Format C ABMs, the terms "first and second Fab domains" and "Fab1 and Fab2 domains" typically refers to the most N-terminal Fab domains.

Certain target molecules, particularly those that have repeated epitopes as may be present in a polypeptide with a repeat motif or a protein with a multimer structure (e.g., a homodimer or homotrimer), may be bound by two or more antibody molecules, leading to the formation of large complexes. The production of large, heterogeneous antibody complexes is referred to as "paper-dolling". Large complexes of antibodies can be rapidly eliminated by phagocytosis, leading to reduced efficacy of the antibody. Large complexes can also increase immunogenicity of a therapeutic antibody. See, e.g., WO2020047067A1. The ABMs of the disclosure can be less prone to aggregation, for example in vivo or ex vivo as compared to parental antibodies from which the Fab domains were obtained. By way of non-limiting example, for a bispecific ABMs where both Fabs bind the same antigen at different epitopes, it was observed (see Example 4 below) that unlike the results obtained with the parental mAb combinations, the ABMs of the disclosure predominantly formed discrete 1:1 complexes with ligand having little to no additional higher order complexes. In contrast, the parental mAb combinations formed multiple higher order structures (multimers) suggesting that these parental antibodies formed bridges between multiple ligands, for example forming unfolded "paper doll" structures. These results demonstrate that the ABMs as disclosed herein are not prone to the aggregation as it is believed that the proximity of the Fab domains favors the formation of 1:1 Fc-Fab ligand complexes over higher order structure. In practice, this could result in higher relative concentrations of single ABM:target molecule complexes than would be expected for the parental antibodies.

In some embodiments, the ABMs of the disclosure specifically bind to at least two different epitopes (and in some instances three or four different epitopes). The at least two different epitopes can be on the same target molecule or different target molecules.

6.2.1. Fab Domains

The ABMs of the disclosure comprise at least one Fab domain in each half antibody. Fab domains were traditionally produced by proteolytic cleavage of immunoglobulin molecules using enzymes such as papain. In the ABMs of the disclosure, the Fab domains are recombinantly expressed as part of a larger molecule.

The Fab domains can comprise constant and variable domain sequences from any suitable species, and thus can be murine, chimeric, human or humanized.

Fab domains typically comprise a CH1 domain attached to a VH domain which pairs with a CL domain attached to a VL domain. In a wild-type immunoglobulin, the VH domain is paired with the VL domain to constitute the Fv region, and the CH1 domain is paired with the CL domain to further stabilize the binding module. A disulfide bond between the two constant domains can further stabilize the Fab domain.

For the ABMs of the disclosure, particularly when the light chain is not a common or universal light chain, it is advantageous to use Fab heterodimerization strategies to permit the correct association of Fab domains belonging to the same ABS and minimize aberrant pairing of Fab domains belonging to different ABSs. For example, the Fab heterodimerization strategies shown in Table B below can be used:

TABLE B

Fab Heterodimerization Strategies

| STRATEGY | VH | CH1 | VL | CL | REFERENCE |
|---|---|---|---|---|---|
| CrossMabCH1-CL | WT | CL domain | WT | CH1 domain | Schaefer et al., 2011, Cancer Cell 2011; 20: 472-86. PMID:22014573. |
| orthogonal Fab VHVRD1CH1CRD2 - VLVRD1CλCRD2 | 39K, 62E | H172A, F174G | 1R, 38D, (36F) | L135Y, S176W | Lewis et al., 2014, Nat Biotechnol 32: 191-8 |
| orthogonal Fab VHVRD2CH1wt- VLVRD2Cλwt | 39Y | WT | 38R | WT | Lewis et al., 2014, Nat Biotechnol 32: 191-8 |
| TCR CaCβ | 39K | TCR Cα | 38D | TCR Cβ | Wu et aL, 2015, MAbs 7: 364-76 |
| CR3 | WT | T192E | WT | N137K, S114A | Golay at al., 2016, J Immunol 196: 3199-211. |
| MUT4 | WT | L143Q, S188V | WT | V133T, S176V | Golay at al., 2016, J Immunol 196: 3199-211. |
| DuetMab | WT | F126C | WT | S121C | Mazor et al., 2015, MAbs 7: 377-89; Mazor et al., 2015, MAbs 7: 461-669. |
| Domain exchanged | WT | CH3 + hole or knob mutation | WT | CH3 + hole or knob mutation | Wozniak-Knopp et al., 2018, PLoSONE13(4): e0195442 |

Accordingly, in certain embodiments, correct association between the two polypeptides of a Fab is promoted by exchanging the VL and VH domains of the Fab for each other or exchanging the CH1 and CL domains for each other, e.g., as described in WO 2009/080251.

Correct Fab pairing can also be promoted by introducing one or more amino acid modifications in the CH1 domain and one or more amino acid modifications in the CL domain of the Fab and/or one or more amino acid modifications in the VH domain and one or more amino acid modifications in the VL domain. The amino acids that are modified are typically part of the VH:VL and CH1:CL interface such that the Fab components preferentially pair with each other rather than with components of other Fabs.

In one embodiment, the one or more amino acid modifications are limited to the conserved framework residues of the variable (VH, VL) and constant (CH1, CL) domains as indicated by the Kabat numbering of residues. Almagro, 2008, Frontiers In Bioscience 13:1619-1633 provides a definition of the framework residues on the basis of Kabat, Chothia, and IMGT numbering schemes.

In one embodiment, the modifications introduced in the VH and CH1 and/or VL and CL domains are complementary to each other. Complementarity at the heavy and light chain interface can be achieved on the basis of steric and hydrophobic contacts, electrostatic/charge interactions or a combination of the variety of interactions. The complementarity between protein surfaces is broadly described in the literature in terms of lock and key fit, knob into hole, protrusion and cavity, donor and acceptor etc., all implying the nature of structural and chemical match between the two interacting surfaces.

In one embodiment, the one or more introduced modifications introduce a new hydrogen bond across the interface of the Fab components. In one embodiment, the one or more introduced modifications introduce a new salt bridge across the interface of the Fab components. Exemplary substitutions are described in WO 2014/150973 and WO 2014/082179, the contents of which are hereby incorporated by reference.

In some embodiments, the Fab domain comprises a 192E substitution in the CH1 domain and 114A and 137K substitutions in the CL domain, which introduces a salt-bridge between the CH1 and CL domains (see, e.g., Golay et al., 2016, J Immunol 196:3199-211).

In some embodiments, the Fab domain comprises a 143Q and 188V substitutions in the CH1 domain and 113T and 176V substitutions in the CL domain, which serves to swap hydrophobic and polar regions of contact between the CH1 and CL domain (see, e.g., Golay et al., 2016, J Immunol 196:3199-211).

In some embodiments, the Fab domain can comprise modifications in some or all of the VH, CH1, VL, CL domains to introduce orthogonal Fab interfaces which promote correct assembly of Fab domains (Lewis et al., 2014 Nature Biotechnology 32:191-198). In an embodiment, 39K, 62E modifications are introduced in the VH domain, H172A, F174G modifications are introduced in the CH1 domain, 1 R, 38D, (36F) modifications are introduced in the VL domain, and L135Y, S176W modifications are introduced in the CL domain. In another embodiment, a 39Y modification is introduced in the VH domain and a 38R modification is introduced in the VL domain.

Fab domains can also be modified to replace the native CH1:CL disulfide bond with an engineered disulfide bond, thereby increasing the efficiency of Fab component pairing. For example, an engineered disulfide bond can be introduced by introducing a 126C in the CH1 domain and a 121 C in the CL domain (see, e.g., Mazor et al., 2015, MAbs 7:377-89).

Fab domains can also be modified by replacing the CH1 domain and CL domain with alternative domains that promote correct assembly. For example, Wu et al., 2015, MAbs 7:364-76, describes substituting the CH1 domain with the constant domain of the a T cell receptor and substituting the CL domain with the b domain of the T cell receptor, and pairing these domain replacements with an additional charge-charge interaction between the VL and VH domains by introducing a 38D modification in the VL domain and a 39K modification in the VH domain.

In lieu of, or in addition to, the use of Fab heterodimerization strategies to promote correct VH-VL pairings, the VL of common light chain (also referred to as a universal light chain) can be used for each Fab VL region of an ABM of the disclosure. In various embodiments, employing a common light chain as described herein reduces the number of inappropriate species of ABMs as compared to employing original cognate VLs. In various embodiments, the VL domains of the ABMs are identified from monospecific antibodies comprising a common light chain. In various embodiments, the VH regions of the ABMs comprise human heavy chain variable gene segments that are rearranged in vivo within mouse B cells that have been previously engineered to express a limited human light chain repertoire, or a single human light chain, cognate with human heavy chains and, in response to exposure with an antigen of interest, generate an antibody repertoire containing a plurality of human VHs that are cognate with one or one of two possible human VLs, wherein the antibody repertoire specific for the antigen of interest. Common light chains are those derived from a rearranged human $V_K1$-$39J_K5$ sequence or a rearranged human $V_K3$-$20J_K1$ sequence, and include somatically mutated (e.g., affinity matured) versions. See, for example, U.S. Pat. No. 10,412,940.

In some embodiments, the Fab is in the format of a single chain Fab ("scFab"), which typically comprises a VH, a CH1, a VL, a CL and a linker. In some embodiments, domains of the scFab are arrange in the following N-terminal to C-terminal order: a) VH-CH1-linker-VL-CL, b) VL-CL-linker-VH-CH1, c) VH-CL-linker-VL-CH1 or d) VL-CH1-linker-VH-CL. The linker can be a linker as described in Section 6.2.3 and is preferably at least 30 amino acids, and in certain aspects between 32 and 50 amino acids. The single chain Fab domains are stabilized via the natural disulfide bond between the CL domain and the CH1 domain.

6.2.2. scFv

Single chain Fv or "scFv" antibody fragments comprise the VH and VL domains of an antibody in a single polypeptide chain, are capable of being expressed as a single chain polypeptide, and retain the specificity of the intact antibodies from which they are derived. Generally, the scFv polypeptide further comprises a polypeptide linker between the VH and VL domain that enables the scFv to form the desired structure for target binding. Examples of linkers suitable for connecting the VH and VL chains of an scFV are the linkers identified in Section 6.2.3.

Unless specified, as used herein an scFv may have the VL and VH variable regions in either order, e.g., with respect to the N-terminal and C-terminal ends of the polypeptide, the scFv may comprise VL-linker-VH or may comprise VH-linker-VL.

The scFv can comprise VH and VL sequences from any suitable species, such as murine, human or humanized VH and VL sequences.

To create an scFv-encoding nucleic acid, the VH and VL-encoding DNA fragments are operably linked to another fragment encoding a linker, e.g., encoding any of the linkers described in Section 6.2.3 (typically a repeat of a sequence containing the amino acids glycine and serine, such as the amino acid sequence (Gly4~Ser)3 (SEQ ID NO:4), such that the VH and VL sequences can be expressed as a contiguous single-chain protein, with the VL and VH regions joined by the flexible linker (see, e.g., Bird et al., 1988, Science 242:423-426; Huston et al., 1988, Proc. Natl. Acad. Sci. USA 85:5879-5883; McCafferty et al., 1990, Nature 348: 552-554).

6.2.3. Linkers

In certain aspects, the present disclosure provides ABM in which two or more domains (e.g., a Fab and an Fc region) are connected to one another by a linker (or "spacer") peptide. Such linkers are referred to herein an "ABM linkers", as opposed to the antibody-drug conjugate ("ADC") linkers used to attach drugs to ABMs as described, for example, in Section 6.4.

Peptide linkers (e.g., polyglycine) are well known in the art and typically allow for proper folding of one or both of the components of the fusion protein. The linker provides a flexible junction region of the component of the fusion protein, allowing the two ends of the molecule to move independently, and may play an important role in retaining each of the two moieties' appropriate functions. Therefore, the junction region acts in some cases as both a linker, which combines the two parts together, and as a spacer, which allows each of the two parts to form its own biological structure and not interfere with the other part.

An ABM linker can range from 2 amino acids to 60 or more amino acids, and in certain aspects a peptide linker ranges from 3 amino acids to 50 amino acids, from 4 to 50 amino acids, from 5 to 25 amino acids, from 10 to 25 amino acids, 10 amino acids to 60 amino acids, from 12 amino acids to 20 amino acids, from 20 amino acids to 50 amino acids, or from 25 amino acids to 35 amino acids in length.

The present disclosure provides ABMs comprising a first polypeptide and a second polypeptide (e.g., a first polypeptide and second polypeptide of the embodiments described in Section 6.2) each comprising a first linker and second linker, respectively. The first linker and the second linker can have a length of from 0 to 60 or 0 to 50 amino acids, such as 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids, for example 0-10, 5-15, 10-20 15-25, 0-30, 5-30, 10-30, 20-30, 0-40, 5-40, 10-40, 15-40, 20-40, 25-40, 30-40, 35-40, 0-50, 5-50, 10-50, 15-50, 20-50, 25-50, 30-50, 35-50, 40-50, or 45-50 amino acids. For the Fc-Fab, Clamp and Tandem Fab format ABMs, a typical linker length is between 5 and 30, e.g., 5-30, amino acid residues. For the Reach format ABMs, a typical linker length is 25 to 45, e.g., 30-40, amino acid residues.

Charged (e.g., charged hydrophilic linkers) and/or flexible linkers are particularly preferred. Examples of flexible linkers that can be used in the ABMs of the disclosure include those disclosed by Chen et al., 2013, Adv Drug Deliv Rev. 65(10):1357-1369 and Klein et al., 2014, Protein Engineering, Design & Selection 27(10):325-330. Particularly useful flexible linkers are repeats of glycines and serines, e.g., monomers or multimers of GnS or SGn, where n is an integer from 1 to 18, e.g., 1, 2, 3, 4, 5, 6, 7, 8, 9, 10, 11, 12, 13, 14, 15, 16, 17, 18. The most common of the GnS or SGn is the $(G4S)_n$ (G4S is disclosed as SEQ ID NO:3) (i.e., $(Gly4Ser)_n$ or $(Gly-Gly-Gly-Gly-Ser)_n$) linker, where n indicates the number of repeats of the motif.

Extended linkers containing 4, 5, 6 or more repeats (e.g., 6, 7, 8, 9 or 10 or more repeats) of G4S (G4S is disclosed as SEQ ID NO:3) and/or another flexible linker motif are particularly useful for the Reach Format, where the extended linker acts as a spacer that is believed to provide more flexible binding that results in greater affinity and/or avidity towards small soluble molecules.

In some embodiments, an ABM linker is a polyGlycine linker, such as Gly-Gly, Gly-Gly-Gly (3Gly), 4Gly (SEQ ID NO:5), 5Gly (SEQ ID NO:6), 6Gly (SEQ ID NO:7), 7Gly (SEQ ID NO:8), 8Gly (SEQ ID NO:9) and 9Gly (SEQ ID NO:10).

In other embodiments, the ABM linker is a Glycine-Serine linker. Examples of such linkers also include Ser-Gly, Gly-Ser, Gly-Gly-Ser, Ser-Gly-Gly, Gly-Gly-Gly-Ser (SEQ ID NO:11), Ser-Gly-Gly-Gly (SEQ ID NO:12), Gly-Gly-Gly-Gly-Ser (SEQ ID NO:3), Ser-Gly-Gly-Gly-Gly (SEQ ID NO:13), Gly-Gly-Gly-Gly-Gly-Ser (SEQ ID NO:14), Ser-Gly-Gly-Gly-Gly-Gly (SEQ ID NO:15), Gly-Gly-Gly-Gly-Gly-Gly-Ser (SEQ ID NO:16), Ser-Gly-Gly-Gly-Gly-Gly-Gly (SEQ ID NO:17), $(Gly-Gly-Gly-Gly-Ser)_n$ (G4S is disclosed as SEQ ID NO:3), and $(Ser-Gly-Gly-Gly-Gly)_n$ (SG4 is disclosed as SEQ ID NO:13), wherein n (the number of repeats of the motif)=1 to 10. $(Gly-Gly-Gly-Gly-Ser)_n$ (G4S is disclosed as SEQ ID NO:3) and $(Ser-Gly-Gly-Gly-Gly)_n$ (SG4 is disclosed as SEQ ID NO:13) are also known as $(G4S)_n$ and $(SG4)_n$, respectively. In one embodiment, the peptide linker is $(Gly-Gly-Gly-Gly-Ser)_1$ (SEQ ID NO:3), $(Gly-Gly-Gly-Gly-Ser)_2$ (SEQ ID NO:18), $(Gly-Gly-Gly-Gly-Ser)_3$ (SEQ ID NO:4), or $(Gly-Gly-Gly-Gly-Ser)_4$ (SEQ ID NO:19). In some embodiments, the first linker and the second linker have identical amino acid sequences. In some embodiments, the poly Glycine and Serine amino acid sequences comprise 2 to 6 repeating GGGGS (SEQ ID NO:3) amino acid sequences, such as 2, 3, 4, 5, or 6 repeating GGGGS (SEQ ID NO:3) amino acid sequences. Extended linkers containing 4, 5, 6 or more repeats (e.g., 6, 7, 8, 9 or 10 or more repeats) of any of the foregoing motifs are contemplated for the Reach Format.

6.2.4. Hinge Regions

In other embodiments, an ABM of the disclosure comprises a hinge region, e.g., a hinge region composed of two hinge domains. A hinge can be used to connect a Fab domain to an Fc domain or to stabilize the ABM configuration.

The hinge region can be a native or a modified hinge region. Hinge regions are typically found at the N-termini of Fc regions; however, in some embodiments, hinge regions can additionally or alternatively be found at the C-termini of Fc regions of the ABMs of the disclosure, for example in the Fc-Fab configurations depicted in FIG. 13B and FIG. 13C.

A native hinge region is the hinge region that would normally be found between Fab and Fc domains in a naturally occurring antibody. A modified hinge region is any hinge that differs in length and/or composition from the native hinge region. Such hinges can include hinge regions from other species, such as human, mouse, rat, rabbit, shark, pig, hamster, camel, llama or goat hinge regions. Other modified hinge regions may comprise a complete hinge region derived from an antibody of a different class or subclass from that of the heavy chain Fc region. Alternatively, the modified hinge region may comprise part of a natural hinge or a repeating unit in which each unit in the repeat is derived from a natural hinge region. In a further alternative, the natural hinge region may be altered by converting one or more cysteine or other residues into neutral residues, such as serine or alanine, or by converting suitably placed residues into cysteine residues. By such means the number of cysteine residues in the hinge region may be increased or decreased. Other modified hinge regions may be entirely synthetic and may be designed to possess desired properties such as length, cysteine composition and flexibility.

A number of modified hinge regions have already been described for example, in U.S. Pat. No. 5,677,425, WO 99/15549, WO 2005/003170, WO 2005/003169, WO 2005/003170, WO 98/25971 and WO 2005/003171 and these are incorporated herein by reference.

In various embodiments, positions 233-236 within a hinge domain may be G, G, G and unoccupied; G, G, unoccupied, and unoccupied; G, unoccupied, unoccupied, and unoccupied; or all unoccupied, with positions numbered by EU numbering.

In some embodiments, the ABMs of the disclosure comprise a modified hinge domain that reduces binding affinity for an Fcγ receptor relative to a wild-type hinge domain of the same isotype (e.g., human IgG1 or human IgG4).

In one embodiment, the Fc region of one or both chains of the ABMs of disclosure possesses an intact hinge domain at its N-terminus.

In one embodiment both the Fc region and the hinge region of an ABM of the disclosure are derived from IgG4 and the hinge region comprises the modified sequence CPPC (SEQ ID NO:20). The core hinge region of human IgG4 contains the sequence CPSC (SEQ ID NO:21) compared to IgG1 that contains the sequence CPPC (SEQ ID NO:20). The serine residue present in the IgG4 sequence leads to increased flexibility in this region, and therefore a proportion of molecules form disulfide bonds within the same protein chain (an intrachain disulfide) rather than bridging to the other heavy chain in the IgG molecule to form the interchain disulfide (Angel et al., 1993, Mol Immunol 30(1): 105-108). Changing the serine residue to a proline to give the same core sequence as IgG1 allows complete formation of inter-chain disulfides in the IgG4 hinge region, thus reducing heterogeneity in the purified product. This altered isotype is termed IgG4P.

6.2.5. Chimeric Hinge Sequences

The hinge region can be a chimeric hinge region.

For example, a chimeric hinge may comprise an "upper hinge" sequence, derived from a human IgG1, a human IgG2 or a human IgG4 hinge region, combined with a "lower hinge" sequence, derived from a human IgG1, a human IgG2 or a human IgG4 hinge region.

In particular embodiments, a chimeric hinge region comprises the amino acid sequence EPKSCDKTH-TCPPCPAPPVA (SEQ ID NO:22) (previously disclosed as SEQ ID NO:8 of WO2014/121087, which is incorporated by reference in its entirety herein) or ESKYGPPCPPCPAPPVA (SEQ ID NO:23) (previously disclosed as SEQ ID NO:9 of WO2014/121087). Such chimeric hinge sequences can be suitably linked to an IgG4 CH2 region (for example by incorporation into an IgG4 Fc domain, for example a human or murine Fc domain, which can be further modified in the CH2 and/or CH3 domain to reduce effector function, for example as described in Section 6.2.7.1).

6.2.6. Hinge Sequences with Reduced Effector Function

In further embodiments, the hinge region can be modified to reduce effector function, for example as described in WO2016161010A2, which is incorporated by reference in its entirety herein. In various embodiments, the positions 233-236 of the modified hinge region are G, G, G and unoccupied; G, G, unoccupied, and unoccupied; G, unoccupied, unoccupied, and unoccupied; or all unoccupied, with positions numbered by EU numbering (as shown in FIG. 1 of WO2016161010A2). These segments can be represented as GGG-, GG--, G--- or ---- with "-" representing an unoccupied position.

Position 236 is unoccupied in canonical human IgG2 but is occupied by in other canonical human IgG isotypes. Positions 233-235 are occupied by residues other than G in all four human isotypes (as shown in FIG. 1 of WO2016161010A2).

The hinge modification within positions 233-236 can be combined with position 228 being occupied by P. Position 228 is naturally occupied by P in human IgG1 and IgG2 but is occupied by S in human IgG4 and R in human IgG3. An S228P mutation in an IgG4 antibody is advantageous in stabilizing an IgG4 antibody and reducing exchange of heavy chain light chain pairs between exogenous and endogenous antibodies. Preferably positions 226-229 are occupied by C, P, P and C respectively.

Exemplary hinge regions have residues 226-236, sometimes referred to as middle (or core) and lower hinge, occupied by the modified hinge sequences designated GGG-(233-236), GG--(233-236), G---(233-236) and no G(233-236). Optionally, the hinge domain amino acid sequence comprises CPPCPAPGGG-GPSVF (SEQ ID NO:24) (previously disclosed as SEQ ID NO:1 of WO2016161010A2), CPPCPAPGG--GPSVF (SEQ ID NO:25) (previously disclosed as SEQ ID NO:2 of WO2016161010A2), CPPCPAPG---GPSVF (SEQ ID NO:26) (previously disclosed as SEQ ID NO:3 of WO2016161010A2), or CPPCPAP----GPSVF (SEQ ID NO:27) (previously disclosed as SEQ ID NO:4 of WO2016161010A2).

The modified hinge regions described above can be incorporated into a heavy chain constant region, which typically include CH2 and CH3 domains, and which may have an additional hinge segment (e.g., an upper hinge) flanking the designated region. Such additional constant region segments present are typically of the same isotype, preferably a human isotype, although can be hybrids of different isotypes. The isotype of such additional human constant regions segments is preferably human IgG4 but can also be human IgG1, IgG2, or IgG3 or hybrids thereof in which domains are of different isotypes. Exemplary sequences of human IgG1, IgG2 and IgG4 are shown in FIGS. 2-4 of WO2016161010A2.

In specific embodiments, the modified hinge sequences can be linked to an IgG4 CH2 region (for example by incorporation into an IgG4 Fc domain, for example a human or murine Fc domain, which can be further modified in the CH2 and/or CH3 domain to reduce effector function, for example as described in Section 6.2.7.1).

6.2.7. Fc Domains

The ABMs of the disclosure can include an Fc region derived from any suitable species. In one embodiment the Fc region is derived from a human Fc domain.

The Fc domain can be derived from any suitable class of antibody, including IgA (including subclasses IgA1 and IgA2), IgD, IgE, IgG (including subclasses IgG1, IgG2, IgG3 and IgG4), and IgM. In one embodiment, the Fc domain is derived from IgG1, IgG2, IgG3 or IgG4. In one embodiment the Fc domain is derived from IgG1. In one embodiment the Fc domain is derived from IgG4.

The two Fc domains within the Fc region can be the same or different from one another. In a native antibody the Fc domains are typically identical, but for the purpose of producing antigen binding molecules, e.g., the ABMs of the disclosure, the Fc domains might advantageously be different to allow for heterodimerization, as described in Section 6.2.7.2 below.

In native antibodies, the heavy chain Fc domain of IgA, IgD and IgG is composed of two heavy chain constant domains (CH2 and CH3) and that of IgE and IgM is composed of three heavy chain constant domains (CH2, CH3 and CH4). These dimerize to create an Fc region.

In ABMs of the present disclosure, the Fc region, and/or the Fc domains within it, can comprise heavy chain constant domains from one or more different classes of antibody, for example one, two or three different classes.

In one embodiment the Fc region comprises CH2 and CH3 domains derived from IgG1.

In one embodiment the Fc region comprises CH2 and CH3 domains derived from IgG2.

In one embodiment the Fc region comprises CH2 and CH3 domains derived from IgG3.

In one embodiment the Fc region comprises CH2 and CH3 domains derived from IgG4.

In one embodiment the Fc region comprises a CH4 domain from IgM. The IgM CH4 domain is typically located at the C-terminus of the CH3 domain.

In one embodiment the Fc region comprises CH2 and CH3 domains derived from IgG and a CH4 domain derived from IgM.

It will be appreciated that the heavy chain constant domains for use in producing an Fc region for the ABMs of the present disclosure may include variants of the naturally occurring constant domains described above. Such variants may comprise one or more amino acid variations compared to wild type constant domains. In one example the Fc region of the present disclosure comprises at least one constant domain that varies in sequence from the wild type constant domain. It will be appreciated that the variant constant domains may be longer or shorter than the wild type constant domain. Preferably the variant constant domains are at least 60% identical or similar to a wild type constant domain. In another example the variant constant domains are at least 70% identical or similar. In another example the variant constant domains are at least 80% identical or similar. In another example the variant constant domains are at least 90% identical or similar. In another example the variant constant domains are at least 95% identical or similar.

IgM and IgA occur naturally in humans as covalent multimers of the common H2L2 antibody unit. IgM occurs as a pentamer when it has incorporated a J-chain, or as a hexamer when it lacks a J-chain. IgA occurs as monomer and dimer forms. The heavy chains of IgM and IgA possess an 18 amino acid extension to the C-terminal constant domain, known as a tailpiece. The tailpiece includes a cysteine residue that forms a disulfide bond between heavy chains in the polymer, and is believed to have an important role in polymerization. The tailpiece also contains a glycosylation site. In certain embodiments, the ABMs of the present disclosure do not comprise a tailpiece.

The Fc domains that are incorporated into the ABMs of the present disclosure may comprise one or more modifications that alter the functional properties of the proteins, for example, binding to Fc-receptors such as FcRn or leukocyte receptors, binding to complement, modified disulfide bond architecture, or altered glycosylation patterns. Exemplary Fc modifications that alter effector function are described in Section 6.2.7.1

The Fc domains can also be altered to include modifications that improve manufacturability of asymmetric ABMs, for example by allowing heterodimerization, which is the preferential pairing of non-identical Fc domains over identical Fc domains. Heterodimerization permits the production of ABMs in which different ABSs are connected to one another by an Fc region containing Fc domains that differ in sequence. Examples of heterodimerization strategies are exemplified in Section 6.2.7.2.

It will be appreciated that any of the modifications mentioned above can be combined in any suitable manner to achieve the desired functional properties and/or combined with other modifications to alter the properties of the ABMs.

6.2.7.1. Fc Domains with Altered Effector Function

In some embodiments, the Fc domain comprises one or more amino acid substitutions that reduces binding to an Fc receptor and/or effector function.

In a particular embodiment the Fc receptor is an Fcγ receptor. In one embodiment the Fc receptor is a human Fc receptor. In one embodiment the Fc receptor is an activating Fc receptor. In a specific embodiment the Fc receptor is an activating human Fcγ receptor, more specifically human FcγRIIIa, FcγRI or FcγRIIa, most specifically human FcγRIIIa. In one embodiment the effector function is one or more selected from the group of complement dependent cytotoxicity (CDC), antibody-dependent cell-mediated cytotoxicity (ADCC), antibody-dependent cellular phagocytosis (ADCP), and cytokine secretion. In a particular embodiment, the effector function is ADCC.

In one embodiment, the Fc region comprises an amino acid substitution at a position selected from the group of E233, L234, L235, N297, P331 and P329 (numberings according to Kabat EU index). In a more specific embodiment, the Fc region comprises an amino acid substitution at a position selected from the group of L234, L235 and P329 (numberings according to Kabat EU index). In some embodiments, the Fc region comprises the amino acid substitutions L234A and L235A (numberings according to Kabat EU index). In one such embodiment, the Fc region is an Igd Fc region, particularly a human Igd Fc region. In one embodiment, the Fc region comprises an amino acid substitution at position P329. In a more specific embodiment, the amino acid substitution is P329A or P329G, particularly P329G (numberings according to Kabat EU index). In one embodiment, the Fc region comprises an amino acid substitution at position P329 and a further amino acid substitution at a position selected from E233, L234, L235, N297 and P331 (numberings according to Kabat EU index). In a more specific embodiment, the further amino acid substitution is E233P, L234A, L235A, L235E, N297A, N297D or P331S. In particular embodiments, the Fc region comprises amino acid substitutions at positions P329, L234 and L235 (numberings according to Kabat EU index). In more particular embodiments, the Fc region comprises the amino acid mutations L234A, L235A and P329G ("P329G LALA", "PGLALA" or "LALAPG").

Typically, the same one or more amino acid substitution is present in each of the two Fc domains of an Fc region. Thus, in a particular embodiment, each Fc domain of the Fc region comprises the amino acid substitutions L234A, L235A and P329G (Kabat EU index numbering), i.e. in each of the first and the second Fc domains in the Fc region the leucine residue at position 234 is replaced with an alanine residue (L234A), the leucine residue at position 235 is replaced with an alanine residue (L235A) and the proline residue at position 329 is replaced by a glycine residue (P329G) (numbering according to Kabat EU index).

In one embodiment, the Fc domain is an IgG1 Fc domain, particularly a human IgG1 Fc domain. In some embodiments, the IgG1 Fc domain is a variant IgG1 comprising D265A, N297A mutations (EU numbering) to reduce effector function.

In another embodiment, the Fc domain is an IgG4 Fc domain with reduced binding to Fc receptors. Exemplary IgG4 Fc domains with reduced binding to Fc receptors may comprise an amino acid sequence selected from Table C below. In some embodiments, the Fc domain includes only the bolded portion of the sequences shown below:

TABLE C

| Fc Domain | Sequence | SEQ ID NO: |
|---|---|---|
| SEQ ID NO: 1 of WO2014/121087 | Asp Lys Arg Val Glu Ser Lys Tyr Gly Pro Pro Cys Pro Pro Cys Pro Ala Pro Pro Val Ala Gly Pro Ser Val Phe Leu Phe Pro Pro Lys Pro Lys Asp Thr Leu Met Ile Ser Arg Thr Pro Glu Val Thr Cys Val Val Val Asp Val Ser Gln Glu Asp Pro Glu Val Gln Phe Asn Trp Tyr Val Asp Gly Val Glu Val His Asn Ala Lys Thr Lys Pro Arg Glu Glu Gln Phe Asn Ser Thr Tyr Arg Val Val Ser Val Leu Thr Val Leu His Gln Asp Trp Leu Asn Gly Lys Glu Tyr Lys Cys Lys Val Ser Asn Lys Gly Leu Pro Ser Ser Ile Glu Lys Thr Ile Ser Lys Ala | 28 |

TABLE C-continued

| Fc Domain | Sequence | SEQ ID NO: |
|---|---|---|
| | Lys Gly Gln Pro Arg Glu Pro Gln Val Tyr Thr Leu Pro Pro Ser Gln Glu Glu Met Thr Lys Asn Gln Val Ser Leu Thr Cys Leu Val Lys Gly Phe Tyr Pro Ser Asp Ile Ala Val Glu Trp Glu Ser Asn Gly Gln Pro Glu Asn Asn Tyr Lys Thr Thr Pro Pro Val Leu Asp Ser Asp Gly Ser Phe Phe Leu Tyr Ser Arg Leu Thr Val Asp Lys Ser Arg Trp Gln Glu Gly Asn Val Phe Ser Cys Ser Val Met His Glu Ala Leu His Asn His Tyr Thr Gln Lys Ser Leu Ser Leu Ser Leu Gly Lys | |
| SEQ ID NO: 2 of WO2014/121087 | Asp Lys Lys Val Glu Pro Lys Ser Cys Asp Lys Thr His Thr Cys Pro Pro Cys Pro Ala Pro Pro Val Ala Gly Pro Ser Val Phe Leu Phe Pro Pro Lys Pro Lys Asp Thr Leu Met Ile Ser Arg Thr Pro Glu Val Thr Cys Val Val Val Asp Val Ser Gln Glu Asp Pro Glu Val Gln Phe Asn Trp Tyr Val Asp Gly Val Glu Val His Asn Ala Lys Thr Lys Pro Arg Glu Glu Gln Phe Asn Ser Thr Tyr Arg Val Val Ser Val Leu Thr Val Leu His Gln Asp Trp Leu Asn Gly Lys Glu Tyr Lys Cys Lys Val Ser Asn Lys Gly Leu Pro Ser Ser Ile Glu Lys Thr Ile Ser Lys Ala Lys Gly Gln Pro Arg Glu Pro Gln Val Tyr Thr Leu Pro Pro Ser Arg Asp Glu Leu Thr Lys Asn Gln Val Ser Leu Thr Cys Leu Val Lys Gly Phe Tyr Pro Ser Asp Ile Ala Val Glu Trp Glu Ser Asn Gly Gln Pro Glu Asn Asn Tyr Lys Thr Thr Pro Pro Val Leu Asp Ser Asp Gly Ser Phe Phe Leu Tyr Ser Lys Leu Thr Val Asp Lys Ser Arg Trp Gln Gln Gly Asn Val Phe Ser Cys Ser Val Met His Glu Ala Leu His Asn His Tyr Thr Gln Lys Ser Leu Ser Leu Ser Pro Gly Lys | 29 |
| SEQ ID NO: 30 of WO2014/121087 | Ala Ser Thr Lys Gly Pro Ser Val Phe Pro Leu Ala Pro Ser Ser Lys Ser Thr Ser Gly Gly Thr Ala Ala Leu Gly Cys Leu Val Lys Asp Tyr Phe Pro Glu Pro Val Thr Val Ser Trp Asn Ser Gly Ala Leu Thr Ser Gly Val His Thr Phe Pro Ala Val Leu Gln Ser Ser Gly Leu Tyr Ser Leu Ser Ser Val Val Thr Val Pro Ser Ser Ser Leu Gly Thr Gln Thr Tyr Ile Cys Asn Val Asn His Lys Pro Ser Asn Thr Lys Val Asp Lys Lys Val Glu Pro Lys Ser Cys Asp Lys Thr His Thr Cys Pro Pro Cys Pro Ala Pro Pro Val Ala Gly Pro Ser Val Phe Leu Phe Pro Pro Lys Pro Lys Asp Thr Leu Met Ile Ser Arg Thr Pro Glu Val Thr Cys Val Val Val Asp Val Ser Gln Glu Asp Pro Glu Val Gln Phe Asn Trp Tyr Val Asp Gly Val Glu Val His Asn Ala Lys Thr Lys Pro Arg Glu Glu Gln Phe Asn Ser Thr Tyr Arg Val Val Ser Val Leu Thr Val Leu His Gln Asp Trp Leu Asn Gly Lys Glu Tyr Lys Cys Lys Val Ser Asn Lys Gly Leu Pro Ser Ser Ile Glu Lys Thr Ile Ser Lys Ala Lys Gly Gln Pro Arg Glu Pro Gln Val Tyr Thr Leu Pro Pro Ser Arg Asp Glu Leu Thr Lys Asn Gln Val Ser Leu Thr Cys Leu Val Lys Gly Phe Tyr Pro Ser Asp Ile Ala Val Glu Trp Glu Ser Asn Gly Gln Pro Glu Asn Asn Tyr Lys Thr Thr Pro Pro Val Leu Asp Ser Asp Gly Ser Phe Phe Leu Tyr Ser Lys Leu Thr Val Asp Lys Ser Arg Trp Gln Gln Gly Asn Val Phe Ser Cys Ser Val Met His Glu Ala Leu His Asn His Tyr Thr Gln Lys Ser Leu Ser Leu Ser Pro Gly Lys | 30 |
| SEQ ID NO: 31 of WO2014/121087 | Ala Ser Thr Lys Gly Pro Ser Val Phe Pro Leu Ala Pro Cys Ser Arg Ser Thr Ser Glu Ser Thr Ala Ala Leu Gly Cys Leu Val Lys Asp Tyr Phe Pro Glu Pro Val Thr Val Ser Trp Asn Ser Gly Ala Leu Thr Ser Gly Val His Thr Phe Pro Ala Val Leu Gln Ser Ser Gly Leu Tyr Ser Leu Ser Ser Val Val Thr Val Pro Ser Ser Ser Leu Gly Thr Lys Thr Tyr Thr Cys Asn Val Asp His Lys Pro Ser Asn Thr Lys Val Asp Lys Arg Val Glu Ser Lys Tyr Gly Pro Pro Cys Pro Pro Cys Pro Ala Pro Pro Val Ala Gly Pro Ser Val Phe Leu Phe Pro Pro Lys Pro Lys Asp Thr Leu Met Ile Ser Arg Thr Pro Glu Val Thr Cys Val Val Val Asp Val Ser Gln Glu Asp Pro Glu Val Gln Phe Asn Trp Tyr Val Asp Gly Val Glu Val His Asn Ala Lys Thr Lys Pro Arg Glu Glu Gln Phe Asn Ser Thr Tyr Arg Val Val Ser Val Leu Thr Val Leu His Gln Asp Trp Leu Asn Gly Lys Glu Tyr Lys Cys Lys Val Ser Asn Lys Gly Leu Pro Ser Ser Ile Glu Lys Thr Ile Ser Lys Ala Lys Gly Gln Pro Arg Glu Pro Gln Val Tyr Thr Leu Pro Pro Ser Gln Glu Glu Met Thr Lys Asn Gln Val Ser Leu Thr Cys Leu Val Lys Gly Phe Tyr Pro Ser Asp Ile Ala Val Glu Trp Glu Ser Asn Gly Gln Pro Glu Asn Asn Tyr Lys Thr Thr Pro Pro Val Leu Asp Ser Asp Gly Ser Phe Phe Leu Tyr Ser Arg Leu Thr Val Asp Lys Ser Arg Trp Gln Glu Gly Asn Val Phe Ser Cys Ser Val Met His Glu Ala Leu His Asn His Tyr Thr Gln Lys Ser Leu Ser Leu Ser Leu Gly Lys | 31 |
| SEQ ID NO: 37 of WO2014/121087 | Ala Ser Thr Lys Gly Pro Ser Val Phe Pro Leu Ala Pro Ser Ser Lys Ser Thr Ser Gly Gly Thr Ala Ala Leu Gly Cys Leu Val Lys Asp Tyr Phe Pro Glu Pro Val Thr Val Ser Trp Asn Ser Gly Ala Leu Thr Ser Gly Val His Thr Phe Pro Ala Val Leu Gln Ser Ser Gly Leu Tyr Ser Leu Ser Ser Val Val Thr Val Pro Ser Ser Ser Leu Gly Thr Gln | 32 |

TABLE C-continued

| Fc Domain | Sequence | SEQ ID NO: |
|---|---|---|
| | Thr Tyr Ile Cys Asn Val Asn His Lys Pro Ser Asn Thr Lys Val Asp<br>Lys Lys Val Glu Pro Lys Ser Cys Asp Lys Thr His Thr Cys Pro<br>Pro Cys Pro Ala Pro Pro Val Ala Gly Pro Ser Val Phe Leu Phe<br>Pro Pro Lys Pro Lys Asp Thr Leu Met Ile Ser Arg Thr Pro Glu<br>Val Thr Cys Val Val Val Asp Val Ser Gln Glu Asp Pro Glu Val<br>Gln Phe Asn Trp Tyr Val Asp Gly Val Glu Val His Asn Ala Lys<br>Thr Lys Pro Arg Glu Glu Gln Phe Asn Ser Thr Tyr Arg Val Val<br>Ser Val Leu Thr Val Leu His Gln Asp Trp Leu Asn Gly Lys<br>Glu Tyr Lys Cys Lys Val Ser Asn Lys Gly Leu Pro Ser Ser Ile<br>Glu Lys Thr Ile Ser Lys Ala Lys Gly Gln Pro Arg Glu Pro Gln<br>Val Tyr Thr Leu Pro Pro Ser Arg Asp Glu Leu Thr Lys Asn<br>Gln Val Ser Leu Thr Cys Leu Val Lys Gly Phe Tyr Pro Ser<br>Asp Ile Ala Val Glu Trp Glu Ser Asn Gly Gln Pro Glu Asn Asn<br>Tyr Lys Thr Thr Pro Pro Val Leu Asp Ser Asp Gly Ser Phe<br>Phe Leu Tyr Ser Lys Leu Thr Val Asp Lys Ser Arg Trp Gln<br>Gln Gly Asn Val Phe Ser Cys Ser Val Met His Glu Ala Leu His<br>Asn Arg Phe Thr Gln Lys Ser Leu Ser Leu Ser Pro Gly Lys | |
| SEQ ID NO: 38 of WO2014/121087 | Ala Ser Thr Lys Gly Pro Ser Val Phe Pro Leu Ala Pro Cys Ser<br>Arg Ser Thr Ser Glu Ser Thr Ala Ala Leu Gly Cys Leu Val Lys<br>Asp Tyr Phe Pro Glu Pro Val Thr Val Ser Trp Asn Ser Gly Ala<br>Leu Thr Ser Gly Val His Thr Phe Pro Ala Val Leu Gln Ser Ser Gly<br>Leu Tyr Ser Leu Ser Ser Val Val Thr Val Pro Ser Ser Ser Leu Gly<br>Thr Lys Thr Tyr Thr Cys Asn Val Asp His Lys Pro Ser Asn Thr<br>Lys Val Asp Lys Arg Val Glu Ser Lys Tyr Gly Pro Pro Cys Pro<br>Pro Cys Pro Ala Pro Pro Val Ala Gly Pro Ser Val Phe Leu Phe<br>Pro Pro Lys Pro Lys Asp Thr Leu Met Ile Ser Arg Thr Pro Glu<br>Val Thr Cys Val Val Val Asp Val Ser Gln Glu Asp Pro Glu Val<br>Gln Phe Asn Trp Tyr Val Asp Gly Val Glu Val His Asn Ala Lys<br>Thr Lys Pro Arg Glu Glu Gln Phe Asn Ser Thr Tyr Arg Val Val<br>Ser Val Leu Thr Val Leu His Gln Asp Trp Leu Asn Gly Lys<br>Glu Tyr Lys Cys Lys Val Ser Asn Lys Gly Leu Pro Ser Ser Ile<br>Glu Lys Thr Ile Ser Lys Ala Lys Gly Gln Pro Arg Glu Pro Gln<br>Val Tyr Thr Leu Pro Pro Ser Gln Glu Glu Met Thr Lys Asn<br>Gln Val Ser Leu Thr Cys Leu Val Lys Gly Phe Tyr Pro Ser<br>Asp Ile Ala Val Glu Trp Glu Ser Asn Gly Gln Pro Glu Asn Asn<br>Tyr Lys Thr Thr Pro Pro Val Leu Asp Ser Asp Gly Ser Phe<br>Phe Leu Tyr Ser Arg Leu Thr Val Asp Lys Ser Arg Trp Gln<br>Glu Gly Asn Val Phe Ser Cys Ser Val Met His Glu Ala Leu His<br>Asn Arg Phe Thr Gln Lys Ser Leu Ser Leu Ser Leu Gly Lys | 33 |

In a particular embodiment, the IgG4 with reduced effector function comprises the bolded portion of the amino acid sequence of SEQ ID NO:31 of WO2014/121087 (corresponding to amino acids 99-326 of SEQ ID NO:31 of the present application), sometimes referred to herein as IgG4s or hIgG4s.

For heterodimeric ABMs, it is possible to incorporate a combination of the variant IgG4 Fc sequences set forth above, for example an Fc region comprising a combination of SEQ ID NO:30 of WO2014/121087 (or the bolded portion thereof, corresponding to amino acids 99-329 of SEQ ID NO:30 of the present application) and SEQ ID NO:37 of WO2014/121087 (or the bolded portion thereof, corresponding to amino acids 99-329 of SEQ ID NO:32 of the present application) or an Fc region comprising a combination of SEQ ID NO:31 of WO2014/121087 (or the bolded portion thereof, corresponding to amino acids 99-326 of SEQ ID NO:31 of the present application) and SEQ ID NO:38 of WO2014/121087 (or the bolded portion thereof, corresponding to amino acids 99-326 of SEQ ID NO:33 of the present application).

6.2.7.2. Fc Heterodimerization Variants

Many multispecific molecule formats entail dimerization between two Fc domains that, unlike a native immunoglobulin, are operably linked to non-identical antigen-binding domains (or portions thereof, e.g., a VH or VH-CH1 of a Fab). Inadequate heterodimerization of two Fc regions to form an Fc domain has can be an obstacle for increasing the yield of desired multispecific molecules and represents challenges for purification. A variety of approaches available in the art can be used in for enhancing dimerization of Fc domains that might be present in the ABMs of the disclosure, for example as disclosed in EP 1870459A1; U.S. Pat. Nos. 5,582,996, 5,731,168, 5,910,573, 5,932,448, 6,833,441 and 7,183,076; U.S. Patent Application Publication No. 2006204493A1; and PCT Publication No. WO2009/089004A1.

The present disclosure provides ABMs comprising Fc heterodimers, i.e., Fc regions comprising heterologous, non-identical Fc domains. Heterodimerization strategies are used to enhance dimerization of Fc regions operably linked to different ABSs (or portions thereof, e.g., a VH or VH-CH1 of a Fab) and reduce dimerization of Fc domains operably linked to identical ABSs. Typically, each Fc domain in the Fc heterodimer comprises a CH3 domain of an antibody. The CH3 domains are derived from the constant region of an antibody of any isotype, class or subclass, and preferably of IgG (IgG1, IgG2, IgG3 and IgG4) class, as described in the preceding section.

Heterodimerization of the two different heavy chains at CH3 domains give rise to the desired ABM, while homodimerization of identical heavy chains will reduce yield of the desired ABM. Thus, in a preferred embodiment, the two half antibodies that associate to form an ABM of the disclosure will contain CH3 domains with modifications that favor heterodimeric association relative to unmodified chains.

In a specific embodiment said modification promoting the formation of Fc heterodimers is a so-called "knob-into-hole" or "knob-in-hole" modification, comprising a "knob" modification in one of the Fc domains and a "hole" modification in the other Fc domain. The knob-into-hole technology is described e.g. in U.S. Pat. Nos. 5,731,168 and 7,695,936; Ridgway et al., 1996, Prot Eng 9:617-621, and Carter, 2001, Immunol Meth 248:7-15. Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g., tyrosine or tryptophan). Compensatory cavities of identical or similar size to the protuberances are created in the interface of the second polypeptide by replacing large amino acid side chains with smaller ones (e.g., alanine or threonine).

Accordingly, in some embodiments, an amino acid residue in the CH3 domain of the first subunit of the Fc domain is replaced with an amino acid residue having a larger side chain volume, thereby generating a protuberance within the CH3 domain of the first subunit which is positionable in a cavity within the CH3 domain of the second subunit, and an amino acid residue in the CH3 domain of the second subunit of the Fc domain is replaced with an amino acid residue having a smaller side chain volume, thereby generating a cavity within the CH3 domain of the second subunit within which the protuberance within the CH3 domain of the first subunit is positionable. Preferably said amino acid residue having a larger side chain volume is selected from the group consisting of arginine (R), phenylalanine (F), tyrosine (Y), and tryptophan (W). Preferably said amino acid residue having a smaller side chain volume is selected from the group consisting of alanine (A), serine (S), threonine (T), and valine (V). The protuberance and cavity can be made by altering the nucleic acid encoding the polypeptides, e.g. by site-specific mutagenesis, or by peptide synthesis. An exemplary substitution is Y470T.

In a specific such embodiment, in the first Fc domain the threonine residue at position 366 is replaced with a tryptophan residue (T366W), and in the Fc domain the tyrosine residue at position 407 is replaced with a valine residue (Y407V) and optionally the threonine residue at position 366 is replaced with a serine residue (T366S) and the leucine residue at position 368 is replaced with an alanine residue (L368A) (numbering according to Kabat EU index). In a further embodiment, in the first Fc domain additionally the serine residue at position 354 is replaced with a cysteine residue (S354C) or the glutamic acid residue at position 356 is replaced with a cysteine residue (E356C) (particularly the serine residue at position 354 is replaced with a cysteine residue), and in the second Fc domain additionally the tyrosine residue at position 349 is replaced by a cysteine residue (Y349C) (numbering according to Kabat EU index). In a particular embodiment, the first Fc domain comprises the amino acid substitutions S354C and T366W, and the second Fc domain comprises the amino acid substitutions Y349C, T366S, L368A and Y407V (numbering according to Kabat EU index).

In some embodiments, electrostatic steering (e.g., as described in Gunasekaran et al., 2010, J Biol Chem 285(25): 19637-46) can be used to promote the association of the first and the second subunit of the Fc domain.

As an alternative, or in addition, to the use of Fc domains that are modified to promote heterodimerization, an Fc domain can be modified to allow a purification strategy that enables selections of Fc heterodimers. In one such embodiment, one half antibody comprises a modified Fc domain that abrogates its binding to Protein A, thus enabling a purification method that yields a heterodimeric protein. See, for example, U.S. Pat. No. 8,586,713. As such, the ABMs comprise a first CH3 domain and a second Ig CH3 domain, wherein the first and second Ig CH3 domains differ from one another by at least one amino acid, and wherein at least one amino acid difference reduces binding of the ABM to Protein A as compared to a corresponding ABM lacking the amino acid difference. In one embodiment, the first CH3 domain binds Protein A and the second CH3 domain contains a mutation/modification that reduces or abolishes Protein A binding such as an H95R modification (by IMGT exon numbering; H435R by EU numbering). The second CH3 may further comprise a Y96F modification (by IMGT; Y436F by EU). Thus class of modifications is referred to herein as "star" mutations.

6.3. Target Molecules

The ABMs of the disclosure comprise at least two Fab domains, Fab1 and Fab2, that each specifically bind to a target molecule, for example a small soluble molecule. In certain embodiments, the ABMs of the disclosure further comprise two additional Fab domains, Fab3 and Fab 4, which can be binding or non-binding. In some embodiments, the target molecules bound by Fab1, Fab2 and, when present, binding forms of Fab3 and Fab4 are protein molecules.

Preferably, Fab1 and Fab2 are selected so that each is capable of specifically binding its respective epitope at the same time. In some embodiments, Fab1 and Fab2 each specifically bind a different target molecule, for example to a pair of molecules capable of interacting with one another (such as a tumor associated antigen and CD3). In other embodiments, Fab1 and Fab2 bind to the same target molecule, either to different epitopes or to the same epitope.

It is believed that the ABMs of the disclosure are particularly advantages for binding small molecular weight proteins, e.g., proteins having a molecule of less than 100 kDa, less than 75 kDa, or less than 60 kDa (inclusive or exclusive of post translational modifications such as glycosylation). In particular embodiments, the proteins bound by the ABMs of the disclosure have a molecular weight ranging from 5 kDa to 75 kDa, from 5 kDa to 60 kDa, from 5 kDa to 45 kDa, from 5 kDa to 30 kDa, from 10 kDa to 75 kDa, from 10 kDa to 60 kDa, from 10 kDa to 45 kDa, or from 10 kDa to 30 kDa, in each case inclusive or exclusive of post-translational modifications such as glycosylation.

Exemplary target molecules to which Fab1 and/or Fab2 can bind include ABCF1, ACVR1, ACVR1B, ACVR2, ACVR2B, ACVRLI, ADORA2A, Aggrecan, AGR2, AICDA, AIF1, AIG1, AKAP1, AKAP2, AMH, AMHR2, ANGPT1, ANGPT2, ANGPTL3, ANGPTL4, ANPEP, APC, APOC1, AR, AZGP1 (zinc-a-glycoprotein), ART-4, B7, B7.1, B7.2, BAD, BAFF, BAGI, BAIi, BCL2, BCL6, BDNF, BLNK, BLRI (MDRIS), BlyS, BMPI, BMP2, BMP3B (GDF10), BMP4, BMP6, BMPS, BMPR1A, BMPR1B, BMPR2, BPAG1 (plectin), BRCA1, Ba-733, BAGE, BrE3-antigen, CA125, CAMEL, CAP-I, CASP-8/m, CCCL19, CCCL21, CD1, CD1a, CD2, CD3, CD4, CDS, CD8, CDI-IA, CD14, CD15, CD16, CD18, CD19, CD20, CD21, CD22, CD23, CD25, CD29, CD30, CD32b, CD33, CD37, CD38, CD40, CD40L, CD45, CD46, CD54, CD55, CD59, CD64, CD66a-e, CD67, CD70, CD74, CD79a, CD80, CD83, CD95, CD126, CD133, CD138, CD147, CD154, CDC27, CDK-4/m, CDKN2A, CXCR4, CXCR7, CXCL12, C19orf10 (IL27w), C3, C4A, CS, CSR1, CANT1, CASPI, CASP4, CAV1, CCBP2 (D6/JAB61), CCLI (I-309), CCLII (eotaxin), CCL13 (MCP-4), CCLIS (MIP-1d), CCL16 (HCC-4), CCL17 (TARC), CCLIS (PARC), CCL19 (MIP-3b), CCL2 (MCP-1), MCAF, CCL20 (MIP-3a), CCL21 (MIP-2), SLC, exodus-2, CCL22 (MDC/STC-1), CCL23 (MPIF-1), CCL24 (MPIF-2/eotaxin-2), CCL2S (TECK), CCL26 (eotaxin-3), CCL27 (CTACK/ILC), CCL2S, CCL3 (MIP1a), CCL4 (MIP-1b), CCLS (RANTES), CCL7 (MCP-3), CCLS (mcp-2), CCNA1, CCNA2, CCND1, CCNE1, CCNE2, CCR1 (CKR1/HM14S), CCR2 (mcp-1RB/RA), CCR3 (CKR3/CMKBR3), CCR4, CCRS (CMKBRSI ChemR13), CCR6 (CMKBR6/CKR-L3/STRL22/DRY6), CCR7 (CKR7/EB1), CCRS (CMKBRS/TER1/CKR-LI), CCR9 (GPR-9-6), CCRLI (VSHK1), CCRL2 (L-CCR), CD164, CDIC, CD200, CD-22, CD24, CD2S, CD3S, CD3E, CD3G, CD3Z, CD4, CD44, CD4SRB, CD47, CD4S, CDS2, CD69, CD72, CD79A, CD79B, CDSO, CDS1, CDS3, CDS6, CD137, CD13S, B7-1, B7-2, ICOSL, B7-H3, B7-H4, CD137L, OX40L, CDH1 (E-cadherin), CDH10, CDH12, CDH13, CDHIS, CDH19, CDH20, CDHS, CDH7, CDHS, CDH9, CDK2, CDK3, CDK4, CDKS, CDK6, CDK7, CDK9, CDKN1A (p21 Wap1/Cip1), CDKN1B (p27Kip1), CDKN1C, CDKN2A (p16INK4a), CDKN2B, CDKN2C, CDKN3, CEBPB, CER1, CHGA, CHGB, Chitinase, CHST10, CKLFSF2, CKLFSF3, CKLFSF4, CKLFSFS, CKLFSF6, CKLFSF7, CKLFSFS, CLDN3, CLDN7 (claudin-7), CLN3, CLU (clusterin), CMKLR1, CMKOR1 (RDC1), CNR1, COLISA1, COLIA1, COL4A3, COL6AI, CR2, CRP, CSF1 (M-CSF), CSF2 (GM-CSF), CSF3 (GCSF), CTLA-4, CTNNB1 (b-catenin), CTSB (cathepsin B), CX3CLI (SCYD1), CX3CR1 (V2S), CXCLI (GRO1), CXCLIO (IP-10), CXCL11 (I-TAC/IP-9), CXCL13, CXCL14, CXCL16, CXCL2 (GR02), CXCL3 (GR03), CXCLS (ENA-7S/LIX), CXCL6 (GCP-2), CXCL9 (MIG), CXCR3 (GPR9/CKR-L2), CXCR6 (TYMSTR/STRL33/Bonzo), CYBS, CYC1, CYSLTR1, HIF-1-a, colon-specific antigen-p (CSAp), CEA (CEACAM5), CEACAM6, c-met, DAB2IP, DES, DKFZp4S1J011S, DNCLI, DPP4, DAM, EGFR, EGFRvIII, EGP-1, EGP-2, ELF2-M, Ep-CAM, E2F1, ECGF1, EDG1, EFNA1, EFNA3, EFNB2, EGF, EGFR, ELAC2, ENG, EN01, EN02, EN03, EPHB4, EPO, EREG, ERKS, ESR1, ESR2, F3 (TF), FADD, FasL, FASN, FCER1A, FCER2, FCGR3A, FGF, FGF1 (aFGF), FGF10, FGF11, FGF12, FGF12B, FGF13, FGF14, FGF16, FGF17, FGF1S, FGF19, FGF2 (bFGF), FGF20, FGF21, FGF22, FGF23, FGF3 (int-2), FGF4 (HST), FGFS, FGF7 (KGF), FGFS, FGF9, FGFR3, FIGF (VEGFD), FILI (EPSILON), FILI (ZETA), FLJ12SS4, FLJ2SS30, FLRT1 (fibronectin), FOS, FOSLI (FRA-1), FY (DARC), FIt-1, FIt-3, folate receptor, G250 antigen, GAGE, GROB, GABRP (GABAa), GAGEB1, GAGEC1, GALNAC4S-6ST, GATA3, GDFS, GFiI, GGTI, GM-CSF, GNAS1, GNRH1, GPR2 (CCR10), GPR31, GPR44, GPRS1 (FKSGSO), GRCC10 (C10), GRP, GSN (Gelsolin), GSTP1, HAVCR2, HDAC4, HDACS, HDAC7A, HDAC9, HGF, HIP1 histamine and histamine receptors, HLA-A, HLA-DRA, HM74, HMOX1, HUMCYT2A, HLA-DR, HMI 24, human chorionic gonadotropin (HCG) and its subunits, HER2/neu, HMGB-1, hypoxia inducible factor (HIF-1), HSP70-2M, HST-2 or 1a, IGF-IR, IFN-γ, IFN-α, IL-2, IL-4R, IL-6R, IL-13R, IL-15R, IL-17R, IL-18R, IL-6, IL-8, IL-12, IL-15, IL-17, IL-18, IL-25, IGBP1, IGF1, IGF1R, IGF2, IGFBP2, IGFBP3, IGFBP6, IL-1, IL-10, IL-10RA, IL-10RB, IL-11, IL-11RA, IL-12, IL-12A, IL-12B, IL-12RB1, IL-12RB2, IL-13, IL-13RA1, IL-13RA2, IL-14, IL-1S, IL-1SRA, IL-16, IL-17, IL-17B, IL-17C, IL-17R, IL-18, IL-18BP, IL-18R1, IL-18RAP, IL-19, IL-IA, IL-1B, IL-1F10, IL-1FS, IL-1F6, IL-1F7, IL-1F8, IL-1F9, IL-1HY1, IL-1R1, IL-1R2, IL-1RAP, IL-1RAPL1, IL-1RAPL2, IL-1RL1, IL-1RL2 IL-1RN, IL-2, IL-20, IL-20RA, IL-21R, IL-22, IL-22R, IL-22RA2, IL-23, IL-24, IL-2S, IL-26, IL-27, IL-28A, IL-28B, IL-29, IL-2RA, IL-2RB, IL-2RG, IL-3, IL-30, IL-3RA, IL-4, IL-4R, IL-S, IL-5RA, IL-6, IL-6R, IL-6ST (glycoprotein 130), IL-7, IL-7R, IL-S, IL-SRA, IL-SRB, IL-9, IL-9R, IL-K, INHA, INHBA, INSL3, INSL4, IRAK1, IRAK2, ITGA1, ITGA2, ITGA3, ITGA6 (a6 integrin), ITGAV, ITGB3, ITGB4 (b 4 integrin) insulin-like growth factor-1 (IGF-1), ICEBERG, ICOSL, ID2, IFN-a, IFNA1, IFNA2, IFNA4 IFNAS, IFNA6, IFNA7, IFNB1, IFNW1, JAG1, JAK1, JAK3, JUN, K6HF, KAi1, KDR, KITLG, KLFS (GC Box BP), KLF6, KLK10, KLK12, KLK13, KLK14, KLK1S, KLK3, KLK4, KLKS, KLK6, KLK9, KRT1, KRT19 (Keratin 19), KRT2A, KRTHB6 (hair-specific type II keratin), KC4-antigen, KS-1-antigen, KS 1-4, Le-Y, LDR/FUT, LAMAS, LEP (leptin), Lingo-p7S, Lingo-Troy, LPS, LTA (TNF-b), LTB, LTB4R (GPR16), LTB4R2, LTBR, MACMARCKS, MAG or Omgp, MAP2K7 (c-Jun), MDK, MIB1, midkine, MIF, MIP-2, MKI67 (Ki-67), MMP2, MMP9, MS4A1, MSMB, MT3 (metallothionectin-III), MTSS1, MUC1 (mucin), MYC, MYD88, macrophage migration inhibitory factor (MIF), MAGE, MAGE-3, MART-1, MART-2, NY-ES0-1, TRAG-3, mCRP, MCP-1, MIP-1A, MIP-1B, MIF, MUC1, MUC2, MUC3, MUC4, MUC5, MUM-1/2, MUM-3, NCA66, NCA95, NCA90, NCK2, neurocan, NFKB1, NFKB2, NGFB (NGF), NGFR, NgR-Lingo, NgR-Nogo66 (Noga), NgRp7S, NgR-Troy, NME1 (NM23A), NOXS, NPPB, NROB1, NROB2, NR1D1, NR1D2, NRIH2, NRIH3, NRIH4, NR1I2, NR1I3, NR2C1, NR2C2, NR2E1, NR2E3, NR2F1, NR2F2, NR2F6, NR3C1, NR3C2, NR4A1, NR4A2, NR4A3, NRSA1, NRSA2, NR6A1, NRP1, NRP2, NTSE, NTN4, ODZ1, OPRD1, PCSK9, P2RX7, PAP, PART1, PATE, PAWR, PCA3, PCNA, PD-1, PD-L1, alpha4beta7, OX40, GITR, TIM-3, Lag-3, B7-H3, B7-H4, GDFS, CGRP, Lingo-I, Factor IXa, Factor X, ICOS, GARP, BTLA, CD160, RORI, 2B4, KIR, CD27, OX40, A2aR, PDGFA, PDGFB, PECAM1, PF4 (CXCL4), PGF, PGR, phosphacan, PIAS2, PIK3CG, PLAU (uPA), PLG, PLXDC1, PPBP (CXCL7), PPID, PR1, PRKCQ, PRKD1, PRL, PROC, PROK2, PSAP, PSCA, PTAFR, PTEN, PTGS2 (COX-2), PTN, pancreatic cancer mucin, placental growth factor, p53, PLAGL2, prostatic acid phosphatase, PSA, PRAME, PSMA, 10 PIGF, ILGF, ILGF-IR, IL-6, RS5, RANTES, RAC2 (p21Rac2), RARB, RGS1, RGS13, RGS3, RNFI10 (ZNF144), ROB02, S100A2, SCGB1D2 (lipophilin B), SCGB2A1 (mammaglobin 2), SCGB2A2 (mammaglobin 1), SCYE1 (endothelial Monocyte-activating cytokine), SDF2, SERPINA1, SERPINA3, SERPINBS (maspin), SERPINE1 (PAI-1), SERPINF1, SHBG, SLA2, SLC2A2, SLC33A1, SLC43A1, SLIT2, SPP1, SPRR1B (SprI), ST6GAL1, STAB1, STATE, STEAP, STEAP2, TIOI, SAGE, 5100, survivin, survivin-2B, TAC, TAG-72, tenascin, TRAIL receptors, TNF-α, Tn-antigen, ThomsonFriedenreich antigens, tumor necrosis antigens, TB4R2, TBX21, TCP10, TDGF1, TEK, TGFA, TGFB1, TGFBIiI, TGFB2, TGFB3, TGFBI, TGFBR1, TGFBR2, TGFBR3, TH1L, THBS1 (thrombospondin-1), THBS2, THBS4, THPO, TIE (Tie-1), TIMP3, tissue factor, TLR10, TLR2, TLR3, TLR4, TLRS, TLR6, TLR7, TLRS, TLR9, TNF, TNF-a, TNFAIP2 (B94), TNFAIP3, TNFRSF11A, TNFRSF1A, TNFRSF1B, TNFRSF21, TNFRSFS, TNFRSF6 (Fas), TNFRSF7, TNFRSFS, TNFRSF9, TNFSF10 (TRAIL), TNFSF11 (TRANCE), TNFSF12 (APO3L), TNFSF13 (April), TNFSF13B, TNFSF14 (HVEM-L), TNFSF1S (VEGI), TNFSF18, TNFSF4 (OX40 ligand), TNFSFS (CD40 ligand), TNFSF6 (FasL), TNFSF7 (CD27 ligand), TNFSFS (CD30 ligand), TNFSF9 (4-IBB ligand), TOLLIP, Toll-like receptors, TOP2A (topoisomerase Iia), TPS3, TPM1, TPM2, TRADD, TRAF1, TRAF2, TRAF3, TRAF4, TRAPS, TRAF6, TREM1, TREM2, TRPC6, TSLP, TWEAK, VEGFR, ED-B fibronectin, WT-1, 17-IA antigen, complement factors C3, C3a, C3b, C5a, CS, an angiogenesis marker, bcI-2, bcI-6, Kras, cMET, CD19/CD3, BCMA/CD3, EGFR, HER3, IL17RA/IL7R, IL-6/IL-23, IL1/IL-8, IL-6, IL-6R/IL-21, IL-21R, ANG2/VEGF, VEGF/PDGFR-beta, Vascular Endothelial Growth Factor (VEGF) acceptor 2/CD3, PSMA/CD3, EPCAM/CD3, VEGFR-1, VEGFR-2, VEGFR-3, VEGFB, VEGFC, versican, VHL CS, VLA-4, c-FMS/CS-FIR, RET, HER3, HER4, IGFR, PDGFR, c-KIT, BCR, integrin, MMPs VEGF, EGF, PlGF, PDGF, HGF, angiopoietin, ERBB-3/C-MET, ERBB-2/C-MET, EGF receptor I/CD3, EGFR/HER3, PSCA/CD3, C-MET/CD3, ENDOSIALIN/CD3, EPCAM/CD3, IGF-1R/CD3, FAPALPHA/CD3, EGFR/IGF-IR, IL 25 17A/F, EGF receptor I/CD3, and CD19/CD16, KHI, Tn-antigen, TF-antigen, CD44, glycolipids, glycosphingolipids such as 30 Gg3, Gb3, GD3, GD2, Gb5, Gm1, Gm2, sialyltetraosylceramide, XCL1 (lymphotactin), XCL2 (SCM-1b), XCR1 (GPRS/CCXCR1), YY1, and ZFPM2.

In some embodiments, an ABM of the disclosure is capable of binding a pair of target molecules, e.g., via Fab1 and Fab2. Exemplary pairs of target molecules include CD137 and CD20, CD137 and EGFR, CD137 and Her-2, CD137 and PD-1, CD137 and PDL-1, VEGF and PD-L1, Lag-3 and TIM-3, OX40 and PD-1, TIM-3 and PD-1, TIM-3 and PDL-1, EGFR and DLL-4, CD138 and CD20, CDI 38 and CD40, CDI 9 and CD20, CD20 and CD3, CD3 and CD33, CD3 and CD133, CD47 and CD20, CD38 and CD138, CD38 and CD20, CD20 and CD22, CD38 and CD40, CD40 and CD20, CD-8 and IL-6, CSPGs and RGM A, CTLA-4 and BTN02, IGF1 and IGF2, IGF1/2 and Erb2B, IGF-1R and EGFR, EGFR and CD13, IGF-1R and ErbB3, EGFR-2 and IGFR, VEGFR-2 and Met, VEGF-A and Angiopoietin-2 (Ang-2), IL-12 and TWEAK, IL-13 and IL-1 beta, PDGFR and VEGF, EpCAM and CD3, Her2 and CD3, CD19 and CD3, EGFR and Her3, CD16a and CD30, CD30 and PSMA, EGFR and CD3, CEA and CD3, TROP-2 and HSG, TROP-2 and CD3, MAG and RGM A, NgR and RGM A, NogoA and RGM A, OMGp and RGM A, PDL-1 and CTLA-4, CTLA-4 and PD-1, PD-1 and TIM-3, RGMA and RGM B, Te38 and TNFa, TNFa and Blys, TNFa and CD-22, TNFa and CTLA-4 domain, TNFa and GP130, TNFa and IL-12p40, and TNFa and RANK ligand.

In some embodiments, an ABM of the disclosure is capable of binding one or more cytokines, cytokine-related proteins, and/or cytokine receptors, e.g., one or a pair of cytokines, cytokine-related proteins, and/or cytokine receptors, e.g., via Fab1 and Fab2. Exemplary cytokines, cytokine-related proteins, and/or cytokine receptors include BMP1, BMP2, BMP3B (GDF10), BMP4, BMP6, BMP8, CSF1 (M-CSF), CSF2 (GM-CSF), CSF3 (G-CSF), EPO, FGF1 (aFGF), FGF2 (bFGF), FGF3 (int-2), FGF4 (HST), FGF5, FGF6 (HST-2), FGF7 (KGF), FGF9, FGF10, FGF11, FGF12, FGF12B, FGF14, FGF16, FGF17, FGF19, FGF20, FGF21, FGF23, IGF1, IGF2, IFNA1, IFNA2, IFNA4, IFNA5, IFNA6, IFNA7, IFNB1, IFNG, IFNW1, FILI, FILI (EPSILON), FILI (ZETA), ILIA, ILIB, IL2, IL3, IL4, IL5, IL6, IL7, IL8, IL9, ILIO, ILi1, ILI2A, ILI2B, ILI3, ILI4, ILI5, ILI6, ILI7, ILI7B, ILI8, ILI9, IL20, IL22, IL23, IL24, IL25, IL26, IL27, IL28A, IL28B, IL29, IL30, PDGFA, FGER1, FGFR2, FGFR3, EGFR, RORI, 2B4, KIR, CD137, CD27, OX40, CD40L, A2aR, CD48, B7-1, B7-2, ICOSL, B7-H3, B7-H4, CD137L, OX40L, CD70, CD40, PDGFB, TGFA, TGFB1, TGFB2, TGFB3, LTA (TNF-b), LTB, TNF (TNF-a), TNFSF4 (OX40 ligand), TNFSF5 (CD40 ligand), TNFSF6 (FasL), TNFSF7 (CD27 ligand), TNFSF8 (CD30 ligand), TNFSF9 (4-1BB ligand), TNFSF10 (TRAIL), TNFSF11 (TRANCE), TNFSF12 (AP03L), TNFSF13 (April), TNFSF13B, TNFSF14 (HVEM-L), TNFSF15 (VEGI), TNFSF18, FIGF (VEGFD), VEGF, VEGFB, VEGFC, ILIR1, ILIR2, ILIRLI, ILIRL2, IL2RA, IL2RB, IL2RG, IL3RA, IL4R, ILSRA, IL6R, IL 7R, ILSRA, ILSRB, IL9R, ILIORA, ILIORB, IL11RA, ILI2RB1, ILI2RB2, ILI3RA1, ILI3RA2, ILI5RA, ILI7R, ILI8R1, IL20RA, IL21R, IL22R, IL1HY1, ILIRAP, ILIRAPLI, ILIRAPL2, ILIRN, IL6ST, ILI8BP, ILI8RAP, IL22RA2, AIF1, HGF, LEP (leptin), PTN, and THPO.

In some embodiments, an ABM of the disclosure is capable of binding one or more chemokines, chemokine-related proteins, and/or chemokine receptors, e.g., one or a pair of chemokines, chemokine-related proteins, and/or chemokine receptors, e.g., via Fab1 and Fab2. Exemplary chemokines, chemokine-related proteins and chemokine receptors include CCLI (I-309), CCL2 (MCP-1/MCAF), CCL3 (MIP1a), CCL4 (MIP-1b), CCL5 (RANTES), CCL7 (MCP-3), CCL8 (mcp-2), CCLII (eotaxin), CCLI3 (MCP-4), CCLI5 (MIP-1 d), CCLI 6 (HCC-4), CCLI 7 (TARC), CCLI 8 (PARC), CCLI9 (MIP-3b), CCL20 (MIP-3a), CCL21 (SLC/exodus-2), CCL22 (MDC/STC-1), CCL23 (MPIF-1), CCL24 (MPIF-2/eotaxin-2), CCL25 (TECK), CCL26 (eotaxin-3), CCL27 (CTACK/ILC), CCL28, CXCLI (GRO1), CXCL2 (GR02), CXCL3 (GR03), CXCL5 (ENA-78), CXCL6 (GCP-2), CXCL9 (MIG), CXCLIO (IP 10), CXCL11 (I-TAC), CXCL12 (SDF1), CXCL13, CXCL14, CXCL16, PF4 (CXCL4), PPBP (CXCL7), CX3CL1 (SCYD1), SCYE1, XCL1 (lymphotactin), XCL2 (SCM-1b), BLR1 (MDR15), CCBP2 (D6/JAB61), CCR1 (CKR1/HM145), CCR2 (mcp-1RB/RA), CCR3 (CKR3/CMKBR3), CCR4, CCR5 (CMKBR5/ChemR13), CCR6 (CMKBR6/CKR-L3/STRL22/DRY6), CCR7 (CKR7/EBI1), CCRS (CMKBR8/TER1/CKR-L1), CCR9 (GPR-9-6), CCRL1 (VSHK1), CCRL2 (L-CCR), XCR1 (GPR5/CCXCR1), CMKLR1, CMKOR1 (RDC1), CX3CR1 (V28), CXCR4, GPR2 (CCR10), GPR31, GPR81 (FKSGSO), CXCR3 (GPR9/CKR-L2), CXCR6 (TYMSTR/STRL33/Bonzo), HM74, ILSRA (IL8Ra), ILSRB (IL8Rb), LTB4R (GPR16), TCP10, CKLFSF2, CKLFSF3, CKLFSF4, CKLFSF5, CKLFSF6, CKLFSF7, CKLFSFS, BDNF, C5R1, CSF3, GRCC10 (010), EPO, FY (DARC), GDF5, HIF1A, ILS, PRL, RGS3, RGS13, SDF2, SLIT2, TLR2, TLR4, TREM1, TREM2, and VHL.

In some embodiments, an ABM of the disclosure is capable of binding a pair of cytokines, cytokine receptors and/or cytokine-related proteins. Exemplary pairs of cytokines include IL-1a and IL-Iβ, IL-12 and IL-18, TNFa and IL-23, TNFa and IL-13, TNF and IL-18, TNF and IL-12, TNF and IL-1beta, TNF and MIF, TNF and IL-6, TNF and IL-6 Receptor, TNF and IL-17, IL-17 and IL-20, IL-17 and IL-23, TNF and IL-15, TNF and VEGF, VEGFR and EGFR, PDGFR and VEGF, IL-13 and IL-9, IL-13 and IL-4, IL-13 and IL-5, IL-13 and IL-25, IL-13 and TARC, IL-13 and MDC, IL-13 and MIF, IL-13 and TGF-β, IL-13 and LHR agonist, IL-13 and CL25, IL-13 and SPRR2a, IL-13 and SPRR2b, IL-13 and ADAM 8, and TNFa and PGE4, IL-13 and PED2, and TNF and PEG2.

In some embodiments, an ABM of the disclosure is capable of binding at least two epitopes on a single cytokine, cytokine receptor or cytokine-related proteins. Exemplary cytokines include TSLP, IL-1a, IL-Iβ, IL-12, IL-18, TNFa, IL-23, IL-13, MIF, IL-6, IL-6 Receptor, IL-17, IL-20, IL-15, VEGF, VEGFR, EGFR, PDGFR, IL-9, IL-4, IL-5, IL-25, TARC, MDC, TGF-13, LHR agonist, CL25, SPRR2a, SPRR2b, ADAM 8, PGE4, PED2, and PEG2.

In some embodiments, an ABM of the disclosure is capable of binding to its antigen target with a similar or greater affinity relative to an antibody or antibody fragment of conventional format.

In some embodiments, an ABM of the disclosure has an agonist function against its target molecule(s). In other embodiments, an ABM of the disclosure has blocking and/or antagonist function against its antigen or target molecule(s).

In certain aspects, an ABM of the disclosure has a similar or lower $IC_{50}$ to its antigen(s) or target molecule(s) relative to a parental antibody (or pair of parental antibodies), such as to a parental IgG1, IgG2, IgG3, IgG4, IgD, IgA, IgE, or IgM antibody, from which the Fabs of the ABM were derived, for example, having similar or lower $IC_{50}$ relative to a conventional IgG format.

In some embodiments, an ABM of the disclosure is bispecific for a single ligand and forms 1:1 ligand complexes at a higher level relative a parental antibody or antibodies.

When Fab1 and Fab2 bind to different epitopes on the same target molecule, binding to the target molecule is preferably non-competitive, i.e., the Fab1 and Fab2 do not compete for binding to the target molecule (which might occur, e.g., if the epitopes were overlapping). Assays for measuring binding competition between antibodies and antibody fragments are known in the art and include, for example, enzyme-linked immunosorbent assays (ELISA), fluorescence activated cell sorting (FACS) assays and surface plasmon resonance assays.

Competition for binding to a target molecule can be determined, for example, using a real time, label-free biolayer interferometry assay on the Octet HTX biosensor platform (Pall ForteBio Corp.). In a specific embodiment of the assay, the entire assay is performed at 25° C. in a buffer of 10 mM HEPES, 150 mM NaCl, 3 mM EDTA, 1 mg/mL BSA, 0.05% v/v Surfactant Tween-20, pH 7.4 (HBS-EBT buffer) with the plate shaking at the speed of 1000 rpm. To assess whether two antibodies or antigen-binding fragments thereof are able to compete with one another for binding to their respective epitopes on their specific target antigen, a penta-His tagged target antigen ("penta-His" is disclosed as SEQ ID NO:34) is first captured on to anti-penta-His antibody ("penta-His" is disclosed as SEQ ID NO:34) coated Octet biosensor tips (Fortebio Inc, #18-5122) by submerging the biosensor tips in wells containing the penta-His tagged target antigen ("penta-His" is disclosed as SEQ ID NO:34). The antigen captured biosensor tips are then saturated with a first antibody or antigen-binding fragment thereof (subsequently referred to as Ab-1) by dipping into wells containing a solution of Ab-1 (e.g., a 50 µg/mL solution). The biosensor tips are then subsequently dipped into wells containing a solution (e.g., a 50 µg/mL solution) of a second antibody or antigen-binding fragment thereof (subsequently referred to as Ab-2). The biosensor tips are washed in HBS-EBT buffer in between every step of the assay. The real-time binding response can be monitored during the entire course of the assay and the binding response at the end of every step can be recorded. The response of Ab-2 binding to the target antigen pre-complexed with Ab-1 can be compared and competitive/non-competitive behavior of different antibodies/antigen-binding fragments against the same target antigen can be determined.

In various embodiments:
The ABM (e.g., a Format A ABM or a Format B ABM) does not include Fab3 and Fab4, and Fab1 and Fab2 bind to the same or different epitopes on the same target molecule;
The ABM (e.g., a Format A ABM or a Format B ABM) does not include Fab3 and Fab4, and Fab1 and Fab2 bind to different target molecules;
The ABM (e.g., a Format C ABM) includes a non-binding Fab3 and a non-binding Fab4, and Fab1 and Fab2 bind to the same or different epitopes on the same target molecule;
The ABM (e.g., a Format C ABM) includes a non-binding Fab3 and a non-binding Fab4, and Fab1 and Fab2 bind to different target molecules;
The ABM (e.g., a Format C ABM) includes a binding Fab3 and a binding Fab4, and Fab1 and Fab2 bind to the same epitope and Fab3 and Fab4 bind to the same epitope that is different from the epitope bound by Fab1 and Fab2, either on the same as the target molecule bound by Fab1 and Fab2 or on a different target molecule;
The ABM (e.g., a Format C ABM) includes a binding Fab3 and a binding Fab4, and Fab1 and Fab3 bind to the same epitope and Fab2 and Fab4 bind to the same epitope that is different from the epitope bound by Fab1 and Fab3, either on the same as the target molecule bound by Fab1 and Fab3 or on a different target molecule.

When two or more of Fab1, Fab2, Fab3 and Fab4 bind to the same epitope on a target molecule, such Fab domains can have the same or different heavy chain CDR sequences and/or the same or different VH sequences. Optionally, they can have the same or different VL sequences.

Without being bound by theory, it is believed that ABMs of the disclosure have the advantage of binding to a target molecule with greater affinity than a parental monospecific antibody or bispecific antibody with a native configuration. Accordingly, the ABMs of the disclosure can in some embodiments bind to one or more target molecules with greater affinity than a parental monospecific antibody or bispecific antibody with a native configuration. For example, ABMs can in some embodiments having a lower $K_D$ for binding to a target molecule and/or have more potent EC50 values in a cell based binding assay than a corresponding parental monospecific antibody or bispecific antibody (e.g., as described in Section 7).

The agonist or antagonist activity of a given antibody or ABM depends on target selection, epitope coverage and choice of format. Identification of agonistic and antagonistic antibodies can be achieved, for example, through functional based screening. The ABM formats of the present disclosure are particularly advantageous for antagonist activity against small soluble molecules.

6.4. Antibody Drug Conjugates

The ABMs of the disclosure can be conjugated, e.g., via a linker, to a drug moiety, particularly where the ABM is intended for use as a cancer therapeutic. Such conjugates are referred to herein as antibody-drug conjugates (or "ADCs") for convenience.

In certain aspects, the drug moiety exerts a cytotoxic or cytostatic activity. In one embodiment, the drug moiety is chosen from a maytansinoid, a kinesin-like protein KIF11 inhibitor, a V-ATPase (vacuolar-type H+-ATPase) inhibitor, a pro-apoptotic agent, a Bcl2 (B-cell lymphoma 2) inhibitor, an MCL1 (myeloid cell leukemia 1) inhibitor, a HSP90 (heat shock protein 90) inhibitor, an IAP (inhibitor of apoptosis) inhibitor, an mTOR (mechanistic target of rapamycin) inhibitor, a microtubule stabilizer, a microtubule destabilizer, an auristatin, a dolastatin, a MetAP (methionine aminopeptidase), a CRM1 (chromosomal maintenance 1) inhibitor, a DPPIV (dipeptidyl peptidase IV) inhibitor, a proteasome inhibitor, an inhibitor of a phosphoryl transfer reaction in mitochondria, a protein synthesis inhibitor, a kinase inhibitor, a CDK2 (cyclin-dependent kinase 2) inhibitor, a CDK9 (cyclin-dependent kinase 9) inhibitor, a kinesin inhibitor, an HDAC (histone deacetylase) inhibitor, a DNA damaging agent, a DNA alkylating agent, a DNA intercalator, a DNA minor groove binder, a RNA polymerase inhibitor, a topoisomerase inhibitor, or a DHFR (di hydrofolate reductase) inhibitor.

In some embodiments, the cytotoxic agent is a maytansinoid having the structure:

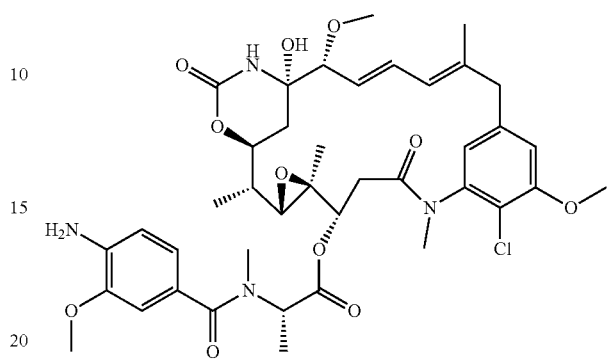

In some embodiments, the cytotoxic agent is a maytansinoid having the structure:

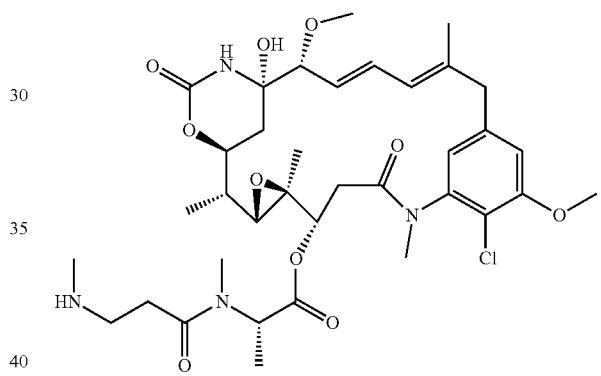

In some embodiments, the ADC comprises an ABM of the disclosure and

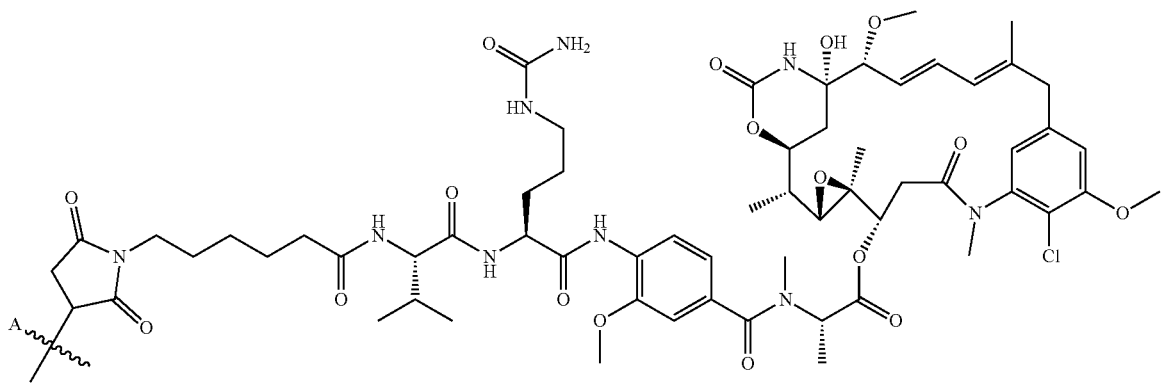

wherein
is a bond to the ABM.
In some embodiments, the antibody-drug conjugate comprises an ABM of the disclosure, and
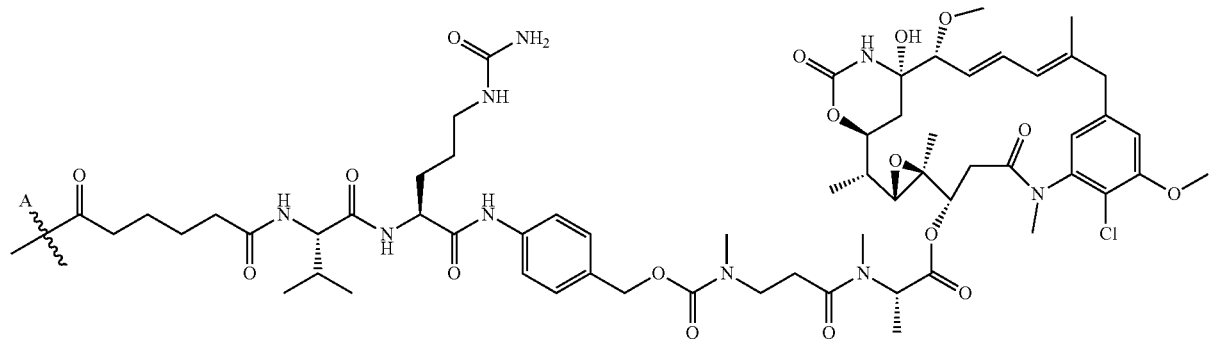
wherein
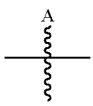
is a bond to the ABM.
In some embodiments, the ADC comprises an ABM of the disclosure and
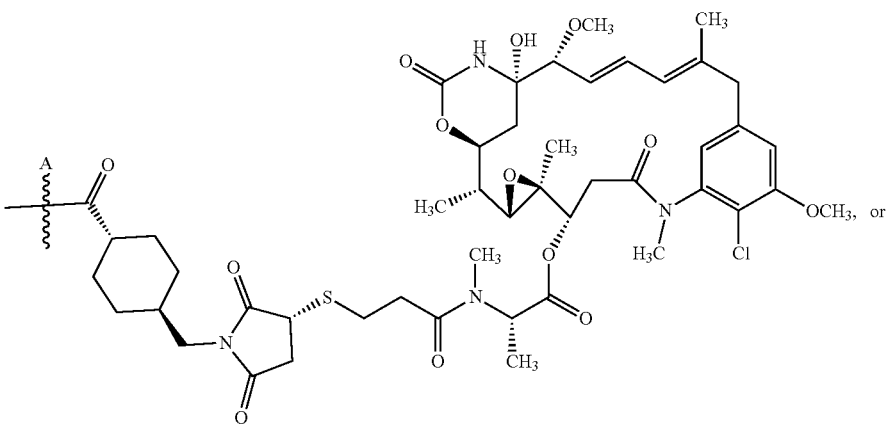

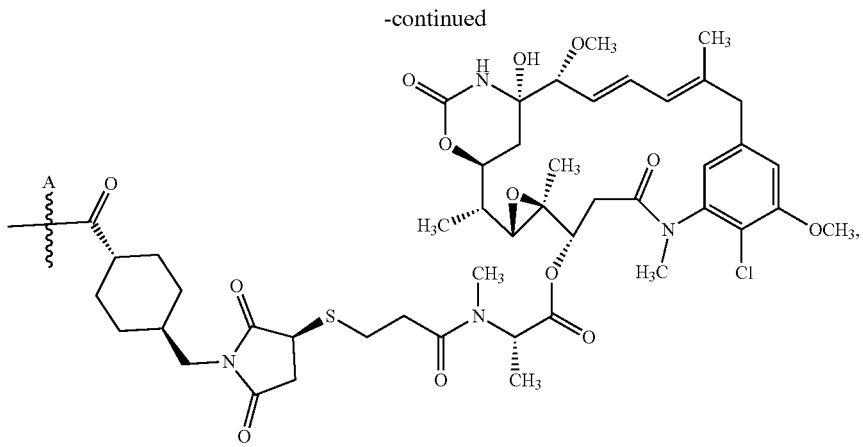

or a mixture thereof,
wherein

is a bond to the ABM of the disclosure.

In some embodiments, the bond is linked to the ABM via a sulfur constituent of a cysteine residue.

In some embodiments, the bond is linked the ABM via a nitrogen constituent of a lysine residue.

In the ADCs of the disclosure, the cytotoxic and/or cytostatic agents are linked to the ABM by way of ADC linkers. The ADC linker linking a cytotoxic and/or cytostatic agent to the ABM of an ADC may be short, long, hydrophobic, hydrophilic, flexible or rigid, or may be composed of segments that each independently have one or more of the above-mentioned properties such that the linker may include segments having different properties. The linkers may be polyvalent such that they covalently link more than one agent to a single site on the ABM, or monovalent such that covalently they link a single agent to a single site on the ABM.

In certain aspects, the linker is chosen from a cleavable linker, a non-cleavable linker, a hydrophilic linker, a procharged linker, or a dicarboxylic acid based linker.

As will be appreciated by skilled artisans, the ADC linkers link cytotoxic and/or cytostatic agents to the ABM by forming a covalent linkage to the cytotoxic and/or cytostatic agent at one location and a covalent linkage to the ABM at another. The covalent linkages are formed by reaction between functional groups on the ADC linker and functional groups on the agents and ABM.

The ADC linkers are preferably, but need not be, chemically stable to conditions outside the cell, and may be designed to cleave, immolate and/or otherwise specifically degrade inside the cell. Alternatively, ADC linkers that are not designed to specifically cleave or degrade inside the cell may be used. Choice of stable versus unstable ADC linker may depend upon the toxicity of the cytotoxic and/or cytostatic agent. For agents that are toxic to normal cells, stable linkers are preferred. Agents that are selective or targeted and have lower toxicity to normal cells may utilize, chemical stability of the ADC linker to the extracellular milieu is less important. A wide variety of ADC linkers useful for linking drugs to ABMs in the context of ADCs are known in the art. Any of these ADC linkers, as well as other ADC linkers, may be used to link the cytotoxic and/or cytostatic agents to the ABM of the ADCs of the disclosure.

Exemplary polyvalent ADC linkers that may be used to link many cytotoxic and/or cytostatic agents to a single ABM molecule are described, for example, in WO 2009/073445; WO 2010/068795; WO 2010/138719; WO 2011/120053; WO 2011/171020; WO 2013/096901; WO 2014/008375; WO 2014/093379; WO 2014/093394; WO 2014/093640, the contents of which are incorporated herein by reference in their entireties. For example, the Fleximer linker technology developed by Mersana et al. has the potential to enable high-DAR ADCs with good physicochemical properties. The Mersana technology is based on incorporating drug molecules into a solubilizing poly-acetal backbone via a sequence of ester bonds. The methodology renders highly-loaded ADCs (DAR up to 20) while maintaining good physicochemical properties.

Exemplary monovalent ADC linkers that may be used are described, for example, in Nolting, 2013, Antibody-Drug Conjugates, Methods in Molecular Biology 1045:71-100; Ducry et al., 2010, Bioconjugate Chem. 21:5-13; Zhao et al., 2011, J. Med. Chem. 54:3606-3623; U.S. Pat. Nos. 7,223,837 and 8,568,728; U.S. Pat. No. 8,535,678; and WO2004010957, each of which is incorporated herein by reference.

By way of example and not limitation, some cleavable and noncleavable ADC linkers that may be included in the ADCs of the disclosure are described below.

In certain embodiments, the ADC linker selected is cleavable in vivo. Cleavable ADC linkers may include chemically or enzymatically unstable or degradable linkages. Cleavable ADC linkers generally rely on processes inside the cell to liberate the drug, such as reduction in the cytoplasm, exposure to acidic conditions in the lysosome, or cleavage by specific proteases or other enzymes within the cell. Cleavable ADC linkers generally incorporate one or more chemical bonds that are either chemically or enzymatically cleavable while the remainder of the ADC linker is noncleavable. In certain embodiments, an ADC linker comprises a chemically labile group such as hydrazone and/or disulfide groups. Linkers comprising chemically labile groups exploit differential properties between the plasma and some cytoplasmic compartments. The intracellular conditions to facilitate drug release for hydrazone containing ADC linkers are the acidic environment of endosomes and lysosomes, while the disulfide containing ADC linkers are reduced in the cytosol, which contains high thiol concentrations, e.g., glutathione. In certain embodiments, the plasma stability of an ADC linker comprising a chemically labile group may be increased by introducing steric hindrance using substituents near the chemically labile group.

Cleavable ADC linkers may include noncleavable portions or segments, and/or cleavable segments or portions may be included in an otherwise non-cleavable ADC linker to render it cleavable. By way of example only, polyethylene glycol (PEG) and related polymers may include cleavable groups in the polymer backbone. For example, a polyethylene glycol or polymer ADC linker may include one or more cleavable groups such as a disulfide, a hydrazone or a dipeptide.

Other degradable linkages that may be included in ADC linkers include ester linkages formed by the reaction of PEG carboxylic acids or activated PEG carboxylic acids with alcohol groups on a biologically active agent, wherein such ester groups generally hydrolyze under physiological conditions to release the biologically active agent. Hydrolytically degradable linkages include, but are not limited to, carbonate linkages; imine linkages resulting from reaction of an amine and an aldehyde; phosphate ester linkages formed by reacting an alcohol with a phosphate group; acetal linkages that are the reaction product of an aldehyde and an alcohol; orthoester linkages that are the reaction product of a formate and an alcohol; and oligonucleotide linkages formed by a phosphoramidite group, including but not limited to, at the end of a polymer, and a 5' hydroxyl group of an oligonucleotide.

In certain embodiments, the ADC linker comprises an enzymatically cleavable peptide moiety, for example a tripeptide or a dipeptide. In particular embodiments, the dipeptide is selected from: Val-Cit; Cit-Val; Ala-Ala; Ala-Cit; Cit-Ala; Asn-Cit; Cit-Asn; Cit-Cit; Val-Glu; Glu-Val; Ser-Cit; Cit-Ser; Lys-Cit; Cit-Lys; Asp-Cit; Cit-Asp; Ala-Val; Val-Ala; Phe-Lys; Val-Lys; Ala-Lys; Phe-Cit; Leu-Cit; Ile-Cit; Phe-Arg; and Trp-Cit. In certain embodiments, the dipeptide is selected from: Cit-Val; and Ala-Val.

In any of the various embodiments of the ADCs discussed above or herein, the ADCs can have a drug:antibody ratio (or, in this instance, a drug:ABM ratio), of 1 to 20, more typically in the range of 2 to 10.

6.5. Nucleic Acids and Host Cells

In another aspect, the disclosure provides nucleic acids encoding the ABMs of the disclosure. In some embodiments, the ABMs are encoded by a single nucleic acid. In other embodiments, the ABMs are encoded by a plurality (e.g., two, three, four or more) nucleic acids.

A single nucleic acid can encode an ABM that comprises a single polypeptide chain, an ABM that comprises two or more polypeptide chains, or a portion of an ABM that comprises more than two polypeptide chains (for example, a single nucleic acid can encode two polypeptide chains of an ABM comprising three, four or more polypeptide chains, or three polypeptide chains of an ABM comprising four or more polypeptide chains). For separate control of expression, the open reading frames encoding two or more polypeptide chains can be under the control of separate transcriptional regulatory elements (e.g., promoters and/or enhancers). The open reading frames encoding two or more polypeptides can also be controlled by the same transcriptional regulatory elements, separated by internal ribosome entry site (IRES) sequences allowing for translation into separate polypeptides.

In some embodiments, an ABM comprising two or more polypeptide chains is encoded by two or more nucleic acids. The number of nucleic acids encoding an ABM can be equal to or less than the number of polypeptide chains in the ABM (for example, when more than one polypeptide chains are encoded by a single nucleic acid).

The nucleic acids of the disclosure can be DNA or RNA (e.g., mRNA).

In another aspect, the disclosure provides host cells and vectors containing the nucleic acids of the disclosure. The nucleic acids may be present in a single vector or separate vectors present in the same host cell or separate host cell, as described in more detail herein below.

6.5.1. Vectors

The disclosure provides vectors comprising nucleotide sequences encoding an ABM or an ABM component described herein, for example one or two of the polypeptide chains of a half antibody. The vectors include, but are not limited to, a virus, plasmid, cosmid, lambda phage or a yeast artificial chromosome (YAC).

Numerous vector systems can be employed. For example, one class of vectors utilizes DNA elements which are derived from animal viruses such as, for example, bovine papilloma virus, polyoma virus, adenovirus, vaccinia virus, baculovirus, retroviruses (Rous Sarcoma Virus, MMTV or MOMLV) or SV40 virus. Another class of vectors utilizes RNA elements derived from RNA viruses such as Semliki Forest virus, Eastern Equine Encephalitis virus and Flaviviruses.

Additionally, cells which have stably integrated the DNA into their chromosomes can be selected by introducing one or more markers which allow for the selection of transfected host cells. The marker may provide, for example, prototropy to an auxotrophic host, biocide resistance (e.g., antibiotics), or resistance to heavy metals such as copper, or the like. The selectable marker gene can be either directly linked to the DNA sequences to be expressed, or introduced into the same cell by co-transformation. Additional elements may also be needed for optimal synthesis of mRNA. These elements may include splice signals, as well as transcriptional promoters, enhancers, and termination signals.

Once the expression vector or DNA sequence containing the constructs has been prepared for expression, the expression vectors can be transfected or introduced into an appropriate host cell. Various techniques may be employed to achieve this, such as, for example, protoplast fusion, calcium phosphate precipitation, electroporation, retroviral transduction, viral transfection, gene gun, lipid based transfection or other conventional techniques. Methods and conditions for culturing the resulting transfected cells and for recovering the expressed polypeptides are known to those skilled in the art, and may be varied or optimized depending upon the specific expression vector and mammalian host cell employed, based upon the present description.

6.5.2. Cells

The disclosure also provides host cells comprising a nucleic acid of the disclosure.

In one embodiment, the host cells are genetically engineered to comprise one or more nucleic acids described herein.

In one embodiment, the host cells are genetically engineered by using an expression cassette. The phrase "expression cassette," refers to nucleotide sequences, which are capable of affecting expression of a gene in hosts compatible with such sequences. Such cassettes may include a promoter, an open reading frame with or without introns, and a termination signal. Additional factors necessary or helpful in effecting expression may also be used, such as, for example, an inducible promoter.

The disclosure also provides host cells comprising the vectors described herein.

The cell can be, but is not limited to, a eukaryotic cell, a bacterial cell, an insect cell, or a human cell. Suitable eukaryotic cells include, but are not limited to, Vero cells, HeLa cells, COS cells, CHO cells, HEK293 cells, BHK cells and MDCKII cells. Suitable insect cells include, but are not limited to, Sf9 cells.

6.6. Pharmaceutical Compositions

The ABMs and/or ADCs of the disclosure may be in the form of compositions comprising the ABM and/or ADC and one or more carriers, excipients and/or diluents, optionally with one or more other agents that provide improved transfer, delivery, tolerance, and the like. The compositions may be formulated for specific uses, such as for pharmaceutical uses in humans or veterinary use. The form of the composition (e.g., dry powder, liquid formulation, etc.) and the excipients, diluents and/or carriers used will depend upon the intended uses of the ABM and/or ADC and, for therapeutic uses, the mode of administration.

The dose of antigen-binding molecule, such as a monospecific antigen-binding molecule or bispecific antigen-binding molecule, administered to a patient may vary depending upon the age and the size of the patient, target disease, conditions, route of administration, and the like. The preferred dose is typically calculated according to body weight or body surface area. When a bispecific antigen-binding molecule of the present disclosure is used for therapeutic purposes in an adult patient, it may be advantageous to intravenously administer the antigen-binding molecule of the present disclosure normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering a antigen-binding molecule may be determined empirically; for example, patient progress can be monitored by periodic assessment, and the dose adjusted accordingly. Moreover, interspecies scaling of dosages can be performed using well-known methods in the art (e.g., Mordenti et al., 1991, Pharmaceut. Res. 8:1351).

For therapeutic uses, the compositions may be supplied as part of a sterile, pharmaceutical composition that includes a pharmaceutically acceptable carrier. This composition can be in any suitable form (depending upon the desired method of administering it to a patient). The pharmaceutical composition can be administered to a patient by a variety of routes such as orally, transdermally, subcutaneously, intranasally, intravenously, intramuscularly, intratumorally, intrathecally, topically or locally. The most suitable route for administration in any given case will depend on the particular antibody and/or ADC, the subject, and the nature and severity of the disease and the physical condition of the subject. Typically, the pharmaceutical composition will be administered intravenously or subcutaneously.

Pharmaceutical compositions can be conveniently presented in unit dosage forms containing a predetermined amount of an ABM and/or ADC of the disclosure per dose. The quantity of ABM and/or ADC included in a unit dose will depend on the disease being treated, as well as other factors as are well known in the art. Such unit dosages may be in the form of a lyophilized dry powder containing an amount of ABM and/or ADC suitable for a single administration, or in the form of a liquid. Dry powder unit dosage forms may be packaged in a kit with a syringe, a suitable quantity of diluent and/or other components useful for administration. Unit dosages in liquid form may be conveniently supplied in the form of a syringe pre-filled with a quantity of ABM and/or ADC suitable for a single administration.

The pharmaceutical compositions may also be supplied in bulk from containing quantities of ADC suitable for multiple administrations.

Pharmaceutical compositions may be prepared for storage as lyophilized formulations or aqueous solutions by mixing an ABM and/or ADC having the desired degree of purity with optional pharmaceutically-acceptable carriers, excipients or stabilizers typically employed in the art (all of which are referred to herein as "carriers"), i.e., buffering agents, stabilizing agents, preservatives, isotonifiers, non-ionic detergents, antioxidants, and other miscellaneous additives. See, Remington's Pharmaceutical Sciences, 16th edition (Osol, ed. 1980). Such additives should be nontoxic to the recipients at the dosages and concentrations employed.

Buffering agents help to maintain the pH in the range which approximates physiological conditions. They may be present at a wide variety of concentrations, but will typically be present in concentrations ranging from about 2 mM to about 50 mM. Suitable buffering agents for use with the present disclosure include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris can be used.

Preservatives may be added to retard microbial growth, and can be added in amounts ranging from about 0.2%-1% (w/v). Suitable preservatives for use with the present disclosure include phenol, benzyl alcohol, meta-cresol, methyl paraben, propyl paraben, octadecyldimethylbenzyl ammonium chloride, benzalconium halides (e.g., chloride, bromide, and iodide), hexamethonium chloride, and alkyl parabens such as methyl or propyl paraben, catechol, resorcinol, cyclohexanol, and 3-pentanol. Isotonicifiers sometimes known as "stabilizers" can be added to ensure isotonicity of liquid compositions of the present disclosure and include polyhydric sugar alcohols, for example trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, a-monothioglycerol and sodium thio sulfate; low molecular weight polypeptides (e.g., peptides of 10 residues or fewer); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trehalose; and trisaccacharides such as raffinose; and polysaccharides such as dextran. Stabilizers may be present in amounts ranging from 0.5 to 10 wt % per wt of ADC.

Non-ionic surfactants or detergents (also known as "wetting agents") may be added to help solubilize the glycoprotein as well as to protect the glycoprotein against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), and pluronic polyols. Non-ionic surfactants may be present in a range of about 0.05 mg/mL to about 1.0 mg/mL, for example about 0.07 mg/mL to about 0.2 mg/mL.

Additional miscellaneous excipients include bulking agents (e.g., starch), chelating agents (e.g., EDTA), antioxidants (e.g., ascorbic acid, methionine, vitamin E), and cosolvents.

6.7. Therapeutic Indications

The ABMs, ADCs, and pharmaceutical compositions of the disclosure can be used for treating conditions associated with an antigen or target molecule bound by an ABM of the disclosure, for example a condition associated with the aberrant expression or activity of an antigen or target molecule or an aberrant cell or tissue that expresses the antigen or target molecule. The ABMs, ADCs, and pharmaceutical compositions of the disclosure can be administered to a subject in need thereof, e.g., a human or non-human animal that exhibits one or more symptoms or indicia of condition associated with the aberrant expression or activity of an antigen or target molecule to which an ABM binds.

In some embodiments, an ABM, ADC, or pharmaceutical composition of the disclosure is administered to treat any disease or disorder in which stimulation, activation and/or targeting of the antigen or target molecule is desired. In particular embodiments, the ABMs of the present invention may be used for the treatment, prevention and/or amelioration of any disease or disorder associated with or mediated by the expression or activity or the antigen or target molecule.

ABMs of the disclosure can are exemplified by ABMs containing one of more Fab domains (e.g., Fab1 and/or Fab2) that bind to thymic stromal lymphopoietin ("TSLP"), e.g., human TSLP. TSLP is an immune cytokine that induces dendritic cell-mediated $CD4^+$ T cell responses with a proalogenic phenotype (Gilliet et al., 2003, J. Exp. Medicine 197(8):1059-1063). TSLP is involved in the initiation of allergic inflammation (Watanabe et al., 2004, Nature Immunology 5:426-434). TSLP acts on a broad range of cell types (e.g., dendritic cells, $CD4^+$ T cells, eosinophils, basophils, mast cells and Type 2 innate lymphoid cells (ILC2) (Mjosberg et al., 2012, Immunity 37(4):649-59) to drive inflammation, and in particular, Type 2 inflammation (characterized by the production of the cytokines IL-5, IL-13 and IL-4). Type 2 inflammation is a feature of asthma and other allergic diseases such as atopic dermatitis and Netherton Syndrome. TSLP has been found to induce fibroblast accumulation and collagen deposition in animals demonstrating an additional role in promoting fibrotic disorders.

Accordingly, ABMs that are TSLP antagonists are useful in the treatment of inflammatory, and particularly allergic inflammatory, as well as fibrotic disorders. ABMs that bind to TSLP (either monospecifically or bispecifically) can be used for treating a conditions associated with TSLP signaling in a subject in need thereof, for example in a human subject. Exemplary conditions associated with TSLP signaling include asthma, idiopathic pulmonary fibrosis, atopic dermatitis, allergic conjunctivitis, allergic rhinitis, Netherton syndrome, eosinophilic esophagitis (EoE), food allergy, allergic diarrhea, eosinophilic gastroenteritis, allergic bronchopulmonary aspergillosis (ABPA), allergic fungal sinusitis, cancer, rheumatoid arthritis, COPD, systemic sclerosis, keloids, ulcerative colitis, chronic rhinosinusitis (CRS), nasal polyposis, chronic eosinophilic pneumonia, eosinophilic bronchitis, coeliac disease, Churg-Strauss syndrome, eosinophilic myalgia syndrome, hypereosinophilic syndrome, eosinophilic granulomatosis with polyangiitis and inflammatory bowel disease.

7. EXAMPLES

7.1. Example 1; Construction of Alternative Format Antigen Binding Molecules Non-competing parental mAbs were selected for construction of alternative format bispecific ABMs for human TSLP, a protein belonging to the cytokine family and having a molecular weight of approximately 15-18 kDa (depending on state of glycosylation). These parental mAbs share a common light chain. All heterodimeric bispecific ABMs were constructed with the "knobs-into-holes" mutations in the Fc region to promote Fc heterodimer formation (Merchant et al., 1998, Nat Biotechnol. 16:677-681). For the Fc-Fab format (FIG. 1B and FIG. 2B), heavy chains were constructed by connecting VH-CH1 fragments to the C-terminal end of Fc using $(G4S)_n$ linkers (G4S is disclosed as SEQ ID NO:3), n=1-6. In the Clamp format (FIG. 3B), the inside Fab fragment is inert and does not bind to TSLP. This inert Fab fragment is replaced with a flexible long $(G4S)_n$ linker (G4S is disclosed as SEQ ID NO:3), n=6-8, in the Reach format (FIG. 3A). In the 2+2 Tandem Fab formats, all four Fab fragments are functional and can bind to the antigen (FIG. 3C-3D). The short linker between Fab fragments in the Clamp and 2+2 Tandem Fab formats is 2xG4S (SEQ ID NO:18) or 3xG4S (SEQ ID NO:4).

Similarly, non-competing parental mAbs were selected for construction of bispecific Fc-Fabs for human Ligand X. These parental anti-Ligand X mAbs share a common light chain.

For cell surface targets, Fc-Fabs were constructed in a similar way, using Fab fragments sharing a common light chain for bispecific Fc-Fabs, and using constant regions of either hIgG4 with reduced effector function (shown as hIgG4s) (U.S. Pat. No. 9,359,437B2) or hIgG1.

All antibodies using human IgG4 constant region contain a S228P (EU) substitution in the hinge region to minimize half antibody formation (Labrijn et al., 2009, Nat Biotechnol 27:767-771).

7.2. Example 2 Expression of Antigen Binding Molecules

All alternative format bispecific ABMs were expressed by transient transfection in Expi293F cells (Thermo Fisher Scientific). ABMs in Expi293F supernatant were purified using the ProteinMaker system (Protein BioSolutions, Gaithersburg, MD) with HiTrap rProteinA FF columns (GE Healthcare). After single step elution, the ABMs were neutralized, dialyzed into a final buffer of phosphate buffered saline (PBS) with 5% glycerol, aliquoted and stored at −80° C.

7.3. Example 3 Activity of Anti-hTSLP Bispecific ABMs in Bioassays

Purified anti-hTSLP bispecific ABMs were evaluated for their ability to inhibit hTSLP activity in a luciferase reporter assay. Baf3 cells stably expressing hIL-7R, hTSLPR, and STAT3-Luciferase reporter were plated at 40,000 cells/well in culture media without IL-3 and incubated overnight. For hTSLP dose response curve, 1:3 serially diluted hTSLP was added to each well, with the final concentration of hTSLP starting at 10 nM (FIG. 4A). To determine blocking activity of anti-hTSLP ABMs, a "Race format" blocking assay was used in which the ABMs and hTSLP were added to the reporter cells at the same time. Anti-hTSLP ABMs were serially diluted at 1:3, with final concentration of each antibody starting at 100 nM. Human TSLP was added to a constant concentration at approximately EC50 of the TSLP dose response curve. After a 5.5-hour incubation, the plates were equilibrated at room temperature for 15 minutes. 100 µl of One-Glo substrate (Promega) was added to each well. After 5-minute incubation at room temperature, luminescence was measured on Envision. Activity of three non-competing anti-hTSLP parental antibodies, 30206, 30217, and 30230, in the STAT3-luciferase reporter assay is shown in FIG. 4B. Three bispecific pairings using these parental mAbs were tested. Conventional hIgG4 bispecific antibodies showed similar blocking activity as the corresponding parental antibody combinations (FIG. 5). For each bispecific pairing, all alternative format bispecific ABMs showed better blocking activity than the conventional hIgG4 bispecific antibody (FIGS. 6A-6C). Overall, the best formats are Fc-Fab (with the hinge configuration shown in FIG. 13A) and 2+2 Tandem Fab_heterodimer for all bispecific pairings tested. IC$_{50}$ values of these ABMs are summarized in Table 5-1.

TABLE 5-1

IC50 values of TSLP ABMs in hTSLP blocking bioassay

| | |
|---|---|
| hTSLP EC50 [M] | 4.35E−11 |
| Constant hTSLP in Inhibition Assay | 100 pM |

| Anti-TSLP | IC50 in Race Format Inhibition Assay |
|---|---|
| 30206-IgG4 | 6.64E−10 |
| 30217-IgG4 | 9.83E−10 |
| 30230-IgG4 | >1.0E−07 |
| 30206x30217 bispecific | |
| Bispecific IgG4 | 1.86E−10 |
| Fc-Fab_2xG4S ("2xG4S" is disclosed as SEQ ID NO: 18) | 7.99E−11 |
| Fc-Fab_4xG4S ("4xG4S" is disclosed as SEQ ID NO: 19) | 6.48E−11 |
| Clamp | 1.27E−10 |
| Reach | 1.07E−10 |
| 2 + 2 Tandem Fab_het | 5.20E−11 |
| 2 + 2 Tandem Fab_ho | 1.08E−10 |
| 30206x30230 bispecific | |
| Bispecific IgG4 | 1.74E−09 |
| Fc-Fab_2xG4S ("2xG4S" is disclosed as SEQ ID NO: 18) | 1.54E−10 |
| Fc-Fab_4xG4S ("4xG4S" is disclosed as SEQ ID NO: 19) | 1.70E−10 |
| Clamp | 4.70E−10 |
| Reach | 1.28E−09 |
| 2 + 2 Tandem Fab_het | 2.33E−10 |
| 2 + 2 tandem Fab_ho | 5.18E−10 |
| 30217x30230 bispecific | |
| Bispecific IgG4 | 1.30E−09 |
| Fc-Fab_2xG4S ("2xG4S" is disclosed as SEQ ID NO: 18) | 7.32E−11 |
| Fc-Fab_4xG4S ("4xG4S" is disclosed as SEQ ID NO: 19) | 7.63E−11 |
| Clamp | 1.39E−10 |
| Reach | 3.82E−10 |
| 2 + 2 Tandem Fab_het | 1.15E−10 |
| 2 + 2 Tandem Fab_ho | 1.66E−10 |

7.4. Example 4 Size Analysis of In Vitro Complexes Formed Between Anti-hTSLP Bispecific Antibodies and Recombinant hTSLP by Asymmetric Flow Field-Flow Fractionation Coupled to Multi-Angle Laser Light Scattering (A4F-MALLS)

7.4.1. Overview

Size analysis of in vitro complexes formed between the following anti-TSLP ABMs identified in Table 5-2 and recombinant hTSLP (REGN4009) was performed using asymmetric flow field-flow fractionation coupled to multi-angle laser light scattering (A4F-MALLS): anti-TSLP parental Ab 30206 hIgG4, anti-TSLP parental Ab 30217 hIgG4, anti-TSLP parental Ab 30230 hIgG4, Fc-Fab_30206x30217-2xG4S ("2xG4S" is disclosed as SEQ ID NO:18), Fc-Fab_30217x30230-2xG4S ("2xG4S" is disclosed as SEQ ID NO:18), Clamp_30206x30217, Clamp_30217x30230, 2+2 Tandem Fab_het_30206x30217 and 2+2 Tandem Fab_het_30217x30230. In this study, the Fc-Fab ABMs had the hinge format shown in FIG. 13A.

7.4.2. Materials & Methods
7.4.2.1. Molecules

Table 5-2 below lists the molecules analyzed by A4F-MALLS and their alternative designation.

TABLE 5-2

Molecules analyzed in A4F-MALLS

| Designation | Description |
|---|---|
| REGN4009 | recombinant hTSLP.mmh |
| H4H30206P2 | anti-TSLP parental Ab 30206 hIgG4 |
| H4H30217P2 | anti-TSLP parental Ab 30217 hIgG4 |
| H4H30230P2 | anti-TSLP parental Ab 30230 hIgG4 |
| TS-FC1-eL1 | Fc-Fab_30206x30217-2xG4S ("2xG4S" is disclosed as SEQ ID NO: 18) |
| TS-FC6-eL2 | Fc-Fab_30217x30230-2xG4S ("2xG4S" disclosed as SEQ ID NO: 18) |
| TS-CL4-eL1 | Clamp_30206x30217 |
| TS-CL6-eL1 | Clamp_30217x30230 |
| TS-CL2-eL2 | 2 + 2 Tandem Fab_het_30206x30217 |
| TS-CL3-eL2 | 2 + 2 Tandem Fab_het_30217x30230 |

7.4.2.2. A4F-MALLS Mobile Phase Buffer

The mobile phase buffer (10 mM sodium phosphate, 500 mM sodium chloride, pH 7.0±0.1) was prepared by combining 1.4 g sodium phosphate monobasic monohydrate, 10.7 g sodium phosphate dibasic heptahydrate, and 500 mL 5 M sodium chloride; the solution was then brought to a volume to 5.0 L with HPLC grade water. The final measured pH of the buffer was 7.0. The mobile phase buffer was filtered (0.2 µm) before use.

7.4.2.3. AF-MALLS

The A4F-MALLS system was composed of an Eclipse™ 3+A4F Separation System coupled to an Agilent 1200 Series HPLC system equipped with a ultraviolet (UV) diode array detector, Wyatt Technology Dawn HELEOS® II laser light scattering instrument (LS), and an Optilab® T-rEX differential refractometer (RI) detector. The detectors were connected in series in the following order: UV-LS-RI. LS and RI detectors were calibrated according to instructions provided by Wyatt Technology.

Defined amounts of anti-TSLP mAb were each combined with REGN4009 (recombinant TSLP) and diluted in 1× DPBS, pH 7.4 to yield the equimolar ratio:1 µM anti-TSLP mAb:1 µM hTSLP. Equimolar combinations of each parental mAb were prepared as combo stock solutions, then each combo stock solution was mixed with an equimolar amount of hTSLP to yield final solution concentrations of 0.5 µM mAb1+0.5 µM mAb2+1 µM hTSLP. All samples were incubated at ambient temperature for 2 hours and maintained unfiltered at 4° C. prior to injection into an Eclipse™ short channel fitted with a W350 spacer foil (350 µm spacer thickness, 2.2 cm spacer width) and using a 10 kDa MWCO regenerated cellulose membrane. The channel was pre-equilibrated with the mobile phase buffer (10 mM sodium phosphate, 500 mM sodium chloride, pH 7.0±0.1), prior to the injection of each sample. Bovine serum albumin (BSA; 2 mg/mL; 10 µg sample load) was injected separately and included as a system suitability control.

The fractionation method consisted of four steps: injection, focusing, elution, and a channel "wash-out" step. The A4F-MALLS mobile phase buffer (10 mM sodium phosphate, 500 mM sodium chloride, pH 7.0±0.1) was used throughout the fractionation method. Each sample (7 µg) was injected at a flow rate of 0.2 mL/min for 1 min and subsequently focused for 3 min with a focus flow rate of 1.0 mL/min. The sample was eluted with a channel flow rate of 1.0 mL/min with the constant cross flow 3.0 mL/min for 15 min, followed by linear gradient cross flow from 3.0 mL/min to 0 mL/min over 5 min. Finally, the cross flow was held at 0 mL/min for an additional 5 min to wash out the channel. BSA was fractionated using the same parameter settings.

7.4.2.4. MALLS Data Analysis

Data were analyzed using ASTRA V software (version 5.3.4.14, Wyatt Technology). The data were fit to the equation that relates the excess scattered light to the solute concentration and weight-average molar mass, Mw (Kendrick et al., 2001, Anal Biochem. 299(2):136-46; Wyatt, 1993, Anal. Chim. Acta 272(1):1-40):

$$\frac{K^*c}{R(\theta,c)} = \frac{1}{MwP(\theta)} + 2A_2c \qquad \text{Equation 1}$$

where c is the solute concentration, $R(f,c)$ is the excess Raleigh ratio from the solute as a function of scattering angle and concentration, Mw is the molar mass, $P(\theta)$ describes the angular dependence of scattered light (~1 for particles with radius of gyration <50 nm), A2 is the second virial coefficient in the expansion of osmotic pressure (which can be neglected since measurements are performed on dilute solutions) and $$K^* = \frac{4\pi^2 n_0^2}{N_A \lambda_0^4}\left(\frac{dn}{dc}\right)^2 \qquad \text{Equation 2}$$

where $n_0$ represents the solvent refractive index, $N_A$ is Avogadro's number, $\lambda 0$ is the wavelength of the incident light in a vacuum, and dn/dc represents the specific refractive index increment for the solute.

The molar mass of BSA monomer served to evaluate the calibration constants of the light scattering and differential refractive index detectors during data collection (system suitability check). The relative standard deviation (% RSD) of the average molar mass of BSA determined from the UV and RI detectors was ≤5.0%.

The normalization coefficients for the light scattering detectors, inter-detector delay volume and band broadening terms were calculated from the BSA chromatograms collected for the A4F-MALLS condition employed. These values were applied to the data files collected for all the other samples to correct for these terms.

The dn/dc value and the extinction coefficient at 215 nm or 280 nm (corrected for glycosylation) were experimentally determined using the protein conjugate analysis provided in the Astra software. The corrected extinction coefficient and do/dc value was used to analyze all protein-protein complex samples.

7.4.3. Results

A4F-MALLS was used to assess the relative size distribution of complexes formed between several anti-hTSLP ABMs and hTSLP. The theoretical molar mass and predicted stoichiometry of potential ABM complexes with hTSLP are shown in Tables 5-3 and 5-4:

TABLE 5-3

Theoretical Molar Mass of Complexes of
parental mAbs and Fc-Fab format with TSLP

| Ratio of ABM:TSLP in Complex | Theoretical Molar Mass (kDa) |
|---|---|
| 1:0 | 152 |
| 0:1 | 25 |
| 1:1 | 177 |
| 1:2 | 202 |
| 2:1 | 329 |
| 2:2 | 354 |

TABLE 5-4

Theoretical Molar Mass of Complexes of
Clamp and 2 + 2 Tandem Fabs with TSLP

| Ratio of ABM:TSLP Complex | Theoretical Molar Mass (kDa) |
|---|---|
| 1:0 | 254 |
| 0:1 | 25 |
| 1:1 | 279 |
| 1:2 | 304 |
| 2:1 | 533 |
| 2:2 | 558 |

As expected, each individual parental anti-TSLP mAb (H4H30206P2, H4H30217P2, H4H30230P2) formed canonical 1:1 and 1:2 complexes with hTSLP when combined at equimolar ratios (Peak 3, ~179 kDa, FIG. 7, Table 5-5).

However, when different combinations of two parental mAbs (H4H30206P2+H4H30217P2 and H4H30217P2+H4H30230P2) were mixed with equimolar amounts of hTSLP, a heterogeneous distribution of heteromeric complexes was observed indicating that each parental mAb can engage the same molecule of hTSLP to form extended antibody-antigen lattices in a process termed "paper-dolling" (FIG. 8). In these samples, a distinct peak (Peak 4) having a molar mass of approximately 342 kDa was observed, followed by a series of broad, poorly-resolved species (Peak 5) having a wide molar mass distribution ranging from ~650-5000 kDa. Based on the calculated molar masses of the individual components, peak 4 likely represents a 2:2 mAb:hTLSP complex, whereas peak 5 corresponds to a heterogeneous distribution of higher order heteromeric complexes composed of ≥4 molecules of mAb coordinating ≥3 molecules of hTSLP (Table 5-6).

TABLE 5-5

Summary of Molar Masses and Retention
Time of Human TSLP Complexes with Parental Abs

| Sample | Molar Ratio (mol:mol) | Peak 1 Free hTSLP Rt, min | Peak 1 Free hTSLP Mw, kDa | Peak 2 Free mAb Rt, min | Peak 2 Free mAb Mw, kDa | Peak 3 [mAb]1:[hTSLP] 1-2 Complex Rt, min | Peak 3 [mAb]1:[hTSLP] 1-2 Complex Mw, kDa | Peak 4 [mAb]2:[hTSLP] 1-2 Complex Rt, min | Peak 4 [mAb]2:[hTSLP] 1-2 Complex Mw, kDa | Peak 5 Higher Order Complexes Rt, min | Peak 5 Higher Order Complexes Mw, kDa |
|---|---|---|---|---|---|---|---|---|---|---|---|
| hTSLP | — | 7.6 | 25.2 | ND | ND | ND | ND | ND | ND | ND | ND |
| H4H30217P2 | — | ND | ND | 9.8 | 151.7 | ND | ND | ND | ND | ND | ND |
| H4H30206P2: hTSHLP | 1:1 | ND | ND | 10.0 | 155.1 | 10.5 | 177.6 | ND | ND | ND | ND |
| H4H30217P2: hTSLP | 1:1 | ND | ND | 10.0 | 147.5 | 10.5 | 169.7 | ND | ND | ND | ND |
| H4H30230P2: hTSLP | 1:1 | ND | ND | 10.2 | 157.1 | 10.4 | 181.4 | ND | ND | ND | ND |

$R_t$: Retention Time; $M_w$: weight average molar mass; NA: Not Applicable; min: minutes; kDa: kiloDaltons.

TABLE 5-6

Summary of Molar Masses and Retention Time of Human TSLP Complexes with Parental Ab Combinations

| Sample | Molar Ratio (mol:mol) | Peak 1 Free hTSLP Rt, min | Peak 1 Free hTSLP Mw, kDa | Peak 2 Free mAb Rt, min | Peak 2 Free mAb Mw, kDa | Peak 3 [mAb]1:[hTSLP] 1-2 Complex Rt, min | Peak 3 [mAb]1:[hTSLP] 1-2 Complex Mw, kDa | Peak 4 [mAb]2:[hTSLP] 1-2 Complex Rt, min | Peak 4 [mAb]2:[hTSLP] 1-2 Complex Mw, kDa | Peak 5 Higher Order Heteromeric Complexes Rt, min | Peak 5 Higher Order Heteromeric Complexes Mw, kDa |
|---|---|---|---|---|---|---|---|---|---|---|---|
| hTSLP | — | 7.6 | 25.2 | ND | ND | ND | ND | ND | ND | ND | ND |
| H4H30217P2 | — | ND | ND | 9.8 | 151.7 | ND | ND | ND | ND | ND | ND |
| H4H30206P2: H4H30217P2: hTSLP | 0.5:0.5:1 | ND | ND | ND | ND | ND | ND | 12.4 | 329 | 15.3 | ~650-5000 |
| H4H30217P2: H4H30230P2: hTSLP | 0.5:0.5:1 | ND | ND | ND | ND | ND | ND | 12.0 | 345.2 | 15.1 | ~800-5000 |

Rt: Retention Time; M$_w$: weight average molar mass; NA: Not Applicable; min: minutes; kDa; kiloDaltons.

In addition, complexes formed between hTSLP and a set of novel bispecific antibodies (TS-FC1-eL1, TS-FC6-eL2) having two unique Fab domains, derived from the same parental mAb combinations tested above, attached to the C-terminus of a human Fc domain (Fc-Fab) were also examined. Unlike the results obtained with the parental mAb combinations, each Fc-Fab bispecific antibody (bsAb) predominantly formed a discrete 1:1 complex with hTLSP (peak 3, ~178 kDa; FIG. 9, Table 5-7) with little to no additional higher order complexes ("paper-dolling") observed.

This suggests that both Fab domains on each of the Fc-Fab bsAbs prefer to engage the same molecule of hTSLP forming a monogamous, bivalent interaction and thus precluding the process of "paper-dolling".

Two additional sets of the ABM formats of the disclosure, having either an extra exterior Fab domain on each binding arm (2+2 Tandem Fabs; TS-CL2-eL2, TS-CL3-eL2) or an extra interior, non-binding Fab on each arm (Clamps; TS-CL4-eL1, TS-CL6-eL1), were also evaluated for complex formation with hTSLP in a similar manner. In general, each Clamp ABM appeared to form a certain degree of 1:1

TABLE 5-7

Summary of Molar Masses and Retention Time of Human TSLP Complexes with Fc-Fabs

| Sample | Molar Ratio (mol:mol) | Peak 1 Free hTSLP Rt, min | Peak 1 Free hTSLP Mw, kDa | Peak 2 Free bsAb Rt, min | Peak 2 Free bsAb Mw, kDa | Peak 3 [bsAb]1:[hTSLP] 1-2 Complex Rt, min | Peak 3 [bsAb]1:[hTSLP] 1-2 Complex Mw, kDa | Peak 4 [bsAb]2:[hTSLP] 1-2 Complex Rt, min | Peak 4 [bsAb]2:[hTSLP] 1-2 Complex Mw, kDa | Peak 5 Higher Order Complexes Rt, min | Peak 5 Higher Order Complexes Mw, kDa |
|---|---|---|---|---|---|---|---|---|---|---|---|
| hTSLP | — | 7.6 | 25.2 | ND | ND | ND | ND | ND | ND | ND | ND |
| TS-FC1-eL1 | — | ND | ND | 9.8 | 156.8 | ND | ND | ND | ND | ND | ND |
| TS-FC6-eL2 | — | ND | ND | 9.8 | 148.1 | ND | ND | ND | ND | ND | ND |
| TS-FC1-eL1:TSLP | 1:1 | ND | ND | ND | ND | 10.1 | 175.7 | 11.0 | 357.7 | ND | ND |
| TS-FC6-eL2:TSLP | 1:1 | ND | ND | ND | ND | 10.2 | 176.1 | 11.1 | 361.4 | ND | ND |

Rt: Retention Time; M$_w$: weight average molar mass; NA: Not Applicable; min: minutes; kDa: kiloDaltons.

complex with hTSLP (peak 3, ~272 kDa; FIG. 10, Table 5-8); however, a broad, heterogeneous distribution of higher order complexes (peak 5, ~650-7000 kDa; FIG. 10, Table 5-8), indicative of varying levels of "paper-dolling", could also be detected in these samples.

blocking activity was seen with Fc-Fabs with linker length between 2-5xG4S (G4S is disclosed as SEQ ID NO:3). Different hinge formats were also evaluated using the 30217×30230 bispecific Fc-Fab as an example (FIG. 13). In Format #1, the hinge sequence is at the N-terminal end of Fc-Fab, as it occurs in the native hIgG4 sequence, with S228P (EU) substitution (FIG. 13A). In Format #2, the same hinge sequence is removed from the N-terminal end of Fc-Fab and inserted between the C-terminus of the Fc CH3 domain and the $(G4S)_n$ linker (G4S is disclosed as SEQ ID NO:3) (FIG. 13B). In Format #3, the hinge is also located between the CH3 domain and the $(G4S)_n$ linker (G4S is disclosed as SEQ ID NO:3). However, the upper hinge sequence is replaced with G4S sequence (G4S is disclosed as SEQ ID NO:3) (FIG. 13C). All three hinge formats were

TABLE 5-8

Summary of Molar Masses and Retention Time of Human TSLP Complexes with Clamps

| Sample | Molar Ratio (mol: mol) | Peak 1 Free hTSLP | | Peak 2 Free bsAb | | Peak 3 [bsAb]1:[hTSLP] 1-2 Complex | | Peak 4 [bsAb]2:[hTSLP] 1-2 Complex | | Peak 5 Higher Order Complexes | |
|---|---|---|---|---|---|---|---|---|---|---|---|
| | | Rt, min | Mw, kDa | Rt, min | Mw, kDa | Rt, min | Mw, kDa | Rt, min | Mw, kDa | Rt, min | Mw, kDa |
| TSLP | — | 7.6 | 25.2 | ND | ND | ND | ND | ND | ND | ND | ND |
| TS-CL4-eL1 | — | ND | ND | 11.0 | 244.3 | ND | ND | ND | ND | ND | ND |
| TS-CL6-eL1 | — | ND | ND | 11.3 | 255.0 | ND | ND | ND | ND | ND | ND |
| TS-CL4-eL1:TSLP | 1:1 | ND | ND | ND | ND | 10.8 | 264.4 | 13.4 | 491.6 | 15.0 | ~650-7000 |
| TS-CL6-eL1:TSLP | 1:1 | ND | ND | ND | ND | 11.4 | 280.4 | 13.8 | 533.9 | 15.1 | ~650-3000 |

Rt: Retention Time; $M_w$: weight average molar mass; NA: Not Applicable; min: minutes; kDa: kiloDaltons.

Finally, when mixed with equimolar amounts of hTLSP, each 2+2 Tandem Fab bsAb displayed the highest propensity for "paper-dolling" of all the novel bispecific formats tested. In these samples, a distinct peak consistent with free 2+2 Tandem Fab bsAb (peak 2; ~255 kDa) could be observed followed by a series of broad, poorly-resolved peaks representative of a heterogeneous distribution of increasingly larger species terminating in very large complexes with molar masses exceeding ten (10) megadaltons (peaks 4-5, ~500-14,000 kDa; FIG. 11, Table 5-9).

TABLE 5-9

Summary of Molar Masses and Retention Time of Human TSLP Complexes with 2 + 2 Tandem Fabs

| Sample | Molar Ratio (mol: mol) | Peak 1 Free hTSLP | | Peak 2 Free bsAb | | Peak 3 [bsAb]1:[hTSLP] 1-2 Complex | | Peak 4 [bsAb]2:[hTSLP] 1-2 Complex | | Peak 5 Higher Order Complexes | |
|---|---|---|---|---|---|---|---|---|---|---|---|
| | | Rt, min | Mw, kDa | Rt, min | Mw, kDa | Rt, min | Mw, kDa | Rt, min | Mw, kDa | Rt, min | Mw, kDa |
| hTSLP | — | 7.6 | 25.2 | ND | ND | ND | ND | ND | ND | ND | ND |
| TS-CL2-eL2 | — | ND | ND | 11.4 | 256.3 | ND | ND | ND | ND | ND | ND |
| TS-CL3-eL2 | — | ND | ND | 11.1 | 260.3 | ND | ND | ND | ND | ND | ND |
| TS-CL2-eL2:hTSLP | 1:1 | ND | ND | 11.0 | 255.0 | ND | ND | 13.7 | 532.1 | 14.6 | ~700-14,000 |
| TS-CL3-eL2:hTSLP | 1:1 | ND | ND | 10.9 | 248.9 | ND | ND | 13.8 | 574.7 | 14.8 | ~700-10,000 |

7.5. Example 5 Optimization of Linkers in Anti-hTSLP Fc-Fab

A series of anti-hTSLP 30217×30230 bispecific Fc-Fabs was constructed using different linkers, from a 2 amino acid GS linker, to a 30 amino acid 6xG4S linker (SEQ ID NO:38). Activity of these Fc-Fabs was evaluated in the hTSLP STAT3-Luciferase reporter assay (FIG. 12). The best combined with either 1xG4S (SEQ ID NO:3) or 4xG4S linker (SEQ ID NO:19) to construct anti-hTSLP 30217×30230 bispecific Fc-Fabs. The activity of these Fc-Fabs was evaluated in the hTSLP STAT3-Luciferase reporter assay (FIG. 13D). For Fc-Fabs with 4xG4S linker (SEQ ID NO:19), the different hinge formats had minor impact on their TSLP blocking activity, with hinge Format #1 showing the best activity. For Fc-Fabs with 1xG4S linker (SEQ ID NO:3), hinge Format #1 had 5 to 10 fold better IC50 than the other two hinge formats.

7.6. Example 6 Biacore Analysis of Fc-Fab Binding to Fc Receptors

Equilibrium dissociation constants ($K_D$ values) for different anti-TSLP Fc-Fab antibodies binding to purified recombinant human FcγR and FcRn receptor subtypes from human were determined using real-time surface plasmon resonance-based MASS-2 (Bruker)/Biacore 3000 (GE Healthcare) biosensor. The Fc-Fab constructs assayed were TSLP 30206×30217 Fc_Fab 2xG4S ("2xG4S" is disclosed as SEQ ID NO:18) (also referred to as REGN8759) and TSLP 30230×30217 Fc_Fab 2xG4S ("2xG4S" is disclosed as SEQ ID NO:18) (also referred to as REGN7860), together with anti-FeID1(-)-IgG1 and IgG4 isotype controls (referred to as REGN1932 and REGN1945, respectively). The Fc receptors assayed were human FcγRIIA (H131)-myc.6× His, human FcγRIIA (R167)-10× His, human FcγRIIB-myc.6× His, human FcγRIIIA (F176)-myc.6× His, human FcγRIIIB-mmh, human FcRn-mmh, and human FcγRI-6× His.

7.6.1. Materials & Methods

All binding studies were performed in 10 mM HEPES, 150 mM NaCl, 3 mM EDTA, and 0.05% v/v Surfactant Tween-20, pH 7.4 (HBS-ET) or PBS, 0.05% v/v Surfactant Tween-20, pH6.0 (PBS-T-pH6.0) running buffer at 25° C. The MASS-2/Biacore 3000 CM5 sensor surface was derivatized by amine coupling with either mouse anti-penta-histidine monoclonal antibody ("penta-histidine" is disclosed as SEQ ID NO:34) (GE Healthcare) or anti-myc monoclonal antibody (REGN642) to capture FcγR and FcRn receptors extracellular domain expressed with a C-terminal myc-myc-hexahistidine ("hexahistidine" is disclosed as SEQ ID NO:35) or histidine regions. Binding studies were performed on different anti-TSLP Fc-Fab and wild-type Fc iso-type control. Different concentrations of anti-TSLP Fc-Fab (ranging from 5 μM to 0.3125 μM, 2-fold dilutions) prepared in HBS-ET or PBS-T pH 7.4 and pH 6.0 running buffer were injected over the FcγR and FcRn receptors captured surface at a flow rate of 50 μL/min. Association of all anti-TSLP Fc-Fabs to each of the captured FcγR and FcRn receptors was monitored for 1.5-2 minutes and their dissociation in HBST running buffer was monitored for 10 minutes. At the end of each cycle, the FcγR and FcRn receptors capture surface was regenerated using either 20-30 sec injection of 10 mM glycine-HCl pH 1.5 for mouse anti-penta-histidine monoclonal antibody ("penta-histidine" is disclosed as SEQ ID NO:34) or anti-myc monoclonal antibody. All the binding kinetics experiments were performed at 25° C.

7.6.2. Data Analysis

Binding dissociation equilibrium constant (KD) and dissociative half-life (t½) were calculated from the kinetic rates as:

$$KD(M) = kd/ka \text{ and } t\frac{1}{2}(min) = \ln2/(60 \times kd)$$

7.6.3. Results

Binding kinetics parameters for different anti-TSLP Fc-Fab and control antibody binding to different FcγR and FcRn receptors of the disclosure at 25° C. are shown in Tables 5-10 and 5-11, respectively. In Table 5-10, NT means Not Tested and IC means Inconclusive. In Table 5-11, NB means No binding and IC means Inconclusive.

TABLE 5-10

Binding Kinetics parameters of FcγR receptor binding to anti-TSLP Fc-Fab and isotype control mAbs at 25° C. in HBS-ET pH7.4

| | | | REGN8759 | | | | | REGN8760 | | | | |
|---|---|---|---|---|---|---|---|---|---|---|---|---|
| Capture Surface | FcRg. Mmh Capture (RU) | Highest Conc. Tested | REGN 8759 Bound (RU) | Ka (1/Ms) | kd (1/s) | KD (M) | t½ (min) | REGN 8760 Bound (RU) | ka (1/Ms) | kd (1/s) | KD (M) | t½ (min) |
| Human FcγRI-6xHis | 344.9 ± 4.1 | 100 nM | 161.1 | 7.03E+05 | 3.77E−03 | 5.37E−09 | 3.1 | 161.1 | 5.54E+05 | 4.54E−03 | 8.20E−09 | 2.5 |
| | | | | Steady-State Kinetics | | Steady-State Kinetics | | | Steady-State Kinetics | | Steady-State Kinetics | |
| Human FcγRIIA (H131)-myc.6xHis | 346.1 ± 1.6 | 5 uM | 42.4 | | | 1.56E−05 | | 42.4 | | | 2.11E−05 | |
| Human FcγRIIA (R167)-10xHis | 323.2 ± 3.6 | 5 uM | 59.6 | | | 1.23E−05 | | 59.6 | | | 1.08E−05 | |
| Human FcγRIIB-myc.6xHis | 353.1 ± 2.8 | 5 uM | 98.5 | | | 3.80E−06 | | 98.5 | | | 6.20E−06 | |
| Human FcγRIIIA (F176)-myc.6xHis | 201.4 ± 0.8 | 5 uM | 18.2 | | | 5.50E−06 | | 18.2 | | | 3.40E−05 | |
| Human FcγRIIIA (V176)-myc.6xHis | NT | NT | | | | NT | | | | | NT | |
| Human FcγRIIIB-10xHis | 192.7 ± 15.8 | 5 uM | 38.9 | | | IC | | 38.9 | | | IC | |

TABLE 5-10-continued

Binding Kinetics parameters of FcγR receptor binding to anti-TSLP Fc-Fab and isotype control mAbs at 25° C. in HBS-ET pH7.4

| Surface Description | FcRg. Mmh Capture (RU) | Highest Conc. Tested | REGN1932 Bound (RU) | Ka (1/Ms) | kd (1/s) | KD (M) | t½ (min) | REGN 1945 Bound (RU) | ka (1/Ms) | kd (1/s) | KD (M) | t½ (min) |
|---|---|---|---|---|---|---|---|---|---|---|---|---|
| Human FcγRI-6xHis | 344.9 ± 4.1 | 100 nM | 183.1 | 4.38E+05 | 7.63E−04 | 1.74E−09 | 15.1 | 130.9 | 4.33E+05 | 2.33E−03 | 5.39E−09 | 4.9 |
| Human FcγRIIA (H131)-myc.6xHis | 346.1 ± 1.6 | 5 uM | 190.0 | Steady-State Kinetics | | 1.07E−06 | Steady-State Kinetics | 60.1 | Steady-State Kinetics | | 1.17E−05 | Steady-State Kinetics |
| Human FcγRIIA (R167)-10xHis | 323.2 ± 3.6 | 5 uM | 167.8 | | | 9.50E−07 | | 86.1 | | | 5.20E−06 | |
| Human FcγRIIB-myc.6xHis | 353.1 ± 2.8 | 5 uM | 141.5 | | | 2.50E−06 | | 105.8 | | | 4.30E−06 | |
| Human FcγRIIA (F176)-myc.6xHis | 201.4 ± 0.8 | 5 uM | 120.1 | | | 1.47E−06 | | 9.5 | | | 7.00E−05 | |
| Human FcγRIIA (V176)-myc.6xHis | NT | NT | NT | | | NT | | NT | | | NT | |
| Human FcγRIIIB-10xHis | 192.7 ± 15.8 | 5 uM | 120.3 | | | 3.00E−06 | | −0.7 | | | NB | |

TABLE 5-11

Binding Kinetics parameters of FcRn receptor binding to anti-TSLP Fc-Fab and isotype control mAbs at 25° C. in PBS-T pH 7.4 and pH6.0

| mAb Tested | Construct | Running Buffer: PBSP, pH 7.4 | | | | | | Running Buffer: PBSP, pH 6.0 | | | | | |
|---|---|---|---|---|---|---|---|---|---|---|---|---|---|
| | | hFcRn. mmh Capture (RU) | 5 uM mAb Bound (RU) | ka (1/Ms) | kd (1/s) | KD (M) | t½ (min) | hFcRn. mmh Capture (RU) | 5 uM mAb Bound (RU) | ka (1/Ms) | kd (1/s) | KD (M) | t½ (min) |
| REGN8759 | Fc-Fab-hIgG4 | 390.7 ± 18.8 | −16.2 | NB | NB | NB | NB | 121.4 ± 5.8 | 45.6 | 4.91E+04 | 1.09E−01 | 2.22E−06 | 0.1 |
| REGN8760 | Fc-Fab-hIgG4 | 331.3 ± 14.1 | −11.6 | NB | NB | NB | NB | 105 ± 3.6 | 42.5 | 6.65E+04 | 1.53E−01 | 2.30E−06 | 0.1 |
| REGN1932 | hIgG1 | 286.3 ± 9.9 | 9.1 | IC | IC | IC | IC | 93 ± 2.4 | 80.3 | 1.12E+05 | 1.18E−01 | 1.06E−06 | 0.1 |
| REGN1945 | hIgG4 | 252.8 ± 8.4 | 8.0 | IC | IC | IC | IC | 82 ± 2.4 | 65.0 | 6.16E+04 | 1.08E−01 | 1.75E−06 | 0.1 |

7.7. Example 7 Pharmacokinetic Assessment of Anti-TSLP Fc-Fab Bispecific Antibodies in Wild Type Mice

7.7.1. Overview

An evaluation of the pharmacokinetic profiles of two anti-TSLP Fc-Fab bispecific binding molecules, (1) 30206× 30217 IgG4 Fc-Fab bispecific with a 2xG4S linker (SEQ ID NO:18) also referred to as REGN8759, and (2) 30230× 30217 IgG4 Fc-Fab bispecific with a 2xG4S linker (SEQ ID NO:18) also referred to as REGN 8760, in comparison to an anti-fel d 1 IgG4 isotype control, REGN1945, an irrelevant conventional bispecific IgG4 control, H4H21237D and a hFcγ homodimer, REGN1627, was conducted in C57BL/6 Wild-Type (WT) mice.

7.7.2. Materials & Methods

Cohorts contained 5 mice per tested antibody. Mice dosed with REGN8759, REGN8760, REGN1945, and H4H21237D received a single sub-cutaneous (SC) 1 mg/kg dose. Mice dosed with the hFcγ homodimer, REGN1627, received a normalized SC dose based on molar equivalence (0.35 mg/kg) to the other antibodies in the study. Blood samples were collected at 6 hours and 1, 2, 3, 4, 7, 10, 14, and 21-days post dosing. Blood was processed into serum and frozen at −80° C. until analyzed. The total and functional serum concentrations of REGN8759 and REGN8760 and the total serum concentrations of REGN1945, H4H21237D, and REGN1627 were measured using the GyroLab xPlore platform (Gyros).

Gyros technology uses an affinity flow-through format for automated immunoassays with laser-induced fluorescence detection. Samples are loaded onto a compact disc (CD) that contains multiple radially arranged nanoliter-scale affinity capture columns. Liquid flow is controlled by centrifugal and capillary forces.

For the measurement of total and functional REGN8759, REGN8760, and for measurement of total REGN1945, H4H21237D and REGN1627 in serum, 100 µg/mL of a test article or control article-specific biotinylated capture reagent (Table 5-11) was added onto a Gyrolab Bioaffy 200 CD containing affinity columns preloaded with streptavidin-coated beads (Dynospheres). The standards used for calibration (Table 5-11) were run at concentrations ranging from 0.488-2000 ng/mL. Serial dilutions of serum samples were prepared in phosphate buffered saline (PBS) containing 0.5% bovine serum albumin (BSA). Serial dilutions of standards were prepared in PBS+0.5% BSA containing 2% normal mouse serum (NMS). Singlets of serum samples diluted at 1:50 and duplicates of standards were added onto the capture reagent-coated affinity columns at room temperature. Captured human IgG was detected using Alexa-647-conjugated mouse anti-human IgG1/hIgG4 monoclonal antibody (REGN2567@ 0.5 µg/mL) diluted in Rexxip F buffer (Gyros); the resultant fluorescent signal was recorded in response units (RU) by the GyroLab xPlore instrument. The respective assay's lower limit of quantitation (LLOQ) was defined as the lowest concentration on the standard curve for which a quality control (QC) sample was determined to consistently deviate less than 25% from the expected concentration (Table 5-12). Sample concentrations were determined by interpolation from a standard curve that was constructed using a 4-parameter logistic curve fit in Gyrolab Evaluator Software. Average concentrations from 2 replicate experiments were used to calculate final concentrations.

TABLE 5-12

Reagents used in PK analysis

| Detected human IgG | Capture Reagent | Standard | LLOQ |
|---|---|---|---|
| REGN8759 (Total) | Biotin-conjugated goat anti-human IgG, Fcγ fragment specific pAb | REGN8759 | 0.195 µg/mL |
| REGN8760 (Total) | | REGN8760 | 0.195 µg/mL |
| REGN1945 (Total) | | REGN1945 | 0.0488 µg/mL |
| H4H21237D (Total) | | H4H21237D | 0.391 µg/mL |
| REGN1627 (Total) | | REGN1627 | 0.195 µg/mL |
| REGN8759 (Functional) | Biotin-conjugated hTSLP-mFc (REGN4010) | REGN8759 | 0.391 µg/mL |
| REGN8760 (Functional) | | REGN8760 | 0.391 µg/mL |

PK parameters were determined by non-compartmental analysis (NCA) using Phoenix®WinNonlin® software Version 6.3 (Certara, L. P., Princeton, NJ) and an extravascular dosing model. Using the respective mean concentration values (total drug) for each antibody, all PK parameters including observed maximum concentration in serum ($C_{max}$), estimated half-life observed ($t_{1/2}$), area under the concentration curve versus time up to the last measurable concentration ($AUC_{last}$) and antibody clearance rates (CI) were determined using a linear trapezoidal rule with linear interpolation and uniform weighting.

7.7.3. Results

Following 1 mg/kg SC administration of anti-TSLP Fc-Fab bispecific antibodies and controls in WT mice, REGN8759 and REGN8760 exhibited similar maximum total concentrations of drug in serum ($C_{max}$=11.7 and 10.7 µg/mL, respectively), while the hIgG4 isotype control, REGN1945, the irrelevant conventional bispecific IgG4 control, H4H21237D, and the hFcγ homodimer, REGN1627 ($C_{max}$ dose normalized) had approximately 1.5-2-fold lower concentrations ($C_{max}$=8.2, 7.8 and 6.4 µg/mL, respectively).

In addition, REGN8759, REGN8760, REGN1945, and H4H21237D all exhibited similar half-life values ($T_{1/2}$=12.1, 12.2, 10.9 and 11.2 days, respectively), while REGN1627 had a faster half-life as compared to all other tested drugs (6.4 days). Additionally, REGN8759 and REGN8760 exhibited better drug exposure ($AUC_{last}$=131, and 122 (d*µg/mL)/(mg/kg), respectively) and slower clearance rates (CI=5.2, 5.5 mL/day/kg, respectively) when compared to REGN1945, H4H21237D, and REGN1627 (AUClast=88.0, 84.1, and 19.7, respectively, $AUC_{last}$/D=56.2 (d*µg/mL)/(mg/kg), respectively; CI=9.5, 8.2, and 45.2 mL/day/kg, respectively).

Furthermore, total and functional TSLP-binding concentrations of REGN8759 and REGN8760 were comparable at all timepoints tested, suggesting that these Fc-Fab molecules are still intact at 21 days. Overall, PK profiles are similar or better for REGN8759 and REGN8760 as compared to hIgG4 isotype control, an irrelevant conventional bispecific IgG4 control, or hFcγ homodimer.

A summary of the data for total and functional REGN8759 and REGN8760 drug concentrations and total REGN1945, H4H21237D, and REGN1627 drug concentrations are summarized in Table 5-13, mean PK parameters are described in Table 5-14 and mean total antibody concentrations versus time are shown in FIG. 14 and FIG. 15.

TABLE 5-13

Mean Concentrations (± SEM) of Total and Functional Drug Concentrations in Serum Following a Single 1 mg/kg (or Dose Equivalent) Subcutaneous Injection of REGN8759 or REGN8760 Anti-TSLP Antibodies or Controls in WT Mice Over Time

| | | Total Drug Concentration | | Functional Drug Concentration | |
|---|---|---|---|---|---|
| | | 1 mg/kg (0.345 mg/kg dose normalized) | | | |
| Antibody | Time (d) | Mean (µg/mL) | +/− SEM | Mean (µg/mL) | +/− SEM |
| REGN8759 | 0.25 | 7.3 | 0.4 | 6.8 | 0.2 |
| | 1 | 11.6 | 0.2 | 11.5 | 0.3 |
| | 2 | 10.7 | 0.6 | 9.8 | 0.4 |
| | 3 | 9.6 | 0.5 | 8.9 | 0.6 |
| | 4 | 8.4 | 0.4 | 8.1 | 0.4 |
| | 7 | 7.2 | 0.4 | 7.1 | 0.4 |
| | 10 | 5.7 | 0.6 | 5.2 | 0.4 |
| | 14 | 4.6 | 0.4 | 4.2 | 0.4 |
| | 21 | 3.8 | 0.3 | 3.3 | 0.2 |
| REGN8760 | 0.25 | 6.6 | 0.4 | 6.2 | 0.2 |
| | 1 | 10.7 | 0.3 | 10.0 | 0.2 |
| | 2 | 9.8 | 0.3 | 8.7 | 0.3 |
| | 3 | 8.8 | 0.4 | 7.9 | 0.6 |
| | 4 | 8.2 | 0.3 | 7.7 | 0.4 |
| | 7 | 6.6 | 0.3 | 5.9 | 0.4 |
| | 10 | 5.1 | 0.5 | 5.0 | 0.2 |
| | 14 | 4.4 | 0.3 | 3.7 | 0.1 |
| | 21 | 3.5 | 0.2 | 3.0 | 0.2 |

TABLE 5-13-continued

Mean Concentrations (± SEM) of Total and Functional Drug Concentrations in Serum Following a Single 1 mg/kg (or Dose Equivalent) Subcutaneous Injection of REGN8759 or REGN8760 Anti-TSLP Antibodies or Controls in WT Mice Over Time

| | | Total Drug Concentration | | Functional Drug Concentration | |
|---|---|---|---|---|---|
| | | 1 mg/kg (0.345 mg/kg dose normalized) | | | |
| Antibody | Time (d) | Mean (µg/mL) | +/− SEM | Mean (µg/mL) | +/− SEM |
| REGN1945 | 0.25 | 5.2 | 0.5 | NT | NT |
| | 1 | 8.9 | 0.9 | NT | NT |
| | 2 | 8.6 | 1.3 | NT | NT |
| | 3 | 8.1 | 0.7 | NT | NT |
| | 4 | 7.1 | 0.8 | NT | NT |
| | 7 | 5.6 | 0.4 | NT | NT |
| | 10 | 4.2 | 0.5 | NT | NT |
| | 14 | 3.4 | 0.4 | NT | NT |
| | 21 | 2.6 | 0.4 | NT | NT |
| H4H21237D | 0.25 | 4.1 | 0.5 | NT | NT |
| | 1 | 7.8 | 0.3 | NT | NT |
| | 2 | 7.2 | 0.2 | NT | NT |
| | 3 | 6.5 | 0.1 | NT | NT |
| | 4 | 5.6 | 0.3 | NT | NT |
| | 7 | 4.5 | 0.2 | NT | NT |
| | 10 | 3.7 | 0.1 | NT | NT |
| | 14 | 2.8 | 0.2 | NT | NT |
| | 21 | 2.4 | 0.1 | NT | NT |
| REGN1627 | 0.25 | 1.3 | 0.1 | NT | NT |
| | 1 | 2.2 | 0.03 | NT | NT |
| | 2 | 2.0 | 0.04 | NT | NT |
| | 3 | 1.9 | 0.04 | NT | NT |
| | 4 | 1.6 | 0.1 | NT | NT |
| | 7 | 1.1 | 0.04 | NT | NT |
| | 10 | 0.8 | 0.04 | NT | NT |
| | 14 | 0.5 | 0.01 | NT | NT |
| | 21 | 0.3 | 0.01 | NT | NT |

TABLE 5-14

Summary of Pharmacokinetic Parameters

| | | 1 mg/kg (0.345 mg/kg dose normalized) | | | | |
|---|---|---|---|---|---|---|
| Parameter | Units | REGN8759 | REGN8760 | REGN1945 | H4H21237D | REGN1627 |
| $C_{max}$ | µg/mL | 11.7 ± 0.17 | 10.7 ± 0.33 | 8.2 ± 1.6 | 7.8 ± 0.3 | 2.2 ± 0.03 |
| $C_{max\_D}$ | (ug/mL)/kg | 11.7 ± 0.17 | 10.7 ± 0.33 | 8.2 ± 1.6 | 7.8 ± 0.3 | 6.4 ± 0.086 |
| $T_{1/2}$ | D | 12.1 ± 0.75 | 12.2 ± 0.58 | 10.9 ± 0.56 | 11.2 ± 0.5 | 6.4 ± 0.094 |
| $AUC_{last}$ | d * µg/mL | 131 ± 8 | 122 ± 4.9 | 88 ± 15 | 84.1 ± 2.1 | 19.7 ± 0.45 |
| $AUC_{last\_D}$ | (day * kg * ug/mL/mg) | 131 ± 8 | 122 ± 4.9 | 88 ± 15 | 84.1 ± 2.1 | 56.2 ± 1.3 |
| Cl | mL/day/kg | 5.2 ± 0.43 | 5.5 ± 0.28 | 9.7 ± 2.4 | 8.2 ± 0.29 | 45.2 ± 1.1 |

PK parameters were derived from mean concentration versus time profiles of total drug concentrations. $T_{1/2}$ and $AUC_{last}$ are based on concentrations out to day 21. The mean±SEM value for each PK parameter is shown for all dose groups.

Abbreviations: $AUC_{last}$=area under the curve from the time of dosing to the last measurable concentration; $AUC_{last}/D$=AUC last dose normalized to 1 mg/kg dosing; t½=terminal half-life of elimination; $C_{max}$=peak concentration; $C_{max}/d$=Cmax dose normalized to 1 mg/kg dosing; $t_{max}$=the time at which $C_{max}$ is observed; Cl=clearance rate of antibody over time; SEM=standard error of the mean.

7.8. Example 8 Biacore Analysis of Anti-Ligand X Fc-Fab Binding to Ligand X

Fab fragments from three non-competing mAbs against human Ligand X, mAbX1, mAbX2, and mAbX3, were used to make bispecific Fc-Fabs for human Ligand X, a soluble monomeric protein having a molecular weight in the 15-20 kDa range, in which the linker is a $G4S_2$ (i.e., GGGGSGGGGS (SEQ ID NO:18)). The Fc-Fabs had the hinge format depicted in FIG. 13A.

Equilibrium dissociation constants (KD values) for Ligand X binding to purified anti-Ligand X antibodies were determined using a real-time surface plasmon resonance biosensor assay on a Biacore T200 instrument. The Biacore sensor surface was derivatized by amine coupling with a monoclonal mouse anti-human Fc antibody (REGN2567) to capture anti-Ligand X antibodies expressed with human Fc constant regions. Biacore binding studies were conducted in HBST running buffer (0.01M HEPES pH 7.4, 0.15M NaCl, 3 mM EDTA, 0.05% v/v Surfactant P20). Human Ligand X was obtained from an in-house source (REGN138). Different concentrations of human Ligand X (ranging from 90 nM to 0.12 nM, 3-fold dilutions) prepared in HBST running buffer were injected over the anti-Ligand X antibody captured surface at a flow rate of 50 µL/min. Association of all the Ligand X reagents to each of the captured monoclonal antibodies was monitored for 4 minutes and their dissociation in HBST running buffer was monitored for 10 minutes. All the binding kinetics experiments were performed at 37° C. Kinetic association (ka) and dissociation (kd) rate constants were determined by fitting the real-time sensorgrams to a 1:1 binding model using biaevaluation curve fitting software. Binding dissociation equilibrium constants (KD) and dissociative half-lives (t½) were calculated from the kinetic rate constants as:

KD(M)=kd/ka and t½(min)=ln2/(60×kd)

Binding kinetic parameters for human Ligand X binding to anti-Ligand X antibodies at 37° C. are shown in Table 5-15. At 37° C., the anti-Ligand X Fc-Fabs of the disclosure bound to human Ligand X with KD values ranging from 0.25 pM to 18.4 pM while Parental mAb bound human Ligand X with respective KD values of 0.56 pM and 557 pM, as shown in Table 5-15.

TABLE 5-15

Binding Kinetics parameters of anti-Ligand X monoclonal antibodies binding to human Ligand X at 37° C.

| Description | mAb Capture (RU) | 90 nM human Ligand X Bound (RU) | ka (1/Ms) | kd (1/s) | KD (M) | t½ (min) |
|---|---|---|---|---|---|---|
| mAbX1 × mAbX2 IgG4 Fc-Fab | 57.2 ± 0.1 | 5.8 | 4.61E+07 | 1.14E−05 | 2.47E−13 | 1016.0 |
| mAbX1 × mAbX3 IgG4 Fc-Fab | 56.2 ± 0.2 | 7.2 | 1.18E+07 | 1.58E−04 | 1.34E−11 | 73.1 |
| mAbX2 × mAbX3 IgG4 Fc-Fab | 62.6 ± 0.2 | 7.6 | 4.78E+07 | 8.80E−04 | 1.84E−11 | 13.1 |
| mAbX1 IgG4 | 106.7 ± 0.7 | 21.4 | 1.24E+06 | 6.05E−05 | 4.86E−11 | 191.1 |
| mAbX2 IgG4 | 77.7 ± 0.3 | 14.2 | 5.19E+07 | 2.89E−02 | 5.57E−10 | 0.4 |
| mAbX3 IgG4 | 63.3 ± 0.1 | 13.8 | 1.81E+07 | 1.00E−05 | 5.51E−13 | ≥1155.2 |
| REGN1945 | 70.6 ± 0.1 | 0.1 | NB | NB | NB | NB |

7.9. Example 9 Activity of Anti-Human Ligand X Bispecific Fc-Fabs in Bioassays Purified anti-human Ligand X bispecific Fc-Fabs were evaluated for their ability to inhibit human Ligand X in Receptor X signaling bioassays. Bioassay for Ligand X signaling through Receptor X was carried out using an engineered luciferase reporter cell line. The reporter cells were plated in Opti-MEM (Gibco) with 0.1% Fetal Bovine Serum (Seradigm) at 10,000 cells/well and incubated overnight. For the Ligand X dose response curve, 1:3 serially diluted Ligand X was added to each well, with the final concentration of Ligand X starting at 2 nM. To determine blocking activity of anti-Ligand X parental mAbs and bispecific Fc-Fabs, a "Race format" blocking assay was used in which the antibodies and Ligand X were added to the reporter cells at the same time. Anti-Ligand X antibodies were serially diluted at 1:3, with final concentration starting at 100 nM. Human Ligand X was added to a constant concentration of 10 pM, 100 pM or 1 nM. After 5.5-hour incubation, the assay plates were equilibrated at room temperature for 15 minutes. 100 μl of One-Glo substrate (Promega) was added to each well. After 5-minute incubation at room temperature, luminescence was measured on Envision.

Activity of three anti-human Ligand X bispecific Fc-Fabs in the Receptor X bioassay is shown in FIGS. 16A-16C (mAbX1×mAbX2), FIGS. 17A-17C (mAbX2×mAbX3), and FIGS. 18A-18C (mAbX1×mAbX3). Their activity was compared to the corresponding anti-human Ligand X parental mAbs in the same assays. The mAbX1×mAbX2 Fc-Fab has the best blocking activity, showing significantly improved IC$_{50}$ values over those of the parental anti-Ligand X mAbs. One of the parental mAbs, mAbX3, does not block Ligand X activity to baseline in the bioassays, even when the mAb is at 100- to 1000-fold molar excess to human Ligand X. Interestingly, the two Fc-Fabs that use the mAbX3 Fab are able to block Ligand X activity to base line (FIGS. 17A-17C and FIGS. 18A-18C). These results demonstrate superior activity of the bispecific Fc-Fabs when compared to their parental anti-Ligand X mAbs. IC$_{50}$ values of these anti-Ligand X antibodies are summarized in Table 5-16.

TABLE 5-16

IC50 values of Ligand X bispecific Fc-Fabs in Ligand X blocking bioassays

| Ligand X EC50 [M] Constant Ligand X in Inhibition Assay | 4.90E−12 10 pM | 1.19E−11 100 pM | 1.19E−11 1 nM |
|---|---|---|---|
| Anti-Ligand X | IC50 in Race Format Inhibition Assay | | |
| mAbX3-hIgG4 | 5.12E−11 | Weak Inhibition | No Inhibition |
| mAbX1-hIgG4 | 4.84E−09 | 2.88E−08 | Weak Inhibition |
| mAbX2-hIgG4 | 9.42E−10 | 5.87E−09 | Weak Inhibition |
| Fc-Fab mAbX3 × mAbX1 | 4.2E−11 | 2.33E−10 | 1.99E−09 |
| Fc-Fab mAbX3 × mAbX2 | 1.36E−11 | 1.49E−10 | 1.72E−09 |
| Fc-Fab mAbX1 × mAbX2 | 7.34E−12 | 1.07E−10 | 9.07E−10 |

7.10. Example 10

Size Analysis of In Vitro Complexes Formed Between Anti-Ligand X Heterodimers and Recombinant Ligand X by Asymmetric Flow Field-Flow Fractionation Coupled to Multi-Angle Laser Light Scattering (A4F-MALLS)

Size analysis of in vitro complexes formed between recombinant Ligand X and bispecific mAbX1×mAbX2 in the Fc-Fab, Clamp and 2+2 Tandem Fab heterodimer formats in comparison to complexes with the parental mAbs was performed using asymmetric flow field-flow fractionation coupled to multi-angle laser light scattering (A4F-MALLS) as described in Section 7.4. The results of this analysis are shown in FIGS. 19A-19E. FIGS. 19A and 19B show the results of in vitro analyses of complexes of Ligand X with parental mAbs (singly or in combination); FIG. 19C shows the results of in vitro analysis of complexes of Ligand X with mAbX1×mAbX2 Fc-Fab; FIG. 19D shows the results of in vitro analysis of complexes of Ligand X with mAbX1×mAbX2 Clamp; and FIG. 19E shows the results of in vitro analysis of complexes of Ligand X with mAbX1× mAbX2 2+2 Tandem Fab heterodimer. As shown in FIG. 19C, the Fc-Fab format shows the least amount of paper dolling or aggregation.

7.11. Example 11 Fc-Fabs Maintain Binding to Cell Surface Targets

In addition to small soluble antigens, cell surface proteins were tested as targets for Fc-Fabs. IgG antibodies against Antigen Y, a cell surface antigen, were reformatted into mono-specific Fc-Fabs (as illustrated in FIG. 1B, with the hinge format depicted in FIG. 13A) using either hIgG1 constant region (FIG. 20A) or hIgG4 constant region with reduced effector function (U.S. Pat. No. 9,359,437B2) (shown as hIgG4s, FIGS. 20B, 20C, 20D). Three different linkers, 1xG4S (SEQ ID NO:3), 2xG4S (SEQ ID NO:18), and 3xG4S (SEQ ID NO:4), were tested for each anti-Antigen Y Fc-Fab. These Fc-Fabs were evaluated for binding to cell surface Antigen Y in flow cytometry (FACS) binding assays. Antigen Y-expressing cells were collected and resuspended in cold FACS wash buffer (PBS+ 1% FBS). For each binding assay, 50,000-100,000 cells were incubated with primary antibodies in FACS wash buffer at 4° C. for 30 minutes. Cells were then washed twice with cold FACS wash buffer, and incubated with 1:200 dilution of APC-F(ab)'2 anti-human IgG Fcγ fragment (Jackson ImmunoResearch Laboratories) for 30 minutes at 4° C. At end of the incubation, cells were washed twice with cold FACS wash buffer and analyzed on FACS Canto (BD Biosciences).

All Fc-Fabs maintained strong binding to cell surface Antigen Y. Two sets of Fc-Fabs had binding activity similar to that of their parental mAbs (FIGS. 20A and 20B). The other two sets of Fc-Fabs showed moderately reduced binding to Antigen Y when compared to their parental mAbs (FIGS. 20C and 20D). Variation in linker length between 1xG4S (SEQ ID NO:3) to 3xG4S (SEQ ID NO:4) had minimal impact on target binding of the anti-Antigen Y Fc-Fabs.

Additional cell surface proteins were tested as targets for Fc-Fabs, including CD3 and a cell surface tumor associated antigen, Antigen Z. The Fc-Fabs had the hinge format depicted in FIG. 13A. In FACS binding assays, anti-CD3 hIgG1 Fc-Fabs showed specific binding to CD3+ Jurkat cells (FIG. 21A), while anti-Antigen Z hIgG1 Fc-Fabs showed specific binding to Antigen Z+ cell line (FIG. 21B). Variation in linker length between 1xG4S (SEQ ID NO:3) to 5xG4S (SEQ ID NO:39) had minor impact on target binding of these Fc-Fabs, with the shortest linker resulting in moderately weaker binding activity to both CD3 and Antigen Z.

7.12. Example 12 Bispecific CD3 x Antigen Z Fc-Fabs are Active in Bioassays Using T Cells as Effector Cells Bispecific Fc-Fabs against CD3 and Antigen Z (a cell surface tumor associated antigen) were generated as described in Example 1, using constant regions of hIgG1. Three different linkers, 1xG4S (SEQ ID NO:3), 2xG4S (SEQ ID NO:18), and 3xG4S (SEQ ID NO:4), were tested for these bispecific Fc-Fabs with the hinge format depicted in FIG. 13A. Activity of the bispecific Fc-Fabs was evaluated in a Jurkat NFAT-Luciferase reporter assay (FIG. 22A) and an in vitro cytotoxicity assay (FIG. 22B). In the Jurkat NFAT-Luciferase reporter assay, a Jurkat/NFAT-Luc reporter cell line was mixed at 1:1 ratio with a Antigen Z+ cell line (50,000 cells each) in 96-well plates. CD3xAntigen Z bispecific Fc-Fabs were added to each well to a final volume of 100 μl. The reactions were incubated at 37° C. for 5 hours. After incubation, the plates were equilibrated at room temperature for 10 minutes before addition of 100 μl of One-Glo substrate (Promega) to each well. Luminescence was measured on Victor. In the cytotoxicity assay, pre-activated human T cells were prepared using human donor PBMCs activated with CD3/CD28 Beads and IL-2 for 7 days. On the day of the cytotoxicity assay, Antigen Z+ cells were harvested and labeled with 8 μM calcein-AM (Invitrogen) for 30 minutes. The labeled target cells were washed twice and mixed with pre-activated human T cells at a 1:10 ratio, with ~10,000 target cells/well. Serial dilutions of CD3xAntigen Z bispecific Fc-Fabs were added to a final volume of 200 μl. The reactions were incubated at 37° C. for 3 hours. Following incubation, the plates were centrifuged and 100 μl of supernatant was transferred to a translucent black clear bottom plate for fluorescence reading. The CD3xAntigen Z bispecific Fc-Fabs were active in both the Jurkat reporter assay (FIG. 22A) and the cytotoxicity assay (FIG. 22B). In both assays, Fc-Fabs with longer linkers showed stronger activity.

8. SPECIFIC EMBODIMENTS

The present disclosure is exemplified by the Group A and Group B specific embodiments below.

In preferred aspects of the specific embodiments below and the claims which follow, the antigen binding domains (e.g., Fab) contain humanized or human VH and VL sequences; the Fc domains comprise human CH2 and/or CH3 domans and variants thereof, for example variants with at least about 90%, at least about 95%, at least about 96%, at least about 97%, at least about 98%, at least about 99% or 100% sequence identity to such human sequence. Further the Fab domains may be Fab domains composed of two polypeptide chains, a VH polypeptide chain and a VL polypeptide chain as described herein, or a single chain Fab ("scFab") in which the VH and VL are present in a single polypeptide chain. Unless explicitly stated otherwise, the Fab domains can also include domain swaps, for example the domain swaps present in the Crossmab format.

8.1. Group A Specific Embodiments

1. An antigen-binding molecule which binds to a first target molecule and:
   (a) comprises:
      (i) an Fc region comprising two Fc domains;
      (ii) a first Fab domain and a second Fab domain,
      wherein the Fc region, the first Fab domain and second Fab domain are in a non-native immunoglobulin configuration;
      wherein the first Fab domain and/or the second Fab domain is capable of binding to the first target molecule; and
   (b) binds the first target molecule with greater affinity and/or avidity than a native immunoglobulin comprising the at least two Fab domains.

2. An antigen-binding molecule, which is optionally an antigen binding molecule according to embodiment 1, which binds to a first target molecule and comprises:
   (a) a first polypeptide comprising in an N-to-C terminal orientation:
      (i) a first Fc domain; and
      (ii) a first Fab domain comprising a first heavy chain variable region (VH) associated with a first light chain variable region (VL); and (b) a second polypeptide comprising in an N-to-C terminal orientation:
    (i) a second Fc domain; and
    (ii) a second Fab domain comprising a second VH associated with a second VL,
wherein the first Fc domain and second Fc domain are associated with one another to form an Fc region and, optionally wherein the first polypeptide and second polypeptide are identical.

3. The antigen-binding molecule of embodiment 2 which comprises a first linker between the first Fc domain and the first VH.

4. The antigen-binding molecule of embodiment 3, wherein the first linker is 5 amino acids to 60 amino acids in length.

5. The antigen-binding molecule of embodiment 3, wherein the first linker is 10 amino acids to 60 amino acids residues in length.

6. The antigen-binding molecule of embodiment 3, wherein the first linker is 5 amino acids to 20 amino acids residues in length.

7. The antigen-binding molecule of embodiment 3, wherein the first linker is 5 amino acids to 30 amino acids residues in length.

8. The antigen-binding molecule of embodiment 3, wherein the first linker is 10 amino acids to 30 amino acids residues in length.

9. The antigen-binding molecule of embodiment 3, wherein the first linker is 10 amino acids to 20 amino acids residues in length.

10. The antigen-binding molecule of embodiment 3, wherein the first linker is 20 amino acids to 50 amino acids in length.

11. The antigen-binding molecule of embodiment 3, wherein the first linker is 25 to 35 amino acids in length.

12. The antigen-binding molecule of any one of embodiments 3 to 11, wherein the first linker comprises a multimer of $G_nS$ or $SG_n$, optionally where n is an integer from 1 to 7.

13. The antigen-binding molecule of embodiment 12, wherein the first linker comprises a multimer of $G_4S$ (SEQ ID NO:3).

14. The antigen-binding molecule of embodiment 13, wherein the first linker comprises 2 to 6 repeats of $G_4S$ (SEQ ID NO:3).

15. The antigen-binding molecule of embodiment 14, wherein first linker comprises $(G_4S)_2$ (SEQ ID NO:18), $(G_4S)_3$ (SEQ ID NO:4) or $(G_4S)_4$ (SEQ ID NO:19).

16. The antigen-binding molecule of any one of embodiments 3 to 15 which comprises a second linker between the second Fc domain and the second VH.

17. The antigen-binding molecule of embodiment 16, wherein the first linker and the second linker have identical amino acid sequences.

18. The antigen binding molecule of embodiment 16 or embodiment 17, wherein the second linker is 5 amino acids to 60 amino acids in length.

19. The antigen binding molecule of embodiment 16 or embodiment 17, wherein the second linker is 10 amino acids to 60 amino acids in length.

20. The antigen-binding molecule of embodiment 16 or embodiment 17, wherein the first linker is 5 amino acids to 20 amino acids residues in length.

21. The antigen-binding molecule of embodiment 16 or embodiment 17, wherein the first linker is 5 amino acids to 30 amino acids residues in length.

22. The antigen-binding molecule of embodiment 16 or embodiment 17, wherein the first linker is 10 amino acids to 30 amino acids residues in length.

23. The antigen-binding molecule of embodiment 16 or embodiment 17, wherein the first linker is 10 amino acids to 20 amino acids residues in length.

24. The antigen-binding molecule of embodiment 16 or embodiment 17, wherein the second linker is 20 amino acids to 50 amino acids in length.

25. The antigen-binding molecule of embodiment 16 or embodiment 17, wherein the second linker is 25 to 35 amino acids in length.

26. The antigen-binding molecule of any one of embodiments 16 to 25, wherein the second linker comprises a multimer of $G_nS$ or $SG_n$, optionally where n is an integer from 1 to 7.

27. The antigen-binding molecule of embodiment 26, wherein the second linker comprises a multimer of $G_4S$ (SEQ ID NO:3).

28. The antigen-binding molecule of embodiment 27, wherein the second linker comprises 2 to 6 repeats of $G_4S$ (SEQ ID NO:3).

29. The antigen-binding molecule of embodiment 28, wherein second linker comprises $(G_4S)_2$ (SEQ ID NO:18), $(G_4S)_3$ (SEQ ID NO:4) or $(G_4S)_4$ (SEQ ID NO:19).

30. The antigen-binding molecule of any one of embodiments 2 to 29, wherein the first polypeptide comprises a first hinge domain N-terminal to the first Fc domain and the second polypeptide comprises a second hinge domain N-terminal to the second Fc domain.

31. The antigen-binding molecule of embodiment 30, wherein the first hinge domain and the second hinge domain are linked via a disulfide bond.

32. The antigen-binding molecule of embodiment 30, wherein the first hinge domain and the second hinge domain are not linked via a disulfide bond.

33. The antigen-binding molecule of any one of embodiments 2 to 32, in which the first polypeptide does not comprise a VH N-terminal to the first Fc domain.

34. The antigen-binding molecule of any one of embodiments 2 to 33, in which the second polypeptide does not comprise a VH N-terminal to the second Fc domain.

35. The antigen-binding molecule of any one of embodiments 2 to 29, which has one hinge region.

36. The antigen-binding molecule of embodiment 35, which has the hinge format illustrated in FIG. 13A.

37. The antigen-binding molecule of embodiment 35, which has the hinge format illustrated in FIG. 13C.

38. The antigen-binding molecule of any one of embodiments 2 to 29, which has two hinge regions.

39. The antigen-binding molecule of embodiment 38, which has the hinge format illustrated in FIG. 13B.

40. The antigen-binding molecule of any one of embodiments 2 to 39 in which the first polypeptide and second polypeptide are non-identical.

41. The antigen-binding molecule of any one of embodiments 2 to 40 in which the first VL and second VL are universal light chains.

42. The antigen-binding molecule of any one of embodiments 2 to 40, in which the light chain constant region and the first heavy chain constant region (CH1) of the first Fab domain or the second Fab domain are in a Crossmab arrangement.

43. The antigen-binding molecule of any one of embodiments 1 to 42 which is bivalent.

44. An antigen-binding molecule, which is optionally an antigen binding molecule according to embodiment 1, comprising:
(a) a first polypeptide comprising in an N-to-C terminal orientation:
(i) a first Fab domain comprising a first VH associated with a first VL;
(ii) a first spacer domain;
(iii) a first Fc domain; and
(b) a second polypeptide comprising in an N-to-C terminal orientation:
(i) a second Fab domain comprising a second VH associated with a second VL;
(ii) a second spacer domain;
(iii) a second Fc domain; and
wherein the first Fab domain and/or the second Fab domain is capable of binding to the first target molecule, wherein the first Fc domain and second Fc domain are associated with one another to form an Fc region and, optionally wherein the first polypeptide and second polypeptide are identical.

45. The antigen-binding molecule of embodiment 44, which comprises hinge domains between the first spacer domain and the first Fc domain and between the second spacer domain and the second Fc domain.

46. The antigen-binding molecule of embodiment 44 or embodiment 45, wherein the hinge domains are linked via a disulfide bond.

47. The antigen-binding molecule of any one of embodiments 44 to 46 in which the first VL and second VL are universal light chains.

48. The antigen-binding molecule of any one of embodiments 44 to 46 in which the light chain constant region and the first heavy chain constant region (CH1) of the first Fab domain or the second Fab domain are in a Crossmab arrangement.

49. The antigen-binding molecule of any one of embodiments 44 to 48, wherein the first spacer domain and the second spacer domain each comprise an extended linker.

50. The antigen-binding molecule of embodiment 49, wherein each extended linker is at least 30 amino acids in length.

51. The antigen-binding molecule of embodiment 49 or embodiment 50, wherein each extended linker is 30 acid residues to 70 amino acids in length.

52. The antigen-binding molecule of embodiment 49 or embodiment 50, wherein each extended linker is 30 acid residues to 55 amino acids in length.

53. The antigen-binding molecule of embodiment 49 or embodiment 50, wherein each extended linker is 30 acid residues to 40 amino acids in length.

54. The antigen-binding molecule of any one of embodiments 49 to 53, wherein each extended linker comprises a multimer of $G_nS$ or $SG_n$, optionally where n is an integer from 1 to 7.

55. The antigen-binding molecule of embodiment 54, wherein each extended linker comprises a multimer of $G_4S$ (SEQ ID NO:3).

56. The antigen-binding molecule of embodiment 55, wherein each extended linker comprises 5 to 12 repeats of $G_4S$ (SEQ ID NO:3).

57. The antigen-binding molecule of embodiment 56, wherein each extended linker comprises $(G_4S)_6$ (SEQ ID NO:38), $(G_4S)_7$ (SEQ ID NO:36) or $(G_4S)_8$ (SEQ ID NO:37).

58. The antigen-binding molecule of any one of embodiments 44 to 57, wherein the first and second spacer domains are identical.

59. The antigen-binding molecule of any one of embodiments 44 to 58 which is bivalent.

60. The antigen-binding molecule of embodiment 44, wherein the first spacer domain comprises a third Fab domain comprising a third VH associated with a third VL and the second spacer domain comprises a fourth Fab domain comprising a fourth VH associated with a fourth VL.

61. The antigen-binding molecule of embodiment 60, wherein the third VL and the fourth VL are universal light chains in which the Fc region.

62. The antigen-binding molecule of embodiment 60 or embodiment 61, wherein the first polypeptide comprises a first linker between the first VH and the third VH and the second polypeptide comprises a second linker between the second VH and the fourth VH.

63. The antigen-binding molecule of embodiment 62, wherein the first linker and the second linker are each 10 amino acids to 60 amino acids in length.

64. The antigen-binding molecule of embodiment 62 or embodiment 63, wherein the first linker and the second linker are each 20 amino acids to 50 amino acids in length.

65. The antigen-binding molecule of embodiment 62 or embodiment 63, wherein the first linker and the second linker are each 25 to 35 amino acids in length.

66. The antigen-binding molecule of embodiment 62 or embodiment 63, wherein the first linker and the second linker each comprises a multimer of $G_nS$ or $SG_n$, optionally where n is an integer from 1 to 7.

67. The antigen-binding molecule of embodiment 66, wherein the first linker and the second linker each comprises a multimer of $G_4S$ (SEQ ID NO:3).

68. The antigen-binding molecule of embodiment 67, wherein the first linker and the second linker each comprises 2 to 6 repeats of $G_4S$ (SEQ ID NO:3).

69. The antigen-binding molecule of embodiment 68, wherein the first linker and the second linker each comprises $(G_4S)_2$ (SEQ ID NO:18), $(G_4S)_3$ (SEQ ID NO:4) or $(G_4S)_4$ (SEQ ID NO:19).

70. The antigen-binding molecule of any one of embodiments 62 to 69, wherein the first linker and the second linker have identical amino acid sequences.

71. The antigen-binding molecule of any one of embodiments 60 to 70, wherein the third Fab domain and the fourth Fab domain are non-binding.

72. The antigen-binding molecule of embodiment 71, wherein the third VH and the fourth VH are universal heavy chains.

73. The antigen-binding molecule of embodiment 71 or embodiment 72, wherein the first Fab domain and the second Fab domain are each capable of binding to the same or different epitopes on the first target molecule.

74. The antigen-binding molecule of any one of embodiments 60 to 73 which is bivalent.

75. The antigen-binding molecule of any one of embodiments 60 to 70, wherein the third Fab domain and the fourth Fab domain are each capable of binding to the same or different epitopes.

76. The antigen-binding molecule of embodiment 75, wherein the third Fab domain and the fourth Fab domain are each capable of binding to the same target molecule.

77. The antigen-binding molecule of embodiment 76, wherein the third Fab domain and the fourth Fab domain are each capable of binding to the first target molecule.

78. The antigen-binding molecule of any one of embodiments 75 to 77, wherein the first and second Fab domains bind to the same epitope.

79. The antigen-binding molecule of embodiment 78, wherein the first and second Fab domains have identical sequences.

80. The antigen-binding molecule any one of embodiments 75 to 79, wherein the third and fourth Fab domains bind to the same epitope.

81. The antigen-binding molecule of embodiment 80, wherein the third and fourth Fab domains have identical sequences.

82. The antigen-binding molecule any one of embodiments 75 to 77, wherein the first and third Fab domains bind to the same epitope.

83. The antigen-binding molecule of embodiment 82, wherein the first and third Fab domains have identical sequences.

84. The antigen-binding molecule of any one of embodiments 75 to 77, 82 and 83, wherein the second and fourth Fab domains bind to the same epitope.

85. The antigen-binding molecule of embodiment 84, wherein the second and fourth Fab domains have identical sequences.

86. The antigen-binding molecule of any one of embodiments 60 to 70 and 75 to 85 which is tetravalent.

87. The antigen-binding molecule of any one of embodiments 1 to 86, which is an antagonist of the first target molecule.

88. The antigen-binding molecule of any one of embodiments 1 to 87, which inhibits the binding of the first target molecule to a binding partner, optionally wherein the binding partner is a receptor of the first target molecule.

89. The antigen-binding molecule of any one of embodiments 1 to 88, in which the Fc region comprises a human Fc sequence.

90. The antigen-binding molecule of any one of embodiments 1 to 89, wherein the Fc region comprises human $IgG_1$ or human $IgG_4$ Fc sequences.

91. The antigen-binding molecule of any one of embodiments 1 to 90, in which the Fc region comprises an Fc heterodimer.

92. The antigen-binding molecule of embodiment 89, wherein the Fc domains in the Fc heterodimer comprise knob-in-hole mutations as compared to a wild type Fc domain.

93. The antigen-binding molecule of embodiment 92, wherein the Fc domain in the first polypeptide comprises a knob mutation and the Fc domain in the second polypeptide comprises a hole mutation.

94. The antigen-binding molecule of embodiment 92, wherein the Fc domain in the second polypeptide comprises a knob mutation and the Fc domain in the first polypeptide comprises a hole mutation.

95. The antigen-binding molecule of embodiment 89, wherein the Fc region comprises star mutations as compared to a wild type Fc region.

96. The antigen-binding molecule of embodiment 89, wherein the Fc domain in the first polypeptide comprises an H435R mutation and a Y436F mutation.

97. The antigen-binding molecule of embodiment 89, wherein the Fc domain in the second polypeptide comprises an H435R mutation and a Y436F mutation.

98. The antigen-binding molecule of any one of embodiments 1 to 97, in which the CL and the CH1 in the first Fab domain are linked by a disulfide bond.

99. The antigen-binding molecule of any one of embodiments 1 to 98, in which the CL and the CH1 in the second Fab domain are linked by a disulfide bond.

100. The antigen-binding molecule of any one of embodiments 1 to 99, wherein the first Fab domain and the second Fab domain bind to the first target molecule.

101. The antigen-binding molecule of any one of embodiments 1 to 100, wherein the first target molecule is a small soluble ligand.

102. The antigen-binding molecule of any one of embodiments 1 to 101, wherein the first target molecule is a cytokine or chemokine.

103. The antigen-binding molecule of any one of embodiments 1 to 100, wherein the first target molecule is a cell surface protein.

104. The antigen-binding molecule of any one of embodiments 1 to 100 and 103, wherein the first target molecule is a tumor associated antigen.

105. The antigen-binding molecule of any one of embodiments 1 to 104, wherein the first target molecule has a molecule has a molecular weight of less than 100 kDa exclusive of post-translational modifications.

106. The antigen-binding molecule of any one of embodiments 1 to 104, wherein the first target molecule has a molecule has a molecular weight of less than 100 kDa inclusive of post-translational modifications.

107. The antigen-binding molecule of any one of embodiments 1 to 104, wherein the first target molecule has a molecule has a molecular weight of less than 75 kDa exclusive of post-translational modifications.

108. The antigen-binding molecule of any one of embodiments 1 to 104, wherein the first target molecule has a molecule has a molecular weight of less than 75 kDa inclusive of post-translational modifications.

109. The antigen-binding molecule of any one of embodiments 1 to 104, wherein the first target molecule has a molecule has a molecular weight of less than 60 kDa exclusive of post-translational modifications.

110. The antigen-binding molecule of any one of embodiments 1 to 104, wherein the first target molecule has a molecule has a molecular weight of less than 60 kDa inclusive of post-translational modifications.

111. The antigen-binding molecule of any one of embodiments 1 to 104, wherein the first target molecule has a molecule has a molecular weight of less than 45 kDa exclusive of post-translational modifications.

112. The antigen-binding molecule of any one of embodiments 1 to 104, wherein the first target molecule has a molecule has a molecular weight of less than 45 kDa inclusive of post-translational modifications.

113. The antigen-binding molecule of any one of embodiments 1 to 112, wherein the first target molecule has a molecule has a molecular weight of at least 5 kDa exclusive of post-translational modifications.

114. The antigen-binding molecule of any one of embodiments 1 to 112, wherein the first target molecule has a molecule has a molecular weight of at least 5 kDa inclusive of post-translational modifications.

115. The antigen-binding molecule of any one of embodiments 1 to 112, wherein the first target molecule has a molecule has a molecular weight of at least 5 kDa exclusive of post-translational modifications.

116. The antigen-binding molecule of any one of embodiments 1 to 112, wherein the first target molecule has a molecule has a molecular weight of at least 5 kDa inclusive of post-translational modifications.

117. The antigen-binding molecule of any one of embodiments 1 to 112, wherein the first target molecule has a molecule has a molecular weight of at least 10 kDa exclusive of post-translational modifications.

118. The antigen-binding molecule of any one of embodiments 1 to 112, wherein the first target molecule has a molecule has a molecular weight of at least 10 kDa inclusive of post-translational modifications.

119. The antigen-binding molecule of any one of embodiments 1 to 118, wherein the first target molecule is glycosylated.

120. The antigen-binding molecule of any one of embodiments 1 to 118, wherein the first target molecule is not glycosylated 121. The antigen-binding molecule of any one of embodiments 1 to 120, wherein the first target molecule is a monomer.

122. The antigen-binding molecule of any one of embodiments 1 to 120, wherein the first target molecule is a dimer.

123. The antigen-binding molecule of embodiment 122, wherein the first target molecule is a homodimer.

124. The antigen-binding molecule of embodiment 122, wherein the first target molecule is a heterodimer.

125. The antigen-binding molecule of any one of embodiments 1 to 120, wherein the first target molecule is a trimer.

126. The antigen-binding molecule of embodiment 125, wherein the first target molecule is a homotrimer.

127. The antigen-binding molecule of any one of embodiments 1 to 120, wherein the first target molecule is a tetramer.

128. The antigen-binding molecule of embodiment 127, wherein the first target molecule is a homotetramer.

129. The antigen-binding molecule of any one of embodiments 1 to 128 which is monospecific.

130. The antigen-binding molecule of any one of embodiments 1 to 128 which is bispecific.

131. The antigen-binding molecule of embodiment 130, which is capable of binding to a first epitope and a second epitope on the first target molecule.

132. The antigen-binding molecule of embodiment 131, which comprises at least one Fab domain that binds to the first epitope and at least one Fab domain that binds to the second epitope on the first target molecule.

133. The antigen-binding molecule of embodiment 132, which is capable of binding to the different epitopes on the first target molecule simultaneously.

134. The antigen-binding molecule of embodiment 130, which is capable of binding to the first target molecule and to a second target molecule.

135. The antigen-binding molecule of embodiment 134, which comprises at least one Fab domain that binds to the first target molecule and at least one Fab domain that binds to the second target molecule.

136. The antigen-binding molecule of embodiment 135 which can bind to the first target molecule and the second target molecule simultaneously.

137. The antigen-binding molecule of any one of embodiments 1 to 136, which blocks the binding of the target molecule to its receptor at a lower $IC_{50}$ relative to a human IgG antibody comprising the first Fab and the second Fab.

138. The antigen-binding molecule of any one of embodiments 1 to 137, which binds to the target molecule with a greater affinity than a human IgG antibody comprising the first Fab and the second Fab.

139. A conjugate comprising the antigen-binding molecule of any one of embodiments 1 to 138 and a cytotoxic or cytostatic agent.

140. A pharmaceutical composition comprising the antigen-binding molecule of any one of embodiments 1 to 138 or the conjugate of embodiment 139 and an excipient.

141. A method of treating a subject having a condition associated with the aberrant expression or activity of a target molecule, comprising administering to the subject an effective amount of an antigen-binding molecule according to any one of embodiments 1 to 138, the conjugate of embodiment 139 or the pharmaceutical composition of embodiment 140.

142. A method of inhibiting a molecular pathway associated with a target molecule in a subject, comprising administering to the subject an effective amount of an antigen-binding molecule according to any one of embodiments 1 to 138, the conjugate of embodiment 139 or the pharmaceutical composition of embodiment 140.

143. Use of an antigen-binding molecule according to any one of embodiments 1 to 138, the conjugate of embodiment 139 or the pharmaceutical composition of embodiment 140 in the manufacture of a medicament for the treatment of a condition associated with a target molecule bound by the antigen-binding molecule, conjugate, or antigen-binding molecule or conjugate present in the pharmaceutical composition, respectively.

144. A nucleic acid molecule or plurality of nucleic acid molecules comprising one or more nucleotide sequences encoding the antigen-binding molecule of any one of embodiments 1 to 138.

145. The nucleic acid molecule or plurality of nucleic acid molecules of embodiment 144, in which the one or more nucleotide sequences are each operably linked to an expression control sequence.

146. A cell engineered to express the antigen-binding molecule of any one of embodiments 1 to 138.

147. A cell transfected with one or more expression vectors comprising one or more nucleic acid sequences encoding the antigen-binding molecule of any one of embodiments 1 to 138 under the control of one or more promoters.

148. A method of producing the antigen-binding molecule of any one of embodiments 1 to 138, comprising:
(a) culturing the cell of embodiment 146 or embodiment 147 in conditions under which the antigen-binding molecule is expressed; and
(b) recovering the antigen-binding molecule from the cell culture 149. The method of embodiment 148, which further comprises enriching for the antigen-binding molecule.

150. The method of embodiment 148 or embodiment 149, which further comprises purifying the antigen-binding molecule.

8.2. Group B Specific Embodiments

1. An antigen-binding molecule comprising:
   (a) a first heavy chain polypeptide, the first heavy chain polypeptide comprising: a first CH amino acid sequence; a first VH amino acid sequence; and a second CH amino acid sequence, wherein the first VH amino acid sequence is between the first CH amino acid sequence and the second CH amino acid sequence; and
   (b) a second heavy chain polypeptide, the second heavy chain polypeptide comprising: a third CH amino acid sequence; a second VH amino acid sequence; and a fourth CH amino acid sequence, wherein the second VH amino acid sequence is between the third CH amino acid sequence and the fourth CH amino acid sequence.

2. The antigen-binding molecule of embodiment 1, wherein the first CH amino acid sequence comprises a first CH3 amino acid sequence located N-terminal to the first VH amino acid sequence.

3. The antigen-binding molecule of embodiment 2, wherein the first CH3 comprises an H435R mutation and a Y436F mutation.

4. The antigen-binding molecule of embodiment 2 or embodiment 3, further comprising a first linker linking a N-terminal end of the first VH amino acid sequence to a C-terminal end of the first CH3 amino acid sequence.

5. The antigen-binding molecule of any one of embodiments 1-4, wherein the third CH amino acid sequence comprises a second CH3 amino acid sequence located N-terminal to the second VH amino acid sequence.

6. The antigen-binding molecule of embodiment 5, further comprising a second linker linking a N-terminal end of the second VH amino acid sequence to a C-terminal end of the second CH3 amino acid sequence.

7. The antigen-binding molecule of any one of embodiments 1-6, wherein the second CH amino acid sequence comprises a first CH1 amino acid sequence located C-terminal to the first VH amino acid sequence.

8. The antigen-binding molecule of any one of embodiments 1-7, wherein the fourth CH amino acid sequence comprises a second CH2 amino acid sequence located C-terminal to the second VH amino acid sequence.

9. The antigen-binding molecule of any one of embodiments 1-8, further comprising a first CH2 amino acid sequence located N-terminal to the first CH3 amino acid sequence.

10. The antigen-binding molecule of any one of embodiments 1-9, further comprising a second CH2 amino acid sequence located N-terminal to the second CH3 amino acid sequence.

11. The antigen-binding molecule of any one of embodiments 1-10, wherein the antigen-binding molecule does not include a hinge region disulfide bond.

12. The antigen-binding molecule of any one of embodiments 1-11, further comprising a first light chain polypeptide, the first light chain polypeptide comprising: a first VL amino acid sequence; and a first CL amino acid sequence.

13. The antigen-binding molecule of embodiment 12, further comprising a disulfide bond linking first CL to the first CH1.

14. The antigen-binding molecule of any one of embodiments 1-13 further comprising a second light chain polypeptide, the second light chain polypeptide comprising: a second VL amino acid sequence; and a second CL amino acid sequence.

15. The antigen-binding molecule of embodiment 14, further comprising a disulfide bond linking second CL to the second CH1.

16. The antigen-binding molecule of any one of embodiments 6-15, wherein the first linker and the second linker each comprises a polypeptide.

17. The antigen-binding molecule of embodiment 16, wherein the first linker and the second linker have a length of from 0 to 50 amino acids.

18. The antigen-binding molecule of any one of embodiments 16-17, wherein the first linker and the second linker have identical amino acid sequences.

19. The antigen-binding molecule of any one of embodiments 16-18, wherein the first linker and the second linker each comprises poly Glycine and Serine amino acid sequences.

20. The antigen-binding molecule of embodiment 19, wherein the poly Glycine and Serine amino acid sequences comprise 2 to 6 repeating GGGGS (SEQ ID NO:3) amino acid sequences.

21. The antigen-binding molecule of embodiment 20, wherein the poly Glycine and Serine amino acid sequences comprise (G4S)$_2$ (SEQ ID NO:18), (G4S)$_3$ (SEQ ID NO:4) or (G4S)$_4$ (SEQ ID NO:19).

22. The antigen-binding molecule of any one of embodiments 14-21, wherein the first light chain polypeptide and the second light chain polypeptide have identical amino acid sequences.

23. The antigen-binding molecule of any one of embodiments 1-22, wherein the first heavy chain polypeptide the second heavy chain polypeptide have identical amino acid sequences.

24. The antigen-binding molecule of any one of embodiments 1-22, wherein the first heavy chain polypeptide the second heavy chain polypeptide have non-identical amino acid sequences.

25. The antigen-binding molecule of any one of embodiments 1-24, wherein the antigen-binding molecule is capable of binding one or more antigens selected from the group consisting of ABCF1, ACVR1, ACVR1B, ACVR2, ACVR2B, ACVRLI, ADORA2A, Aggrecan, AGR2, AICDA, AIF1, AIG1, AKAP1, AKAP2, AMH, AMHR2, ANGPT1, ANGPT2, ANGPTL3, ANGPTL4, ANPEP, APC, APOC1, AR, AZGP1 (zinc-a-glycoprotein), ART-4, B7, B7.1, B7.2, BAD, BAFF, BAGI, BAIi, BCL2, BCL6, BDNF, BLNK, BLRI (MDRIS), BIyS, BMPI, BMP2, BMP3B (GDF10), BMP4, BMP6, BMPS, BMPR1A, BMPR1B, BMPR2, BPAG1 (plectin), BRCA1, Ba-733, BAGE, BrE3-antigen, CA125, CAMEL, CAP-I, CASP-8/m, CCCL19, CCCL21, CD1, CD1a, CD2, CD3, CD4, CDS, CD8, CDI-IA, CD14, CD15, CD16, CD18, CD19, CD20, CD21, CD22, CD23, CD25, CD29, CD30, CD32b, CD33, CD37, CD38, CD40, CD40L, CD45, CD46, CD54, CD55, CD59, CD64, CD66a-e, CD67, CD70, CD74, CD79a, CD80, CD83, CD95, CD126, CD133, CD138, CD147, CD154, CDC27, CDK-4/m, CDKN2A, CXCR4, CXCR7, CXCL12, C19orf10 (IL27w), C3, C4A, CS, CSR1, CANT1, CASPI, CASP4, CAV1, CCBP2 (D6/JAB61), CCLI (1-309), CCLII (eotaxin), CCL13 (MCP-4), CCLIS (MIP-1d), CCL16 (HCC-4), CCL17 (TARC), CCLIS (PARC), CCL19 (MIP-3b), CCL2 (MCP-1), MCAF, CCL20 (MIP-3a), CCL21 (MIP-2), SLC, exodus-2, CCL22 (MDC/STC-1), CCL23 (MPIF-1), CCL24 (MPIF-2/eotaxin-2), CCL2S (TECK), CCL26 (eotaxin-3), CCL27 (CTACK/ILC), CCL2S, CCL3 (MIP1a), CCL4 (MIP-1b), CCLS (RANTES), CCL7 (MCP-3), CCLS (mcp-2), CCNA1, CCNA2, CCND1, CCNE1, CCNE2, CCR1 (CKR1/HM14S), CCR2 (mcp-1RB/RA), CCR3 (CKR3/CMKBR3), CCR4, CCRS (CMKBRSI ChemR13), CCR6 (CMKBR6/CKR-L3/STRL22/DRY6), CCR7 (CKR7/EB1), CCRS (CMKBRS/TER1/CKR-LI), CCR9 (GPR-9-6), CCRLI (VSHK1), CCRL2 (L-CCR), CD164, CDIC, CD200, CD-22, CD24, CD2S, CD3S, CD3E, CD3G, CD3Z, CD4, CD44, CD4SRB, CD47, CD4S, CDS2, CD69, CD72, CD79A, CD79B, CDSO, CDS1, CDS3, CDS6, CD137, CD13S, B7-1, B7-2, ICOSL, B7-H3, B7-H4, CD137L, OX40L, CDH1 (E-cadherin), CDH10, CDH12, CDH13, CDHIS, CDH19, CDH20, CDHS, CDH7, CDHS, CDH9, CDK2, CDK3, CDK4, CDKS, CDK6, CDK7, CDK9, CDKN1A (p21 Wap1/Cip1), CDKN1B (p27Kip1), CDKN1C, CDKN2A (p16INK4a), CDKN2B, CDKN2C, CDKN3, CEBPB, CER1, CHGA, CHGB, Chitinase, CHST1O, CKLFSF2, CKLFSF3, CKLFSF4, CKLFSFS, CKLFSF6, CKLFSF7, CKLFSFS, CLDN3, CLDN7 (claudin-7), CLN3, CLU (clusterin), CMKLR1, CMKOR1 (RDC1), CNR1, COLISA1, COLIA1, COL4A3, COL6AI, CR2, CRP, CSF1 (M-CSF), CSF2 (GM-CSF), CSF3 (GCSF), CTLA-4, CTNNB1 (b-catenin), CTSB (cathepsin B), CX3CLI (SCYD1), CX3CR1 (V2S), CXCLI (GRO1), CXCLIO (IP-10), CXCL11 (I-TAC/IP-9), CXCL13, CXCL14, CXCL16, CXCL2 (GR02), CXCL3 (GR03), CXCLS (ENA-7S/LIX), CXCL6 (GCP-2), CXCL9 (MIG), CXCR3 (GPR9/CKR-L2), CXCR6 (TYMSTR/STRL33/Bonzo), CYBS, CYC1, CYSLTR1, HIF-1-a, colon-specific antigen-p (CSAp), CEA (CEACAM5), CEACAM6, c-met, DAB2IP, DES, DKFZp4S1J011S, DNCLI, DPP4, DAM, EGFR, EGFRvIII, EGP-1, EGP-2, ELF2-M, Ep-CAM, E2F1, ECGF1, EDG1, EFNA1, EFNA3, EFNB2, EGF, EGFR, ELAC2, ENG, EN01, EN02, EN03, EPHB4, EPO, EREG, ERKS, ESR1, ESR2, F3 (TF), FADD, FasL, FASN, FCER1A, FCER2, FCGR3A, FGF, FGF1 (aFGF), FGF10, FGF11, FGF12, FGF12B, FGF13, FGF14, FGF16, FGF17, FGF1S, FGF19, FGF2 (bFGF), FGF20, FGF21, FGF22, FGF23, FGF3 (int-2), FGF4 (HST), FGFS, FGF7 (KGF), FGFS, FGF9, FGFR3, FIGF (VEGFD), FILI (EPSILON), FILI (ZETA), FLJ12SS4, FLJ2SS30, FLRT1 (fibronectin), FOS, FOSLI (FRA-1), FY (DARC), FIt-1, FIt-3, folate receptor, G250 antigen, GAGE, GROB, GABRP (GABAa), GAGEB1, GAGEC1, GALNAC4S-6ST, GATA3, GDFS, GFiI, GGTI, GM-CSF, GNAS1, GNRH1, GPR2 (CCR10), GPR31, GPR44, GPRSI (FKSGSO), GRCC10 (C10), GRP, GSN (Gelsolin), GSTP1, HAVCR2, HDAC4, HDACS, HDAC7A, HDAC9, HGF, HIP1 histamine and histamine receptors, HLA-A, HLA-DRA, HM74, HMOX1, HUMCYT2A, HLA-DR, HMI 24, human chorionic gonadotropin (HCG) and its subunits, HER2/neu, HMGB-1, hypoxia inducible factor (HIF-1), HSP70-2M, HST-2 or 1a, IGF-IR, IFN-γ, IFN-α, IL-2, IL-4R, IL-6R, IL-13R, IL-15R, IL-17R, IL-18R, IL-6, IL-8, IL-12, IL-15, IL-17, IL-18, IL-25, IGBP1, IGF1, IGF1R, IGF2, IGFBP2, IGFBP3, IGFBP6, IL-1, IL-10, IL-10RA, IL-10RB, IL-11, IL-11RA, IL-12, IL-12A, IL-12B, IL-12RB1, IL-12RB2, IL-13, IL-13RA1, IL-13RA2, IL-14, IL-1S, IL-1SRA, IL-16, IL-17, IL-17B, IL-17C, IL-17R, IL-18, IL-18BP, IL-18R1, IL-18RAP, IL-19, IL-IA, IL-1B, IL-1F10, IL-1FS, IL-1F6, IL-1F7, IL-1F8, IL-1F9, IL-1HY1, IL-1R1, IL-1R2, IL-1RAP, IL-1RAPL1, IL-1RAPL2, IL-1RL1, IL-1RL2 IL-1RN, IL-2, IL-20, IL-20RA, IL-21R, IL-22, IL-22R, IL-22RA2, IL-23, IL-24, IL-2S, IL-26, IL-27, IL-28A, IL-28B, IL-29, IL-2RA, IL-2RB, IL-2RG, IL-3, IL-30, IL-3RA, IL-4, IL-4R, IL-S, IL-5RA, IL-6, IL-6R, IL-6ST (glycoprotein 130), IL-7, IL-7R, IL-S, IL-SRA, IL-SRB, IL-9, IL-9R, IL-K, INHA, INHBA, INSL3, INSL4, IRAK1, IRAK2, ITGA1, ITGA2, ITGA3, ITGA6 (a6 integrin), ITGAV, ITGB3, ITGB4 (b 4 integrin) insulin-like growth factor-I (IGF-1), ICEBERG, ICOSL, ID2, IFN-a, IFNA1, IFNA2, IFNA4 IFNAS, IFNA6, IFNA7, IFNB1, IFNW1, JAG1, JAK1, JAK3, JUN, K6HF, KAi1, KDR, KITLG, KLFS (GC Box BP), KLF6, KLK10, KLK12, KLK13, KLK14, KLK1S, KLK3, KLK4, KLKS, KLK6, KLK9, KRT1, KRT19 (Keratin 19), KRT2A, KRTHB6 (hair-specific type II keratin), KC4-antigen, KS-1-antigen, KS 1-4, Le-Y, LDR/FUT, LAMAS, LEP (leptin), Lingo-p7S, Lingo-Troy, LPS, LTA (TNF-b), LTB, LTB4R (GPR16), LTB4R2, LTBR, MACMARCKS, MAG or Omgp, MAP2K7 (c-Jun), MDK, MIB1, midkine, MIF, MIP-2, MKI67 (Ki-67), MMP2, MMP9, MS4A1, MSMB, MT3 (metallothionectin-III), MTSS1, MUC1 (mucin), MYC, MYD88, macrophage migration inhibitory factor (MIF), MAGE, MAGE-3, MART-1, MART-2, NY-ES0-1, TRAG-3, mCRP, MCP-1, MIP-1A, MIP-1B, MIF, MUC1, MUC2, MUC3, MUC4, MUC5, MUM-1/2, MUM-3, NCA66, NCA95, NCA90, NCK2, neurocan, NFKB1, NFKB2, NGFB (NGF), NGFR, NgR-Lingo, NgR-Nogo66 (Noga), NgRp7S, NgR-Troy, NME1 (NM23A), NOXS, NPPB, NROB1, NROB2, NR1D1, NR1D2, NRIH2, NRIH3, NRIH4, NR1I2, NR1I3, NR2C1, NR2C2, NR2E1, NR2E3, NR2F1, NR2F2, NR2F6, NR3C1, NR3C2, NR4A1, NR4A2, NR4A3, NRSA1, NRSA2, NR6A1, NRP1, NRP2, NTSE, NTN4, ODZ1, OPRD1, PCSK9, P2RX7, PAP, PART1, PATE, PAWR, PCA3, PCNA, PD-1, PD-L1, alpha4beta7, OX40, GITR, TIM-3, Lag-3, B7-H3, B7-H4, GDFS, CGRP, Lingo-I, Factor IXa, Factor X, ICOS, GARP, BTLA, CD160, RORI, 2B4, KIR, CD27, OX40, A2aR, PDGFA, PDGFB, PECAM1, PF4 (CXCL4), PGF, PGR, phosphacan, PIAS2, PIK3CG, PLAU (uPA), PLG, PLXDC1, PPBP (CXCL7), PPID, PR1, PRKCQ, PRKD1, PRL, PROC, PROK2, PSAP, PSCA, PTAFR, PTEN, PTGS2 (COX-2), PTN, pancreatic cancer mucin, placental growth factor, p53, PLAGL2, prostatic acid phosphatase, PSA, PRAME, PSMA, 10 PIGF, ILGF, ILGF-IR, IL-6, RS5, RANTES, RAC2 (p21Rac2), RARB, RGS1, RGS13, RGS3, RNFI10 (ZNF144), ROB02, S100A2, SCGB1D2 (lipophilin B), SCGB2A1 (mammaglobin 2), SCGB2A2 (mammaglobin 1), SCYE1 (endothelial Monocyte-activating cytokine), SDF2, SERPINA1, SERPINA3, SERPINBS (maspin), SERPINE1 (PAI-1), SERPINF1, SHBG, SLA2, SLC2A2, SLC33A1, SLC43A1, SLIT2, SPP1, SPRR1B (Sprl), ST6GAL1, STAB1, STATE, STEAP, STEAP2, T1O1, SAGE, 5100, survivin, survivin-2B, TAC, TAG-72, tenascin, TRAIL receptors, TNF-α, Tn-antigen, ThomsonFriedenreich antigens, tumor necrosis antigens, TB4R2, TBX21, TCP10, TDGF1, TEK, TGFA, TGFB1, TGFBIiI, TGFB2, TGFB3, TGFBI, TGFBR1, TGFBR2, TGFBR3, TH1L, THBS1 (thrombospondin-1), THBS2, THBS4, THPO, TIE (Tie-1), TIMP3, tissue factor, TLR10, TLR2, TLR3, TLR4, TLRS, TLR6, TLR7, TLRS, TLR9, TNF, TNF-a, TNFAIP2 (B94), TNFAIP3, TNFRSF11A, TNFRSF1A, TNFRSF1B, TNFRSF21, TNFRSFS, TNFRSF6 (Fas), TNFRSF7, TNFRSFS, TNFRSF9, TNFSF10 (TRAIL), TNFSF11 (TRANCE), TNFSF12 (APO3L), TNFSF13 (April), TNFSF13B, TNFSF14 (HVEM-L), TNFSF1S (VEGI), TNFSF18, TNFSF4 (OX40 ligand), TNFSFS (CD40 ligand), TNFSF6 (FasL), TNFSF7 (CD27 ligand), TNFSFS (CD30 ligand), TNFSF9 (4-IBB ligand), TOLLIP, Toll-like receptors, TOP2A (topoisomerase Iia), TPS3, TPM1, TPM2, TRADD, TRAF1, TRAF2, TRAF3, TRAF4, TRAPS, TRAF6, TREM1, TREM2, TRPC6, TSLP, TWEAK, VEGFR, ED-B fibronectin, WT-1, 17-IA antigen, complement factors C3, C3a, C3b, C5a, CS, an angiogenesis marker, bcI-2, bcI-6, Kras, cMET, CD19/CD3, BCMA/CD3, EGFR, HER3, IL17RA/IL7R, IL-6/IL-23, IL1/IL-8, IL-6, IL-6R/IL-21, IL-21R, ANG2/VEGF, VEGF/PDGFR-beta, Vascular Endothelial Growth Factor (VEGF) acceptor 2/CD3, PSMA/CD3, EPCAM/CD3, VEGFR-1, VEGFR-2, VEGFR-3, VEGFB, VEGFC, versican, VHL CS, VLA-4, c-FMS/CS-FIR, RET, HER3, HER4, IGFR, PDGFR, c-KIT, BCR, integrin, MMPs VEGF, EGF, PIGF, PDGF, HGF, angiopoietin, ERBB-3/C-MET, ERBB-2/C-MET, EGF receptor I/CD3, EGFR/HER3, PSCA/CD3, C-MET/CD3, ENDO-SIALIN/CD3, EPCAM/CD3, IGF-1R/CD3, FAPALPHA/CD3, EGFR/IGF-IR, IL 25 17A/F, EGF receptor I/CD3, and CD19/CD16, KHI, Tn-antigen, TF-antigen, CD44, glycolipids, glycosphingolipids such as 30 Gg3, Gb3, GD3, GD2, Gb5, Gm1, Gm2, sialyltetraosylceramide, XCL1 (lymphotactin), XCL2 (SCM-1b), XCR1 (GPRS/CCXCR1), YY1, and ZFPM2.

26. The antigen-binding molecule of any one of embodiments 1-24, wherein the antigen-binding molecule is capable of binding pairs of target antigens selected from the group consisting of CD137 and CD20, CD137 and EGFR, CD137 and Her-2, CD137 and PD-1, CD137 and PDL-1, VEGF and PD-L1, Lag-3 and TIM-3, OX40 and PD-1, TIM-3 and PD-L1, TIM-3 and PDL-1, EGFR and DLL-4, CD138 and CD20, CDI 38 and CD40, CDI 9 and CD20, CD20 and CD3, CD3 and CD33, CD3 and CD133, CD47 and CD20, CD38 and CD138, CD38 and CD20, CD20 and CD22, CD38 and CD40, CD40 and CD20, CD-8 and IL-6, CSPGs and RGM A, CTLA-4 and BTN02, IGF1 and IGF2, IGF1/2 and Erb2B, IGF-1R and EGFR, EGFR and CD13, IGF-1R and ErbB3, EGFR-2 and IGFR, VEGFR-2 and Met, VEGF-A andAngiopoietin-2 (Ang-2), IL-12 and TWEAK, IL-13 and IL-1 beta, PDGFR and VEGF, EpCAM and CD3, Her2 and CD3, CD19 and CD3, EGFR and Her3, CD16a and CD30, CD30 and PSMA, EGFR and CD3, CEA and CD3, TROP-2 and HSG, TROP-2 and CD3, MAG and RGM A, NgR and RGM A, NogoA and RGM A, OMGp and RGM A, PDL-1 and CTLA-4, CTLA-4 and PD-1, PD-1 and TIM-3, RGMA and RGM B, Te38 and TNFa, TNFa and Blys, TNFa and CD-22, TNFa and CTLA-4 domain, TNFa and GP130, TNFa and IL-12p40, and TNFa and RANK ligand.

27. The antigen-binding molecule of any one of embodiments 1-24, wherein the antigen-binding molecule is capable of binding one or two cytokines, cytokine-related proteins, and cytokine receptors selected from the group consisting of BMP1, BMP2, BMP3B (GDF10), BMP4, BMP6, BMP8, CSF1 (M-CSF), CSF2 (GM-CSF), CSF3 (G-CSF), EPO, FGF1 (aFGF), FGF2 (bFGF), FGF3 (int-2), FGF4 (HST), FGF5, FGF6 (HST-2), FGF7 (KGF), FGF9, FGF10, FGF11, FGF12, FGF12B, FGF14, FGF16, FGF17, FGF19, FGF20, FGF21, FGF23, IGF1, IGF2, IFNA1, IFNA2, IFNA4, IFNA5, IFNA6, IFNA7, IFNB1, IFNG, IFNW1, FILI, FILI (EPSILON), FILI (ZETA), ILIA, ILIB, IL2, IL3, IL4, IL5, IL6, IL7, IL8, IL9, ILIO, ILi1, ILI2A, ILI2B, ILI3, ILI4, ILI5, ILI6, ILI7, ILI7B, ILI8, ILI9, IL20, IL22, IL23, IL24, IL25, IL26, IL27, IL28A, IL28B, IL29, IL30, PDGFA, FGER1, FGFR2, FGFR3, EGFR, RORI, 2B4, KIR, CD137, CD27, OX40, CD40L, A2aR, CD48, B7-1, B7-2, ICOSL, B7-H3, B7-H4, CD137L, OX40L, CD70, CD40, PDGFB, TGFA, TGFB1, TGFB2, TGFB3, LTA (TNF-b), LTB, TNF (TNF-a), TNFSF4 (OX40 ligand), TNFSF5 (CD40 ligand), TNFSF6 (FasL), TNFSF7 (CD27 ligand), TNFSF8 (CD30 ligand), TNFSF9 (4-1BB ligand), TNFSF10 (TRAIL), TNFSF11 (TRANCE), TNFSF12 (AP03L), TNFSF13 (April), TNFSF13B, TNFSF14 (HVEM-L), TNFSF15 (VEGI), TNFSF18, FIGF (VEGFD), VEGF, VEGFB, VEGFC, ILIR1, ILIR2, ILIRLI, ILIRL2, IL2RA, IL2RB, IL2RG, IL3RA, IL4R, ILSRA, IL6R, IL 7R, ILSRA, ILSRB, IL9R, ILIORA, ILIORB, IK11RA, ILI2RB1, ILI2RB2, ILI3RA1, ILI3RA2, ILI5RA, ILI7R, ILI8R1, IL20RA, IL21R, IL22R, IL1HY1, ILIRAP, ILI-RAPLI, ILIRAPL2, ILIRN, IL6ST, ILI8BP, ILI8RAP, IL22RA2, AIF1, HGF, LEP (leptin), PTN, and THPO.

28. The antigen-binding molecule of any one of embodiments 1-24, wherein the antigen-binding molecule is capable of binding one or more chemokines, chemokine receptors, and chemokine-related proteins selected from the group consisting of CCLI (I-309), CCL2 (MCP-1/MCAF), CCL3 (MIP1a), CCL4 (MIP-1b), CCL5 (RANTES), CCL7 (MCP-3), CCL8 (mcp-2), CCLII (eotaxin), CCLI3 (MCP-4), CCLI5 (MIP-1 d), CCLI 6 (HCC-4), CCLI 7 (TARC). CCLI 8 (PARC), CCLI9 (MIP-3b), CCL20 (MIP-3a), CCL21 (SLC/exodus-2), CCL22 (MDC/STC-1), CCL23 (MPIF-1), CCL24 (MPIF-2/eotaxin-2), CCL25 (TECK), CCL26 (eotaxin-3), CCL27 (CTACK/ILC), CCL28, CXCLI (GRO1), CXCL2 (GR02), CXCL3 (GR03), CXCL5 (ENA-78), CXCL6 (GCP-2), CXCL9 (MIG), CXCLIO (IP 10), CXCL11 (I-TAC), CXCL12 (SDF1), CXCL13, CXCL14, CXCL16, PF4 (CXCL4), PPBP (CXCL7), CX3CL1 (SCYD1), SCYE1, XCL1 (lymphotactin), XCL2 (SCM-1b), BLR1 (MDR15), CCBP2 (D6/JAB61), CCR1 (CKR1/HM145), CCR2 (mcp-1RB/RA), CCR3 (CKR3/CMKBR3), CCR4, CCR5 (CMKBR5/ChemR13), CCR6 (CMKBR6/CKR-L3/STRL22/DRY6), CCR7 (CKR7/EBI1), CCRS (CMKBR8/TER1/CKR-L1), CCR9 (GPR-9-6), CCRL1 (VSHK1), CCRL2 (L-CCR), XCR1 (GPR5/CCXCR1), CMKLR1, CMKOR1 (RDC1), CX3CR1 (V28), CXCR4, GPR2 (CCR10), GPR31, GPR81 (FKSGSO), CXCR3 (GPR9/CKR-L2), CXCR6 (TYMSTR/STRL33/Bonzo), HM74, ILSRA (IL8Ra), ILSRB (IL8Rb), LTB4R (GPR16), TCP10, CKLFSF2, CKLFSF3, CKLFSF4, CKLFSF5, CKLFSF6, CKLFSF7, CKLFSFS, BDNF, C5R1, CSF3, GRCC10 (C10), EPO, FY (DARC), GDF5, HIF1A, ILS, PRL, RGS3, RGS13, SDF2, SLIT2, TLR2, TLR4, TREM1, TREM2, and VHL.

29. The antigen-binding molecule of any one of embodiments 1-24, wherein the antigen-binding molecule is capable of wherein the bispecific antigen-binding molecule is capable of binding pairs of cytokines.

30. The antigen-binding molecule of embodiment 29, wherein the bispecific antigen-binding molecule is capable of binding pairs of cytokines selected from the group consisting of TSLP, IL-1a and IL-Iβ, IL-12 and IL-18, TNFa and IL-23, TNFa and IL-13, TNF and IL-18, TNF and IL-12, TNF and IL-1beta, TNF and MIF, TNF and IL-6, TNF and IL-6 Receptor, TNF and IL-17, IL-17 and IL-20, IL-17 and IL-23, TNF and IL-15, TNF and VEGF, VEGFR and EGFR, PDGFR and VEGF, IL-13 and IL-9, IL-13 and IL-4, IL-13 and IL-5, IL-13 and IL-25, IL-13 and TARC, IL-13 and MDC, IL-13 and MIF, IL-13 and TGF-8, IL-13 and LHR agonist, IL-13 and CL25, IL-13 and SPRR2a, IL-13 and SPRR2b, IL-13 and ADAM 8, and TNFa and PGE4, IL-13 and PED2, and TNF and PEG2.

31. The antigen-binding molecule of any one of embodiments 1-30, wherein the antigen-binding molecule is capable of wherein the bispecific antigen-binding molecule binds to each epitope with similar or greater affinity relative to a monospecific antibody or antibody fragment specific for each epitope.

32. The antigen-binding molecule of any one of embodiments 1-31, wherein the antigen-binding molecule has an agonist function.

33. The antigen-binding molecule of any one of embodiments 1-31, wherein the antigen-binding molecule has blocking function, having a similar or lower IC50 relative a parental antibody, optionally wherein the parental antibody is a human antibody of IgG isotype.

34. The antigen-binding molecule of any one of embodiments 1-33, wherein the antigen-binding molecule is a bispecific for a single ligand and forms 1:1 ligand complexes at a higher level relative a parental antibody or antibodies.

35. An antigen-binding molecule comprising:
   a first antigen-binding Fab domain that specifically binds a first epitope;
   a second antigen-binding Fab domain that specifically binds a second epitope that is distinct from the first epitope;
   an Fc domain comprising a first heavy chain polypeptide and a second heavy chain polypeptide;

a first linker linking the N-terminal end of the heavy chain of the first antigen-binding Fab domain to the C-terminal end of the first heavy chain polypeptide; and a second linker linking the N-terminal end of the heavy chain of the second antigen-binding Fab domain to the C-terminal end of the second heavy chain polypeptide.

36. The antigen-binding molecule of embodiment 35, wherein the first heavy chain polypeptide comprises:
   a first CH amino acid sequence;
   a first VH amino acid sequence; and
   a second CH amino acid sequence, wherein the first VH amino acid sequence is between the first CH amino acid sequence and the second CH amino acid sequence.

37. The antigen-binding molecule of embodiment 36, wherein the first CH amino acid sequence comprises a first CH3 amino acid sequence located N-terminal to the first VH amino acid sequence.

38. The antigen-binding molecule 36, wherein the first CH3 comprises an H435R mutation and a Y436F mutation 39. The antigen-binding molecule of any one of embodiments 35-38, wherein the second heavy chain polypeptide comprises:
   a third CH amino acid sequence;
   a second VH amino acid sequence; and
   a fourth CH amino acid sequence, wherein the second VH amino acid sequence is between the third CH amino acid sequence and the fourth CH amino acid sequence.

40. The antigen-binding molecule of embodiment 39, wherein the first CH amino acid sequence comprises a first CH3 amino acid sequence located N-terminal to the first VH amino acid sequence.

41. The antigen-binding molecule of embodiment 40, wherein the first CH3 comprises an H435R mutation and a Y436F mutation 42. The antigen-binding molecule of embodiment 40 or embodiment 41, further comprising a first linker linking a N-terminal end of the first VH amino acid sequence to a C-terminal end of the first CH3 amino acid sequence.

43. The antigen-binding molecule of any one of embodiments 35-42, wherein the third CH amino acid sequence comprises a second CH3 amino acid sequence located N-terminal to the second VH amino acid sequence.

44. The antigen-binding molecule of embodiment 43, further comprising a second linker linking a N-terminal end of the second VH amino acid sequence to a C-terminal end of the second CH3 amino acid sequence.

45. The antigen-binding molecule of any one of embodiments 35-44, wherein the second CH amino acid sequence comprises a first CH1 amino acid sequence located C-terminal to the first VH amino acid sequence.

46. The antigen-binding molecule of any one of embodiments 35-45, wherein the fourth CH amino acid sequence comprises a second CH1 amino acid sequence located C-terminal to the second VH amino acid sequence.

47. The antigen-binding molecule of any one of embodiments 35-46, further comprising a first CH2 amino acid sequence located N-terminal to the first CH3 amino acid sequence.

48. The antigen-binding molecule of any one of embodiments 35-47, further comprising a second CH2 amino acid sequence located N-terminal to the second CH3 amino acid sequence.

49. The antigen-binding molecule of any one of embodiments 35-48, wherein the antigen-binding molecule does not include a hinge region disulfide bond.

50. The antigen-binding molecule of any one of embodiments 35-49, further comprising a first light chain polypeptide, the first light chain polypeptide comprising: a first VL amino acid sequence; and a first CL amino acid sequence.

51. The antigen-binding molecule of embodiment 50, further comprising a disulfide bond linking first CL to the first CH1.

52. The antigen-binding molecule of any one of embodiments 35-51 further comprising a second light chain polypeptide, the second light chain polypeptide comprising: a second VL amino acid sequence; and a second CL amino acid sequence.

53. The antigen-binding molecule of embodiment 521, further comprising a disulfide bond linking second CL to the second CH1.

54. The antigen-binding molecule of any one of embodiments 44-53, wherein the first linker and the second linker each comprises a polypeptide.

55. The antigen-binding molecule of embodiment 54, wherein the first linker and the second linker have a length of from 0 to 50 amino acids.

56. The antigen-binding molecule of any one of embodiments 54-55, wherein the first linker and the second linker have identical amino acid sequences.

57. The antigen-binding molecule of any one of embodiments 54-56, wherein the first linker and the second linker each comprises poly Glycine and Serine amino acid sequences.

58. The antigen-binding molecule of embodiment 57, wherein the poly Glycine and Serine amino acid sequences comprise 2 to 6 repeating GGGGS (SEQ ID NO:3) amino acid sequences.

59. The antigen-binding molecule of embodiment 58, wherein the poly Glycine and Serine amino acid sequences comprise $(G4S)_2$ (SEQ ID NO:18), $(G4S)_3$ (SEQ ID NO:4) or $(G4S)_4$ (SEQ ID NO:19).

60. The antigen-binding molecule of any one of embodiments 52-59, wherein the first light chain polypeptide and the second light chain polypeptide have identical amino acid sequences.

61. The antigen-binding molecule of any one of embodiments 35-60, wherein the first heavy chain polypeptide the second heavy chain polypeptide have identical amino acid sequences.

62. The antigen-binding molecule of any one of embodiments 35-60, wherein the first heavy chain polypeptide the second heavy chain polypeptide have non-identical amino acid sequences.

63. The antigen-binding molecule of any one of embodiments 35-61, wherein the antigen-binding molecule is capable of binding one or more antigens selected from the group consisting of ABCF1, ACVR1, ACVR1B, ACVR2, ACVR2B, ACVRLI, ADORA2A, Aggrecan, AGR2, AICDA, AIF1, AIG1, AKAP1, AKAP2, AMH, AMHR2, ANGPT1, ANGPT2, ANGPTL3, ANGPTL4, ANPEP, APC, APOC1, AR, AZGP1 (zinc-a-glycoprotein), ART-4, B7, B7.1, B7.2, BAD, BAFF, BAGI, BAIi, BCL2, BCL6, BDNF, BLNK, BLRI (MDRIS), BIyS, BMPI, BMP2, BMP3B (GDF10), BMP4, BMP6, BMPS, BMPR1A, BMPR1B, BMPR2, BPAG1 (plectin), BRCA1, Ba-733, BAGE, BrE3-antigen, CA125, CAMEL, CAP-I, CASP-8/m, CCCL19, CCCL21, CD1, CD1a, CD2, CD3, CD4, CDS, CD8, CDI-IA, CD14, CD15, CD16, CD18, CD19, CD20, CD21, CD22, CD23, CD25, CD29, CD30, CD32b, CD33, CD37, CD38, CD40, CD40L, CD45, CD46, CD54, CD55, CD59, CD64, CD66a-e, CD67, CD70, CD74, CD79a, CD80, CD83, CD95, CD126, CD133, CD138, CD147, CD154, CDC27, CDK-4/m, CDKN2A, CXCR4, CXCR7, CXCL12, C19orf10 (IL27w), C3, C4A, CS, CSR1, CANT1, CASPI, CASP4, CAV1, CCBP2 (D6/JAB61), CCLI (1-309), CCLII (eotaxin), CCL13 (MCP-4), CCLIS (MIP-1d), CCL16 (HCC-4), CCL17 (TARC), CCLIS (PARC), CCL19 (MIP-3b), CCL2 (MCP-1), MCAF, CCL20 (MIP-3a), CCL21 (MIP-2), SLC, exodus-2, CCL22 (MDC/STC-1), CCL23 (MPIF-1), CCL24 (MPIF-2/eotaxin-2), CCL2S (TECK), CCL26 (eotaxin-3), CCL27 (CTACK/ILC), CCL2S, CCL3 (MIP1a), CCL4 (MIP-1b), CCLS (RANTES), CCL7 (MCP-3), CCLS (mcp-2), CCNA1, CCNA2, CCND1, CCNE1, CCNE2, CCR1 (CKR1/HM14S), CCR2 (mcp-1RB/RA), CCR3 (CKR3/CMKBR3), CCR4, CCRS (CMKBRSI ChemR13), CCR6 (CMKBR6/CKR-L3/STRL22/DRY6), CCR7 (CKR7/EB1), CCRS (CMKBRS/TER1/CKR-LI), CCR9 (GPR-9-6), CCRLI (VSHK1), CCRL2 (L-CCR), CD164, CDIC, CD200, CD-22, CD24, CD2S, CD3S, CD3E, CD3G, CD3Z, CD4, CD44, CD4SRB, CD47, CD4S, CDS2, CD69, CD72, CD79A, CD79B, CDSO, CDS1, CDS3, CDS6, CD137, CD13S, B7-1, B7-2, ICOSL, B7-H3, B7-H4, CD137L, OX40L, CDH1 (E-cadherin), CDH10, CDH12, CDH13, CDHIS, CDH19, CDH20, CDHS, CDH7, CDHS, CDH9, CDK2, CDK3, CDK4, CDKS, CDK6, CDK7, CDK9, CDKN1A (p21 Wap1/Cip1), CDKN1B (p27Kip1), CDKN1C, CDKN2A (p16INK4a), CDKN2B, CDKN2C, CDKN3, CEBPB, CER1, CHGA, CHGB, Chitinase, CHST1O, CKLFSF2, CKLFSF3, CKLFSF4, CKLFSFS, CKLFSF6, CKLFSF7, CKLFSFS, CLDN3, CLDN7 (claudin-7), CLN3, CLU (clusterin), CMKLR1, CMKOR1 (RDC1), CNR1, COLISA1, COLIA1, COL4A3, COL6A1, CR2, CRP, CSF1 (M-CSF), CSF2 (GM-CSF), CSF3 (GCSF), CTLA-4, CTNNB1 (b-catenin), CTSB (cathepsin B), CX3CLI (SCYD1), CX3CR1 (V2S), CXCLI (GRO1), CXCLIO (IP-10), CXCL11 (I-TAC/IP-9), CXCL13, CXCL14, CXCL16, CXCL2 (GR02), CXCL3 (GR03), CXCLS (ENA-7S/LIX), CXCL6 (GCP-2), CXCL9 (MIG), CXCR3 (GPR9/CKR-L2), CXCR6 (TYMSTR/STRL33/Bonzo), CYBS, CYC1, CYSLTR1, HIF-1-a, colon-specific antigen-p (CSAp), CEA (CEACAM5), CEACAM6, c-met, DAB2IP, DES, DKFZp4S1J011S, DNCLI, DPP4, DAM, EGFR, EGFRvIII, EGP-1, EGP-2, ELF2-M, Ep-CAM, E2F1, ECGF1, EDG1, EFNA1, EFNA3, EFNB2, EGF, EGFR, ELAC2, ENG, EN01, EN02, EN03, EPHB4, EPO, EREG, ERKS, ESR1, ESR2, F3 (TF), FADD, FasL, FASN, FCER1A, FCER2, FCGR3A, FGF, FGF1 (aFGF), FGF10, FGF11, FGF12, FGF12B, FGF13, FGF14, FGF16, FGF17, FGF1S, FGF19, FGF2 (bFGF), FGF20, FGF21, FGF22, FGF23, FGF3 (int-2), FGF4 (HST), FGFS, FGF7 (KGF), FGFS, FGF9, FGFR3, FIGF (VEGFD), FILI (EPSILON), FILI (ZETA), FLJ12SS4, FLJ2SS30, FLRT1 (fibronectin), FOS, FOSLI (FRA-1), FY (DARC), FIt-I, FIt-3, folate receptor, G250 antigen, GAGE, GROB, GABRP (GABAa), GAGEB1, GAGEC1, GALNAC4S-6ST, GATA3, GDFS, GFiI, GGTI, GM-CSF, GNAS1, GNRH1, GPR2 (CCR10), GPR31, GPR44, GPRSI (FKSGSO), GRCC10 (010), GRP, GSN (Gelsolin), GSTP1, HAVCR2, HDAC4, HDACS, HDAC7A, HDAC9, HGF, HIP1 histamine and histamine receptors, HLA-A, HLA-DRA, HM74, HMOX1, HUMCYT2A, HLA-DR, HMI 24, human chorionic gonadotropin (HCG) and its subunits, HER2/neu, HMGB-1, hypoxia inducible factor (HIF-1), HSP70-2M, HST-2 or 1a, IGF-IR, IFN-γ, IFN-α, IL-2, IL-4R, IL-6R, IL-13R, IL-15R, IL-17R, IL-18R, IL-6, IL-8, IL-12, IL-15, IL-17, IL-18, IL-25, IGBP1, IGF1, IGF1R, IGF2, IGFBP2, IGFBP3, IGFBP6, IL-1, IL-10, IL-10RA, IL-10RB, IL-11, IL-11RA, IL-12, IL-12A, IL-12RB1, IL-12RB2, IL-13, IL-13RA1, IL-13RA2, IL-14, IL-1S, IL-1SRA, IL-16, IL-17, IL-17B, IL-17C, IL-17R, IL-18, IL-18BP, IL-18R1, IL-18RAP, IL-19, IL-IA, IL-1B, IL-1F10, IL-1FS, IL-1F6, IL-1F7, IL-1F8, IL-1F9, IL-1HY1, IL-1R1, IL-1R2, IL-1RAP, IL-1RAPL1, IL-1RAPL2, IL-1RL1, IL-1RL2 IL-1RN, IL-2, IL-20, IL-20RA, IL-21R, IL-22, IL-22R, IL-22RA2, IL-23, IL-24, IL-2S, IL-26, IL-27, IL-28A, IL-28B, IL-29, IL-2RA, IL-2RB, IL-2RG, IL-3, IL-30, IL-3RA, IL-4, IL-4R, IL-S, IL-5RA, IL-6, IL-6R, IL-6ST (glycoprotein 130), IL-7, IL-7R, IL-S, IL-SRA, IL-SRB, IL-9, IL-9R, IL-K, INHA, INHBA, INSL3, INSL4, IRAK1, IRAK2, ITGA1, ITGA2, ITGA3, ITGA6 (a6 integrin), ITGAV, ITGB3, ITGB4 (b 4 integrin) insulin-like growth factor-1 (IGF-1), ICEBERG, ICOSL, ID2, IFN-a, IFNA1, IFNA2, IFNA4 IFNAS, IFNA6, IFNA7, IFNB1, IFNW1, JAG1, JAK1, JAK3, JUN, K6HF, KAi1, KDR, KITLG, KLFS (GC Box BP), KLF6, KLK10, KLK12, KLK13, KLK14, KLK1S, KLK3, KLK4, KLKS, KLK6, KLK9, KRT1, KRT19 (Keratin 19), KRT2A, KRTHB6 (hair-specific type II keratin), KC4-antigen, KS-1-antigen, KS 1-4, Le-Y, LDR/FUT, LAMAS, LEP (leptin), Lingo-p7S, Lingo-Troy, LPS, LTA (TNF-b), LTB, LTB4R (GPR16), LTB4R2, LTBR, MACMARCKS, MAG or Omgp, MAP2K7 (c-Jun), MDK, MIB1, midkine, MIF, MIP-2, MKI67 (Ki-67), MMP2, MMP9, MS4A1, MSMB, MT3 (metallothionectin-III), MTSS1, MUC1 (mucin), MYC, MYD88, macrophage migration inhibitory factor (MIF), MAGE, MAGE-3, MART-1, MART-2, NY-ES0-1, TRAG-3, mCRP, MCP-1, MIP-1A, MIP-1B, MIF, MUC1, MUC2, MUC3, MUC4, MUC5, MUM-1/2, MUM-3, NCA66, NCA95, NCA90, NCK2, neurocan, NFKB1, NFKB2, NGFB (NGF), NGFR, NgR-Lingo, NgR-Nogo66 (Noga), NgRp7S, NgR-Troy, NME1 (NM23A), NOXS, NPPB, NROB1, NROB2, NR1D1, NR1D2, NRIH2, NRIH3, NRIH4, NR1I2, NR1I3, NR2C1, NR2C2, NR2E1, NR2E3, NR2F1, NR2F2, NR2F6, NR3C1, NR3C2, NR4A1, NR4A2, NR4A3, NRSA1, NRSA2, NR6A1, NRP1, NRP2, NTSE, NTN4, ODZ1, OPRD1, PCSK9, P2RX7, PAP, PART1, PATE, PAWR, PCA3, PCNA, PD-1, PD-L1, alpha4beta7, OX40, GITR, TIM-3, Lag-3, B7-H3, B7-H4, GDFS, CGRP, Lingo-I, Factor IXa, Factor X, ICOS, GARP, BTLA, CD160, RORI, 2B4, KIR, CD27, OX40, A2aR, PDGFA, PDGFB, PECAM1, PF4 (CXCL4), PGF, PGR, phosphacan, PIAS2, PIK3CG, PLAU (uPA), PLG, PLXDC1, PPBP (CXCL7), PPID, PR1, PRKCQ, PRKD1, PRL, PROC, PROK2, PSAP, PSCA, PTAFR, PTEN, PTGS2 (COX-2), PTN, pancreatic cancer mucin, placental growth factor, p53, PLAGL2, prostatic acid phosphatase, PSA, PRAME, PSMA, 10 PIGF, ILGF, ILGF-IR, IL-6, RS5, RANTES, RAC2 (p21Rac2), RARB, RGS1, RGS13, RGS3, RNFI10 (ZNF144), ROB02, S100A2, SCGB1D2 (lipophilin B), SCGB2A1 (mammaglobin 2), SCGB2A2 (mammaglobin 1), SCYE1 (endothelial Monocyte-activating cytokine), SDF2, SERPINA1, SERPINA3, SERPINBS (maspin), SERPINE1 (PAI-1), SERPINF1, SHBG, SLA2, SLC2A2, SLC33A1, SLC43A1, SLIT2, SPP1, SPRR1B (SprI), ST6GAL1, STAB1, STATE, STEAP, STEAP2, T1O1, SAGE, 5100, survivin, survivin-2B, TAC, TAG-72, tenascin, TRAIL receptors, TNF-α, Tn-antigen, ThomsonFriedenreich antigens, tumor necrosis antigens, TB4R2, TBX21, TCP10, TDGF1, TEK, TGFA, TGFB1, TGFBIiI, TGFB2, TGFB3, TGFBI, TGFBR1, TGFBR2, TGFBR3, TH1L, THBS1 (thrombospondin-1), THBS2, THBS4, THPO, TIE (Tie-1), TIMP3, tissue factor, TLR10, TLR2, TLR3, TLR4, TLRS, TLR6, TLR7, TLRS, TLR9, TNF, TNF-a, TNFAIP2 (B94), TNFAIP3, TNFRSF11A, TNFRSF1A, TNFRSF1B, TNFRSF21, TNFRSFS, TNFRSF6 (Fas), TNFRSF7, TNFRSFS, TNFRSF9, TNFSF10 (TRAIL), TNFSF11 (TRANCE), TNFSF12 (AP03L), TNFSF13 (April), TNFSF13B, TNFSF14 (HVEM-L), TNFSF1S (VEGI), TNFSF18, TNFSF4 (OX40 ligand), TNFSFS (CD40 ligand), TNFSF6 (FasL), TNFSF7 (CD27 ligand), TNFSFS (CD30 ligand), TNFSF9 (4-IBB ligand), TOLLIP, Toll-like receptors, TOP2A (topoisomerase Iia), TPS3, TPM1, TPM2, TRADD, TRAF1, TRAF2, TRAF3, TRAF4, TRAPS, TRAF6, TREM1, TREM2, TRPC6, TSLP, TWEAK, VEGFR, ED-B fibronectin, WT-1, 17-IA antigen, complement factors C3, C3a, C3b, C5a, CS, an angiogenesis marker, bcI-2, bcI-6, Kras, cMET, CD19/CD3, BCMA/CD3, EGFR, HER3, IL17RA/IL7R, IL-6/IL-23, IL1/IL-8, IL-6, IL-6R/IL-21, IL-21R, ANG2/VEGF, VEGF/PDGFR-beta, Vascular Endothelial Growth Factor (VEGF) acceptor 2/CD3, PSMA/CD3, EPCAM/CD3, VEGFR-1, VEGFR-2, VEGFR-3, VEGFB, VEGFC, versican, VHL CS, VLA-4, c-FMS/CS-FIR, RET, HER3, HER4, IGFR, PDGFR, c-KIT, BCR, integrin, MMPs VEGF, EGF, PIGF, PDGF, HGF, angiopoietin, ERBB-3/C-MET, ERBB-2/C-MET, EGF receptor I/CD3, EGFR/HER3, PSCA/CD3, C-MET/CD3, ENDOSIALIN/CD3, EPCAM/CD3, IGF-1R/CD3, FAPALPHA/CD3, EGFR/IGF-IR, IL 25 17A/F, EGF receptor I/CD3, and CD19/CD16, KHI, Tn-antigen, TF-antigen, CD44, glycolipids, glycosphingolipids such as 30 Gg3, Gb3, GD3, GD2, Gb5, Gm1, Gm2, sialyltetraosylceramide, XCL1 (lymphotactin), XCL2 (SCM-1b), XCR1 (GPRS/CCXCR1), YY1, and ZFPM2.

64. The antigen-binding molecule of any one of embodiments 35-61, wherein the antigen-binding molecule is capable of binding pairs of target antigens selected from the group consisting of CD137 and CD20, CD137 and EGFR, CD137 and Her-2, CD137 and PD-1, CD137 and PDL-1, VEGF and PD-L1, Lag-3 and TIM-3, 0X40 and PD-1, TIM-3 and PD-1, TIM-3 and PDL-1, EGFR and DLL-4, CD138 and CD20, CDI 38 and CD40, CDI 9 and CD20, CD20 and CD3, CD3 and CD33, CD3 and CD133, CD47 and CD20, CD38 and CD138, CD38 and CD20, CD20 and CD22, CD38 and CD40, CD40 and CD20, CD-8 and IL-6, CSPGs and RGM A, CTLA-4 and BTN02, IGF1 and IGF2, IGF1/2 and Erb2B, IGF-1R and EGFR, EGFR and CD13, IGF-1R and ErbB3, EGFR-2 and IGFR, VEGFR-2 and Met, VEGF-A andAngiopoietin-2 (Ang-2), IL-12 and TWEAK, IL-13 and IL-1 beta, PDGFR and VEGF, EpCAM and CD3, Her2 and CD3, CD19 and CD3, EGFR and Her3, CD16a and CD30, CD30 and PSMA, EGFR and CD3, CEA and CD3, TROP-2 and HSG, TROP-2 and CD3, MAG and RGM A, NgR and RGM A, NogoA and RGM A, OMGp and RGM A, PDL-1 and CTLA-4, CTLA-4 and PD-1, PD-1 and TIM-3, RGMA and RGM B, Te38 and TNFa, TNFa and Blys, TNFa and CD-22, TNFa and CTLA-4 domain, TNFa and GP130, TNFa and IL-12p40, and TNFa and RANK ligand.

65. The antigen-binding molecule of any one of embodiments 35-61, wherein the antigen-binding molecule is capable of binding one or two cytokines, cytokine-related proteins, and cytokine receptors selected from the group consisting of BMP1, BMP2, BMP3B (GDF10), BMP4, BMP6, BMP8, CSF1 (M-CSF), CSF2 (GM-CSF), CSF3 (G-CSF), EPO, FGF1 (aFGF), FGF2 (bFGF), FGF3 (int-2), FGF4 (HST), FGF5, FGF6 (HST-2), FGF7 (KGF), FGF9, FGF10, FGF11, FGF12, FGF12B, FGF14, FGF16, FGF17, FGF19, FGF20, FGF21, FGF23, IGF1, IGF2, IFNA1, IFNA2, IFNA4, IFNA5, IFNA6, IFNA7, IFNB1, IFNG, IFNW1, FILI, FILI (EPSILON), FILI (ZETA), ILIA, ILIB, IL2, IL3, IL4, IL5, IL6, IL7, IL8, IL9, ILIO, ILi1, ILI2A, ILI2B, ILI3, ILI4, ILI5, ILI6, ILI7, ILI7B, IL18, IL19, IL20, IL22, IL23, IL24, IL25, IL26, IL27, IL28A, IL28B, IL29, IL30, PDGFA, FGER1, FGFR2, FGFR3, EGFR, RORI, 2B4, KIR, CD137, CD27, OX40, CD40L, A2aR, CD48, B7-1, B7-2, ICOSL, B7-H3, B7-H4, CD137L, OX40L, CD70, CD40, PDGFB, TGFA, TGFB1, TGFB2, TGFB3, LTA (TNF-b), LTB, TNF (TNF-a), TNFSF4 (OX40 ligand), TNFSFS (CD40 ligand), TNFSF6 (FasL), TNFSF7 (CD27 ligand), TNFSF8 (CD30 ligand), TNFSF9 (4-1BB ligand), TNFSF10 (TRAIL), TNFSF11 (TRANCE), TNFSF12 (AP03L), TNFSF13 (April), TNFSF13B, TNFSF14 (HVEM-L), TNFSF15 (VEGI), TNFSF18, FIGF (VEGFD), VEGF, VEGFB, VEGFC, ILIR1, ILIR2, ILIRLI, ILIRL2, IL2RA, IL2RB, IL2RG, IL3RA, IL4R, IL5RA, IL6R, IL 7R, IL8RA, IL8RB, IL9R, ILIORA, ILIORB, IL11RA, ILI2RB1, ILI2RB2, ILI3RA1, ILI3RA2, ILI5RA, ILI7R, ILI8R1, IL20RA, IL21R, IL22R, IL1HY1, ILIRAP, ILI-RAPLI, ILIRAPL2, ILIRN, IL6ST, ILI8BP, ILI8RAP, IL22RA2, AIF1, HGF, LEP (leptin), PTN, and THPO.

66. The antigen-binding molecule of any one of embodiments 35-61, wherein the antigen-binding molecule is capable of binding one or more chemokines, chemokine receptors, and chemokine-related proteins selected from the group consisting of CCLI (I-309), CCL2 (MCP-1/MCAF), CCL3 (MIP1a), CCL4 (MIP-1b), CCLS (RANTES), CCL7 (MCP-3), CCL8 (mcp-2), CCLII (eotaxin), CCLI3 (MCP-4), CCLIS (MIP-1 d), CCLI 6 (HCC-4), CCLI 7 (TARC), CCLI 8 (PARC), CCLI9 (MIP-3b), CCL20 (MIP-3a), CCL21 (SLC/exodus-2), CCL22 (MDC/STC-1), CCL23 (MPIF-1), CCL24 (MPIF-2/eotaxin-2), CCL25 (TECK), CCL26 (eotaxin-3), CCL27 (CTACK/ILC), CCL28, CXCLI (GRO1), CXCL2 (GR02), CXCL3 (GR03), CXCLS (ENA-78), CXCL6 (GCP-2), CXCL9 (MIG), CXCLIO (IP 10), CXCL11 (I-TAC), CXCL12 (SDF1), CXCL13, CXCL14, CXCL16, PF4 (CXCL4), PPBP (CXCL7), CX3CL1 (SCYD1), SCYE1, XCL1 (lymphotactin), XCL2 (SCM-1b), BLR1 (MDR15), CCBP2 (D6/JAB61), CCR1 (CKR1/HM145), CCR2 (mcp-1RB/RA), CCR3 (CKR3/CMKBR3), CCR4, CCR5 (CMKBR5/ChemR13), CCR6 (CMKBR6/CKR-L3/STRL22/DRY6), CCR7 (CKR7/EBI1), CCRS (CMKBR8/TER1/CKR-L1), CCR9 (GPR-9-6), CCRL1 (VSHK1), CCRL2 (L-CCR), XCR1 (GPR5/CCXCR1), CMKLR1, CMKOR1 (RDC1), CX3CR1 (V28), CXCR4, GPR2 (CCR10), GPR31, GPR81 (FKSGSO), CXCR3 (GPR9/CKR-L2), CXCR6 (TYMSTR/STRL33/Bonzo), HM74, ILSRA (IL8Ra), ILSRB (IL8Rb), LTB4R (GPR16), TCP10, CKLFSF2, CKLFSF3, CKLFSF4, CKLFSF5, CKLFSF6, CKLFSF7, CKLFSFS, BDNF, C5R1, CSF3, GRCC10 (C10), EPO, FY (DARC), GDF5, HIF1A, ILS, PRL, RGS3, RGS13, SDF2, SLIT2, TLR2, TLR4, TREM1, TREM2, and VHL.

67. The antigen-binding molecule of any one of embodiments 35-61 wherein the antigen-binding molecule is capable of wherein the antigen-binding molecule is capable of binding pairs of cytokines.

68. The antigen-binding molecule of embodiment 67, wherein the antigen-binding molecule is capable of binding pairs of cytokines selected from the group consisting TSLP, IL-1a and IL-Iβ, IL-12 and IL-18, TNFa and IL-23, TNFa and IL-13, TNF and IL-18, TNF and IL-12, TNF and IL-1beta, TNF and MIF, TNF and IL-6, TNF and IL-6 Receptor, TNF and IL-17, IL-17 and IL-20, IL-17 and IL-23, TNF and IL-15, TNF and VEGF, VEGFR and EGFR, PDGFR and VEGF, IL-13 and IL-9, IL-13 and IL-4, IL-13 and IL-5, IL-13 and IL-25, IL-13 and TARO, IL-13 and MDC, IL-13 and MIF, IL-13 and TGF-β, IL-13 and LHR agonist, IL-13 and CL25, IL-13 and SPRR2a, IL-13 and SPRR2b, IL-13 and ADAM 8, and TNFa and PGE4, IL-13 and PED2, and TNF and PEG2.

69. The antigen-binding molecule of any one of embodiments 35-68, wherein the antigen-binding molecule is capable of wherein the antigen-binding molecule binds to each epitope with similar or greater affinity relative to a monospecific antibody or antibody fragment specific for each epitope.

70. The antigen-binding molecule of any one of embodiments 35-69, wherein the antigen-binding molecule has an agonist function.

71. The antigen-binding molecule of any one of embodiments 35-70, wherein the antigen-binding molecule has blocking function, having a similar or lower IC50 relative to a parental antibody, optionally wherein the parental antibody is a human antibody of IgG isotype.

72. The antigen-binding molecule of any one of embodiments 35-71, wherein the antigen-binding molecule is a bispecific for a single ligand and forms 1:1 ligand complexes at a higher level relative a parental antibody or antibodies.

73. The antigen-binding molecule of any one of embodiments 35 to 72, wherein the antigen-binding molecule is conjugated to an agent selected from the group consisting of an immunoadhesin molecule, an imaging agent, a therapeutic agent, and a cytotoxic agent.

74. A pharmaceutical composition comprising the antigen-binding of any one of embodiments 1 to 73, and a pharmaceutically acceptable carrier.

75. A nucleic acid molecule encoding the antigen-binding molecule of any one of embodiments 1 to 73.

76. The nucleic acid molecule of embodiment 74, wherein the nucleic acid molecule is operatively linked to an expression control sequence.

77. An expression vector comprising the nucleic acid molecule of embodiment 75 or 76.

78. A host cell comprising the nucleic acid molecule of embodiment 75 or 76 or the vector of embodiment 77.

79. The host cell of embodiment 78, wherein the cell is a eukaryotic cell.

80. The host cell of embodiment 78 or 79, wherein the cell is an animal cell.

81. The host cell of any one of embodiments 78 to 79, wherein the cell is a mammalian cell, optionally a CHO cell.

82. A method of treating a subject having a condition associated with any one or more of the antigens recited in embodiment 63, comprising administering to the subject an effective amount of the antigen-binding molecule of any one of embodiments 1-73.

83. A method of inhibiting a molecular pathway in a subject, comprising administering to the subject an effective amount of the antigen-binding molecule of any one of embodiments 1-73 to inhibit the molecular pathway.

84. A method of activating a molecular pathway in a subject, comprising administering to the subject an effective amount of the antigen-binding molecule of any one of embodiments 1-73 to activate the molecular pathway.

85. Use of the antigen-binding molecule of any one of embodiments 1-73 in the manufacture of a medicament for the treatment of a condition associated with any one or more of the antigens recited in embodiment 63.

9. CITATION OF REFERENCES

All publications, patents, patent applications and other documents cited in this application are hereby incorporated by reference in their entireties for all purposes to the same extent as if each individual publication, patent, patent application or other document were individually indicated to be incorporated by reference for all purposes. In the event that there is an inconsistency between the teachings of one or more of the references incorporated herein and the present disclosure, the teachings of the present specification are intended.

What is claimed is:

1. A bispecific antigen-binding molecule comprising:
   (a) a first polypeptide chain comprising in an N-to-C terminal orientation:
      (i) a first Fc domain; and
      (ii) a first Fab domain that binds to a cytokine and comprises a first heavy chain variable region (VH) domain associated with a first light chain variable region (VL) domain; and
   (b) a second polypeptide chain comprising in an N-to-C terminal orientation:
      (i) a second Fc domain associated with the first Fc domain to form an Fc heterodimer; and
      (ii) a second Fab domain that is non-identical to the first Fab domain, binds to the cytokine, and comprises a second VH domain associated with a second VL domain;
   (c) a third polypeptide chain associated with the first polypeptide, the third polypeptide comprising in an N-to-C terminal orientation:
      (i) the first VL domain; and
      (ii) a first constant domain of the light chain (CL) domain; and
   (d) a fourth polypeptide chain associated with the second polypeptide, the fourth polypeptide comprising in an N-to-C terminal orientation:
      (i) the second VL domain; and
      (ii) a second CL domain,
   wherein the first Fab domain and the second Fab domain are the only antigen-binding domains in the antigen-binding molecule.

2. The antigen-binding molecule of claim 1, which comprises a first linker between the first Fc domain and the first VH domain and a second linker between the second Fc domain and the second VH domain.

3. The antigen-binding molecule of claim 2, wherein the first linker and the second linker have identical amino acid sequences.

4. The antigen-binding molecule of claim 1, wherein the first polypeptide chain comprises a first hinge domain N-terminal to the first Fc domain and the second polypeptide chain comprises a second hinge domain N-terminal to the second Fc domain.

5. The antigen-binding molecule of claim 1, which has one hinge region.

6. The antigen-binding molecule of claim 1, which has two hinge regions.

7. The antigen-binding molecule of claim 1, wherein the Fc domains in the Fc heterodimer comprise knob-in-hole mutations as compared to a wild type Fc domain.

8. A pharmaceutical composition comprising the antigen-binding molecule of claim 1 and an excipient.

9. The antigen-binding molecule of claim 1, which is complexed at a 1:1 ratio with the cytokine.

10. The antigen-binding molecule of claim 1, wherein the cytokine is thymic stromal lymphopoietin (TSLP), IL-1α, IL-1β, IL-12, IL-18, TNFα, IL-23, IL-13, macrophage migration inhibitory factor (MIF), IL-6, IL-17, IL-20, IL-15, IL-9, IL-4, IL-5, IL-25, TGF-β, CCL25.

11. The antigen-binding molecule of claim 1, wherein the cytokine is human thymic stromal lymphopoietin (TSLP).

* * * * *